(12) United States Patent
Mendizabal-Ruiz et al.

(10) Patent No.: US 12,310,625 B2
(45) Date of Patent: May 27, 2025

(54) AUTONOMOUS INSEMINATION IN AN INTELLIGENT AUTOMATED IN VITRO FERTILIZATION AND INTRACYTOPLASMIC SPERM INJECTION PLATFORM

(71) Applicant: Conceivable Life Sciences Inc., New York, NY (US)

(72) Inventors: Gerardo Mendizabal-Ruiz, Guadalajara (MX); Joshua Abram, Lyme, CT (US); Roberto Valencia-Murillo, Las Paz (MX); Vladimir C. Ocegueda Hernandez, Zapopan (MX); Nuno Costa-Borges, Barcelona (ES); Estefania Hernandez, Guadalajara (MX); Johann Aguayo, Guadalajara (MX); William Nicholas Garbarini, Jr., Cranford, NJ (US); Alejandro Chavez-Badiola, Mexico City (MX); Alan Murray, Greenwich, CT (US); Jacques Cohen, New York, NY (US); Adolfo Flores-Saiffe Farias, Zapopan (MX)

(73) Assignee: Conceivable Life Sciences Inc., New York, NY (US)

( * ) Notice: Subject to any disclaimer, the term of this patent is extended or adjusted under 35 U.S.C. 154(b) by 0 days.

(21) Appl. No.: 18/431,259

(22) Filed: Feb. 2, 2024

(65) Prior Publication Data

US 2024/0423673 A1  Dec. 26, 2024

Related U.S. Application Data

(63) Continuation of application No. PCT/US2024/013428, filed on Jan. 30, 2024.

(Continued)

(51) Int. Cl.
*A61B 17/43* (2006.01)
*A61B 17/425* (2006.01)
(Continued)

(52) U.S. Cl.
CPC ............ *A61B 17/43* (2013.01); *A61B 17/425* (2013.01); *A61B 34/30* (2016.02); *C12M 21/06* (2013.01);
(Continued)

(58) Field of Classification Search
CPC .............................. A61B 17/43; A61B 17/425
See application file for complete search history.

(56) References Cited

U.S. PATENT DOCUMENTS

| | | | |
|---|---|---|---|
| 11,494,578 B1 | 11/2022 | Chian | |
| 2007/0291798 A1* | 12/2007 | Kenny | ............... G02B 21/0032 359/368 |

(Continued)

FOREIGN PATENT DOCUMENTS

| | | |
|---|---|---|
| CN | 112401994 A | 2/2021 |
| WO | 0004929 A1 | 2/2000 |
| WO | 2016001754 A2 | 1/2016 |

OTHER PUBLICATIONS

Zhu et al. "Study of Robotic System for Automated Oocyte Manipulation" (2017), IEEE, 2017 Intern'l Conf on Manipulation, Automation, and Robotics at Small Scales (MARSS).

(Continued)

*Primary Examiner* — Samuel G Gilbert
(74) *Attorney, Agent, or Firm* — Miller Johnson

(57) ABSTRACT

A method for automated ICSI includes receiving at least one droplet containing an egg in a dish placed on a stage. The method includes using an artificial intelligence/machine learning system (AI/ML system) and an imaging system to detect a zona pellucida. The imaging system includes a (Continued)

microscopy system, a camera system, and a lighting system. The method includes holding the egg using a robotic microtool and lowering a robotic pipettor into the droplet. The method includes using the AI/ML system and imaging system to determine an area at which to hold the egg and positioning the robotic microtool to that area. The method includes using the AI/ML system and imaging system to instruct the robotic microtool to apply negative pressure to hold the egg to the robotic pipettor. The method includes using the AI/ML system and imaging system to determine a target location where zona ablation should be performed.

20 Claims, 74 Drawing Sheets

Related U.S. Application Data

(60) Provisional application No. 63/523,258, filed on Jun. 26, 2023.

(51) Int. Cl.
*A61B 34/30* (2016.01)
*C12M 1/00* (2006.01)
*C12M 1/02* (2006.01)
*C12M 1/22* (2006.01)
*C12M 1/26* (2006.01)
*C12M 1/36* (2006.01)
*C12M 3/00* (2006.01)
*C12N 5/073* (2010.01)
*G01N 33/50* (2006.01)
*G01N 35/00* (2006.01)
*G01N 35/10* (2006.01)
*G06T 7/20* (2017.01)
*G06T 7/70* (2017.01)
*G06V 10/82* (2022.01)
*G06V 20/69* (2022.01)
*A61B 34/32* (2016.01)

(52) U.S. Cl.
CPC ............ *C12M 23/10* (2013.01); *C12M 23/48* (2013.01); *C12M 23/50* (2013.01); *C12M 33/04* (2013.01); *C12M 41/06* (2013.01); *C12M 41/18* (2013.01); *C12M 41/48* (2013.01); *C12N 5/0604* (2013.01); *G01N 33/5091* (2013.01); *G01N 35/0099* (2013.01); *G01N 35/10* (2013.01); *G01N 35/1011* (2013.01); *G06T 7/20* (2013.01); *G06T 7/70* (2017.01); *G06V 10/82* (2022.01); *G06V 20/693* (2022.01); *A61B 34/32* (2016.02); *G06T 2207/20081* (2013.01); *G06T 2207/30024* (2013.01); *G06V 20/69* (2022.01); *G06V 20/698* (2022.01); *G06V 2201/03* (2022.01)

(56) References Cited

U.S. PATENT DOCUMENTS

| | | | |
|---|---|---|---|
| 2013/0023052 A1* | 1/2013 | Tanaka | G02B 21/32 |
| | | | 435/461 |
| 2013/0071002 A1* | 3/2013 | Otsuka | G06T 7/0012 |
| | | | 382/133 |
| 2013/0337487 A1 | 12/2013 | Loewke | |
| 2014/0087412 A1* | 3/2014 | Fouras | G01N 11/00 |
| | | | 435/287.1 |
| 2014/0297199 A1 | 10/2014 | Osten | |
| 2015/0031012 A1* | 1/2015 | Palermo | C12M 23/16 |
| | | | 435/2 |
| 2015/0252328 A1 | 9/2015 | Woodruff | |
| 2017/0140535 A1 | 5/2017 | Hamamah | |
| 2020/0126233 A1* | 4/2020 | Shinoda | C12M 41/46 |
| 2020/0305967 A1 | 10/2020 | Getman | |
| 2022/0189640 A1 | 6/2022 | Wessels Wells | |
| 2022/0358655 A1 | 11/2022 | Wessels Wells | |
| 2023/0093989 A1 | 3/2023 | Mahajan | |
| 2023/0303959 A1 | 9/2023 | Blanchard | |
| 2023/0410309 A1* | 12/2023 | Alvarez Fernandez | |
| | | | G06V 20/698 |

OTHER PUBLICATIONS

Abdullah et al., "Automation in ART: Paving the Way for the Future of Infertility Treatment," Published online Aug. 2022, Reproductive Sciences, vol. 30: 1006-1016.

Casciani et al., "Are we approaching automated assisted reproductive technology? Sperm analysis oocyte manipulation, and insemination," Fertil Steril, vol. 2, No. 3: 189-203, 2021.

Trottmann, et al., "Ex vivo investigations on the potential of optical coherence tomography (OCT) as a diagnostic tool for reproductive medicine in a bovine model," vol. 9, No. 1-2: 129-137, 2016.

Fan, et al., "Optimized Optical Coherence Tomography Imaging with Hough Transform-Based Fixed-Pattern Noise Reduction," IEEE Access, vol. 6, 32087-32096, 2018.

Zhai, et al., "Automated Denudation of Oocytes," Micromachines, 2022.

Targosz, et al., "Semantic segmentation of human oocyte images using deep neural networks," BioMedical Engineering, 20:40, 2021.

* cited by examiner

600

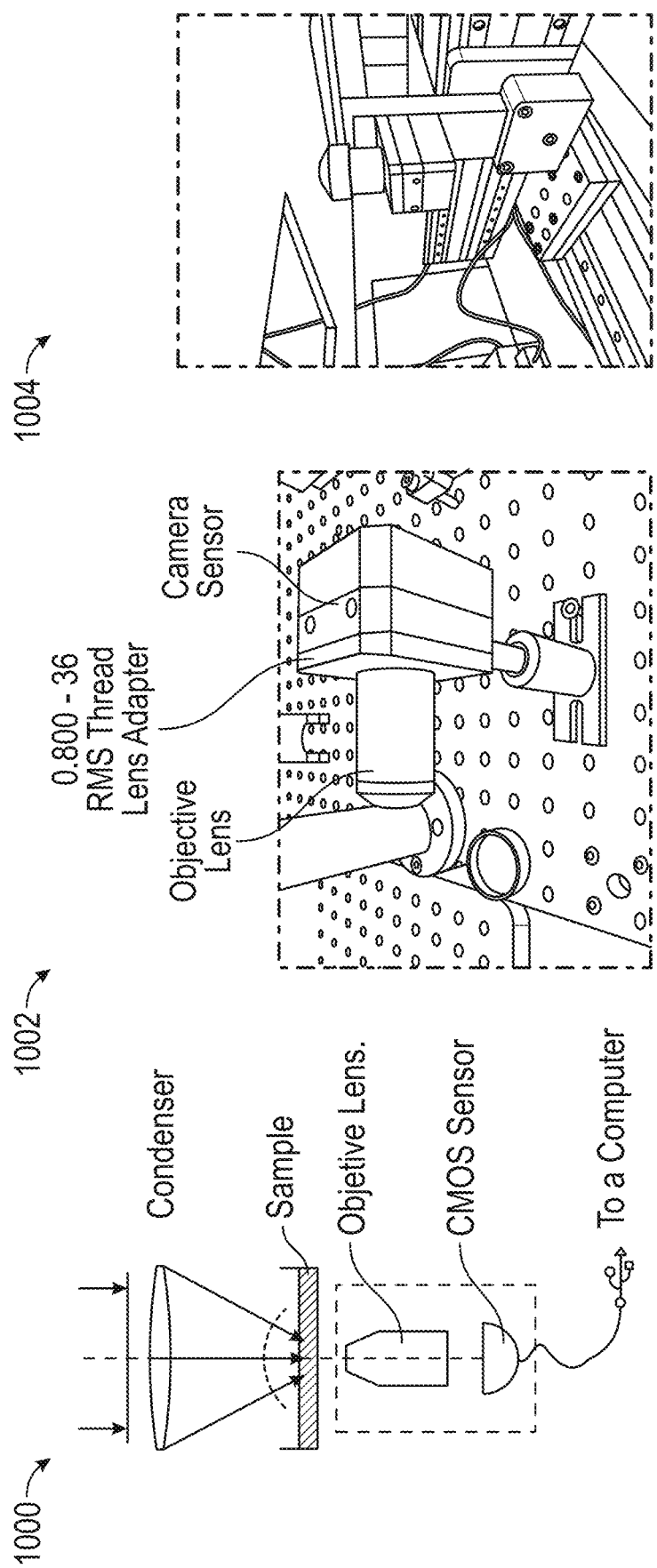

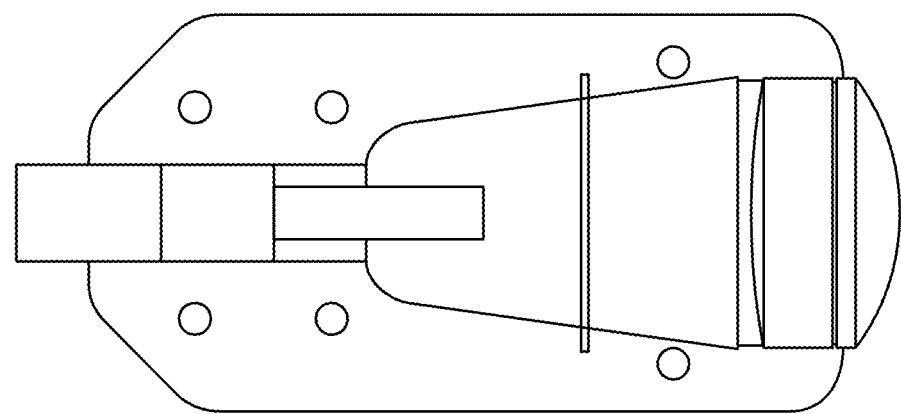
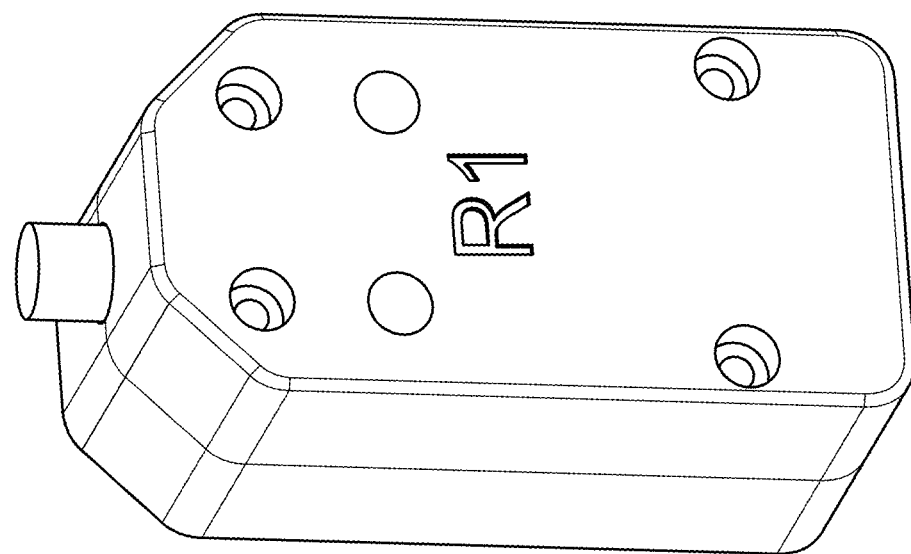
FIG. 13C

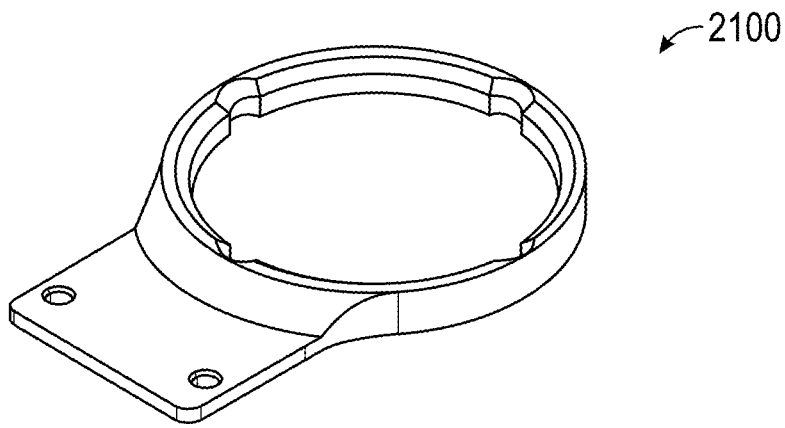
FIG. 21
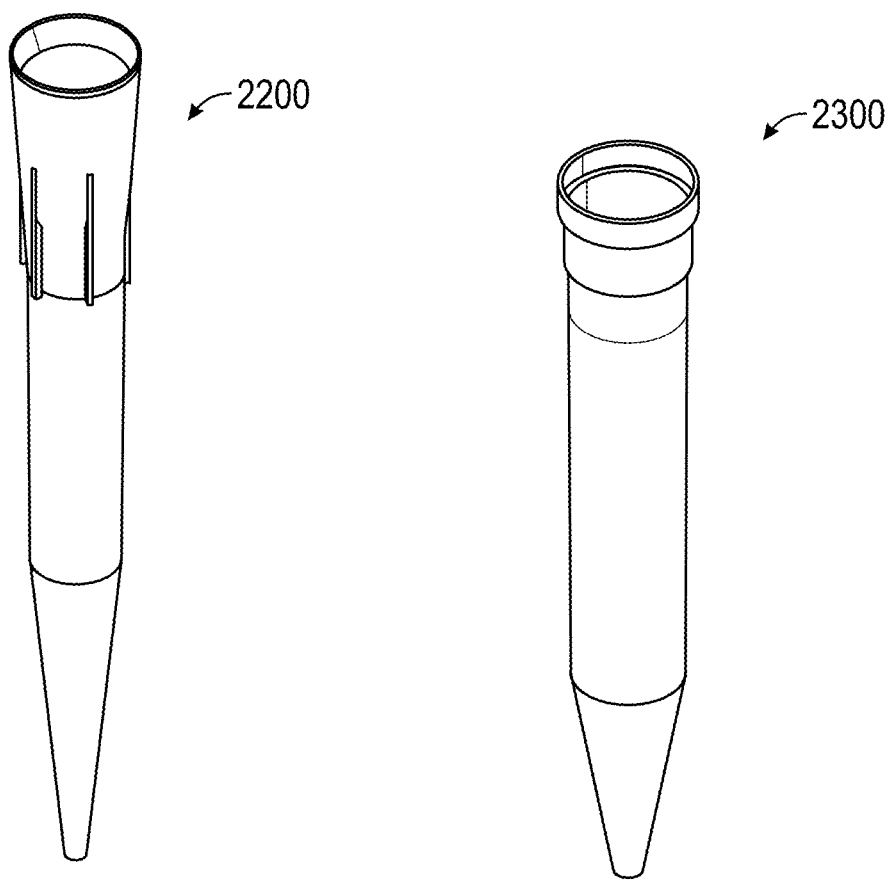
FIG. 22  FIG. 23

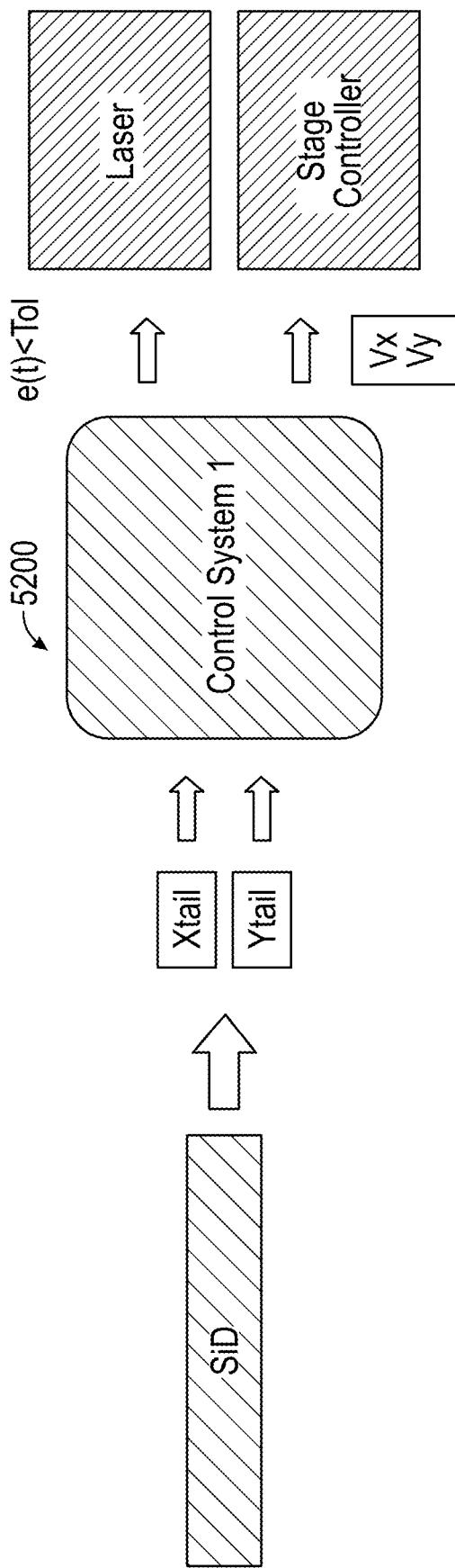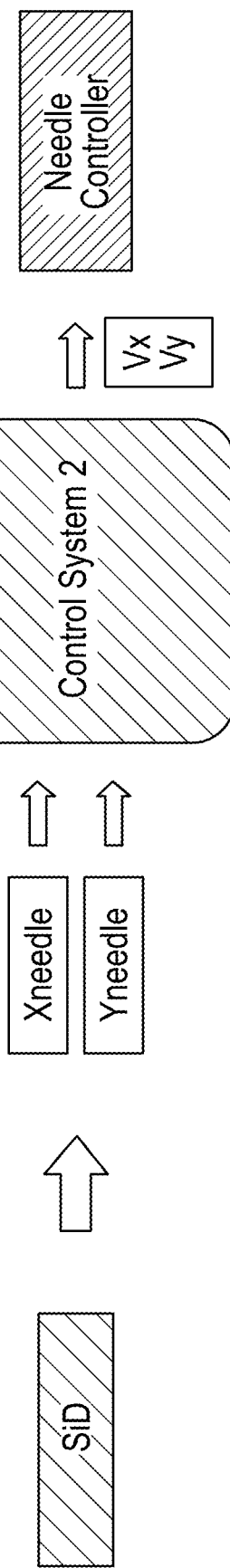
FIG. 52
FIG. 53

- ⊕ Backfeed Data/Sensor Input Cell
- ○ Data/Sensor Input Cell
- ⊘ Noisy Input Sell
- □ Hidden Cell
- ▨ Probabillistic Hidden Cell
- ▩ Spiking Hidden Cell
- ◇ Output Cell
- ◈ Match Input/Output Cell
- ⬠ Recurrent Cell
- ▰ Memory Cell
- ▰ Different Memory Cell
- ⬡ Kernel
- ⬢ Convolution or Pool
6900
FIG. 69
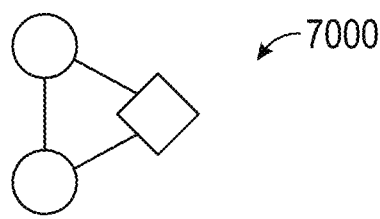
7000
FIG. 70
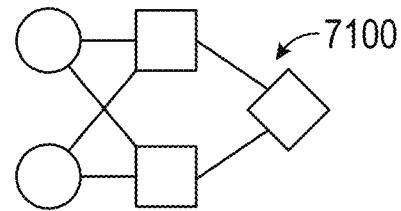
7100
FIG. 71
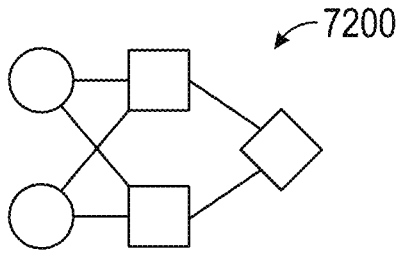
7200
FIG. 72
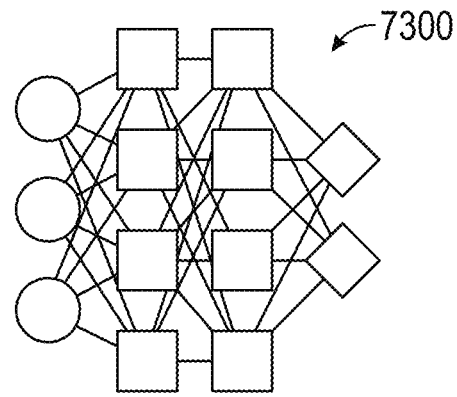
7300
FIG. 73

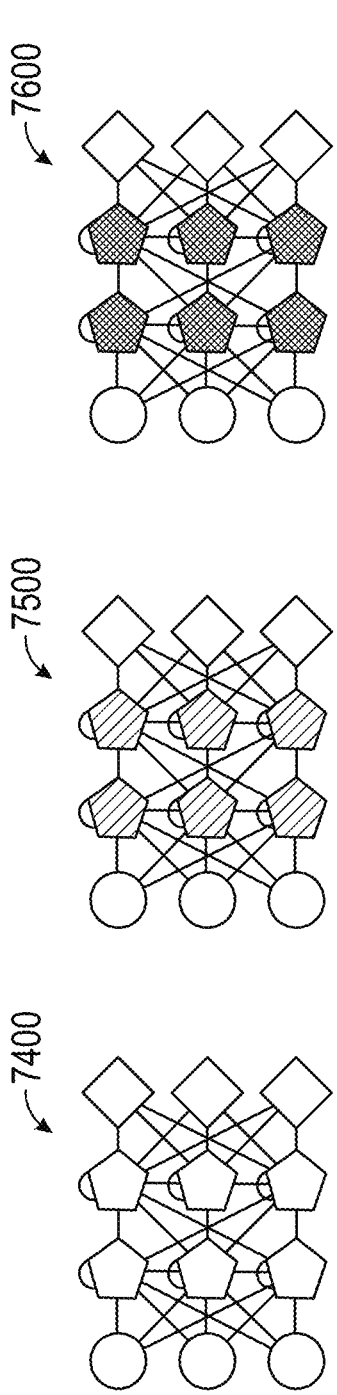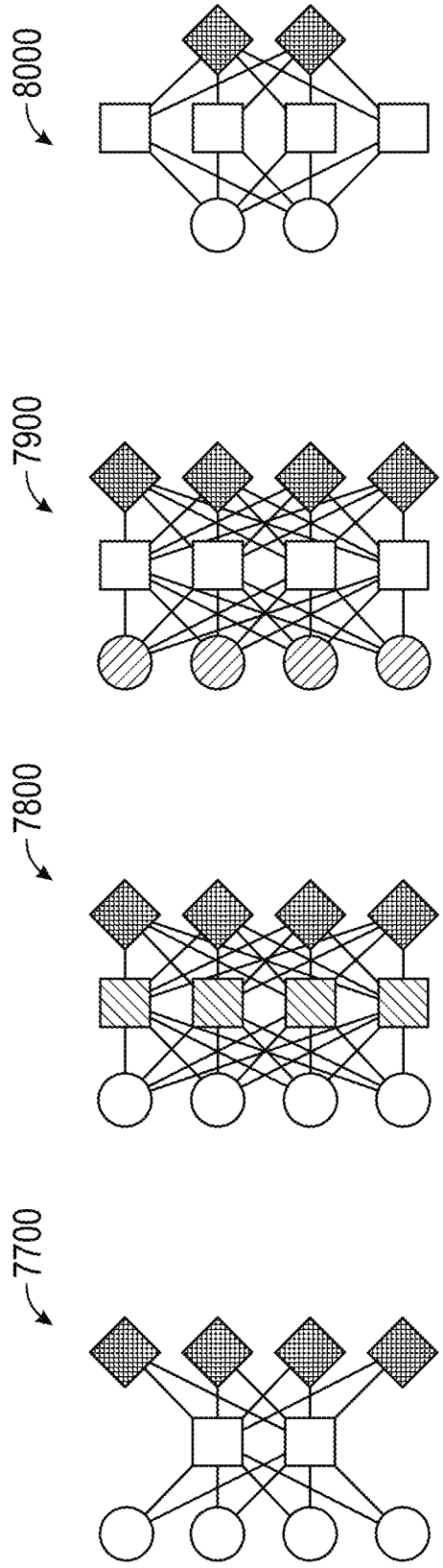

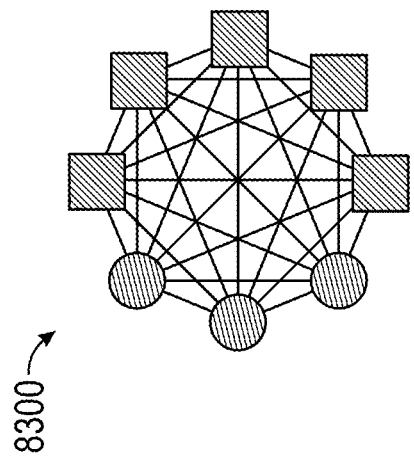
FIG. 83
FIG. 82
FIG. 81
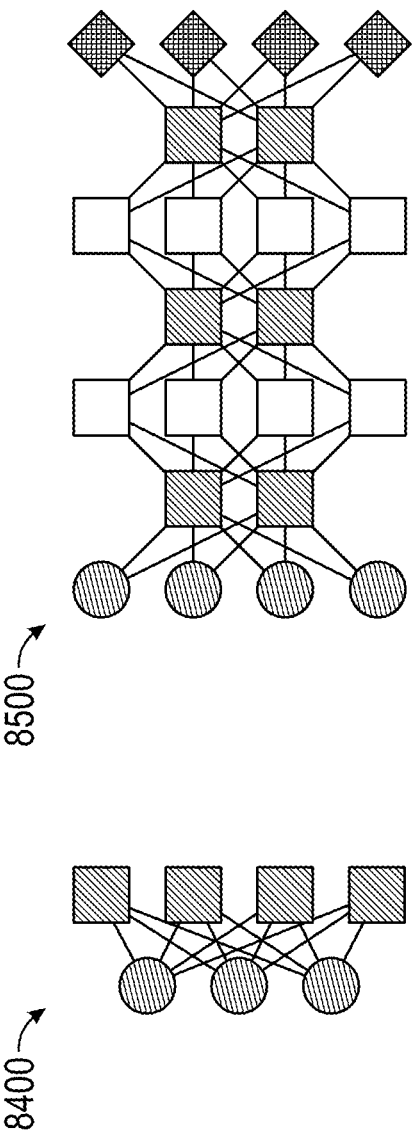
FIG. 85
FIG. 84

8800

8900

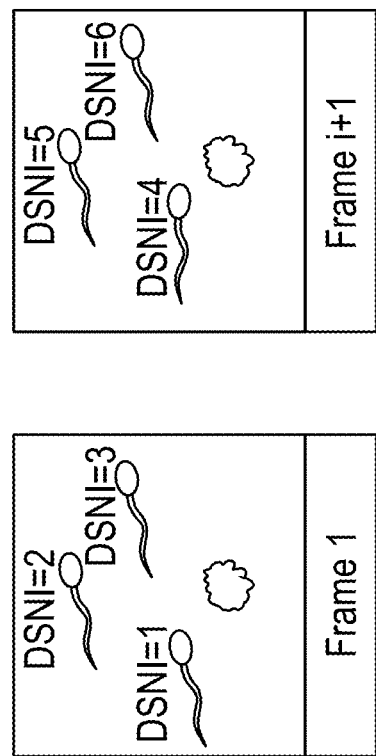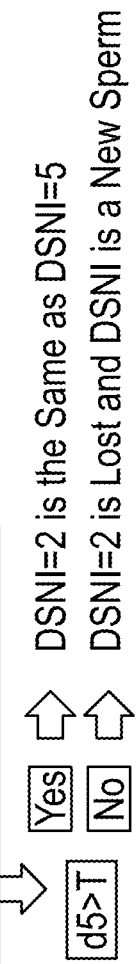
FIG. 109

AUTONOMOUS INSEMINATION IN AN INTELLIGENT AUTOMATED IN VITRO FERTILIZATION AND INTRACYTOPLASMIC SPERM INJECTION PLATFORM

CROSS-REFERENCE TO RELATED APPLICATIONS

This application is a continuation of PCT International Application No. PCT/US2024/013428 filed Jan. 30, 2024, which claims the benefit of U.S. Provisional Application No. 63/523,258 filed Jun. 26, 2023. The entire disclosures of the above applications are incorporated by reference.

FIELD

The present disclosure relates to fertility treatment automation and more particularly to automated in vitro fertilization and more particularly to automated in vitro fertilization and intracytoplasmic sperm injection.

BACKGROUND

Traditional in vitro fertilization (IVF) technologies have largely been dependent upon the assistance of human clinical embryologists and/or andrologists to perform, evaluate, and/or respond to the requirements of IVF processes. This has resulted in expensive IVF intervention that limits access to IVF due to economic constraints, geographic and other limitations, and which is subject to the vagaries of human performance and inconsistencies across clinical settings, equipment, and expertise.

SUMMARY

The present disclosure includes methods and systems for providing an intelligent, automated system of interconnected robotic IVF modules, including intracytoplasmic sperm injection (ICSI) techniques, supported by imaging and artificial intelligence/machine learning (AI/ML) processes, for obtaining, storing, analyzing, performing and reporting on a plurality of materials, data, processes, actions and outcomes relating to IVF/ICSI.

In embodiments, the method for automated, artificial-intelligence-based ICSI, comprising receiving at least one droplet containing an egg in a dish placed on a stage. An artificial intelligence/machine learning system (AI/ML system) and an imaging system may be used to detect a zona pellucida, wherein the imaging system includes a microscopy system, a camera system, and a lighting system. A robotic microtool may be used to hold the egg. A robotic pipettor may lower into the droplet. The AI/ML system and imaging system may be used to determine an area at which to hold the egg and positioning the robotic microtool to that area. The AI/ML system and imaging system may be used to instruct the robotic microtool to apply negative pressure to hold the egg to the robotic pipettor. The AI/ML system and imaging system may be used to determine a target location where zona ablation should be performed, and move the egg to the target location. The AI/ML system and imaging system may be used to assess a thickness of the zona and determine an ablation action, may generate a laser to ablate a pre-designated section and depth of the zona pellucida. The AI/ML system and imaging system may be used to define an injection path into the egg.

In embodiments, the stage may be a microscope stage.

In embodiments, the microscope stage may be in proximity to an inverted microscope, a stercomicroscope, a movable microscope, an optical coherence tomography device, an optical coherence microscopy device, or a lensless microscope.

In embodiments, the robotic microtool may be a robotic holding pipettor.

In embodiments, the robotic pipettor may be a plurality of pipettes.

In embodiments, the dish may be heated.

In embodiments, the imaging system may produce at least one image having a mixed reality in which simulated imagery and real-life imagery are combined.

In embodiments, ablation action may be produced at an intensity and radius needed to ablate an adequate portion of the zona pellucida to facilitate an entry of an ICSI needle through the zona pellucida without distorting the egg.

In embodiments, the method for automated, artificial-intelligence-based ICSI, comprising receiving an egg in a dish placed on a stage of a microscope. The artificial intelligence/machine learning system (AI/ML system) and an imaging system may be used to apply a combination of positive and negative pressures within a robotic ICSI needle to position a sperm at a desired position. The robotic ICSI needle may be moved forward into the egg at a predetermined and controlled speed, stopping once it reaches the end point of the path specified by the AI/ML system, breaking the egg membrane (oolemma) using a piezoelectric pulse, wherein the AI/ML system and the imaging system may be used to determine if a piezo pulse is needed to break the membrane and how many pulses are required. The AI/ML system and the imaging system may be used to apply positive pressure in the robotic ICSI needle to deposit the sperm in the egg. The AI/ML system and the imaging system may be used to confirm that the sperm is out of the needle and move the needle out of the egg; and may be used to apply positive pressure in the holding pipette until the egg is released into a droplet.

In embodiments, the breaking of an egg membrane may be done mechanically.

In embodiments, positive pressure in the ICSI needle may push the sperm to a tip of the ICSI needle in preparation for injection into the cytoplasm, reducing foreign media to be injected into the egg.

In embodiments, the desired position may be determined based in part by using convention microscopy, optical coherence tomography, optical coherence microscopy, or a three-dimensional simulation of the egg morphology.

In embodiments of the present disclosure, a semen preparation module may include a robotic system for semen preparation, retrieval and movement to ICSI dish. In embodiments of the present disclosure, the semen preparation module may include AI for automated detection, identification, and classification. In embodiments of the present disclosure, the semen preparation module may include AI for automated measurement and testing. In embodiments of the present disclosure, the semen preparation module may include AI for optimization. In embodiments of the present disclosure, the semen preparation module may include AI for prediction. In embodiments of the present disclosure, the semen preparation module may include AI for selection/ranking. In embodiments of the present disclosure, the semen preparation module may include AI for semi-autonomous, supervised, or autonomous robotics. In embodiments of the present disclosure, the semen preparation module may include AI for system configuration and control. In embodiments of the present disclosure, the semen preparation module may include fully autonomous AI. In embodiments of the present disclosure, the semen preparation module may include optical, image and machine vision components, systems, and processes. In embodiments of the present disclosure, the semen preparation module may include robotic handling systems and processes. In embodiments of the present disclosure, the semen preparation module may include sensor components, systems, and processes. In embodiments of the present disclosure, the semen preparation module may include semen preparation components, systems, and processes. In embodiments of the present disclosure, the semen preparation module may include specimen management components, systems, and processes. In embodiments of the present disclosure, the semen preparation module may include laser components, systems, and processes.

In embodiments of the present disclosure, an egg preparation module may include egg retrieval components, systems, and processes. In embodiments of the present disclosure, the egg preparation module may include AI for automated detection, identification, and classification. In embodiments of the present disclosure, the egg preparation module may include AI for automated measurement and testing. In embodiments of the present disclosure, the egg preparation module may include AI for optimization. In embodiments of the present disclosure, the egg preparation module may include AI for prediction. In embodiments of the present disclosure, the egg preparation module may include AI for selection/ranking. In embodiments of the present disclosure, the egg preparation module may include AI for semi-autonomous, supervised, or autonomous robotics. In embodiments of the present disclosure, the egg preparation module may include AI for system configuration and control. In embodiments of the present disclosure, the egg preparation module may include fully autonomous AI. In embodiments of the present disclosure, the egg preparation module may include optical, image and machine vision components, systems, and processes. In embodiments of the present disclosure, the egg preparation module may include robotic handling systems and processes. In embodiments of the present disclosure, the egg preparation module may include sensor components, systems, and processes. In embodiments of the present disclosure, the egg preparation module may include specimen management components, systems, and processes. In embodiments of the present disclosure, the egg preparation module may include enzymatic oocyte denudation processes, systems and components. In embodiments of the present disclosure, the egg preparation module may include advanced microscopy systems and components.

In embodiments of the present disclosure, an insemination module may include insemination. In embodiments of the present disclosure, the insemination module may include insemination components, systems, and processes. In embodiments of the present disclosure, the insemination module may include AI for automated detection, identification, and classification. In embodiments of the present disclosure, the insemination module may include AI for automated measurement and testing. In embodiments of the present disclosure, the insemination module may include AI for optimization. In embodiments of the present disclosure, the insemination module may include AI for prediction. In embodiments of the present disclosure, the insemination module may include AI for selection/ranking. In embodiments of the present disclosure, the insemination module may include AI for semi-autonomous, supervised, or autonomous robotics. In embodiments of the present disclosure, the insemination module may include AI for system configuration and control. In embodiments of the present disclosure, the insemination module may include fully autonomous AI. In embodiments of the present disclosure, the insemination module may include optical, image and machine vision components, systems, and processes. In embodiments of the present disclosure, the insemination module may include robotic handling systems and processes. In embodiments of the present disclosure, the insemination module may include sensor components, systems, and processes. In embodiments of the present disclosure, the insemination module may include specimen management components, systems, and processes.

In embodiments of the present disclosure, an incubation module may include incubation components, systems, and processes. In embodiments of the present disclosure, the incubation module may include sensor components, systems, and processes. In embodiments of the present disclosure, the incubation module may include specimen management components, systems, and processes. In embodiments of the present disclosure, the incubation module may include AI for automated measurement and testing. In embodiments of the present disclosure, the incubation module may include AI for optimization. In embodiments of the present disclosure, the incubation module may include AI for prediction. In embodiments of the present disclosure, the incubation module may include AI for selection/ranking. In embodiments of the present disclosure, the incubation module may include AI for semi-autonomous, supervised, or autonomous robotics. In embodiments of the present disclosure, the incubation module may include AI for system configuration and control. In embodiments of the present disclosure, the incubation module may include fully autonomous AI. In embodiments of the present disclosure, the incubation module may include robotic handling systems and processes. In embodiments of the present disclosure, the incubation module may include advanced microscopy systems and components.

In embodiments of the present disclosure, a vitrification and cryo-storage module may include freezing components, systems, and processes. In embodiments of the present disclosure, the vitrification and cryo-storage module may include AI for automated measurement and testing. In embodiments of the present disclosure, the vitrification and cryo-storage module may include AI for optimization. In embodiments of the present disclosure, the vitrification and cryo-storage module may include AI for system configuration and control. In embodiments of the present disclosure, the vitrification and cryo-storage module may include AI for semi-autonomous, supervised, or autonomous robotics. In embodiments of the present disclosure, the vitrification and cryo-storage module may include fully autonomous AI. In embodiments of the present disclosure, the vitrification and cryo-storage module may include sensor components, systems, and processes. In embodiments of the present disclosure, the vitrification and cryo-storage module may include specimen management components, systems, and processes. In embodiments of the present disclosure, the vitrification and cryo-storage module may include robotic handling systems and processes. In embodiments of the present disclosure, the vitrification and cryo-storage module may include storage components, systems, and processes. In embodiments of the present disclosure, the vitrification and cryo-storage module may include AI for automated measurement and testing. In embodiments of the present disclosure, the vitrification and cryo-storage module may include AI for optimization. In embodiments of the present disclosure, the vitrification and cryo-storage module may include AI for system configuration and control. In embodiments of the present disclosure, the vitrification and cryo-storage module may include AI for semi-autonomous, supervised, or autonomous robotics. In embodiments of the present disclosure, the vitrification and cryo-storage module may include fully autonomous AI. In embodiments of the present disclosure, the vitrification and cryo-storage module may include sensor components, systems, and processes. In embodiments of the present disclosure, the vitrification and cryo-storage module may include robotic handling systems and processes.

BRIEF DESCRIPTION OF THE DRAWINGS

The present disclosure will become more fully understood from the detailed description and the accompanying drawings.

FIG. 10A illustrates a microscope comprising the combination of a CMOS camera sensor and a microscope objective.

FIGS. 10B and 10C illustrate an assembled microscope and its appearance when utilized as an inverted microscope within the IVF/ICSI platform robotics, respectively.

FIG. 13C illustrates an example mechanical illustration for this light.

FIG. 21 illustrates a holder for an intracytoplasmic sperm injection (ISCI) dish.

FIGS. 22 and 23 depict a pipette tip having a custom geometry to facilitate a sperm "swim-up" protocol.

FIG. 52 illustrates a simplified system control diagram for laser sperm ablation.

FIG. 53 illustrates a simplified system control diagram for fine positioning of a needle.

FIG. 69 to FIG. 96 are schematic diagrams of embodiments of neural net systems that may connect to, be integrated in, and be accessible by the platform for enabling intelligent transactions including ones involving expert systems, self-organization, machine learning, artificial intelligence and including neural net systems trained for pattern recognition, for classification of one or more parameters, characteristics, or phenomena, for support of autonomous control, and other purposes in accordance with embodiments of the present disclosure.

FIG. 109 is a representation of the process to verify the correspondence of the identity of a sperm within successive frames.

DETAILED DESCRIPTION

Figure 1:
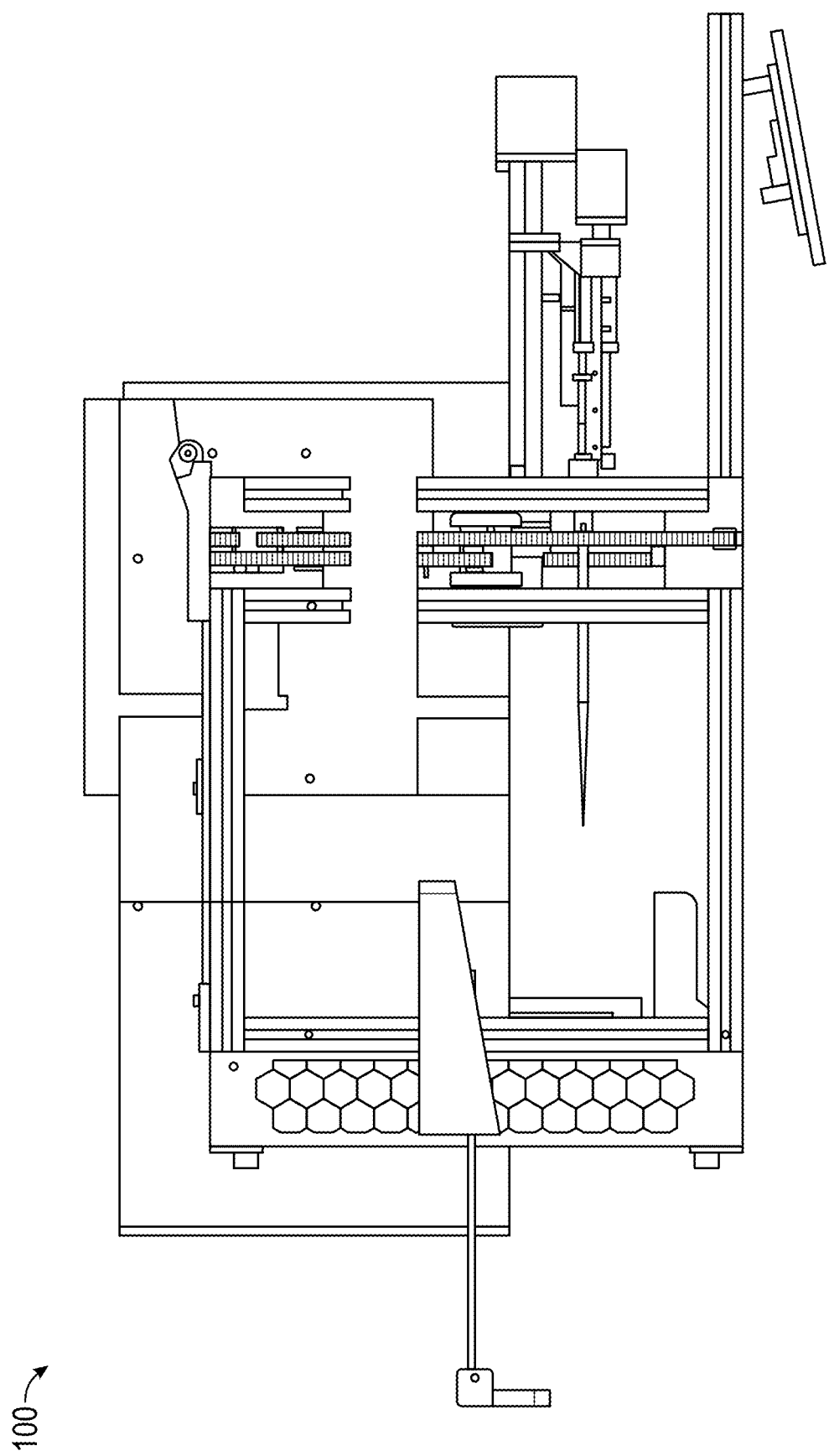
FIG. 1 illustrates the left-side view of the semen preparation module of the IVF/ICSI platform.

In embodiments of the present invention, an IVF/ICSI platform, as described herein, may include automation of traditionally manual laboratory activities between robotic systems used in assisted reproduction (inter-robotic), and automation of traditionally manual laboratory activities preparing for specific robotic procedures (intra-robotic), including but not limited to 1) diagnostic semen analysis, such as computer assisted sperm analysis; 2) continuous embryo culture, including employing robotic handling of dishes combined with time-lapse microscopy technology with manual or automated embryo development annotation; 3) cryo-storage automation, including automated cryo-storage processes in clinical IVF allowing for precise sample location monitoring and continuous environmental status monitoring; and 4) micromanipulator usage, including robotic systems for single-cell surgery, offering fine and coarse control movement modulators, some with digital control for precise tool manipulation.

In embodiments, the IVF/ICSI platform, as described herein, improves upon existing methods and systems, in part, by automating intra- or inter-patient pipette and tool setup, dish preparation, or tracking of disposables and biological materials by integrating traditional IVF laboratory processes into a conveyor-type robotic line (linear or otherwise), including but not limited to automated semen analysis, sperm preparation, petri dish preparation, egg retrieval, oocyte vitrification, egg denudation, time-lapse incubation, ICSI, embryo selection, embryo vitrification, robotic plunging into liquid nitrogen, embryo transfer, cryo-storage, and other IVF systems, methods, processes and procedures. In embodiments, the conveyance system used by the IVF/ICSI platform to transport tools, equipment, biological material, human samples, refuse, and other facilities, components, material and/or objects used by the IVF/ICSI platform to transport such from a first location or position to a second location or position may include, but is not limited to, a conveyor belt, a rail-based conveyance, a sequential robotic movement, a roller conveyor, a chain conveyor, a gravity conveyer, an overhead conveyor, a flexible conveyor, a pneumatic conveyor, an auger conveyor, a screw conveyor, a vacuum conveyor, a vibrating conveyor, or some other type of conveyance.

In embodiments, the IVF/ICSI platform may include an inter-robotic IVF system protocol that includes processes for coordinating robotic elements across distinct IVF procedures, specifically addressing the interconnection of robotic stages within the IVF/ICSI platform, thereby reducing human intervention, minimizing costs, enhancing operational speed, and ensuring the secure and efficient transfer of samples between different robotic modules of the IVF/ICSI platform.

In embodiments, the IVF/ICSI platform may include a comprehensive documentation system to record, monitor and report on the performance of the inter-robotic IVF system, including parameters related to sample transfer, system efficiency, and any incidents for analysis and continuous improvement. The IVF/ICSI platform may be adaptable to changes in IVF laboratory setup and scalable to accommodate future expansions or modifications.

In embodiments, the IVF/ICSI platform may include intra-robotic systems and procedures for configuring an intra-robotic IVF system, encompassing microscopy and non-microscopy robotic elements involved in a specific procedure. Such intra-robotic systems and procedures may standardize setup for each patient, ensuring the incorporation of both disposable and non-disposable components into each robotic platform. In an example intra-robotic IVF system procedure, the availability of necessary components for a specific patient procedure may be verified and the procedure may ensure that both disposable and non-disposable items are in stock and within the designated sterile environment. Sterile and non-sterile components may be positioned on the robotic platform according to a standardized layout, in part to allow flexibility in the positioning of individual components, accommodating variations in patient or procedural requirements and to facilitate adjustments to the setup. Sterility protocols may be implemented by the system when handling and placing sterile components on the robotic platform, which may also regularly assess and maintain the integrity of sterile barriers throughout the procedure. The system may document the configuration of the intra-robotic IVF system for each patient procedure and include details on the positioning of disposable and non-disposable components, allowing for comprehensive records and potential future optimizations.

In embodiments, the inter- and intra-robotic systems of the IVF/ICSI platform may include a comprehensive software system for the coordination and management of IVF processes and integrated laboratory robots. This system may track samples, monitor environmental conditions, monitor and instruct robotic systems, control the timing of all procedures, detect faults or inefficiencies, and report to electronic medical records (EMR) to allow for patient scheduling and patient instructions. The software system may monitor the safety aspects of the robotic system, including maintenance and service requirements.

Figure 2:
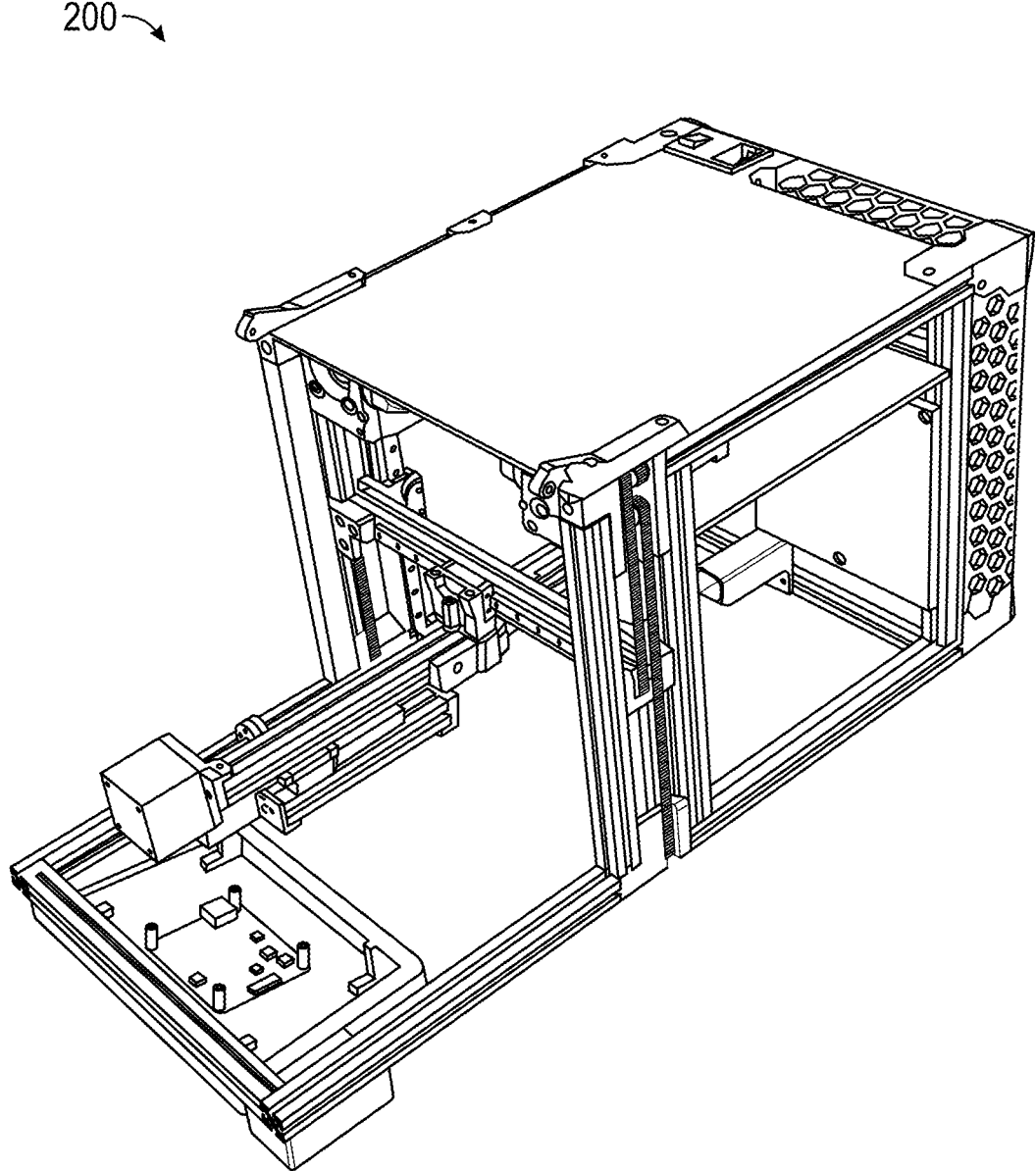
FIG. 2 illustrates a partial assembly view of the semen preparation module of the IVF/ICSI platform.
Figure 3:
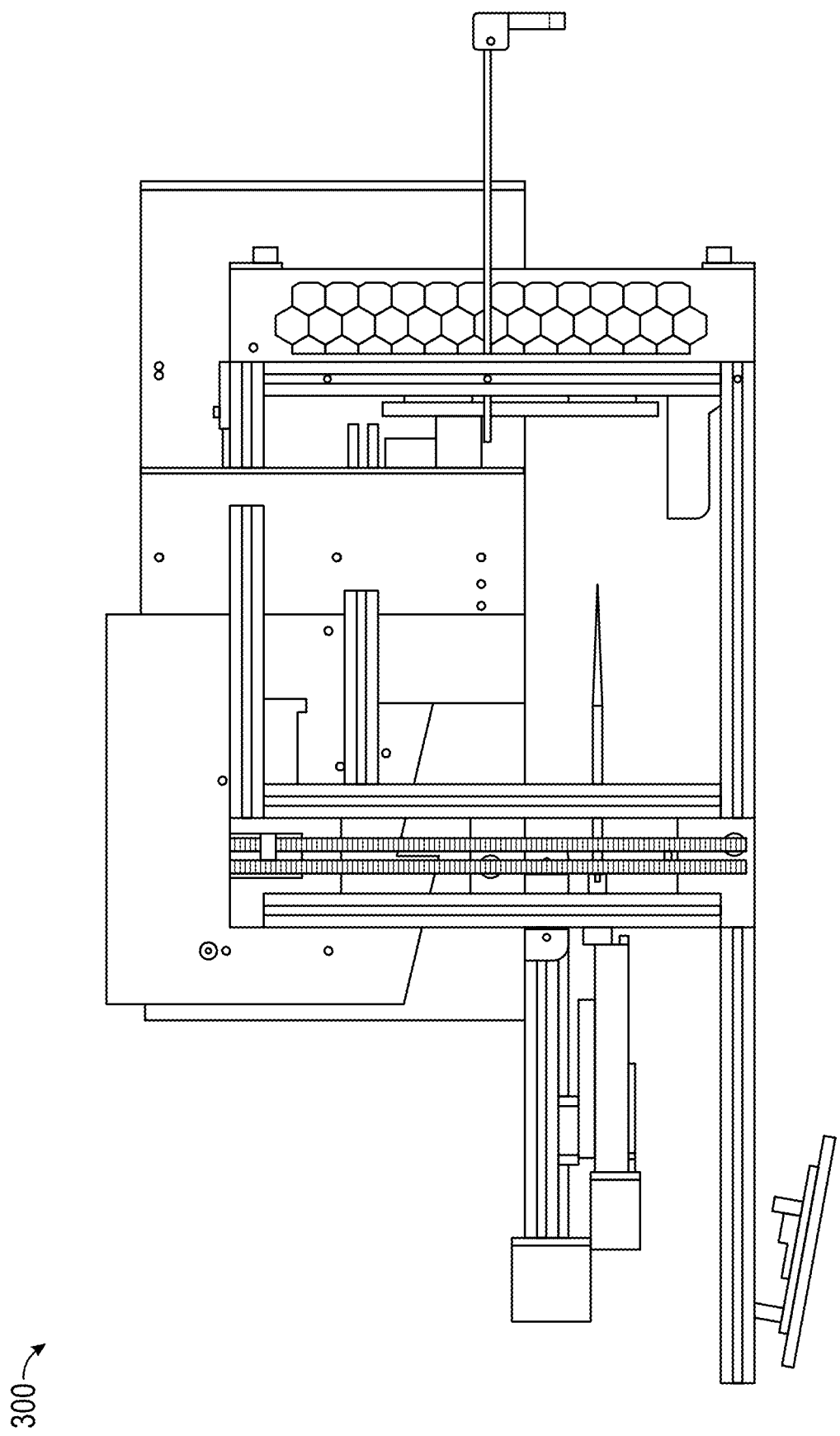
FIG. 3 illustrates a right-side view of the semen preparation module of the IVF/ICSI platform.
Figure 4:
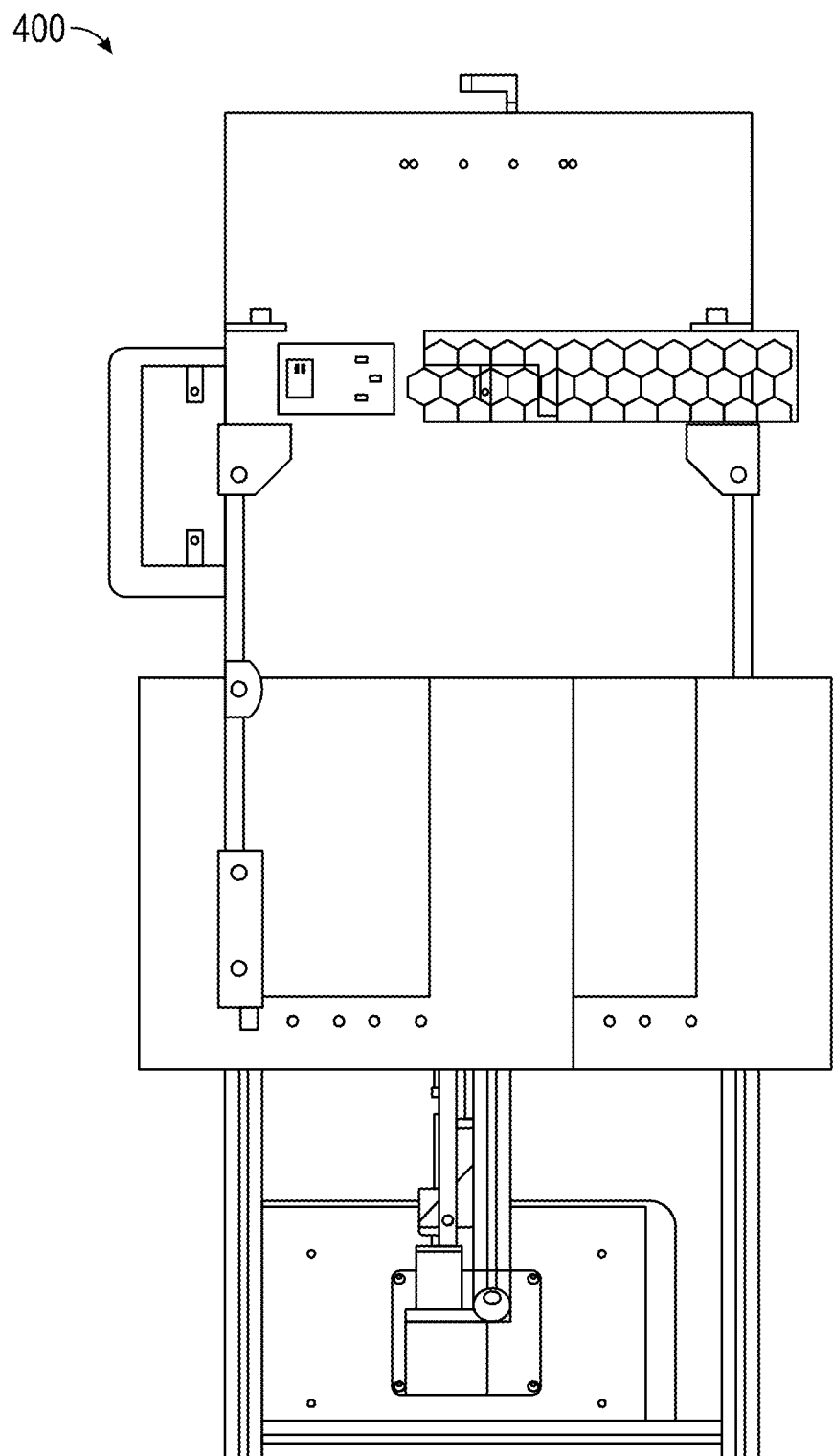
FIG. 4 illustrates a top-side view of the semen preparation module of the IVF/ICSI platform.
Figure 5:
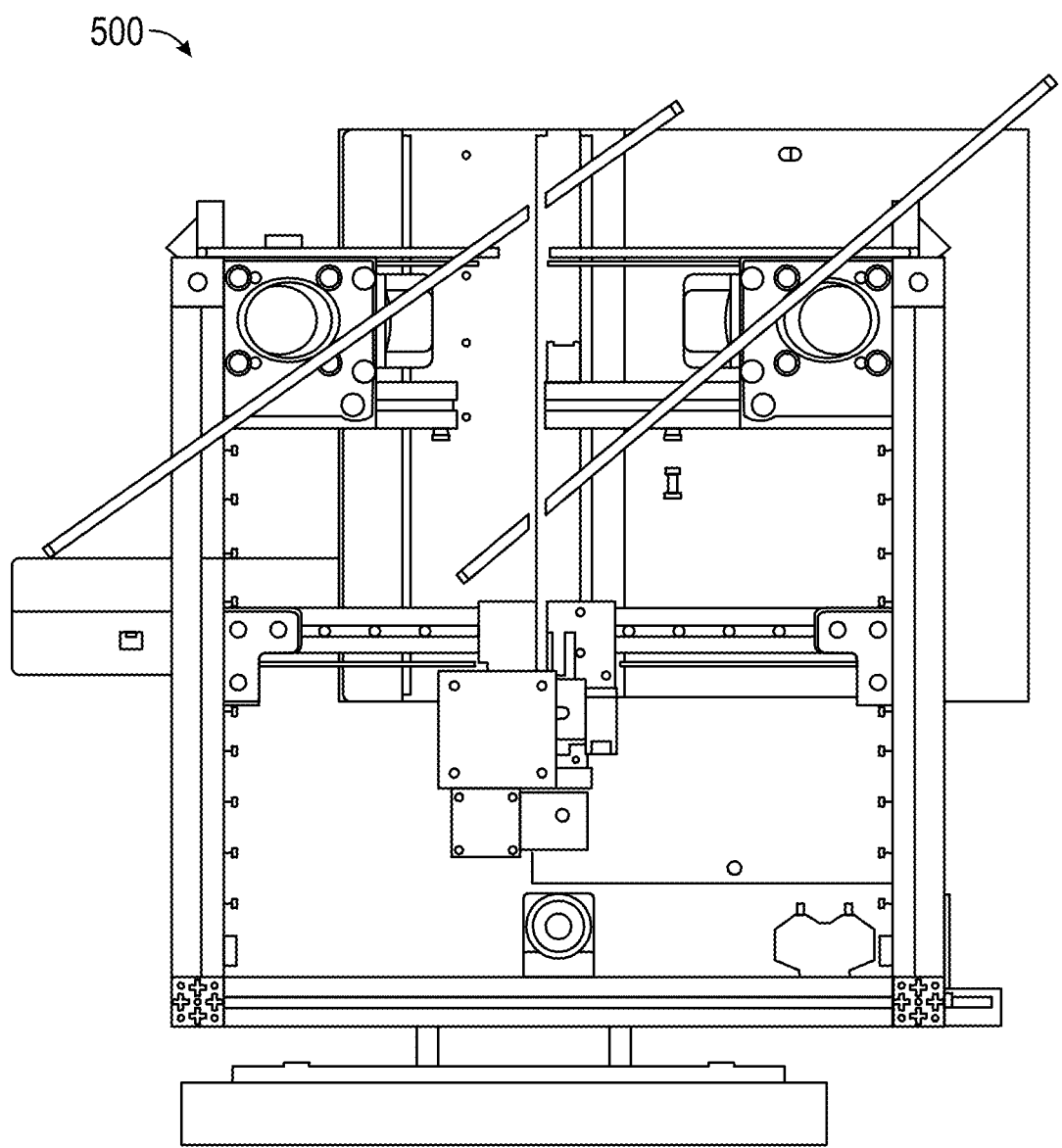
FIG. 5 illustrates a front view of the semen preparation module of the IVF/ICSI platform.
Figure 6:
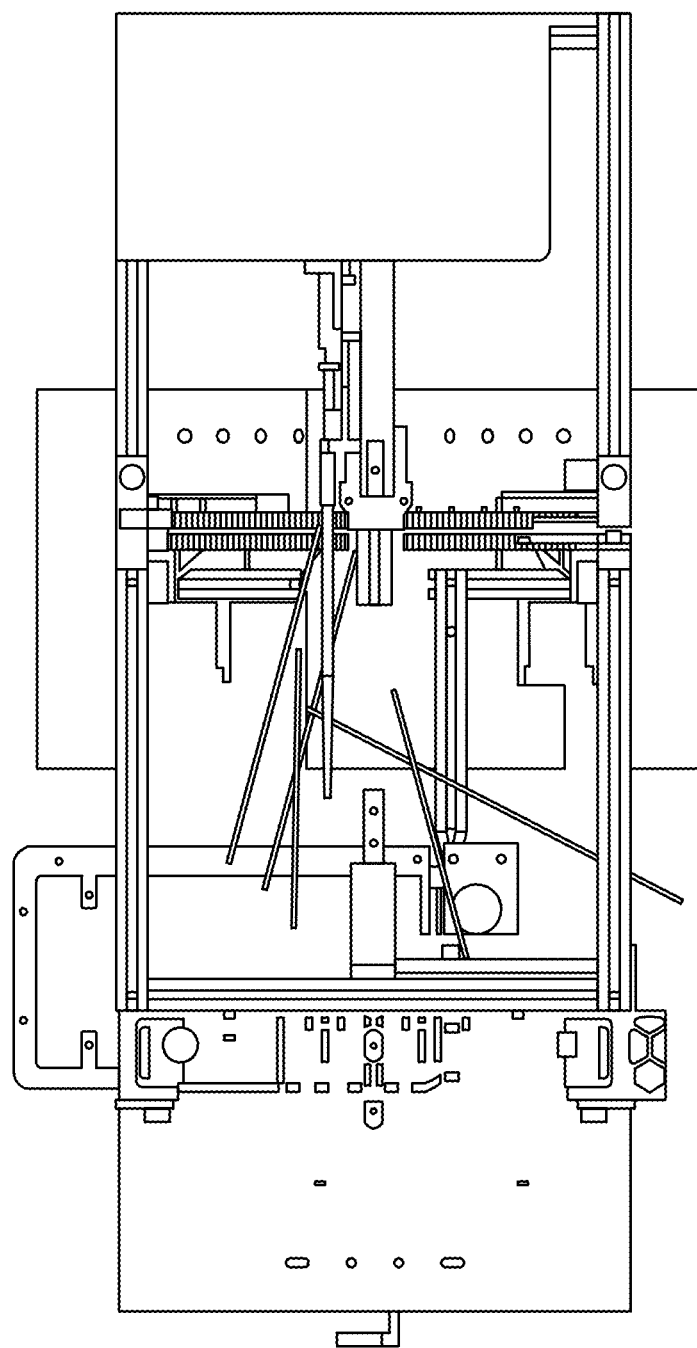
FIG. 6 illustrates a bottom view of the semen preparation module of the IVF/ICSI platform.

In embodiments of the present invention, an IVF/ICSI platform, as described herein, may receive a semen sample from, for example, a human manually placing the semen sample within a semen preparation module of the IVF/ICSI platform, from a robotic device, such as a handling robot, a liquid handling machine, or some other type of automated process. FIG. 1 illustrates the left-side view of a semen preparation module 100 of the IVF/ICSI platform. FIG. 2 illustrates a partial assembly view of the semen preparation module 200 of the IVF/ICSI platform. FIG. 3 illustrates a right-side view of the semen preparation module 300 of the IVF/ICSI platform. FIG. 4 illustrates a top-side view of the semen preparation module 400 of the IVF/ICSI platform. FIG. 5 illustrates a front view of the semen preparation module 500 of the IVF/ICSI platform. FIG. 6 illustrates a bottom view of the semen preparation module 600 of the IVF/ICSI platform.

In embodiments, the semen preparation module may be fully automated, use robotics for the handling and movement of materials, including biological specimens, automated robotic pipetting, and connected to a network infrastructure, as described herein, for remotely controlling the activities of the semen preparation module as one component of the fully automated and robotic IVF/ICSI platform. Semen is a complex biological fluid composed of a mixture of spermatozoa and fluid produced mainly by the seminal vesicles and prostate. The fluid, or seminal plasma, serves multiple functions including transport and protection of sperm cells among other functions. To be functional and maintain motility and viability, sperm may be separated from seminal plasma within approximately an hour of production.

In embodiments, the automated, robotic pipette systems and methods, as described herein may be fully automated, use robotics for the handling and movement of materials, including biological specimens, and operate within a connected network infrastructure for remotely controlling the activities of single-cell-based methods, processes, protocols and the like, including but not limited to single-cell isolation methods, methods for rapid live cell isolation into a container (e.g., a PCR tube), methods for isolating live single cells in sub-microliter volumes (e.g., suitable for single-cell PCR analysis and RNA-sequencing), robotic pipette ("robotic pipettor") methods using a single-cell pipette (SCP), for example consisting of an air-displacement pipette and SCP-Tip, and its application in single-cell isolation for sequencing (e.g., RNA-sequencing), and other robotic pipette systems and methods, as described herein.

In embodiments of the present invention, the term "selection" may refer to processes that use certain criteria (e.g., sperm morphology, sperm motility pattern, and the like) to choose a particular sperm cell from a group. For example, the semen preparation module, as described herein, may select an individual sperm based on, for example, the pattern of the cell's motility. The terms "preparation" or "separation," as used herein may be used in relation to semen and the processes it undergoes before sperm can be used for IVF. Thus, there is an element of selection in the preparation of sperm (selecting for populations of progressively motile sperm) and the term "preparation" as used herein to disclose the semen preparation module fully encompasses the processes of selection, preparation and separation as well as other functionalities, as described herein.

In embodiments, in the context of semen and sperm preparation, the term "automation" as used herein may refer to robotics, robotics-assisted, and/or processes and protocols that involve the use of robotics, including robotics operating without human intervention for the duration of a process or protocol. Thus, processes, methods and protocols performed in the semen preparation module that ordinarily require a human operator may be performed by a robotic system, as described herein.

In embodiments, for insemination of oocytes in vitro, or artificial intrauterine delivery of sperm in vivo, semen is processed in order to remove the seminal plasma, cellular and acellular debris, and immotile sperm cells, and collect a mostly motile sperm fraction free of seminal fluid. Seminal plasma is toxic to oocytes and embryos. General processes involved in semen preparation are listed in Table 1. Traditional manual methods, except microfluidic separation (e.g., for intracytoplasmic sperm injection (ICSI)), require centrifugation of a mixture of semen and handling media. For standard IVF insemination, microfluidic device separation requires centrifugation to remove traces of seminal fluid.

Table 1, below, lists processes involved in traditional, manual semen preparation via three methods (swim up, density gradient, and microfluidics), noting the role of the human operator in the traditional, non-robotic, procedure.

TABLE 1

| Action | Density Gradient (DG) Separation | Swim up (SU) Separation | Microfluidic (MF) Separation | Human operator dependent | Human operator role |
| --- | --- | --- | --- | --- | --- |
| Receipt & identification of semen sample | Yes | Yes | Yes | Yes | Document verification; patient contact; Human judgment |
| Allow semen sample to liquefy | Yes | Yes | Yes | Yes | Time keeping; Microscopic examination; Human judgment |
| Semen Assessment (count, motility) | Yes | Yes | Yes | Yes | Manual pipetting; Microscopic examination; Human judgment |
| Preparation of DG tube/s | Yes | n/a | n/a | Yes | Manual pipetting |
| Preparation of SU tube/s | n/a | Yes | n/a | Yes | Manual pipetting |
| Preparation of the MF chamber | n/a | n/a | Yes | Yes | Manual pipetting |
| Centrifugation of DG tube/s | Yes | n/a | n/a | Yes | Manual handling of tubes; Transport |
| Identity verification during transfer of semen to other containers/devices | Yes | Yes | Yes | Yes | Witnessing; Human judgment |
| Placement of SU tubes at 37 C. for designated time | n/a | Yes | n/a | Yes | Manual handling of tubes; Transport; Timekeeping |
| Placement of MF chamber at 37 C. for designated time | n/a | n/a | Yes | Yes | Manual handling of tubes; Transport; Timekeeping |
| Removal of the layer/portion with separated/selected sperm | Yes | Yes | Yes | Yes | Manual pipetting |
| Dilution of selected sperm suspension & centrifugation of the tube/s (once or twice) | Yes | Possible | Possible if used for standard insemination | Yes | Manual pipetting |
| Removal of the supernatant & dilution of the final sample | Yes | Possible | Possible | Yes | Manual pipetting |

TABLE 1-continued

| Action | Density Gradient (DG) Separation | Swim up (SU) Separation | Microfluidic (MF) Separation | Human operator dependent | Human operator role |
|---|---|---|---|---|---|
| Assessment of prepared sample | Yes | Yes | Yes | Yes | Microscopic examination |
| Maintenance of chain of custody through insemination | Yes | Yes | Yes | Yes | Document verification; witnessing; Human judgment |

In embodiments, a non-diagnostic semen assessment pre-preparation for insemination may include measurement of volume (mL), viscosity (normal/high), sperm concentration (×106/mL), and progressive and non-progressive motility (%). Time required for liquefaction may also be assessed. Liquefaction is temperature-dependent and should be completed within 15-30 minutes post-production. Assessment post-preparation may include sperm concentration and progressive motility.

In embodiments, a robot, liquid handling machine, or other type of automated process may be controlled within the IVF/ICSI platform and/or remotely from the IVF/ICSI platform, for example, using computer code, commands, instructions and the like that are received from a system associated with, but physically remote to, the IVF/ICSI platform. For example, an operator, such as a clinical embryologist and/or andrologist, in a location that is remote from the IVF/ICSI platform may utilize a user interface to select a sperm sample, verify that it is the sperm sample that is intended for preparation and instruct a robot, liquid handling machine, or other type of automated process to move the sperm sample from a first location (e.g., secured storage) to the IVF/ICSI platform for preparation.

In embodiments, a semen specimen may be received by the semen preparation module in a container, for example a container made of plastic or some other material. Processing of the semen specimen by the semen preparation module may proceed within the same container or in another container.

In embodiments, the semen specimen may be placed within the semen preparation module in a container, vessel, dish or other holder that is in contact with a plate that may be moved to optimally position the semen specimen, for example to optimize computer imaging of the sample, sperm detection, or some other activity.

The semen specimen may be placed on, near, above or next to a plate to which temperature control may be applied (e.g., heating). In an example, the plate may be heated to a sustained temperature of 37-degrees Celsius (or some other temperature target), for the duration of a pipetting process. In another example, the plate may have its temperature adjusted throughout the duration of the pipetting process, for example, based upon a detected condition or datum relating to the pipetting process. This temperature adjustment may be made automatically, for example using AI/ML processes, as described herein. Alternatively, the semen specimen may be placed on, near, above or next to a plate to which temperature control is not applied.

In embodiments, the semen preparation module may receive a specimen and automatically place the specimen for viewing with a microscope, computer or machine vision, or some other imaging device, in order to perform sperm identification, discovery, analysis and evaluation. In an example embodiment, the specimen may be viewed within the semen preparation module using one or more flexible or fixed-position microscope objectives, an inverted microscope, a digital microscope, or some other type of microscope.

Figure 7:
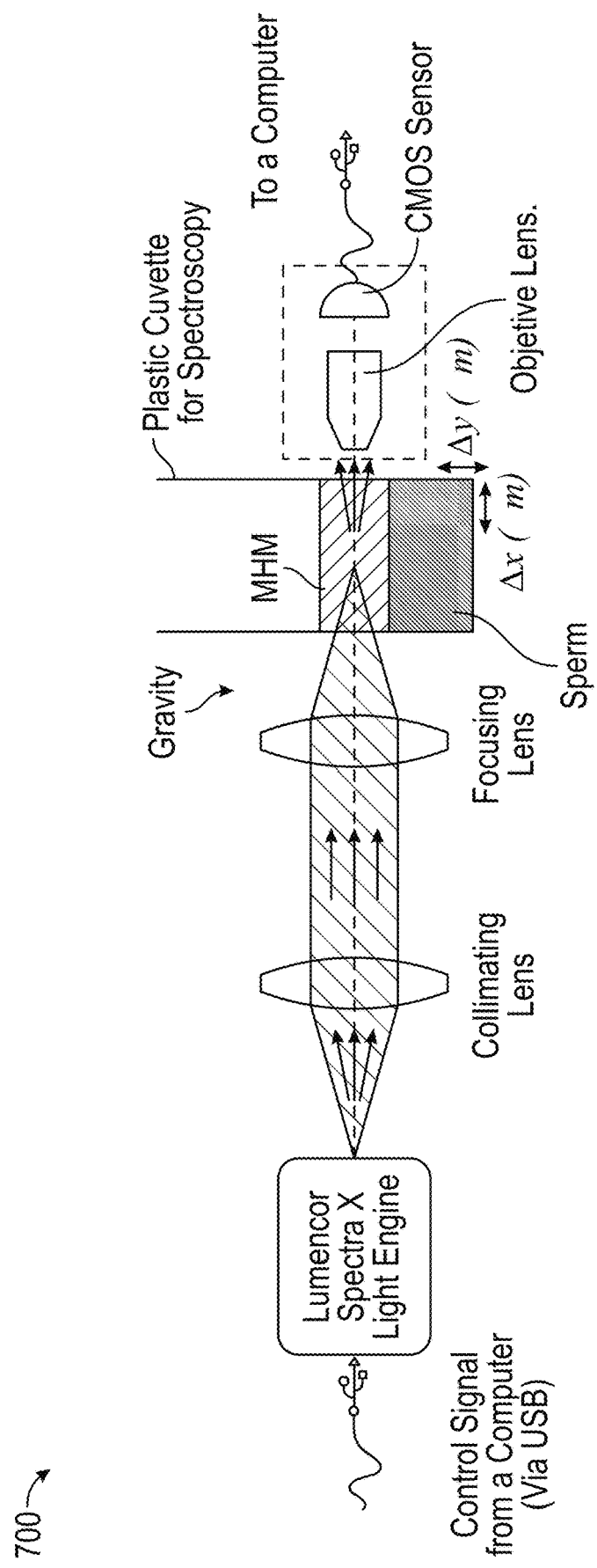
FIG. 7 illustrates a microscope in a horizontal configuration positioned close to a rectangular cuvette containing a biological sample.
Figure 8:
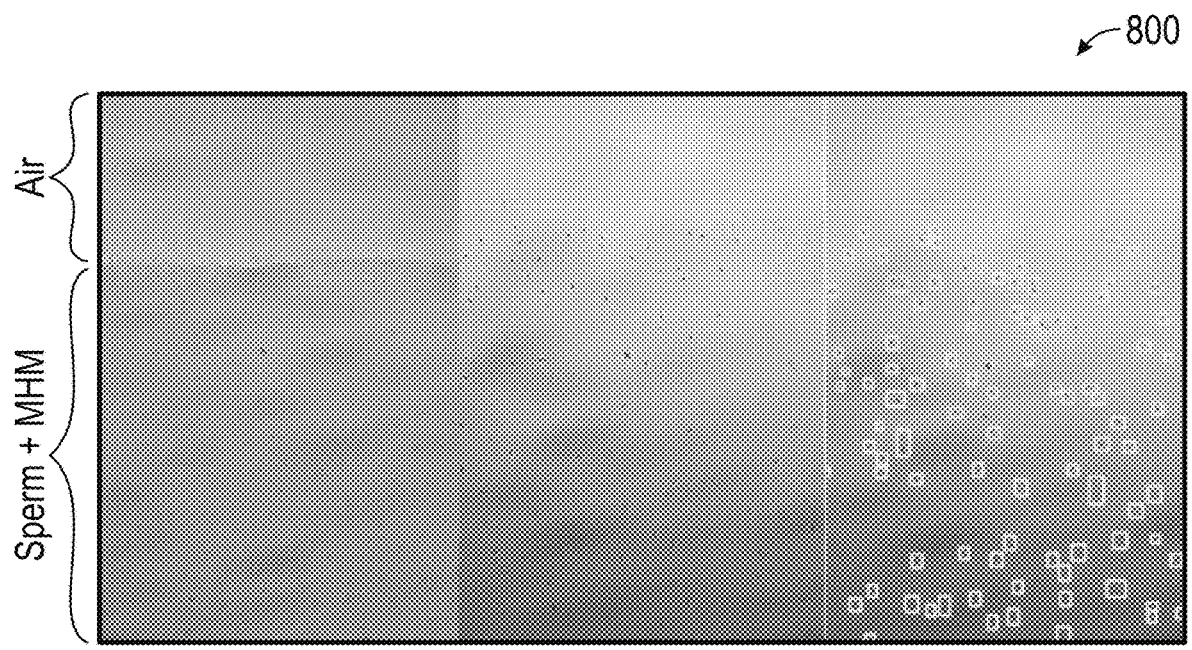
FIG. 8 is an illustrative example of images obtained using a microscope in a horizontal configuration positioned close to a rectangular cuvette containing a biological sample.
Figure 9:
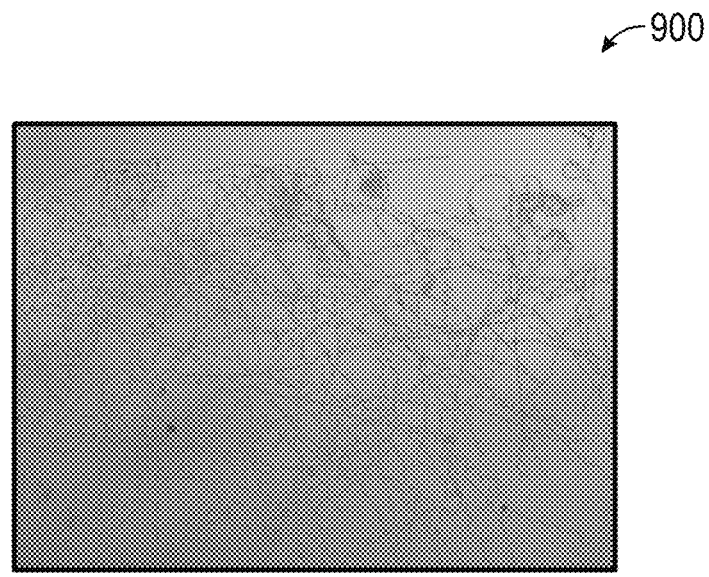
FIG. 9 illustrates a sample screen for sperm tracking analysis.

In embodiments, the IVF platform may include imaging systems and methods for tracking sperm movements as they swim against the direction of gravity, providing direct measurements for sperm statistics, including concentration, swimming direction, position, and speed. In contrast to conventional methods, where sperm are observed, for example, through a counting chamber on a microscope, this method may enable direct observation of sperm behavior in a test tube. In embodiments, this method may include employing a microscope in a horizontal configuration positioned close to a rectangular cuvette containing the sample 700 (see FIG. 7). The sample may comprise two phases of liquid. At the bottom is a semen sample and at the top is a cell handling medium ("medium" and "media" as used herein may include, but is not limited to multipurpose handling medium (MHM), a medium solution, or another culture or handling medium). A lamp designed for fluorescence experiments may emit light, which is focused on the handling medium layer to create an illumination field. Since the two layers are in contact, sperm may swim from the bottom layer to the top layer, aligning with accepted recommendations for sperm preparation in IVF procedures. By positioning the microscope in proximity to the cuvette, images may be captured on, for example, a CMOS sensor, enabling the observation of sperm swimming into the handling medium ("image," "images," and "optics" as used herein includes, but is not limited to, images taken from real life without alteration, enhanced images, hybrid images, including images combining elements of real life imagery, simulated imagery, virtual reality imagery, augmented reality imagery, graphic elements, animation, three-dimensional images, two-dimensional images, still images, time-lapse images, video images, or some other type of image and/or visual depiction). To facilitate this, the sample may be mounted on an X,Y,Z micromanipulator. FIG. 8 provides an illustrative example of images obtained through this setup. FIG. 8 is an illustrative example of images obtained using a microscope in a horizontal configuration positioned close to a rectangular cuvette containing a biological sample 800. FIG. 9 displays a screen for sperm tracking analysis using custom software 900.

In embodiments, the IVF platform may include a microscope specifically crafted for observing various types of cells associated with IVF procedures and to generate microscopic images closely resembling those produced by commercial stereo microscopes, using an optimization process to ensure that its size, shape, and weight are configured to integrate into a robotic system without compromising image quality. The primary cell types intended for observation with this microscope include sperm, oocytes, and cumulus cells. In embodiments, one core component of a microscope is the objective lens. Irrespective of its size or unique functionalities, a pivotal element of this instrument is the set of lenses that facilitate formation of a magnified image of the object under examination. This resultant image may be observed either directly on the human retina or, via its electronic counterpart, for example on a CMOS camera. As illustrated in FIG. 10A, the microscope may comprise the combination of a CMOS camera sensor (e.g., IMX477) and a microscope objective 1000. In this setup, the microscope objective may assume the function of the camera lens.

In embodiments, to improve image contrast, a condenser lens may be positioned above a sample. The condenser's function includes focusing light onto the sample while imparting specific properties to the light, such as polarization, phase, or structural characteristics. The image captured by the CMOS sensor may be accessed through various image systems, webcam, imaging, and optic applications (including machine and computer vision, as described herein, and referred collectively as "optics," "image system," "imaging system," and the like). Additionally, the resulting imaging may be accessible through programming languages like Python, MATLAB, UNITY, and others via a USB port, or other means of connectivity, which may facilitate automation.

Figure 11A:
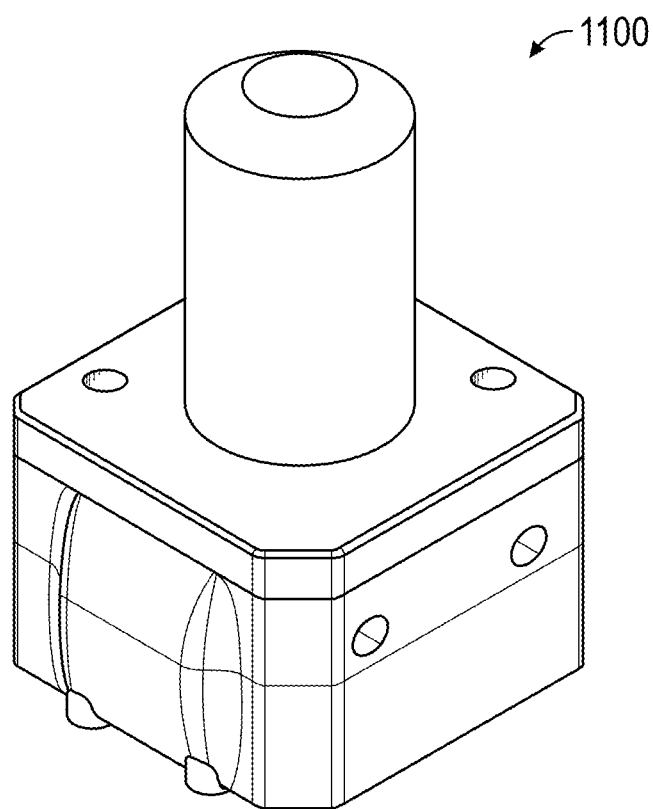
FIGS. 11A though 11F provide simplified component views of an inverted microscope assembly.
Figure 11B:
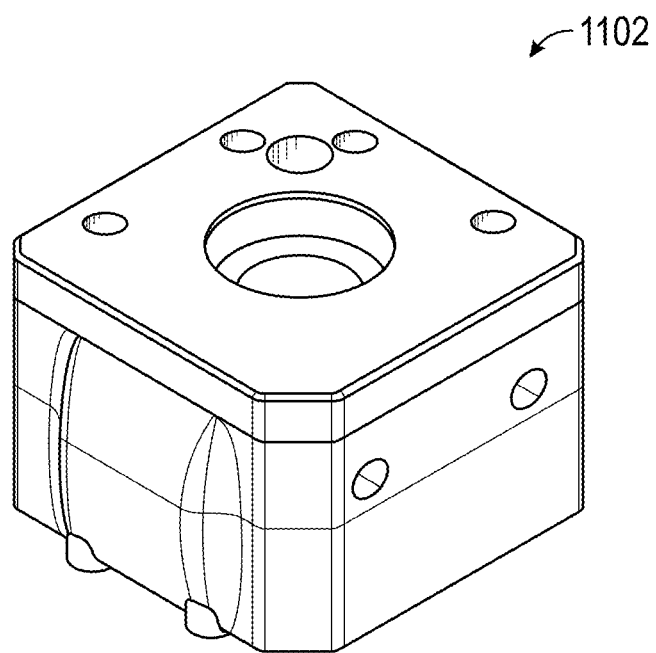
Figure 11C:
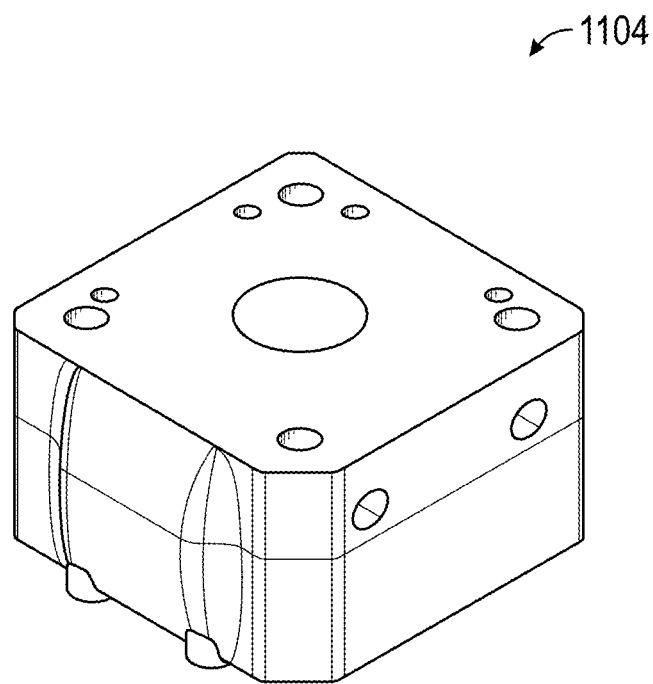
Figure 11D:
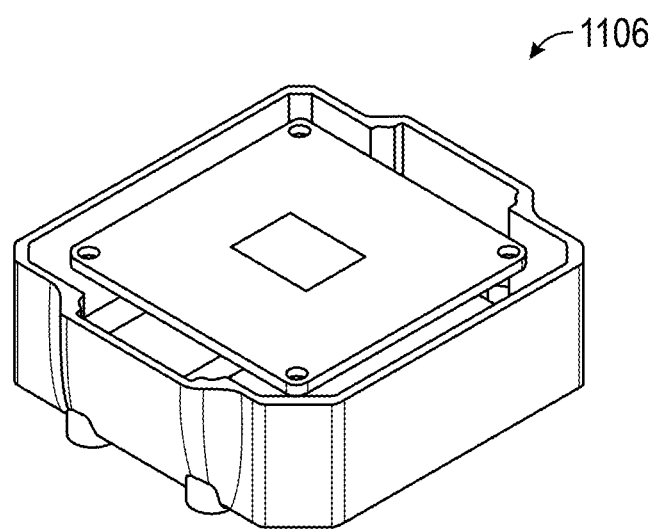
Figure 11E:
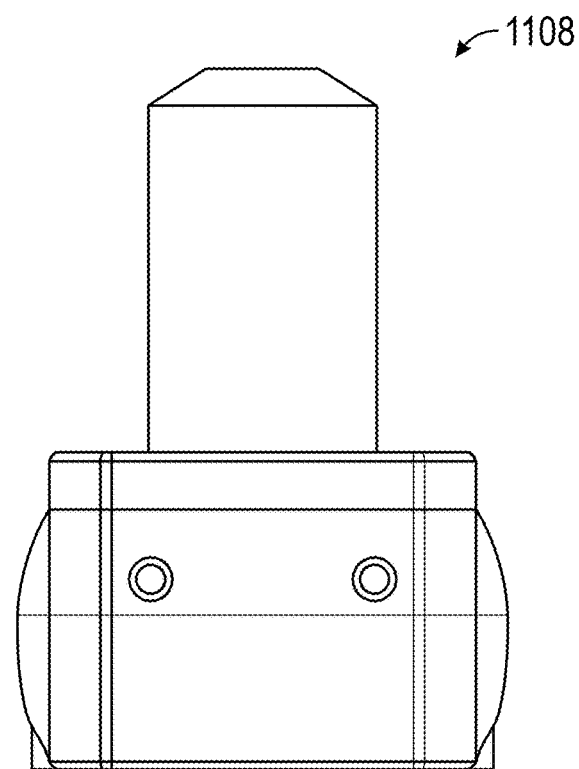
Figure 11F:
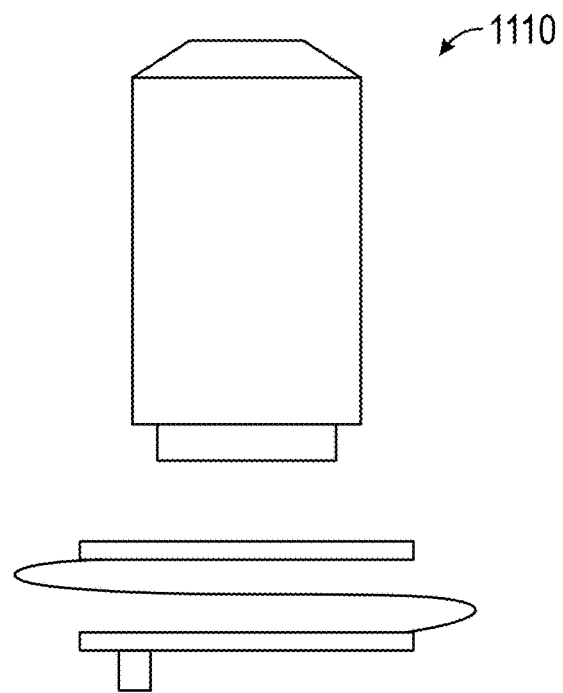
Figure 12:
FIG. 12 illustrates sample images captured with the inverted microscope.

FIG. 10B and FIG. 10C display the assembled microscope 1002 and its appearance when utilized as an inverted microscope within the IVF/ICSI platform robotics 1004, respectively. FIGS. 11A though 11F (1100-1110) provide simplified component views of the inverted microscope assembly FIG. 12 depicts two examples of images captured with the inverted microscope 1200.

Figure 13A:
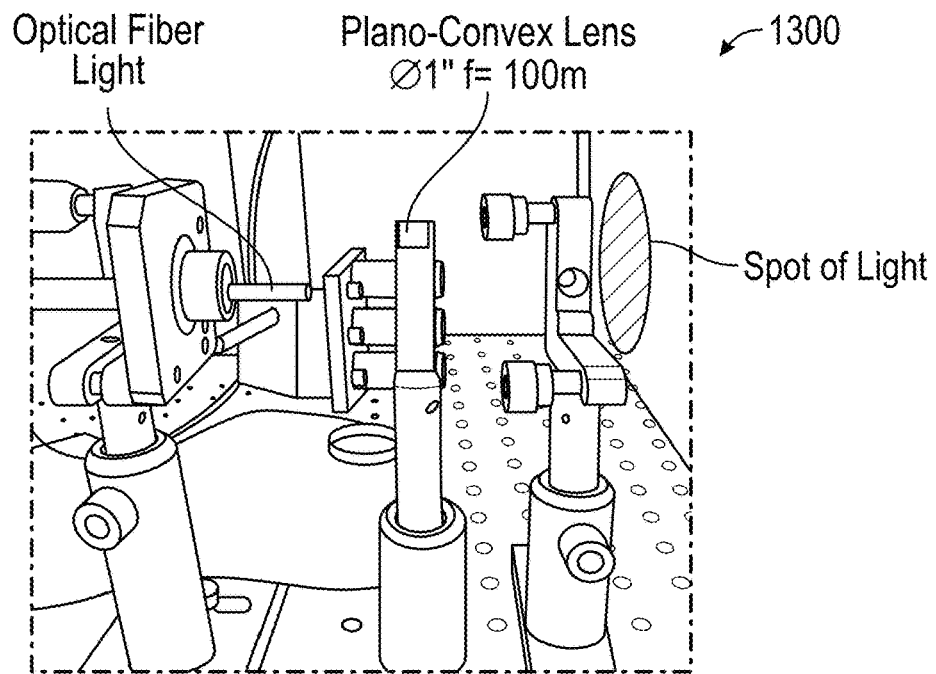
FIG. 13A illustrates a microscope light source comprising a tunable Lumencor lamp adapted to a fiber optic and accompanied by a plano-convex lens.
Figure 13B:
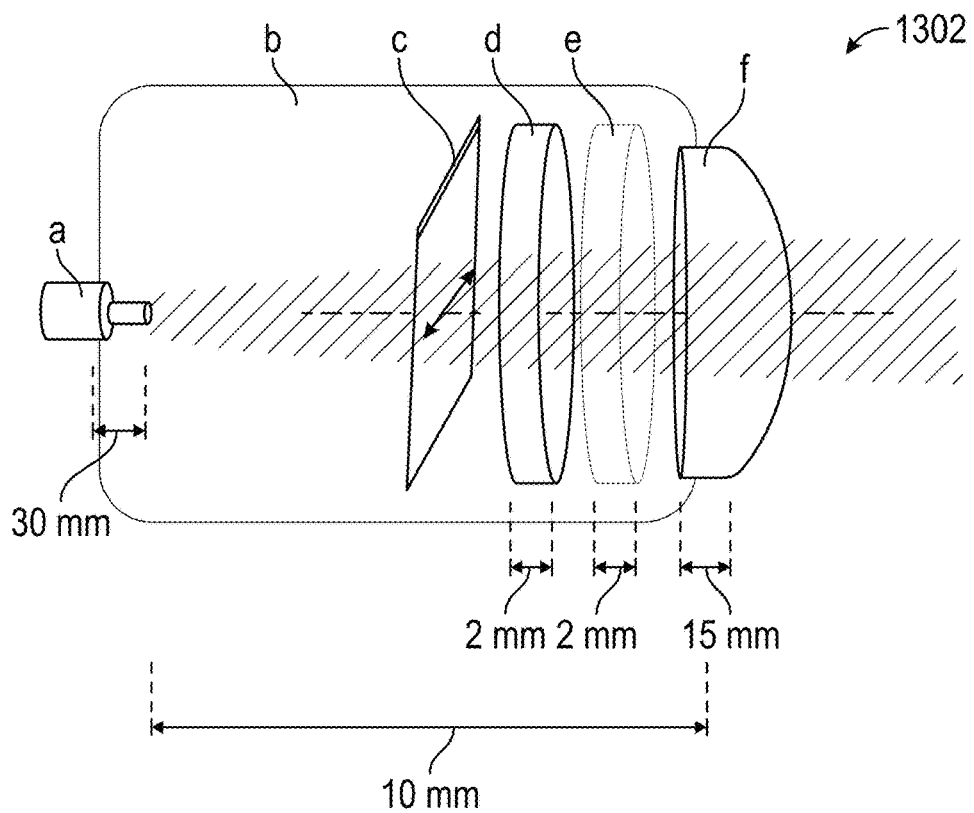
FIG. 13B illustrates a detailed view of the microscope light source.
Figure 14A:
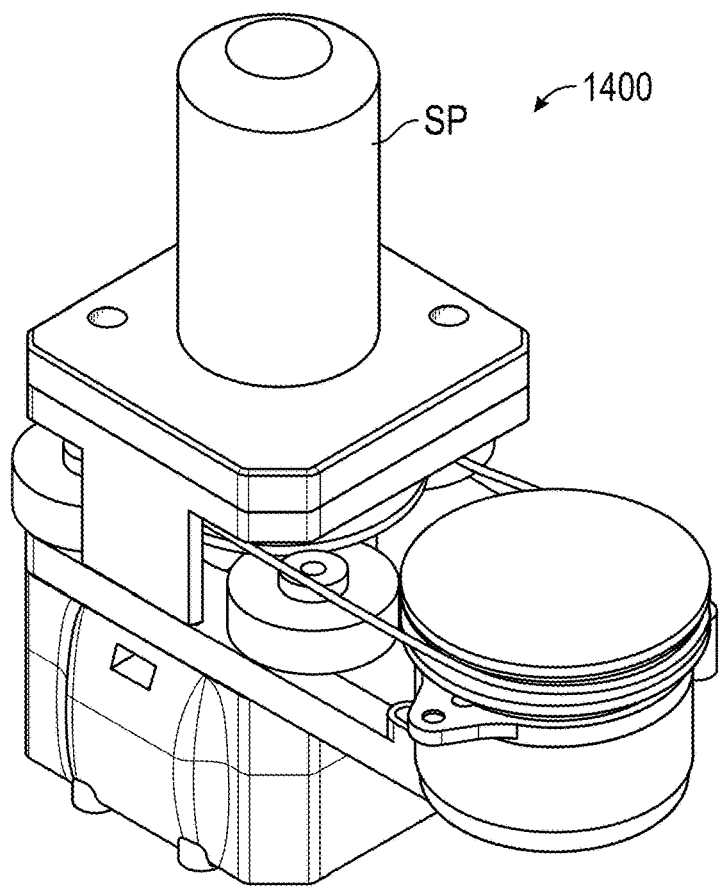
FIGS. 14A through 14H illustrate an imaging system using a rotation stage that is mechanically coupled to a microscope to measure, in part, linear polarization properties of light transmitted through a sample.
Figure 14B:
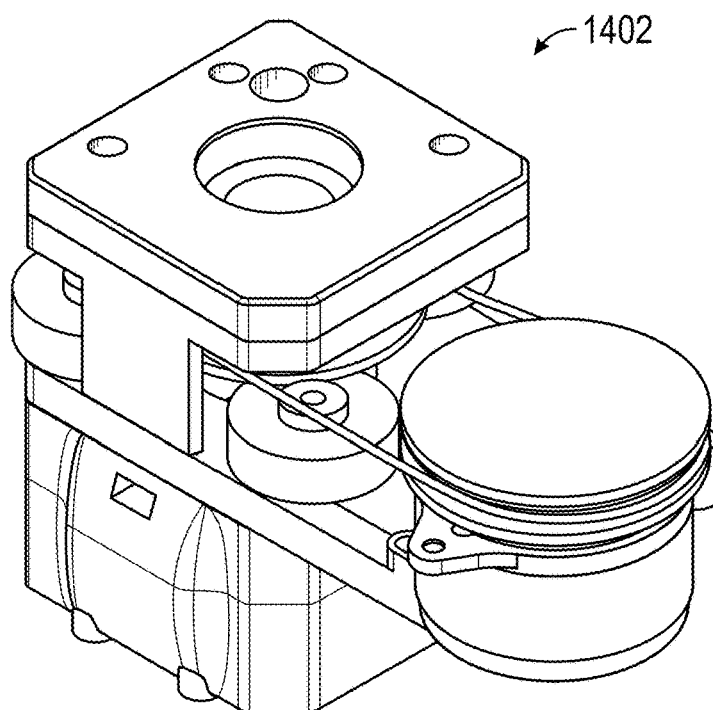
Figure 14C:
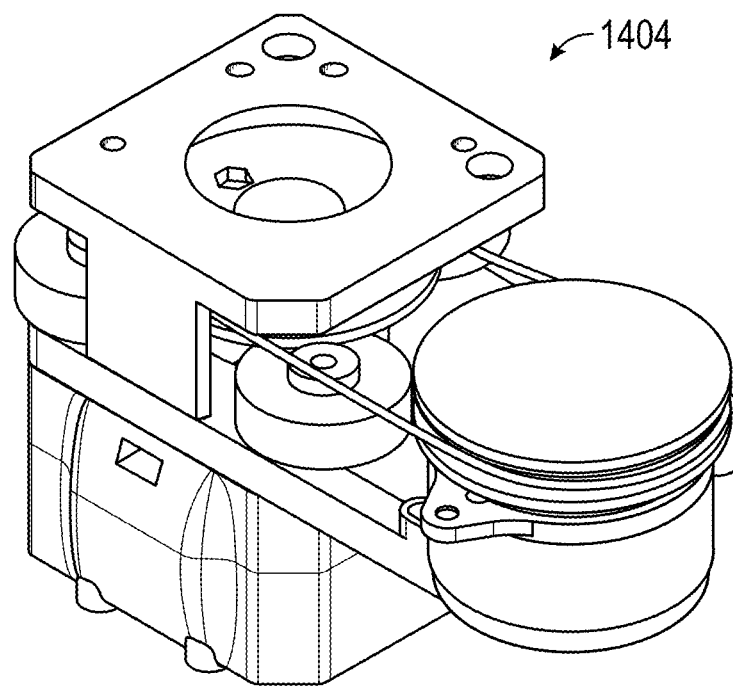
Figure 14D:
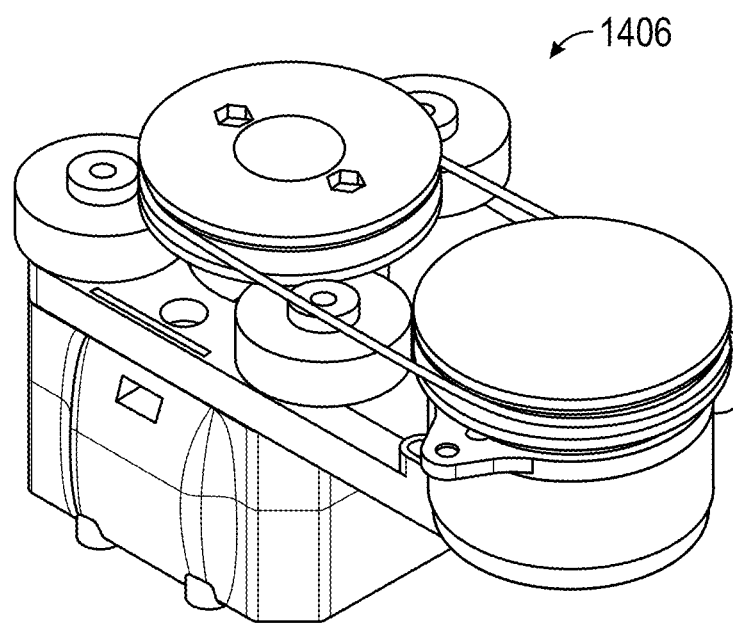
Figure 14E:
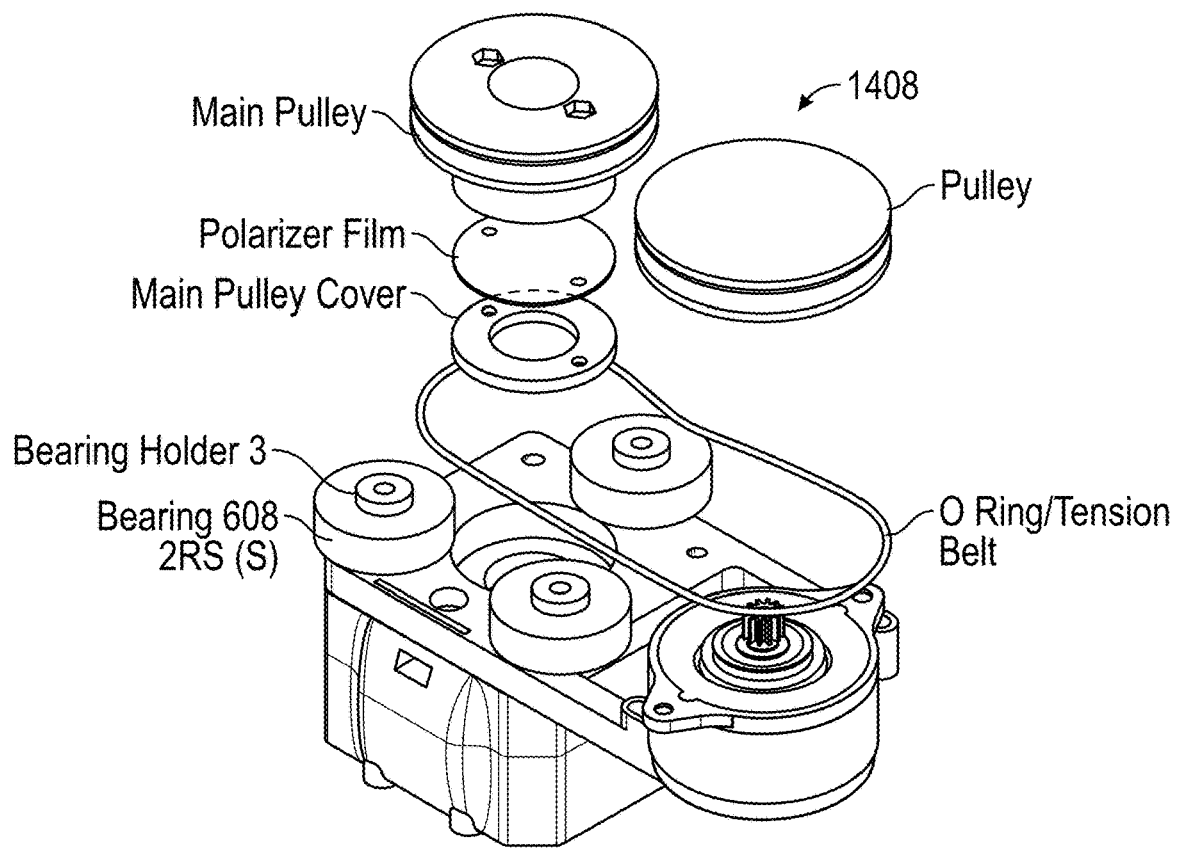
Figure 14F:
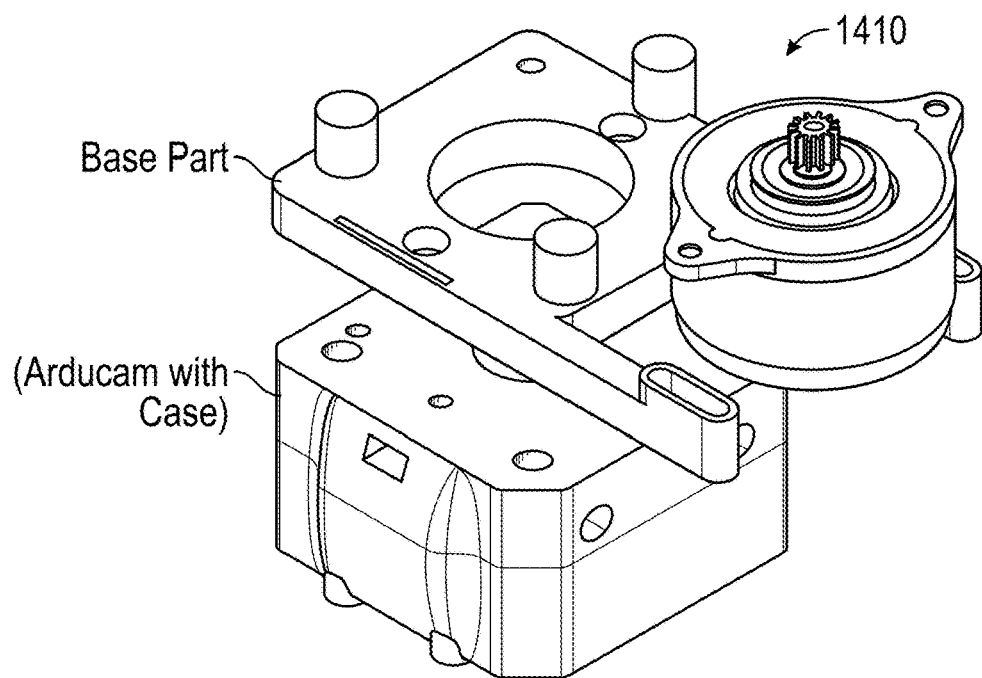
Figure 14G:
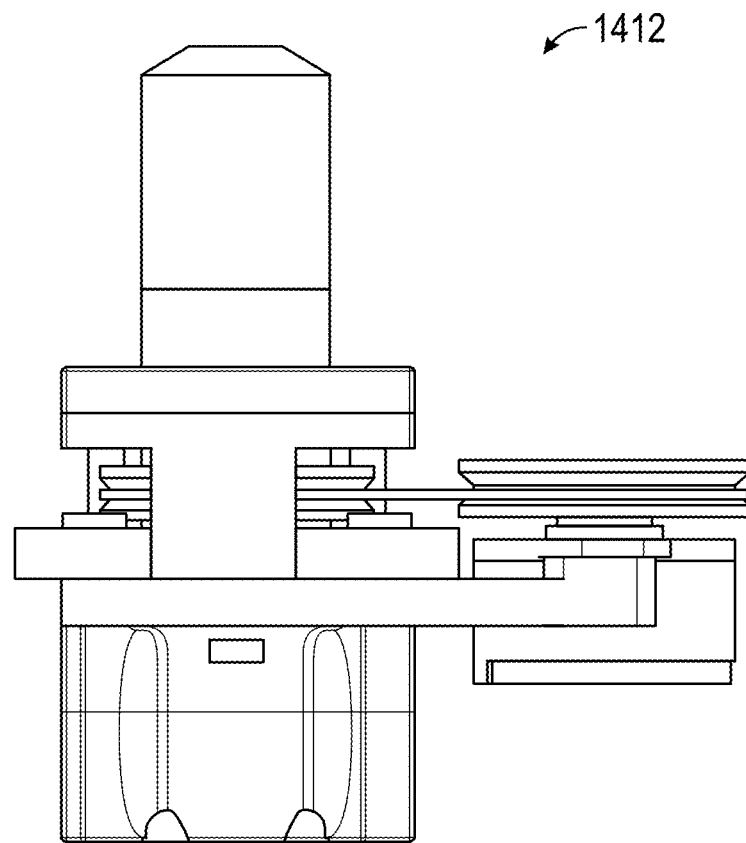
Figure 14H:
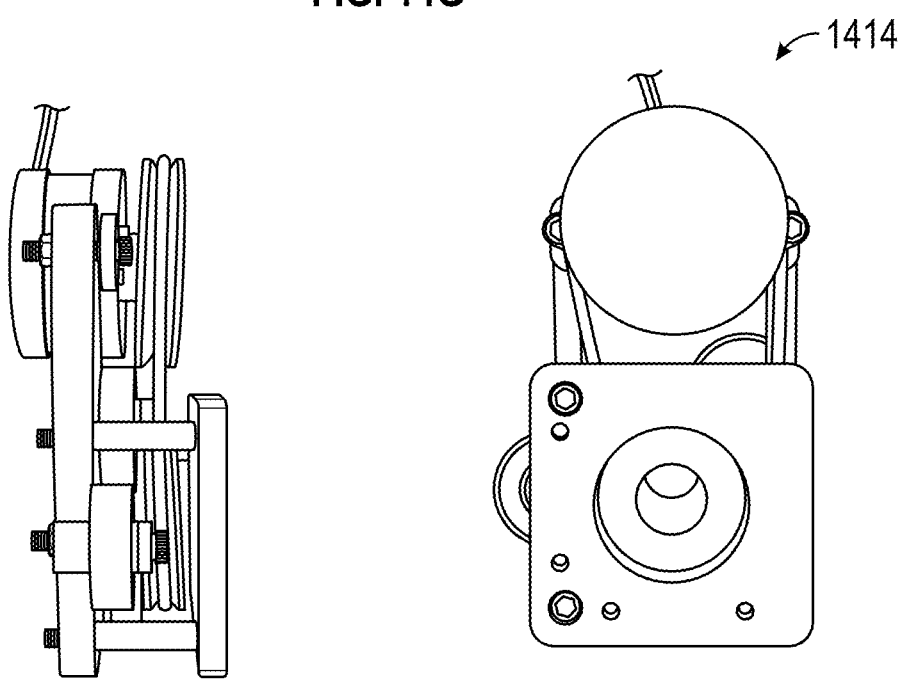

In embodiments, high-quality imaging often relies on effective lighting. Even the most advanced microscope models may fall short of delivering optimal results without a good light source. Achieving a uniform spot and quality contrast for imaging biological samples is important for obtaining useful imaging results. In embodiments, the IVF/ICSI platform may include a microscope light source capable of generating high-quality images that may generate a homogeneous light spot with a favorable intensity to generate a balanced contrast in the images. As depicted in FIG. 13A, the microscope light source may comprise, for example, a tunable Lumencor lamp adapted to a fiber optic and accompanied by a plano-convex lens with, for example, measurements of 25 mm in diameter and focal length of 100 mm 1300. This optical arrangement may produce collimated light characterized by a spot diameter of 40 mm. In FIG. 13B, a detailed view of the microscope light source 1302 is presented. This configuration may incorporate a linear polarizer, and a neutral density (ND5) filter for precise control over light intensity to prevent sensor saturation. Ground glass may be strategically employed to diffuse and homogenize the outgoing light, enhancing the overall quality of illumination. An example mechanical illustration for this light source 1304 is shown in FIG. 13C In embodiments, the IVF/ICSI platform imaging systems and methods may use a rotation stage that is mechanically coupled to the microscope to measure, in part, linear polarization properties for the light transmitted through a sample. The microscope may be equipped with an analyzing polarization feature to enable the observation of birefringence phenomena in biological samples. The mechanism may consist of a linear polarizer positioned between the objective lens and the camera sensor of a microscope. To secure the polarizer, a set of mechanical components may be placed, as illustrated in FIGS. 14A through 14H (1400-1414). The rotation feature may facilitate analyzing polarization states, requiring the polarizer to be set at angles of, for example, 0°, 45°, −45°, and 90°. Rotating the polarizer at a constant angular velocity may facilitate the observation of blinking at certain image points, indicating variations in optical properties at those locations. Control may be provided by, for example, a stepper motor, connected to an electronic interface and control software, as described herein.

Figure 59:
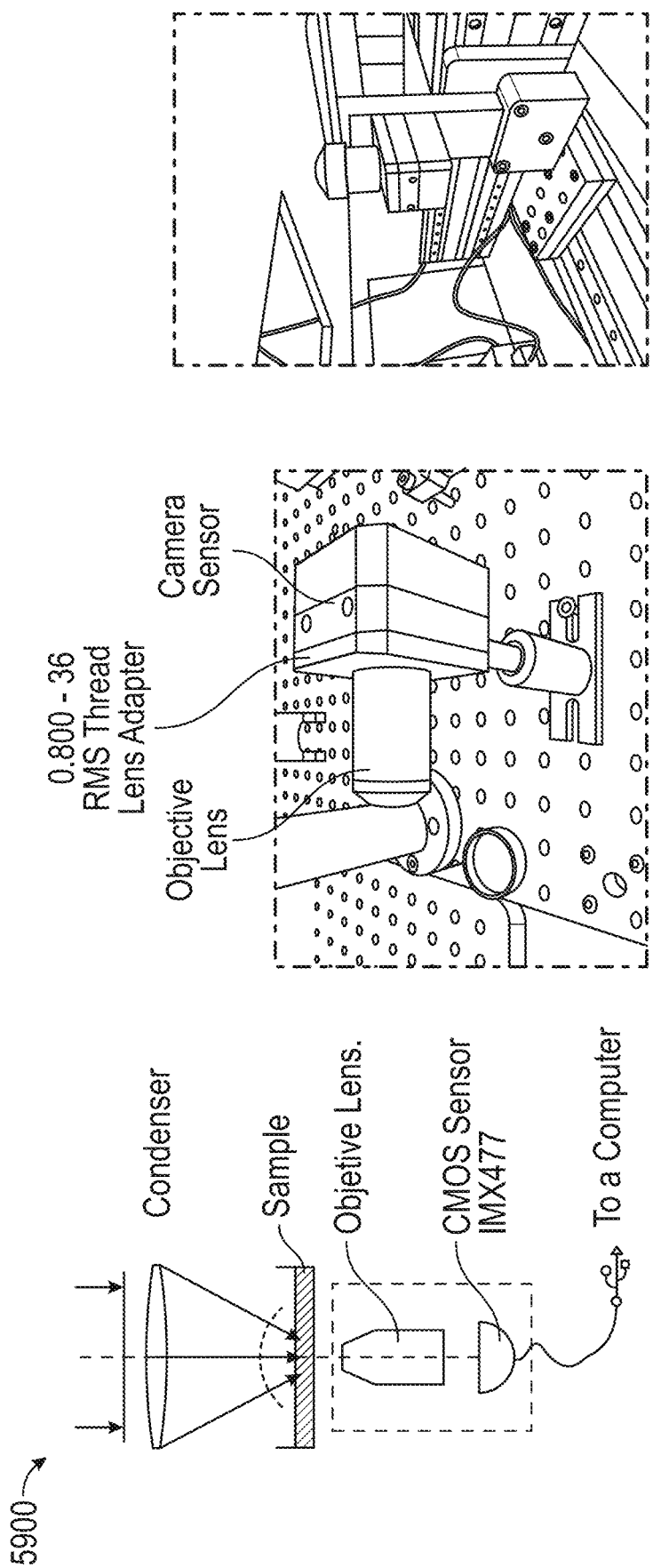
FIG. 59 illustrates an example setup for an inverted microscope assembly that may be used by the IVF/ICSI platform.
Figure 60:
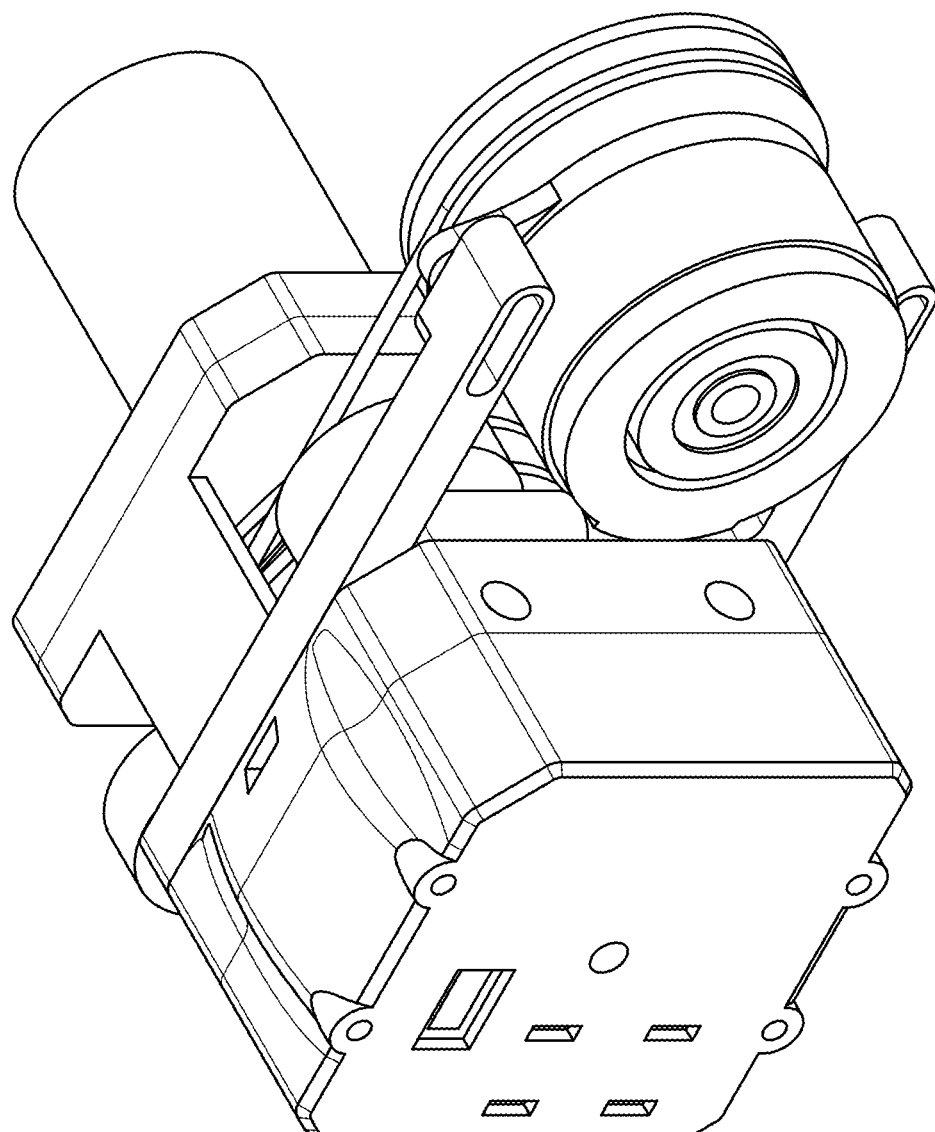
FIG. 60 illustrates an example assembly for a lens, lens adapter, camera and stage assembly that may be used by the IVF/ICSI platform.

The IVF/ICSI platform, as described herein, may use optical coherence tomography (OCT) in the context of an IVF/ICSI platform. OCT is a non-invasive imaging technique that provides high-resolution, three-dimensional images of biological tissues. For example, the IVF/ICSI platform may use OCT to gather detailed information about sperm, oocytes, embryos, or other biological material. The OCT system of the IVF/ICSI platform may be modified to better suit the specific requirements of the process. For example, the head of the OCT system may be moved to the bottom of the sample, similar to an inverted microscope, to better visualize samples in a liquid state. Additionally, the OCT system may be adapted to be controlled by AI/ML and/or custom software, as described herein, allowing for more precise and automated control of the imaging process. FIG. 59 illustrates an example setup for an inverted microscope assembly 5900 that may be used by the IVF/ICSI platform. FIG. 60 illustrates an example assembly for a lens, lens adapter, camera and stage assembly 6000 that may be used by the IVF/ICSI platform.

In embodiments, the IVF/ICSI platform may include a computer-assisted sperm analysis system and semen preparation robot. Before preparation, a semen sample may be assessed by performing a limited semen analysis. After preparation, the same assessment may be repeated to determine sperm recovery and quality. Computer-assisted sperm analysis may do this automatically by inserting samples into the computer-assisted sperm analysis robotic system. The robotics of the semen preparation module may control computer-assisted sperm analysis, move samples into the computer-assisted sperm analysis system, and trigger alerts when specific criteria, such as acceptable sperm concentration or motility, are or are not met. The semen preparation robot may also adapt the preparation protocol based on initial or intermediate computer-assisted sperm analysis findings. Other functions and procedures may include, but are not limited to:

Prostate-specific antigen (PSA) test: Development of a PSA test of the final sperm suspension may be considered to confirm absence of seminal plasma components.

Swim-up efficiency and intelligent sperm preparation: A swim-up efficiency robot based on optical assessment during swim-up may be integrated to develop optimization of each sample processing. The robot may adjust the sperm preparation protocol and also provide detailed reporting for each sample.

Safe storage of prepared samples: The sperm preparations may be stored separately, in a "sperm prep apartment" (part of the semen preparation robot) with a witness system to ensure strict separation of the samples.

Sample scheduling (AI-optimized): This system may schedule samples and also optimize the flow of procedures, ensuring efficiency and minimal manual intervention. The system may determine which samples are needed for specific stages of the IVF process. Multiple simultaneous processing may be considered depending on laboratory size.

Follicular fluid handling: Automation may include collecting follicular fluid in tubes and automatic decanting of such fluid into Petri dishes of different diameters, eliminating the need for manual intervention. Automation may include a decanting process or large volume pipetting system which automatically spreads the follicular fluid into dishes of different diameters.

Disposable Pasteur pipette suction system (PPSS): The PPSS may be pre-manufactured and pre-assembled and sterilized, consisting of a Pasteur-pipette-like glass tip of a specified length connected to tubing using a gastro-intestinal-like tubing similar to a Nutricat. The PPSS may connect to the pipettor like a Sartorius or equivalent pipettor. A stepper system may be applicable if volume restriction is small enough, or otherwise a control system may be applied that is contiguous.

Rail conveyor system: A robotic rail system may be used for transporting dishes containing fluids, eggs, sperm preparations, embryos, biopsy samples, embryos or oocytes for cryo-storage to various robotic systems. It may be equipped with versatile pre-cut forms for housing the dishes or tubes. The system may move material fast enough to minimize exposure to room conditions, and plate-holders may be temperature controlled to ensure that dishes are kept between room-temperature and 37 degrees Celsius. Changes in pH may be minimized requiring gentle yet progressive maneuvering of the plate/tube-holder conveyor system.

Dish handling: This system may seamlessly transport dishes with eggs from incubation to the ICSI platform and back, ensuring the integrity of the samples and minimal disruption.

ICSI platform: The ICSI platform may be equipped with an area for receiving dishes, and off-loading, and check-in/check-out procedures may be recorded and verified using a witness system.

Disposable microtool assembly (DMA) for ICSI: The DMA system may comprise a syringe, tubing, and a microtool-holder system for precise control of microtools, such as ICSI needles and holding pipettes. The assembly may be pre-manufactured, simplifying the traditional system and fit the various options for micromanipulation systems with adapters suitable for different micromanipulator models.

Robotic arms: Robotic arms may place DMAs, for example, bilaterally using an AI/ML and optics system, as described herein, ensuring precise alignment, positioning, and optimal tool orientation, which may be verified by the AI/ML and optics system.

ICSI dish placement: An ICSI dish with gametes may be positioned under the DMAs and microtool-tips using robotic arms.

Alignment and ICSI procedure: The DMAs may be lowered into place and the ICSI procedure initiated, including the alignment of tool tips.

Adding and removing eggs and sperm during ICSI: This system may allow pipetting by a third micromanipulator during ICSI in case of unexpected events.

Oocyte verification: Before and after the ICSI procedure, mature oocytes may be re-evaluated, and their maturity re-confirmed.

The platform may autonomously execute the 20-30 protocols on the sperm-injected eggs.

Sperm-injected egg handling: Sperm-injected eggs may be checked for survival, imaged, and placed into an incubator robot using the conveyor system.

Incubator confirmation: The incubator may confirm the receipt of petri dishes and monitor embryo development and predict blastocyst formation based on time-lapse (TL) data.

Timing of vitrification: The system may predict the optimal timing for vitrification, considering blastocyst development and expansion. Multiple vitrification options may be supported, and the system may optimize the timing. Blastocysts may be vitrified as a cohort (one after the other) or singly.

Blastocysts allocated to the vitrification or embryo transfer robot: Optimal development of embryos in a cohort may be confirmed, at least in part by (a) The TL-system may confirm optimal development, (b) Non-invasive PGT or niPGT may provide a representation of euploidy, or (c) AI/ML systems aimed at optimizing embryo selection such as ERICA may be used. After embryo selection and scoring is completed, the petri dish may be moved to a vitrification robot or one or more of the selected embryos may be transferred to the embryo transfer robot.

Individual embryo treatment: Fast or slow embryos may be assessed individually to decide culture duration and optimal timing of vitrification. This may require automated pipetting in a separate robotic system aimed at moving eggs and embryos between dishes or inside a dish.

Cryo-device handling: A modified RFID cryovial may be used.

In embodiments, the terms "pipette," "pipetting," "automated pipetting," "robotic pipetting" and the like, as used herein, refer to the processes of transferring fluids, cell suspensions, and individual or groups of cells (eggs and embryos) and/or single cells, from container to container, and/or from a first location to a second location, using devices that can create controlled positive and negative pressure. The processes may entail precise aspiration and dispensing, layering, and/or mixing of fluids. Pipetting is fundamental to IVF laboratory techniques (e.g., semen preparation, media and culture dish preparation, egg retrieval, ICSI, vitrification, embryo transfer, and the like) and may be carried out in a sterile fashion, without losing cells, and without creating air bubbles that could be disruptive, lead to loss of cells, or create potentially infectious aerosols. Traditionally, pipetting has remained manual in IVF. Manual pipetting requires precision, dexterity, and hand-eye coordination. It may or may not require a microscope, depending on the procedure.

Figure 15:
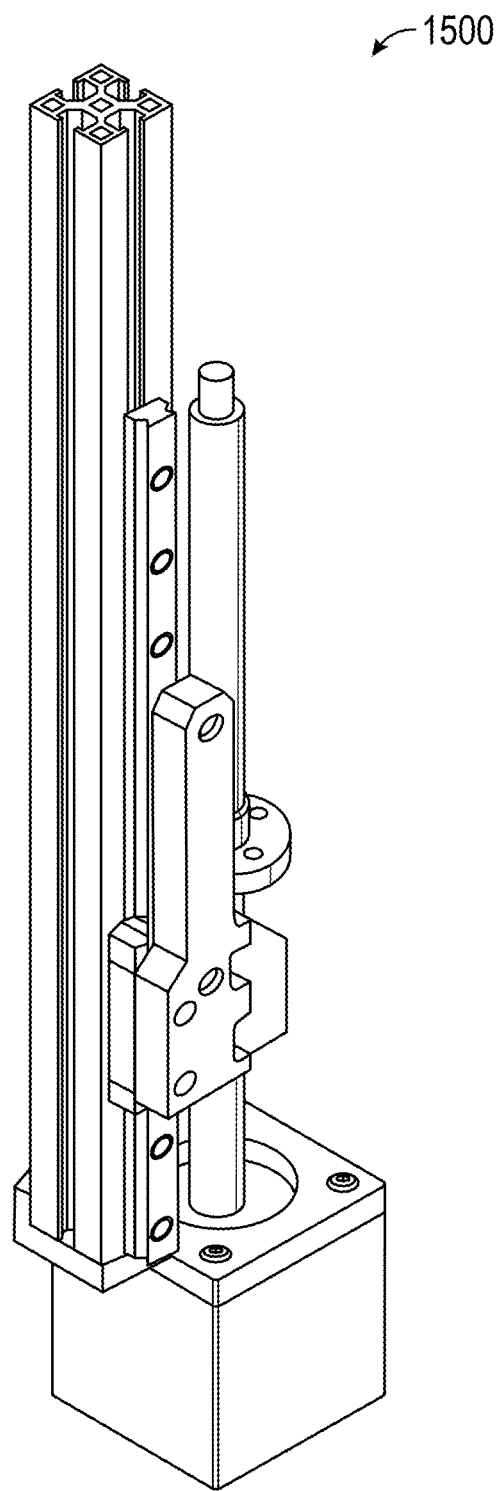
FIG. 15 illustrates a linear axis for toolhead movement of a pipette apparatus of the IVF/ICSI platform.
Figure 16:
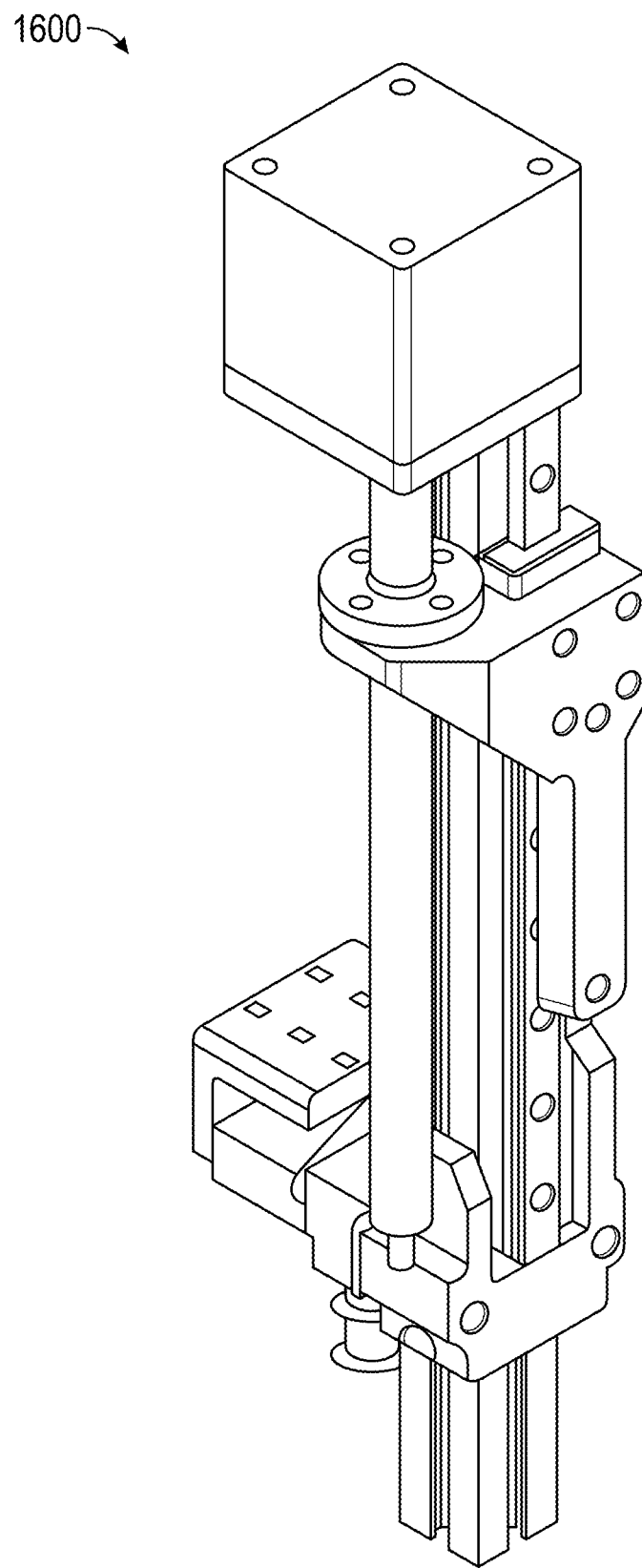
FIG. 16 illustrates a conglomerate of equipment within a pipette apparatus for toolhead movement of the pipette apparatus on the X and Y planes.
Figure 17:
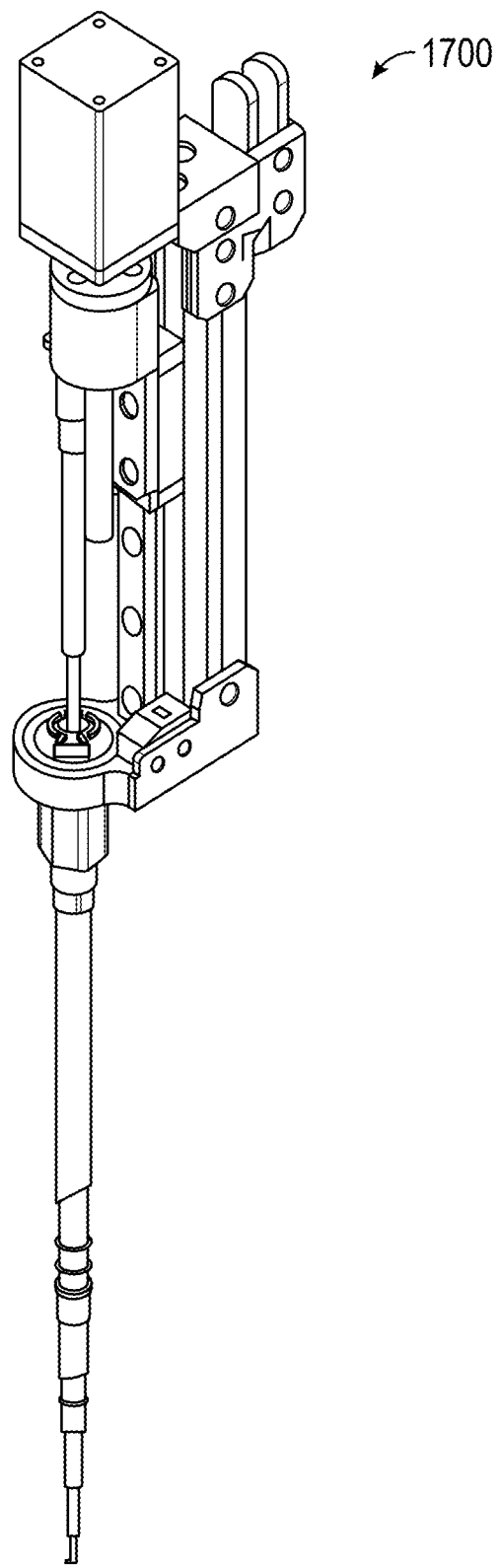
FIG. 17 depicts a pipette used in the pipette apparatus of the IVF/ICSI platform that may create positive or negative pressure.

In embodiments, the semen preparation module may include a robotic pipette capable of a Cartesian movement within X, Y, and/or Z planes, and with independent freedom of movement between the pipette and the pipette apparatus to which the pipette is attached. Referring to FIG. 15, a linear axis for toolhead movement of the pipette apparatus is presented 1500. FIG. 16 illustrates a conglomerate of equipment within the pipette apparatus for toolhead movement of the pipette apparatus on the X and Y planes 1600. As depicted in FIG. 17, the pipette used in the pipette apparatus may create positive or negative pressure 1700.

In embodiments, different types of pipettes may be used during semen preparation, some may be used during other IVF procedures.

Serological pipettes: Made of polystyrene, long, slender pipettes (typically 1-5 mL) to measure semen volume, to prepare density gradients (typically 1-2 mL), to transfer handling medium and semen into tubes (typically 1-5 mL). Serological pipettes are often used in conjunction with a motorized pipettor or "pipette-controller," equipped with a filter, and able to operate with different speeds (slow and fast).

Pasteur pipettes: Made of borosilicate glass, in variable lengths, and used in conjunction with rubber pipette bulbs, to transfer smaller volumes of media or sperm suspension.

Pasteur pipettes may be "drawn" using a flame to create very narrow (and long) tips that can handle single cells/embryos.

Transfer pipettes: Low density polyethylene pipettes molded into one-piece units to eliminate rubber bulbs and reduce operator exposure to samples.

Eppendorf pipettes: Instruments equipped with a piston and a spring-loaded tip cone, single-channel and adjustable volumes (1-1000 µL units with specific ranges), used in conjunction with Eppendorf tips, to aspirate and dispense precise (usually low) volumes.

In embodiments, the IVF/ICSI platform, as described herein, may incorporate pipetting using robotics to replace manual human pipetting. The IVF/ICSI platform may not require centrifugation during semen preparation for conventional insemination and ICSI. Robotic controlled, highly precise pipetting, as described herein, may significantly reduce both complexity and costs associated with microfluidic chambers, while obviating the need for centrifugation. Centrifugation of semen can lead to generation of oxygen free radicals which can damage sperm membranes, and potentially reduce their viability and fertilizing ability. Although samples prepared using microfluidic devices can be used for ICSI procedures, the likelihood of contamination of the final sample with seminal plasma due to design and imprecise manual pipetting makes these samples unsuitable for conventional insemination procedures, requiring addition of a "washing" process via centrifugation.

In embodiments, the IVF/ICSI platform may include a metal plate maintained at 37° C. (e.g., continuously monitored through sensors and a digital readout) 1800, or some other temperature (see FIG. 18). The surface area of the plate may be heated/cooled to a specified temperature, avoiding fluctuations, and an even heat distribution. The plate may incorporate a sensor and vary the temperature (e.g., between room temperature and body temperature). An algorithm may be used to set and maintain temperature.

Figure 19A:
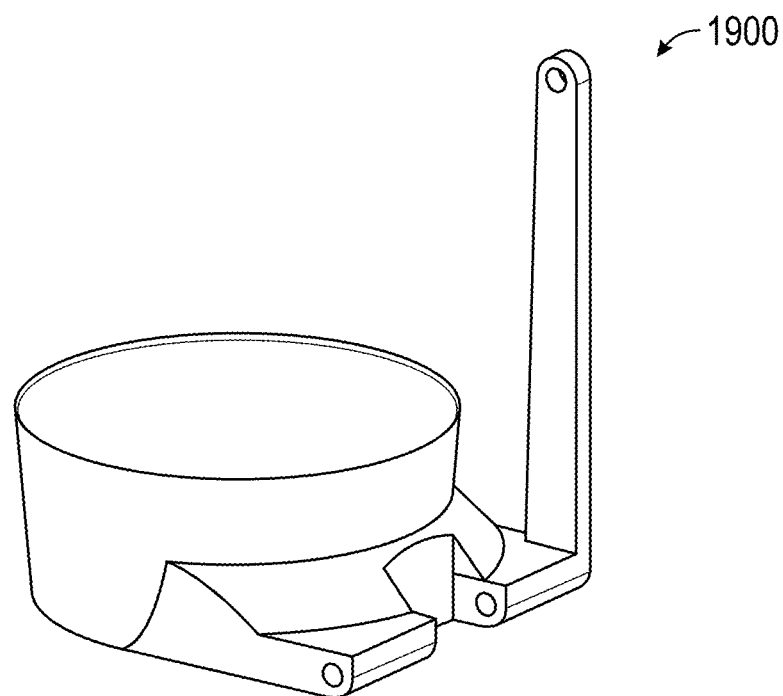
FIGS. 19A and 19B illustrates a semen cup holder that may be directly installed on a temperature-controlled plate and/or in proximity to the temperature-controlled plate.
Figure 19B:
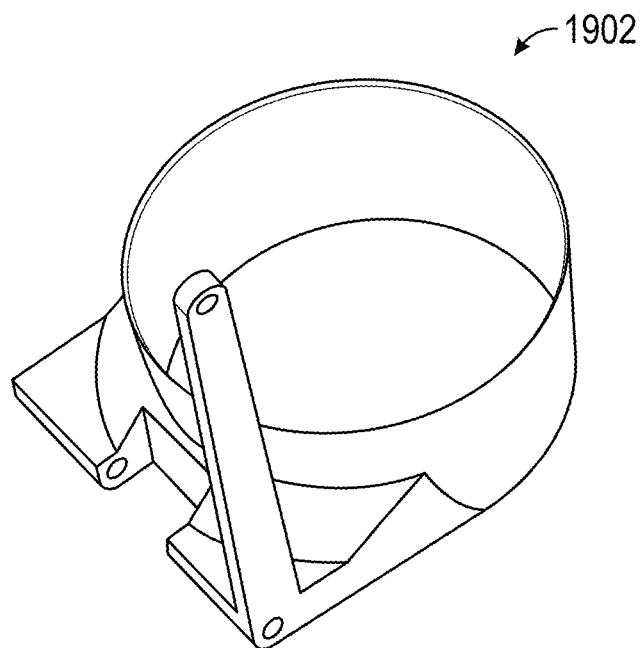

In embodiments, the IVF/ICSI platform may include a semen cup holder installed directly on top of the warming plate and/or in proximity to the warming plate 1900, 1902. (see FIGS. 19A and 19B)

In embodiments, the IVF/ICSI platform may include a 3-D printed specimen holder. The holder may be made of plastic, metal, or some other material. The holder may allow full contact of the specimen cup bottom with the heating plate. The holder may be adapted to accommodate different sizes and shapes of specimen container.

Figure 20A:
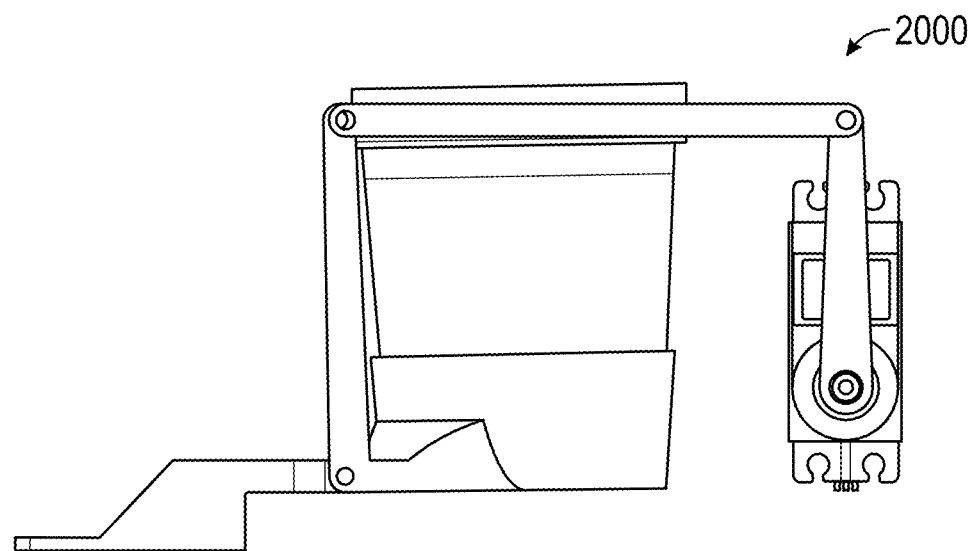
FIGS. 20A through 20C illustrate a robotic titling mechanism in which a specimen or other material may be held.
Figure 20B:
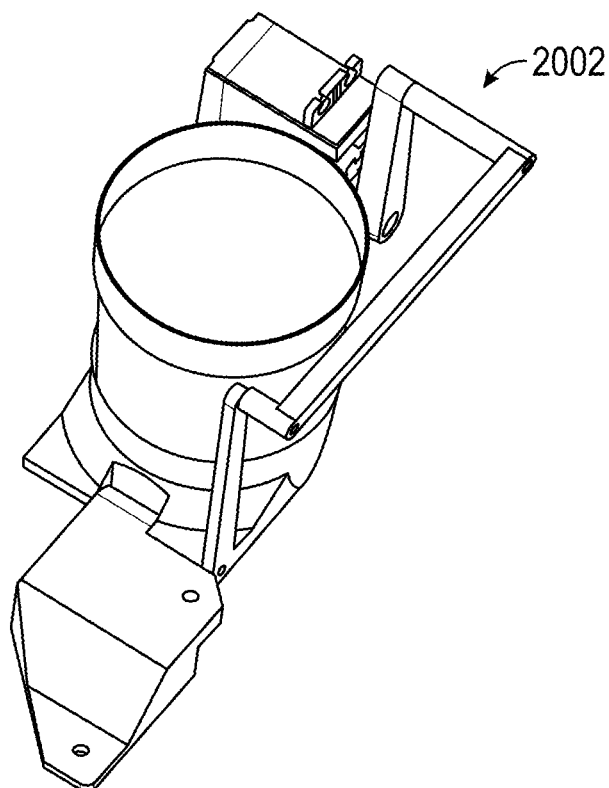
Figure 20C:
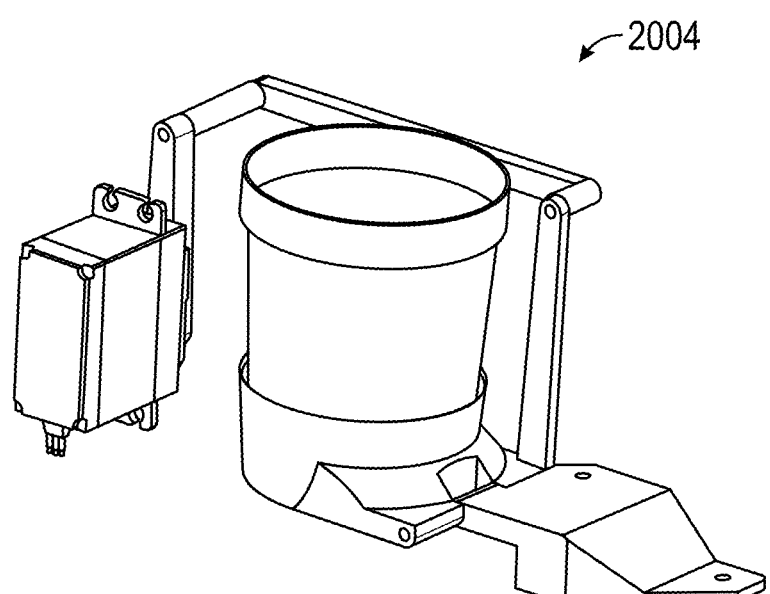

In embodiments, the IVF/ICSI platform may include a robotic titling mechanism in which a specimen or other material may be held 2000, 2002, 2004. (see FIGS. 20A through 20C). In embodiments, rocking movements may be orchestrated using software code, optics, AI/ML and other processes as described herein to control position, timing and speed of the holder. In embodiments, the tilting mechanism may incorporate a servomotor with feedback capability (e.g., equipped with sensors) that may be controlled to specify the degree of tilting and the speed of the rocking motion. The holder may be held at a specific angle depending on the process that is being performed.

In embodiments, the tilting action, degree of tilt, rate of tilt, duration of tilt and other tilt dynamics may be automatically adjusted and optimized by the IVF/ICSI platform to improve sperm processing and improve the fluid dynamics and mechanical benefits present in human handling of sperm specimens, affecting fluid volumes/densities and viscosity normalization. In an embodiment, FIG. 21 illustrates a holder for an intracytoplasmic sperm injection (ISCI) dish 2100. In an embodiment, FIGS. 22 and 23 depict a pipette tip having a custom geometry to facilitate a sperm "swim-up" protocol 2200, 2300.

Figure 24:
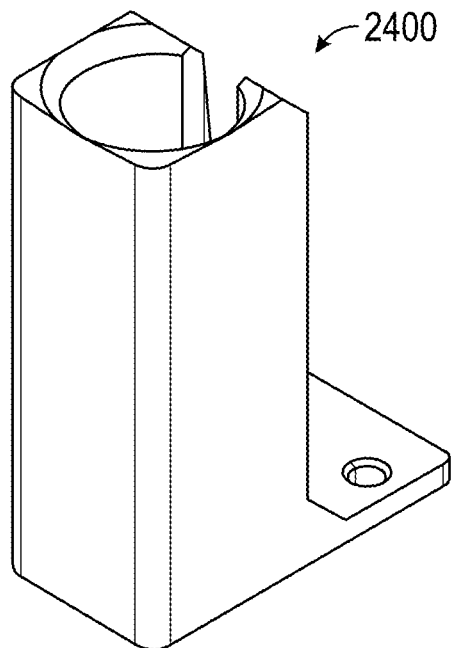
FIG. 24 illustrates a tube holder designed to hold tubes having a conical bottom.
Figure 25:
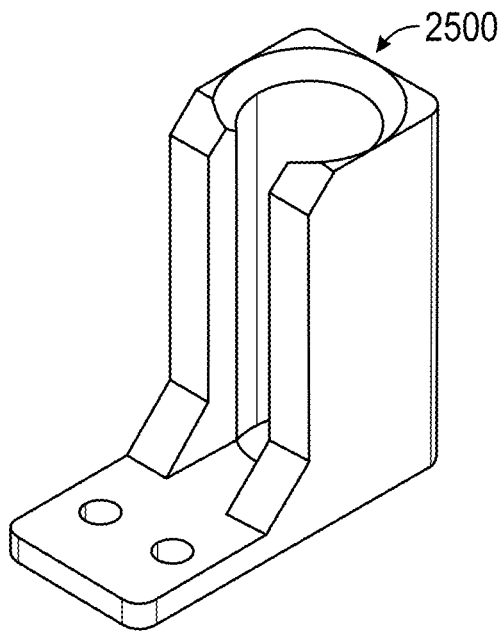
FIG. 25 illustrates a tube holder designed to hold tubes having a round bottom.
Figure 26:
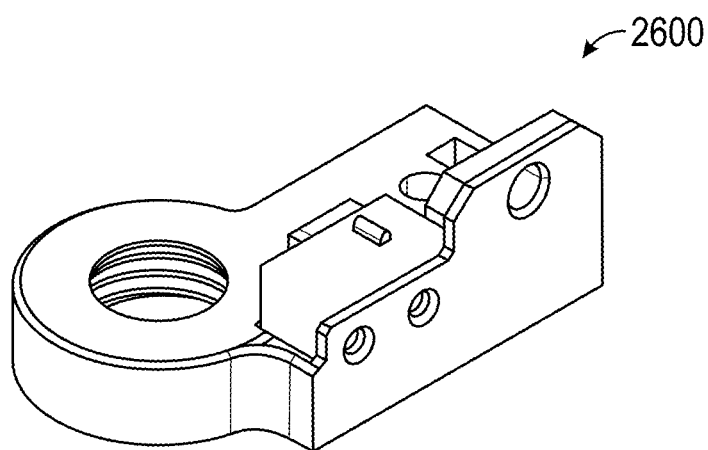
FIG. 26 illustrates a pipette attachment mechanism that may be affixed to the pipette mechanism.
Figure 27:
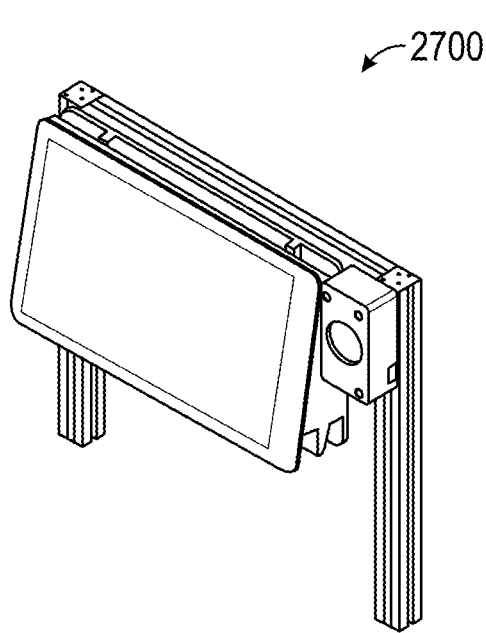
FIG. 27 depicts a pipette tip holder, and a pipette discarder for automatically discarding pipette tips within the semen preparation module.
Figure 28:
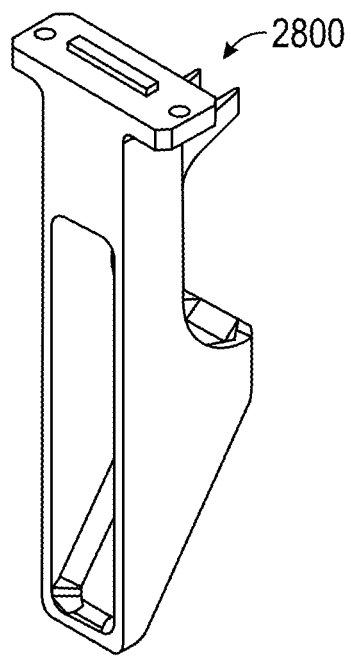
FIG. 28 illustrates a mechanism for discarding pipette tips.
Figure 29:
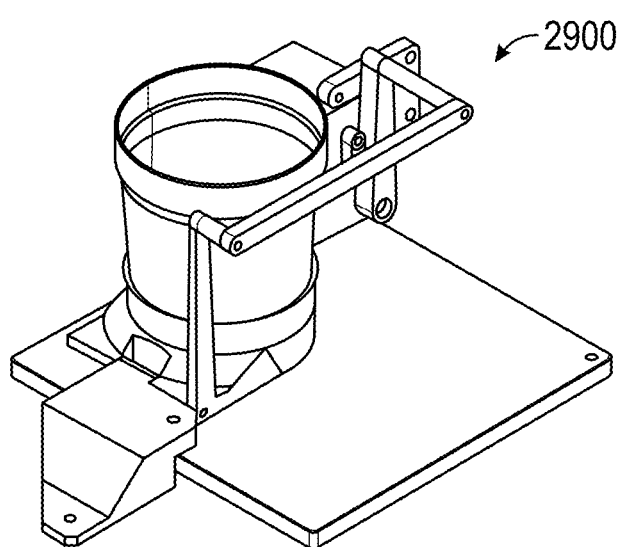
FIG. 29 depicts an angle-controlled holder for the clinical samples.
Figure 30:
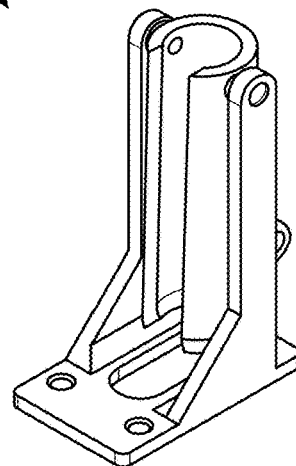
FIG. 30 depicts an angle-controlled holder for clinical tubes.
Figure 31:
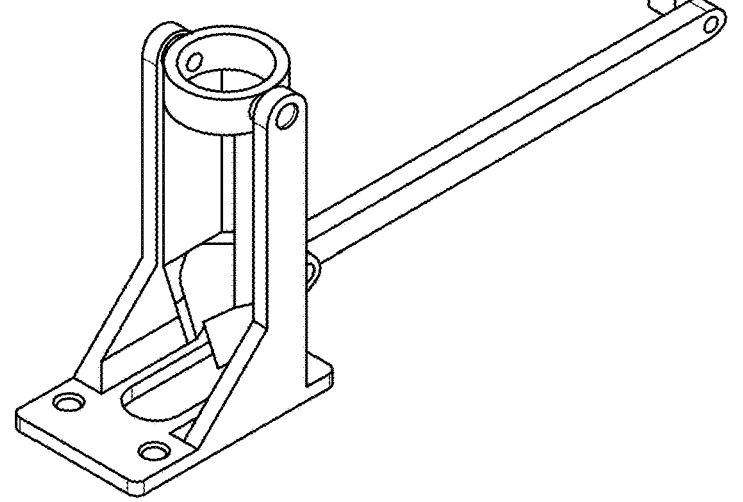
FIG. 31 illustrates an angle-controlled holder for clinical tubes.

In an embodiment, a tube holder may be designed to hold tubes having a conical bottom 2400 (see FIG. 24), a round bottom 2500 (see FIG. 25), flat bottom, or some other configuration. A pipette attachment mechanism 2600, such as shown in FIG. 26, may be affixed to the pipette mechanism 2600. As shown in FIG. 27, the semen preparation module may include a pipette tip holder 2700, and a pipette discarder for automatically discarding pipette tips 2800 (FIG. 28). Tilting of the sperm specimen may include the use of an angle-controlled holder for the clinical samples 2900 (FIG. 29), an angle-controlled holder for clinical tubes 3000 (FIG. 30), and a tilting mechanism 3100 (FIG. 31).

Figure 32A:
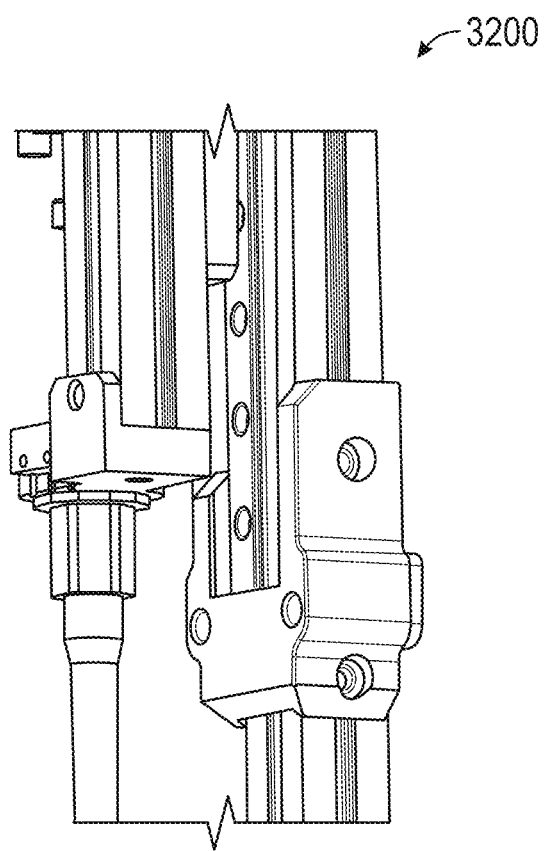
FIGS. 32A though 32H illustrate a robotic pipettor for the IVF/ICSI platform.
Figure 32B:
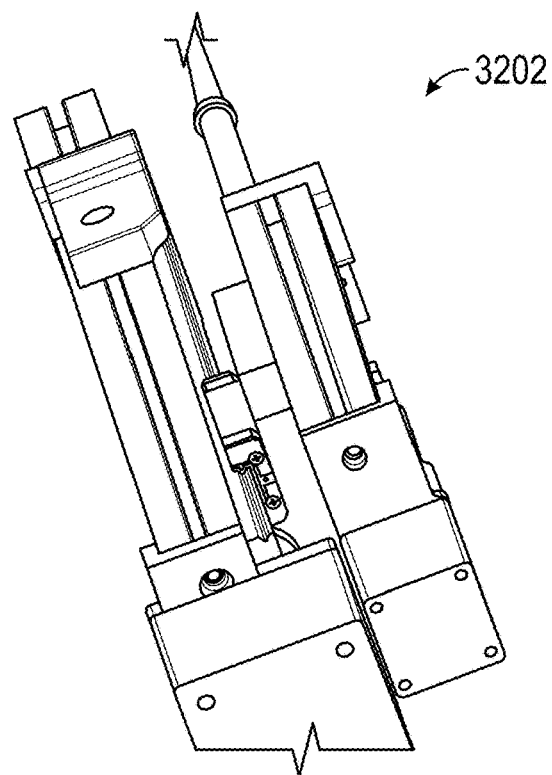
Figure 32C:
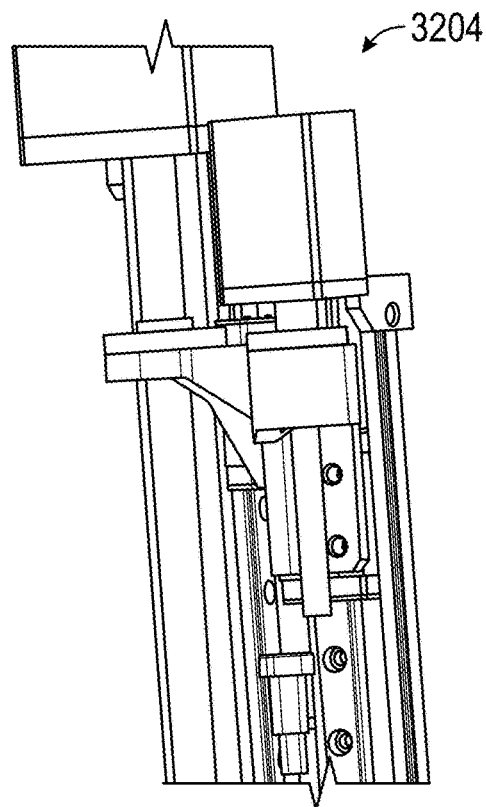
Figure 32D:
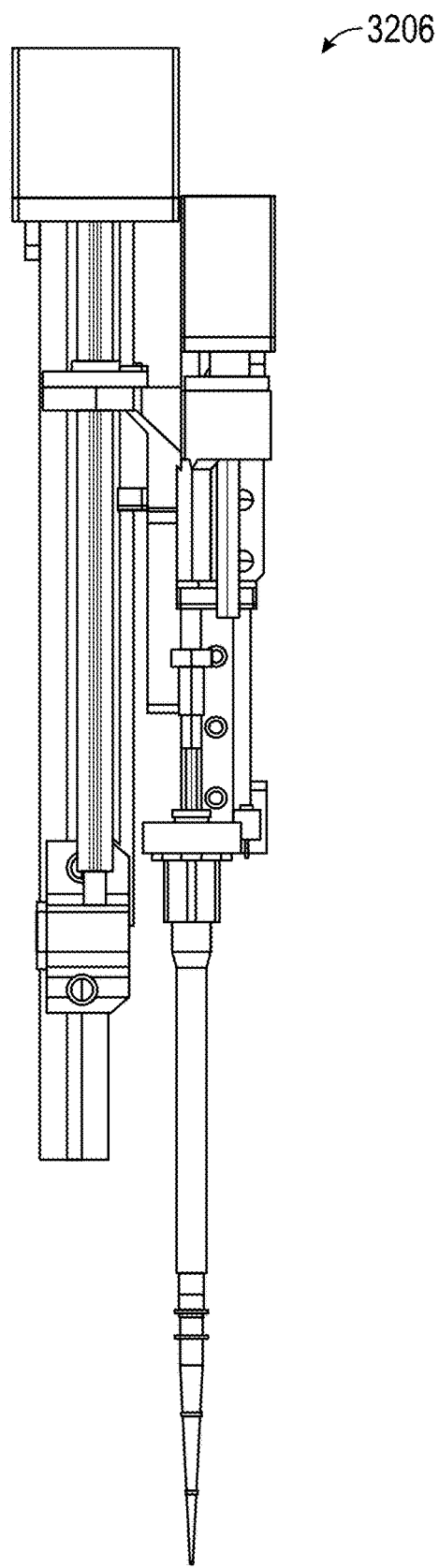
Figure 32E:
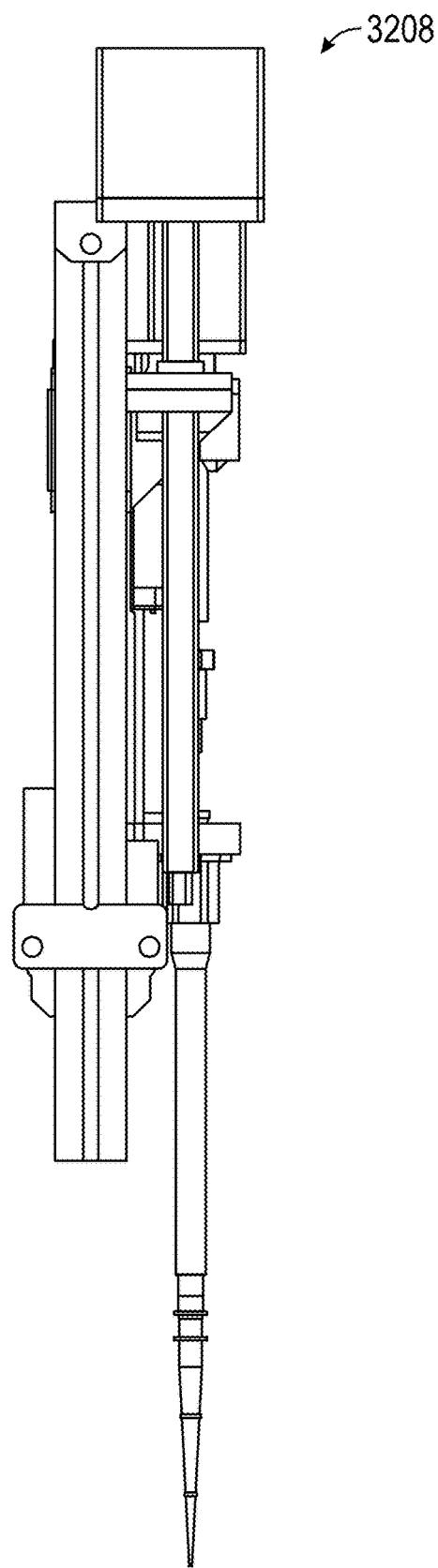
Figure 32F:
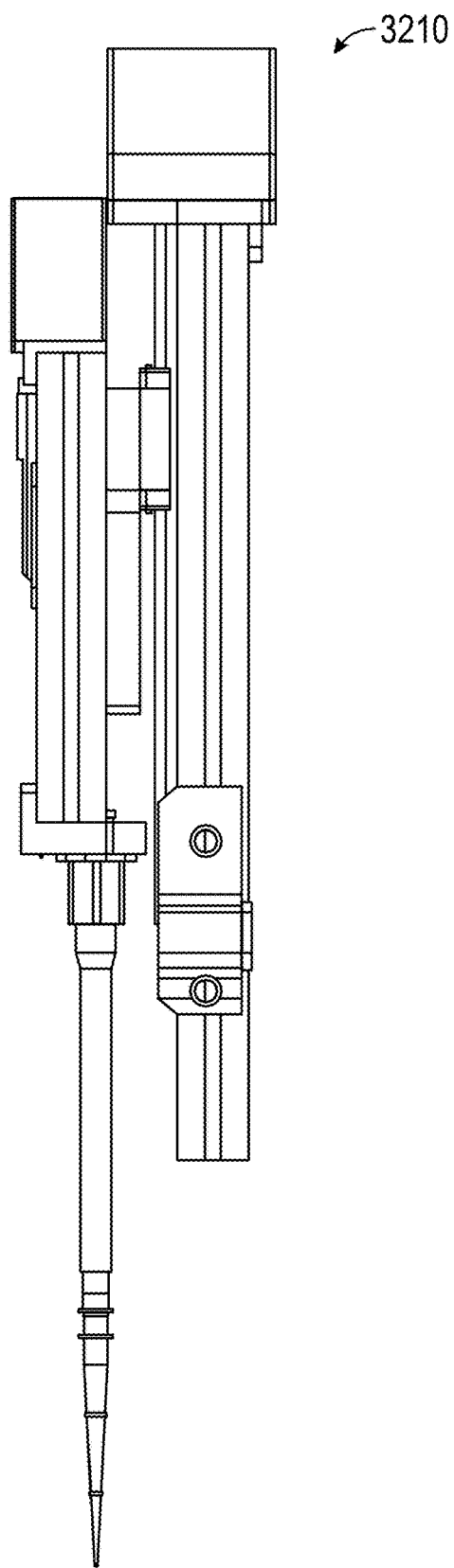
Figure 32G:
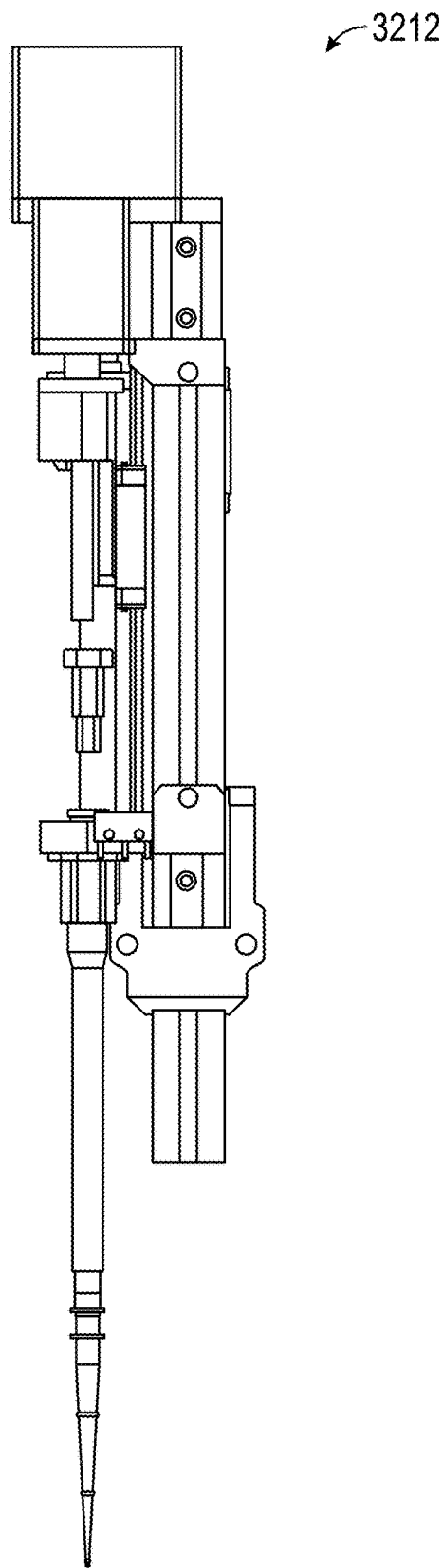
Figure 32H:
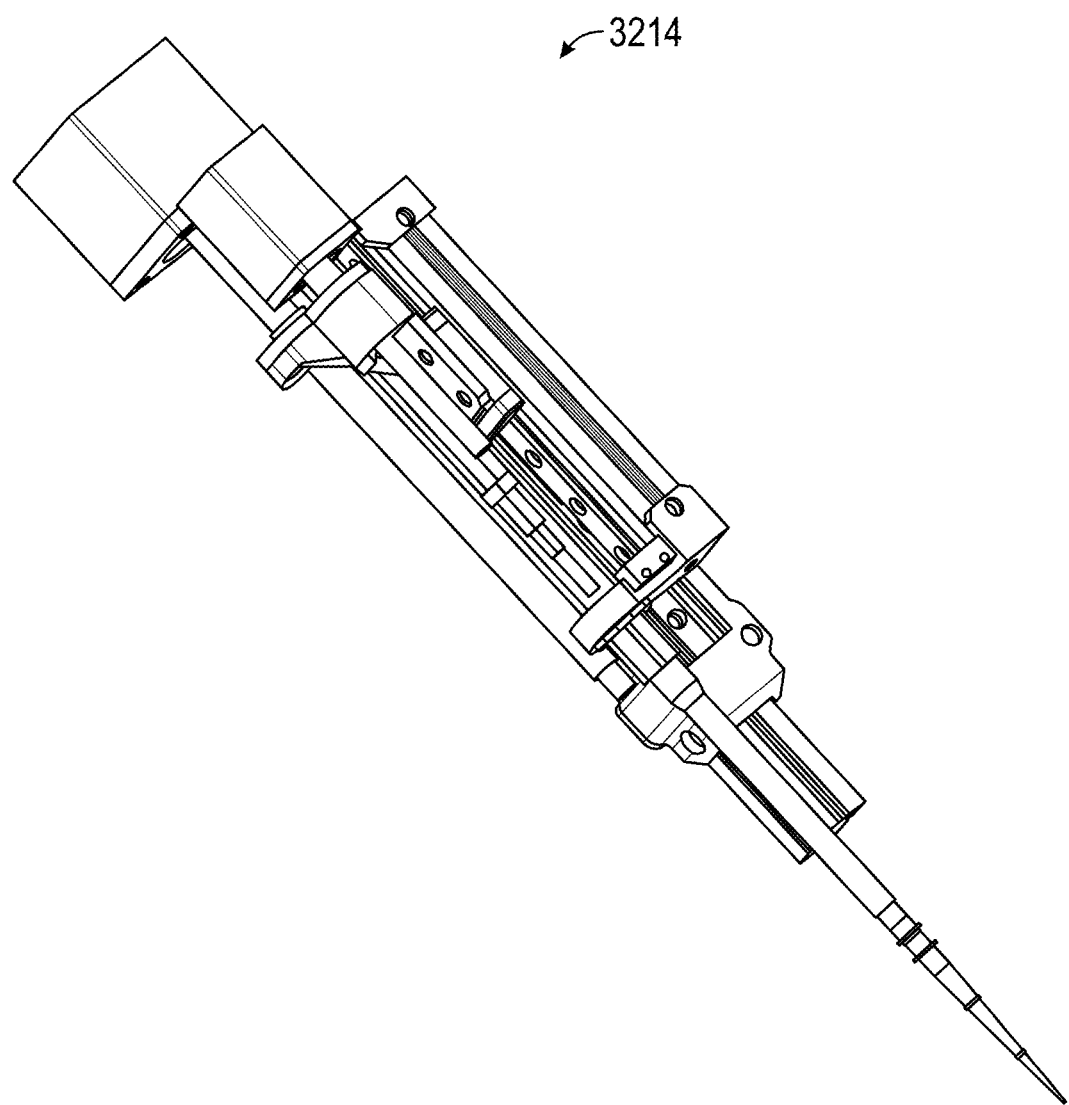

In embodiments, the IVF/ICSI platform may include a robotic pipettor (3200-3214) (see FIGS. 32A though 32H). In embodiments, a robotic pipettor assembly may include, but is not limited to: 1) the functional components of a manual pipettor, for example, consisting of a plunger, spring with lubrication, and the body/cylinder; 2) high precision motor (e.g., stepper motor) that drives the plunger; the plunger moves on a linear rail/track; 3) a second stronger motor with a second rail that drives components 1 and 2 in the Z direction. Components 1, 2, and 3 can move in X and Y directions at a controlled speed and acceleration using proprietary software.

In embodiments, the robotic pipettor of the IVF/ICSI platform may include a cartridge for pipette tips (3300-3304) (see FIGS. 33A through 33C) and include a 3D-printed piece (plastic or metal) to accommodate a plurality of numbers and sizes of pipette tips for handling different volumes, tip brands, and different tube heights.

Figure 34A:
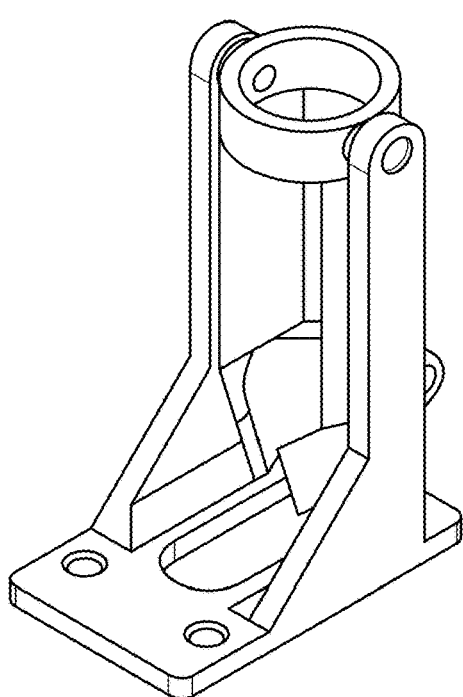
FIGS. 34A through 34C illustrate a robotic tilting mechanism that may be used for the swim-up tube as part of the semen preparation module.
Figure 34B:
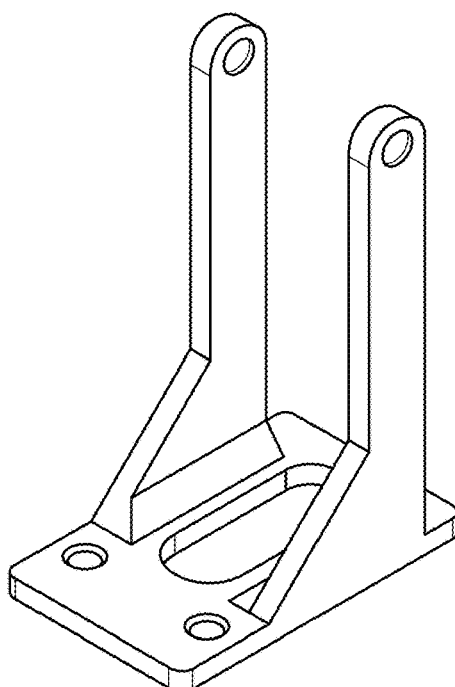
Figure 34C:
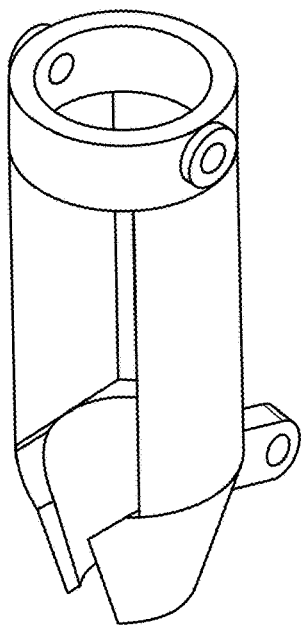

In embodiments, the robotic tilting mechanism, as described herein, may be used for the swim-up tube as part of the semen preparation module (3400-3406) (see FIGS. 34A through 34C). The IVF/ICSI platform assembly may include a tube holder, motor, a bracket that holds the motor to the robot frame, and control arms. Tilting movements may be orchestrated using software code, optics, image systems, AI/ML, as described herein, and other processes to control position, timing and speed of movement of the tube holder, and may incorporate a motor with feedback capability (e.g., equipped with sensors) that can be controlled to specify the degree of tilting and the speed of the tilting motion. The holder position may be held at a specific angle depending on the process that is being performed. The holder may incorporate a window or cut out to allow visualization of the tube during the procedure. In embodiments, a plurality of tube holder types may be incorporated in the IVF/ICSI platform. In an example, two of the three tubes may remain stationary/static in an upright position, while another third may tilt. The holders may be designed to hold multiple sizes of tubes and allow visualization of the contents via a window/cut out.

Figure 35A:
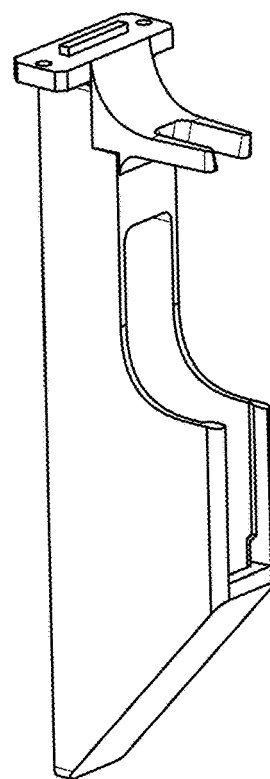
FIGS. 35A and 35B illustrate an automated ejection mechanism that may be used by the IVF/ICSI platform.
Figure 35B:
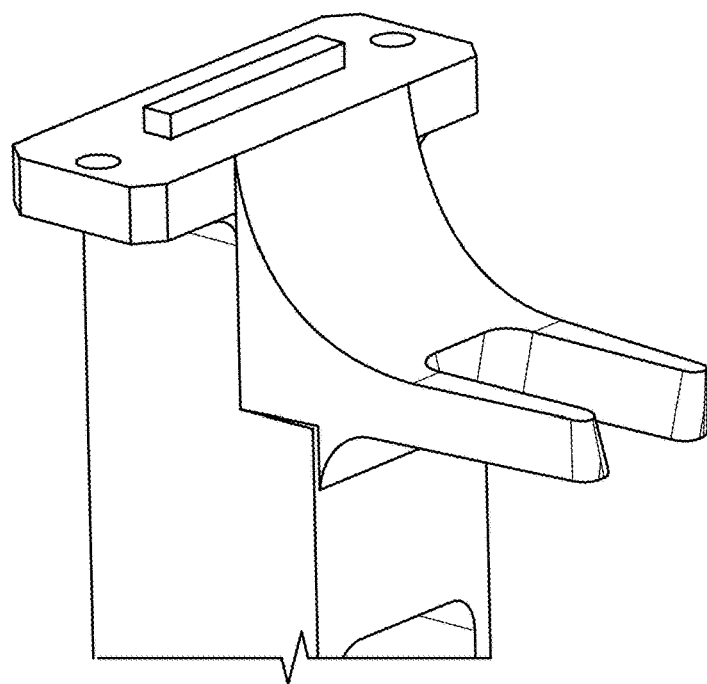

In embodiments, the IVF/ICSI platform may include an automated ejection mechanism 3500, 3502 (see FIGS. 35A and 35B). In an example, an automated ejection mechanism may include a 3-D-printed (plastic or metal) piece, a vertical piece with a fork like appendage that fits the top part of the manual pipettor body and allows an upward movement (facilitated by the z-motor, as described herein) of the pipettor to capture the pipette tip and separate it from the pipettor body.

Figure 18:
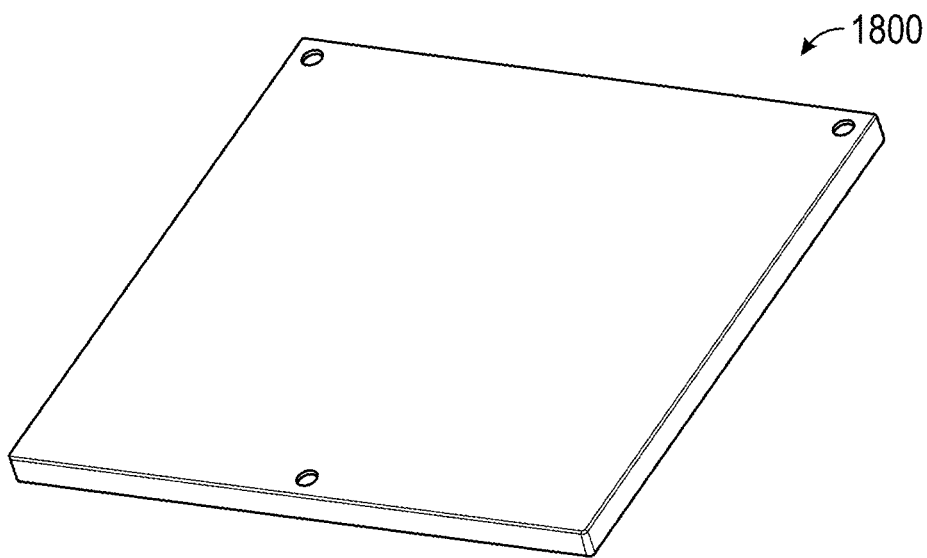
FIG. 18 illustrates a temperature-controlled plate.
Figure 33A:
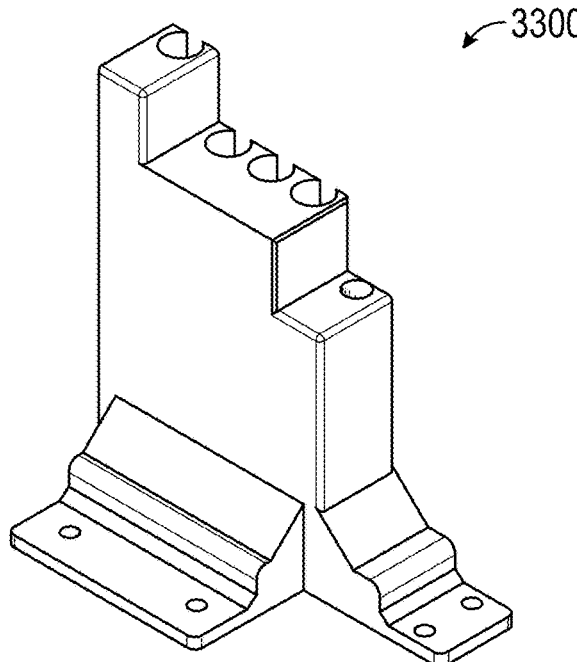
FIGS. 33A through 33C illustrates cartridge examples for holding pipette tips.
Figure 33B:
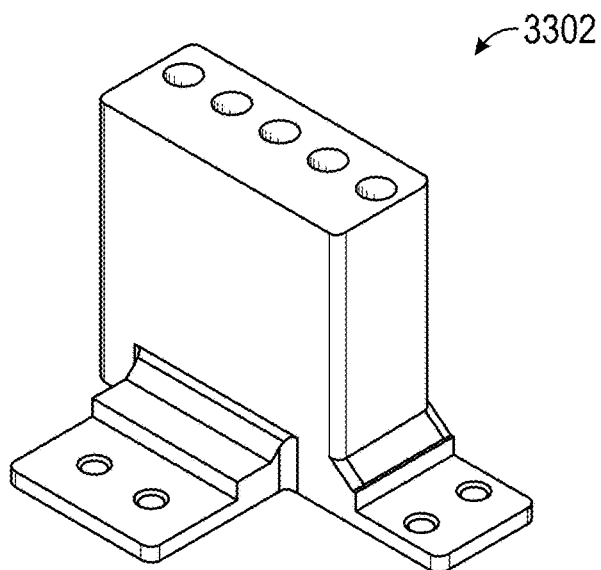
Figure 33C:
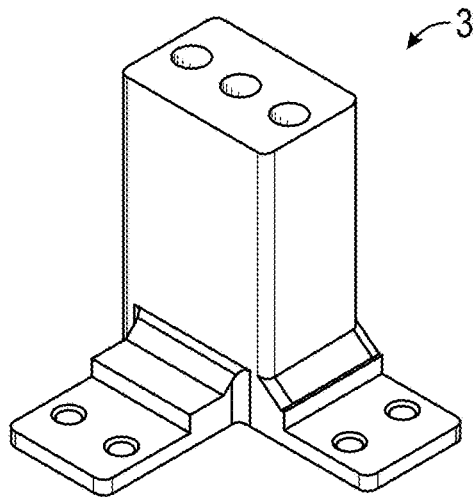

In embodiments, in an example usage of the IVF/ICSI platform, automated, robotic pipetting within the semen preparation module may follow the simplified course of action described below:

1. A human operator may prepare the semen preparation module robotic processing sequence by placing tubes in specified tube holders (3400-3406) (FIGS. 34A through 34C) and multiple pipette tips in a tip cartridge (FIGS. 33A through 33C). Alternatively, as described herein, this process may also be performed robotically, not using a human operator.
2. A discard bag may be attached to the outside of the frame for disposal of used pipette tips.
3. A human operator may place the specimen cup in the cup holder 1900, 1902 (FIGS. 19A an 19B) over a heating plate 1800 (FIG. 18). Alternatively, as described herein, this process may also be performed robotically, not using a human operator.
4. A human operator may issue a single command, or plurality of commands, to the IVF/ICSI platform to begin processes (as well as a calibration routine) in the semen preparation program. Alternatively, as described herein, this process may also be performed automatically, not using a human operator.
5. A robotic tilting mechanism (FIGS. 20A through 20C) may tilt the cup to a designated degree and then bring the cup back to its original upright position 2000, 2002, 2004. This may be repeated several times (to facilitate liquefaction). The tilting may be performed in accordance with a preset operation and/or may be adjusted in real time according to an ML/AI-based algorithm. For example, during a tilting process, machine vision may detect a characteristic (e.g., viscosity) of the sample held within the cup held by the tilting mechanism and, based at least in part on this characteristic, the IVF/ICSI platform may command a new operational parameter, including but not limited to a robotic control setting impacting the angle of tilt of the cup, the speed of movement during a tilting operation, a duration of a tilting operation, and the like.
6. The robotic pipettor (FIGS. 32A through 32H) may move (X and Y axes) to the position of the pipette tip cartridge, and/or move down (Z axis) to attach a pipette tip to the pipettor and move (Z axis) back up to the zero position (uppermost position) (3200-3214).
7. Once a tip is attached, the robotic pipettor may move (X and Y axes) to the position of the specimen cup and lower (Z axis) the pipetter/tip into the cup while the cup is tilted by the robotic tilting mechanism.
8. The robotic pipettor may aspirate a designated volume of semen and expel the volume back into the specimen cup (simulating mixing).
9. The robotic pipettor may lift out (Z axis) of the specimen cup and remain stationary in that position (at a designated height or the zero or uppermost position) for a designated length of time.
10. Processes may be repeated over a designated length of time to achieve liquefaction.
11. After a designated time has lapsed, the robotic pipettor may lower (Z axis) into the specimen cup while the cup is in the tilted position, aspirate a designated volume of semen, and lift out (Z axis) of the specimen cup to a designated height while the robotic rocker goes back to the upright position.
12. The robotic pipettor may move (X and Y axes) to a position precisely above the swim up tube, and lower (Z axis) into the tube to the bottom and expel semen, at a designated speed and acceleration, into the tube without creating air bubbles or aerosols. Processes 11 or 12 may be repeated until the desired final volume is achieved.
13. The robotic pipettor may move (X and Y axes) and stop above the discard bag, and eject (using X, Y and Z motion) (FIGS. 35A and 35B) the used pipette tip into the discard bag 3500, 3502.
14. The robotic pipettor may then move (X and Y axes) to the position of the pipette tip cartridge, and lower (Z axis) to attach a new pipette tip to the pipettor.
15. The robotic pipettor may move (X and Y axes) to a position directly above a tube containing sperm handling/wash medium, lower (Z axis) into the medium at a designated depth, aspirate a designated volume of medium, lift out (Z axis) of the tube, move to the tube containing semen, lower (Z axis) into the tube to a precise position above the semen meniscus, and "layer" the medium at a designated speed and acceleration over the semen. Process 15 may be repeated until the desired final volume is achieved.
16. The robotic pipettor may then move up (Z axis) and out of the tube. Process 13 may be performed to eject the used pipette tip and the pipettor may remain stationary in a designated position next to the discard bag for a designated length of time while the swim up proceeds.
17. After the designated time for swim up has elapsed, process 14 may be repeated for a new pipette tip to be attached.
18. Then the robotic pipettor may move (X and Y axes) to a position directly above the swim up tube, move down (Z axis) to a specified depth of the swim up layer, aspirate a designated volume of the cell suspension, move (X and Y axes) to a position above the final tube, and lower (Z axis) into the tube and expel the volume at the bottom of the tube.
19. The robotic pipettor may then lift out of the tube, move to the discard bag, and eject the used pipette tip.
20. The procedure is then complete.

In embodiments, the IVF/ICSI platform may include patient sample labeling. For example, to prevent sample mix up, the system may incorporate labeling systems, for tracking and to allow safe processing of multiple semen samples in a confined space.

In embodiments, the IVF/ICSI platform may include liquefaction testing. For example, the platform may assess whether semen clumps, clusters or coagula have resolved, and the sample is liquid, using computer vision (e.g., microscopic examination.) alone or in combination with pipetting and preparation protocols, as described herein.

In embodiments, the IVF/ICSI platform may include viscosity testing. For example, the platform may assess sample viscosity through periodic "string" formation testing using pipetting, measured by video recording, using the optics and machine vision processes as described herein, to assess string length and breakage. (e.g., macroscopic examination).

In embodiments, the IVF/ICSI platform may include viscosity reduction techniques. For example, the platform may incorporate methods such as vigorous pipetting (mechanical), ultrasound, enzymatic or other means to reduce viscosity when required.

In embodiments, the IVF/ICSI platform may include processes that may perform an overlay or an underlay. For example, the platform may include an underlay that would involve layering the semen under the handling medium to facilitate swim-up.

In embodiments, the semen preparation module may apply ultrasound to the sperm specimen to facilitate breakdown of the protein structures within the seminal plasma.

For example, an ultrasound transducer may be used to transmit ultrasound waves to manipulate protein structures to improve the viscosity and density of the specimen and thereby improve the overall sample preparation and pipette performance, such as more robust, adequate, dense filling of the pipette tip. As depicted in FIGS. 22 and 23, a pipette tip may have a custom geometry, according to the embodiments described herein, to facilitate a sperm swim-up protocol. In embodiments, pipetting of a sample may include automatically optimizing, using AI/ML processes as described herein, the motion of the pipette (e.g., the upwards and downwards movement of the pipette, the plane of movement and the like) and the coordination of the tilting mechanism, including the tilting action, degree of tilt, rate of tilt, duration of tilt and other tilt dynamics. Additional processes, such as the application of protein-rich media to the sperm sample may be further coordinated and optimized using AI/ML processes as described herein, during the pipetting process.

In embodiments, multipurpose handling medium (MHM) or another culture or handling medium may be used by the semen preparation module as part of the preparation of the sperm specimen for pipetting.

In embodiments, the IVF/ICSI platform may include an intra-pipette bilayer or multilayer system for semen preparation, reducing the number of preparation processes (and consumables) and avoiding seminal fluid cross contamination. This process may begin by drawing up handling medium into the pipette tip, and then, without releasing the pressure, continuing to draw up semen so that the semen is positioned at the bottom of the pipette tip and the handling medium is positioned above it. The residual pressure in the pipette tip prevents the bilayer from leaking out from the open end of the pipette tip. The pipette tip may be held in place for a designated period to allow swim up of sperm into the medium layer. After swim-up is completed, the semen layer along with a designated volume of the handling medium may be expelled through the opening at the end of the pipette tip. The remaining handling medium layer containing motile sperm may be retained and transferred into a clean sterile tube. The preparation can be used for both IVF and ICSI.

In embodiments, the IVF/ICSI platform may include efficient separation of sperm from seminal plasma/fluid. For example, the platform may collect final samples without any contamination with seminal plasma due to the precision of the robotic pipetting system.

In embodiments, the IVF/ICSI platform may include optical assessment of the swim-up layer. For example, the platform may use a light detector or a camera and monitor the swim-up process. ML/AI, as described herein, may be used to estimate the number of motile spermatozoa in the swim-up fraction and determine the time required for collection of an adequate sperm suspension. With incorporation of ML/AI, the platform may 'stop' the procedure or issue a warning to a human operator or continue with the next process in the procedure, which is collection of the sample.

In embodiments, the IVF/ICSI platform may include a "composite pipette tip" (e.g., a 10 µL tip attached to a 1000 µL tip at the tip) that may obviate the need for multiple size pipettors. This composite pipette tip may be used in other modules of the IVF/ICSI platform, as described herein.

In embodiments, the IVF/ICSI platform may include expandability. For example, the platform may be expanded to accommodate the simultaneous processing of multiple semen samples, based on clinical needs.

In an example embodiment, computer vision, machine vision and the like may be used to image the sample within the pipette to determine the adequacy of the volume, density or some other characteristic of the pipetted sperm sample. The image(s) of the pipetted sample(s) may be processed using artificial intelligence, machine learning and the like, as described herein, to test the sample against criteria to determine the quality of the sample. Continuing the example, if the pipetted sample is determined to not be adequate by the automated AI/ML system, a repeat of the pipetting process may begin, followed by further imaging and processing by the AI/ML processes. After a specified number of pipette attempts are made, if a satisfactory sample not obtained, the IVF/ICSI platform may issue an alert of the failure. The semen preparation module may also include an emergency stop activator (e.g., a button), such as within the user interface associated with the IVF/ICSI platform 2700 (see FIG. 27). The alert regarding the unsatisfactory pipetting event that is issued may be within the IVF/ICSI platform, for example presented on an IVF/ICSI platform user interface used by an operator that is interacting with the IVF/ICSI platform. Alternatively, the alert may be issued to a system or platform external to the IVF/ICSI platform, including but not limited to a telecommunications platform (e.g., sending an SMS text message, phone call, video of the pipetting, machine-generated audio narration of data summarizing the pipette processing failure, or some other message type), an email platform, an electronic medical record, a lab platform, a medical payor and/or reimbursement platform, a physician practice platform, or some other external platform type. Upon the detection of a pipette failure, the semen preparation module may produce a listing of a set of instructions that may be used by a human and/or robotic intervener to continue and or restart the pipetting operation. Alternatively, the continuation or restart of the pipetting operation may be automatically invoked according to a set of criteria stored by the IVF/ICSI platform. In embodiments, the stored criteria may be further associated with selection rules relating to data associated with a pipetting event. The unique data of a given pipetting event may be processed by the IVF/ICSI platform according to the rules and the appropriate set of instructions selected to determine the next processes and the actions to be taken, based at least in part on what has occurred during the given pipetting event.

In embodiments, the semen preparation module may include a biological residue trash receptacle into which used or discarded pipette tips may be automatically deposited. For example, within the semen preparation module, a first pipette may be used to begin preparation of the raw semen specimen, such as performing a flush routine. This same pipette may then be used to fill a vessel with the preliminarily prepared sperm specimen, and then automatically discarded by the semen preparation module. The semen preparation module may then obtain a second pipette to use for handling the MHM and placing it on top of the semen that was previously placed within the vessel. Once the MHM is placed, the second pipette may be discarded, and a third pipette automatically obtained by the semen preparation module. The third pipette may then be used to selectively obtain material from the top portion of the layered sample, and automatically discarded following its use.

In embodiments, the semen preparation module may include labeling of samples, apparatuses, and devices that permits automated imaging and tracking of each process performed by the semen preparation module. For example, cameras within the semen preparation module may image, record, store and analyze specimens, containers, pipettes, equipment and the like, including the clinical sequence, actions, performance and outcomes of each process, such as the separation of liquids, the degree of separation within, for example the bilayer, and the like. Labeling may also be used to track the human from whom a sperm sample derives, the physician, laboratory professional, office, company, insurer, payor or some other party that is further associated with the sperm specimen processing. Data derived from the completion of each process carried out in the semen preparation module may be recorded and stored within the IVF platform or within a platform associated with the IVF platform, such as an electronic medical record or other data repository.

In embodiments of the present invention, the IVF platform, as described herein, may include a system for the completely autonomous preparation of semen, for example, for ART or IUI.

In embodiments of the present invention, the IVF platform, as described herein, may include automated semen preparation by layering simulating a human-interphase process but claiming advanced efficiency in separating seminal plasma.

In embodiments of the present invention, the IVF platform, as described herein, may include the ability to process semen samples from multiple sources automatically in confined spaces secured by alert systems to avoid mix-up errors.

In embodiments of the present invention, the IVF platform, as described herein, may include an automated built-in system to reduce viscosity and promote liquefaction.

In embodiments of the present invention, the IVF platform, as described herein, may include a centrifuge-free robotic system allowing completely autonomous preparation of spermatozoa for ART or IUI from all male factor etiologies without swim-up. In embodiments, such robotic processing by the IVF platform may replace an andrologist or embryologist preparing semen samples.

In embodiments, the IVF/ICSI platform may include a robotic sperm preparation system for human clinical and/or veterinary purpose without using sperm swim-up, centrifugation or microfluidics. This robotic sperm preparation system may be used for the automated preparation, selection, and handling of single sperm cells from any mammal. The robotic sperm preparation system includes direct single sperm pick-up from seminal plasma/medium suspensions or from seminal-plasma-free media droplets following horizontal swim into culture medium from droplets. The robotic sperm preparation system be used for any mammal with functional spermatozoa in testicles or semen, including those with the lowest sperm counts, including, but not limited to, azoospermic males in whom spermatozoa may be surgically retrieved from the epididymis or testicle.

In embodiments, the robotic sperm preparation system may include robotic cell isolation, pipetting droplets, and using medium channels under mineral oil in dishes or on slides and merging single motile sperm selection with sperm immobilization and injection techniques. The robotic sperm preparation system processes may be orchestrated by a series of autonomous commands or protocols, as described herein, ensuring efficient and accurate execution, and may be combined to achieve complete autonomy. Parallel sperm preparation from different males may be achieved by combining multiple systems (e.g., semen preparation modules, as described herein) horizontally, stacked, and/or in a mobile manner, such as robotic controlled semen preparation modules that may be moved relative to one another, and to other modules of the IVF/ICSI platform, as necessary to facilitate parallel processes of the IVF/ICSI platform. Yields and protocols of the IVF/ICSI platform may be tailored to allow IUI, IVF or ICSI at will. The robotic sperm preparation system may not require using microfluidics, but microfluidic disposables may be incorporated if necessary. The robotic sperm preparation system may not require centrifugation or swim-up layering systems.

In embodiments, the robotic sperm preparation system may include:

Linking to a semen analysis system or perform semen analysis directly.

Using pipetting from multiple robotic pipettors placed at any angle.

Observing spermatozoa microscopically at different locations within the system, and/or using direct digital camera observation. Multiple observations of a preparation simultaneously may be possible.

Pipetting semen and surgical fluids obtained from epididymal or testicular sperm aspirations. A temperature-controlled receiving dock for surgical tubes may be integrated.

Preparing dishes and pipette droplets using, for example, 100 nL micro-droplets to 100 microliter droplets. Oil-covered for microdroplet covering may use larger volumes in the 1-5 mL range.

Making round droplets as well as any linear and non-linear forms and connecting droplets according to any programmable design commanded by the IVF/ICSI platform.

Interrupting horizontal sperm migration using, for example, a system of continuously measuring sperm migration optically.

Producing any culture medium dish using a programmable system commanded by the IVF/ICSI platform.

In embodiments, the robotic sperm preparation system may include sperm handling: (a) non-surgical sperm collection. Semen samples may be assessed using semen analysis after liquefaction. If liquefaction is absent, it may be initiated using vigorous robotic pipetting or using a mix with proteolytic enzymes such as chymotrypsin. If the latter, enzymes may be removed swiftly by single robotic sperm pipetting out of the enzymatic solution into small media droplets until no enzyme is present depending on the pipetting protocol. The samples, naturally liquefied, may be mixed with buffered cultured medium and robotic arms may retrieve motile spermatozoa, for example, one by one after motility and morphology assessment using AI/ML and optics, as described herein. AI/ML and optics may be applied when liquefaction is absent, and enzyme has been used. The system may retrieve enough spermatozoa to provide a secondary sperm identification and selection (SiD) analysis after the spermatozoa are mixed with a droplet containing, for example, a 5-10% solution of PVP under oil in a prepared ICSI dish. This may be included in a final step before robotic sperm selection and immobilization using, for example, robotic ICSI.

In embodiments, the robotic sperm preparation system may include sperm washing and selection. The system may employ SiD technology, optionally supplemented with morphology assessment and segmentation analysis, to choose optimal spermatozoa rapidly during an initial preparation and later when spermatozoa are injected into a droplet containing PVP to reduce their forward progression for immobilization and ICSI. The seminal plasma may be removed by repeatedly and robotically picking up single spermatozoa in narrow pipettes in groups of, for example, 5-300 and serially pipetting the spermatozoa through buffered medium. Multiple pipettors may be used simultaneously. For surgical preparations, large clumps of cells and tissue may be removed using larger pipettes. The system may operate with one robotic pipettor or several simultaneously. The robotic system using sperm pickup without horizontal sperm preparation may be considerably faster than standard manual procedures. The horizontal sperm prep procedure may also be equipped with SiD AI to allow timing to optimal concentration of horizontal swim-out into seminal-plasma-free culture medium. The timing may be dependent on sperm progression and velocity and may vary from sample to sample. Optimization of medium droplet size and placement and connecting medium channels may be dependent on the quality of the semen sample. The shape of the configuration may vary and be optimized with experience. AI/ML and optics of the IVF/ICSI platform may be used to optimize each droplet and channel configuration.

In embodiments, the robotic sperm preparation system may be fully automated, leveraging advanced robotics and 3D motorized systems, including integration with cameras and computer vision to facilitate autonomous control of the system, ensuring precise movements throughout the process.

In embodiments, the robotic sperm preparation system may autonomously manage autofocusing and zoom-in and zoom-out using software and hardware systems of the IVF/ICSI platform for clear and accurate imaging at all stages.

In embodiments, sperm tracking within the robotic sperm preparation system may be a continuous process, allowing for the real-time monitoring of sperm movement and location throughout a procedure. The optimal sperm preparation concentration may be maintained by interrupting the horizontally placed channel using a blunt pipette tip automatically interrupting the sperm channel.

In embodiments, the robotic sperm preparation system may identify and track various components of the sperm, including the tail, acrosome, head, and midpiece. This segmentation process may ensure precise handling of live motile sperm.

In embodiments, the robotic sperm preparation system may include the reassessment of sperm. For example, after selection, the semen preparation module may provide an option for additional SiD assessment either before or after immobilization to confirm the suitability of a chosen sperm.

In embodiments, the robotic sperm preparation system may include data management and record-keeping by, for example, incorporating automatic patient identification and data recording capabilities, ensuring comprehensive documentation and quality management of each procedure.

In embodiments, the robotic sperm preparation system may be housed in a space that is temperature and humidity controlled with HEPA and carbon filtration.

In embodiments, the robotic sperm preparation system may include quality management, including but not limited to operational functions (such as disposables, fluids, pipette tips, discarded disposable bags, and the like) controlled by a fully automated quality management process(es).

In embodiments, the robotic sperm preparation system may include a command-based operation system and method. For example, a single command may initiate a predefined sequence of events, streamlining the process and reducing the potential for human error. This feature may enhance efficiency and reproducibility and also may be interrupted by an engineer or specialized embryologist or andrology technician. The interphase may be adapted to digitally control aspects such as channeling, sperm concentration determination, focusing, positioning of sperm, changing lenses or cameras, moving the stage and/or cameras or lenses, moving the microtools, adjusting light, inserting different microscopic systems, determining droplet location, or some other action of the IVF/ICSI platform.

Figure 61:
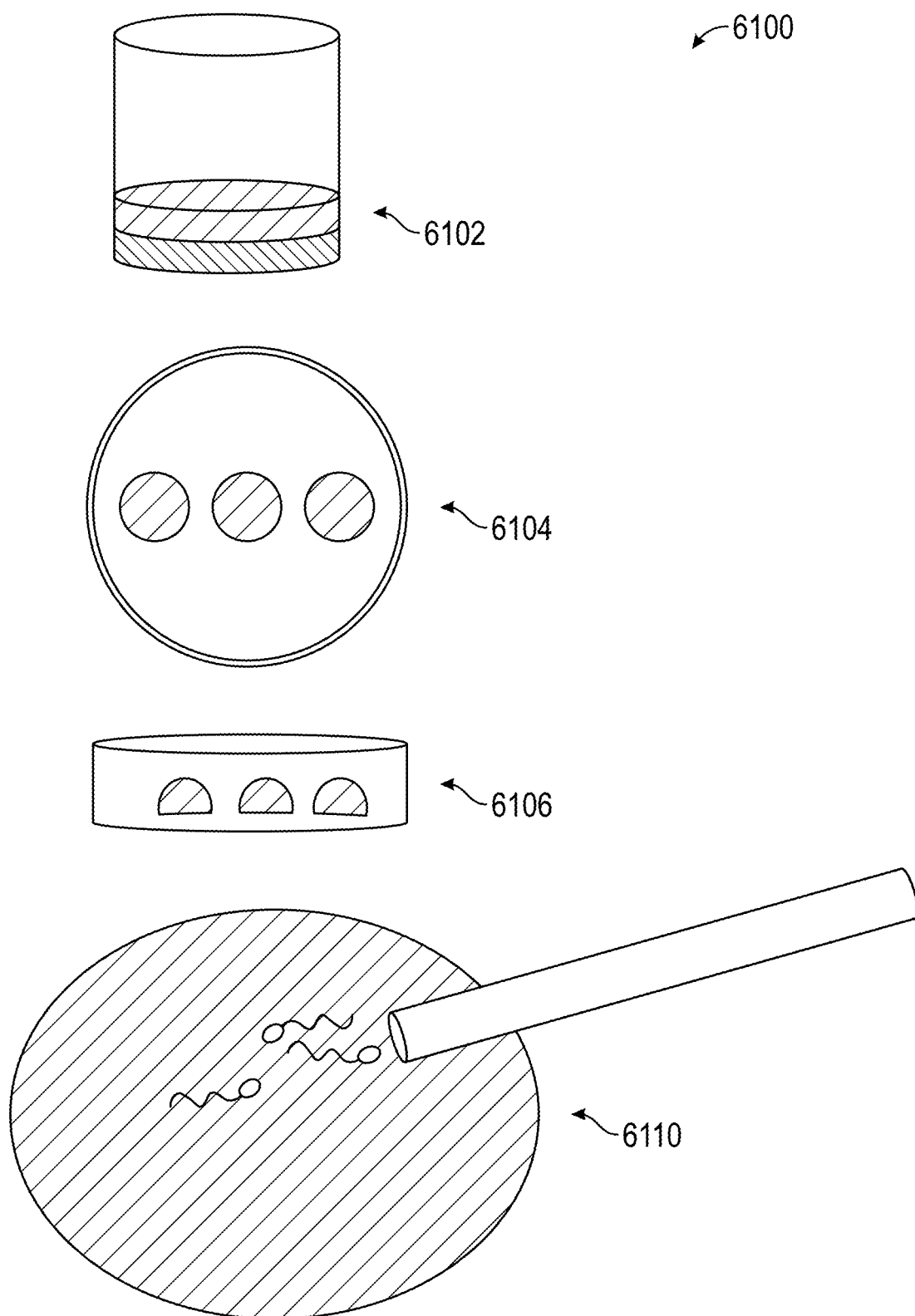
FIG. 61 illustrates an example robotic sperm preparation 6100 that may be performed by the IVF/ICSI platform using semen/medium mixing and spermatozoa tracing systems to pipette single spermatozoa in groups and diluting seminal plasma using a droplet washing system.

FIG. 61 illustrates an example robotic sperm preparation 6100 that may be performed by the IVF/ICSI platform using semen/medium mixing and spermatozoa tracing systems to pipette single spermatozoa in groups and diluting seminal plasma using a droplet washing system. In embodiments, a collection jar 6102 may be used to mix semen (lower layer) with culture medium (upper layer) using a robotic pipette, for example, by collecting ejaculates into a dry jar or by collecting the ejaculate into a jar filled with (e.g., 2-5 mL) of culture medium. The robotics of the IVF/ICSI platform may mix the semen (spermatozoa and seminal fluid-seminal plasma) and culture medium. Droplets of culture medium/seminal plasma/spermatozoa may be pipetted by a robotic arm onto bottom of dish 6104. Followed by covering the droplets robotically with mineral oil. The semen/medium mixtures may be placed onto a microscope stage 6106 and spermatozoa may be visualized using the optics and imaging system, as described herein. A plurality of robotic pipetting arms, for example, with narrow glass or plastic pipette tips may be used to pick up the spermatozoa 6110.

Figure 62:
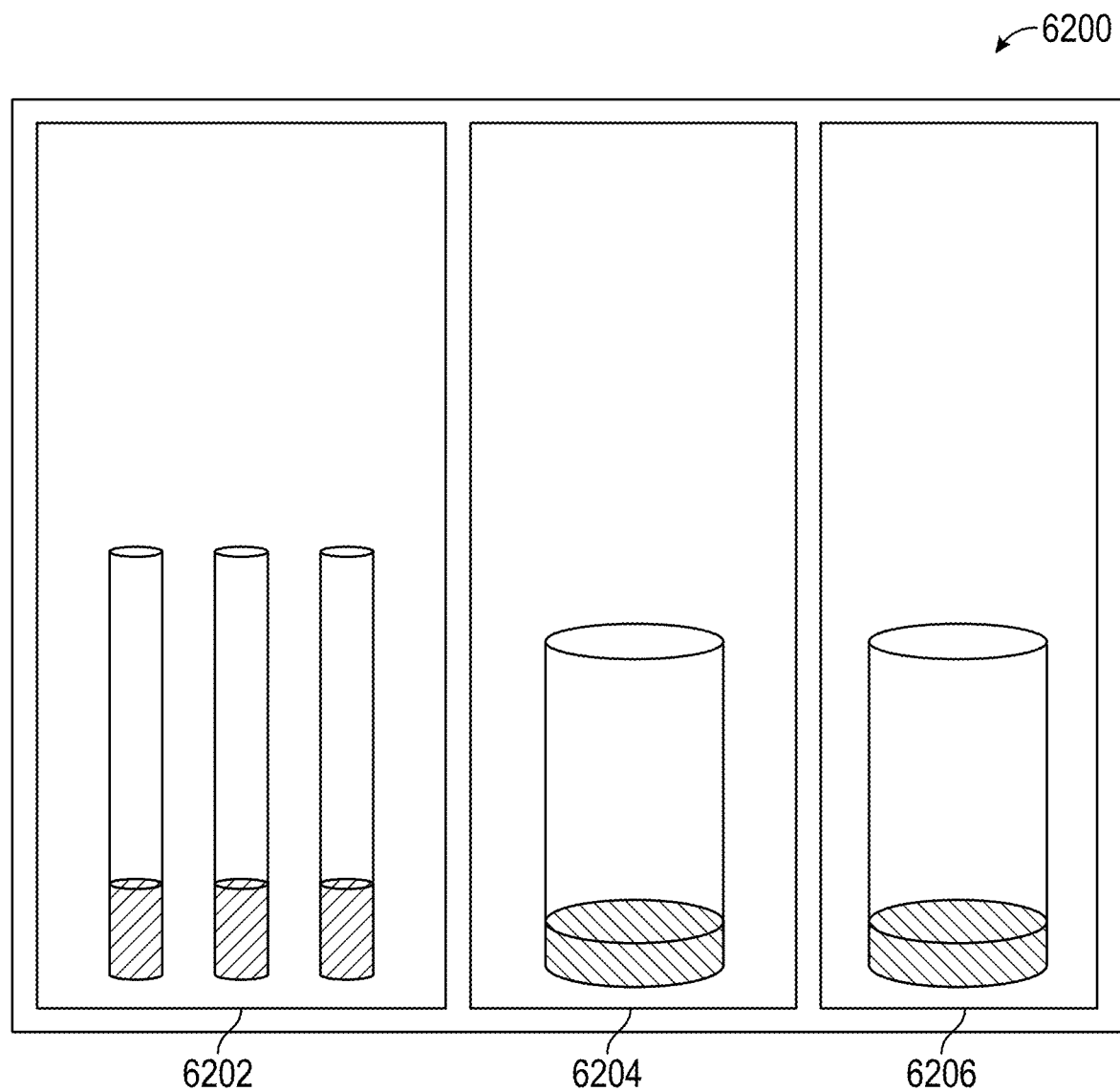
FIG. 62 illustrates collection tubes 6202 filled with biopsies from testicular or epididymal aspirates.

Referring to FIG. 62, collection tubes 6200 may be filled with biopsies from testicular or epididymal aspirates (shaded region) 6202, 6204, 6206. Robotics of the IVF/ICSI platform may place the tubes in temperature-controlled racks. Collection jars with ejaculates 6204, 6206 (shaded) from individual patients or donors may be placed in separately controlled and monitored compartments within the modular system of the IVF/ICSI platform. Each compartment handling specimens from a single patient may perform robotic activities needed to complete sperm preparation or perform a horizontal swim-out under mineral oil using a microdroplet and micro-channel medium system. In embodiments, the compartment system may be modular and expandable. Each compartment may be environmentally isolated with its own material supply and disposable sections and equipped with labelling recognition systems.

Figure 63:
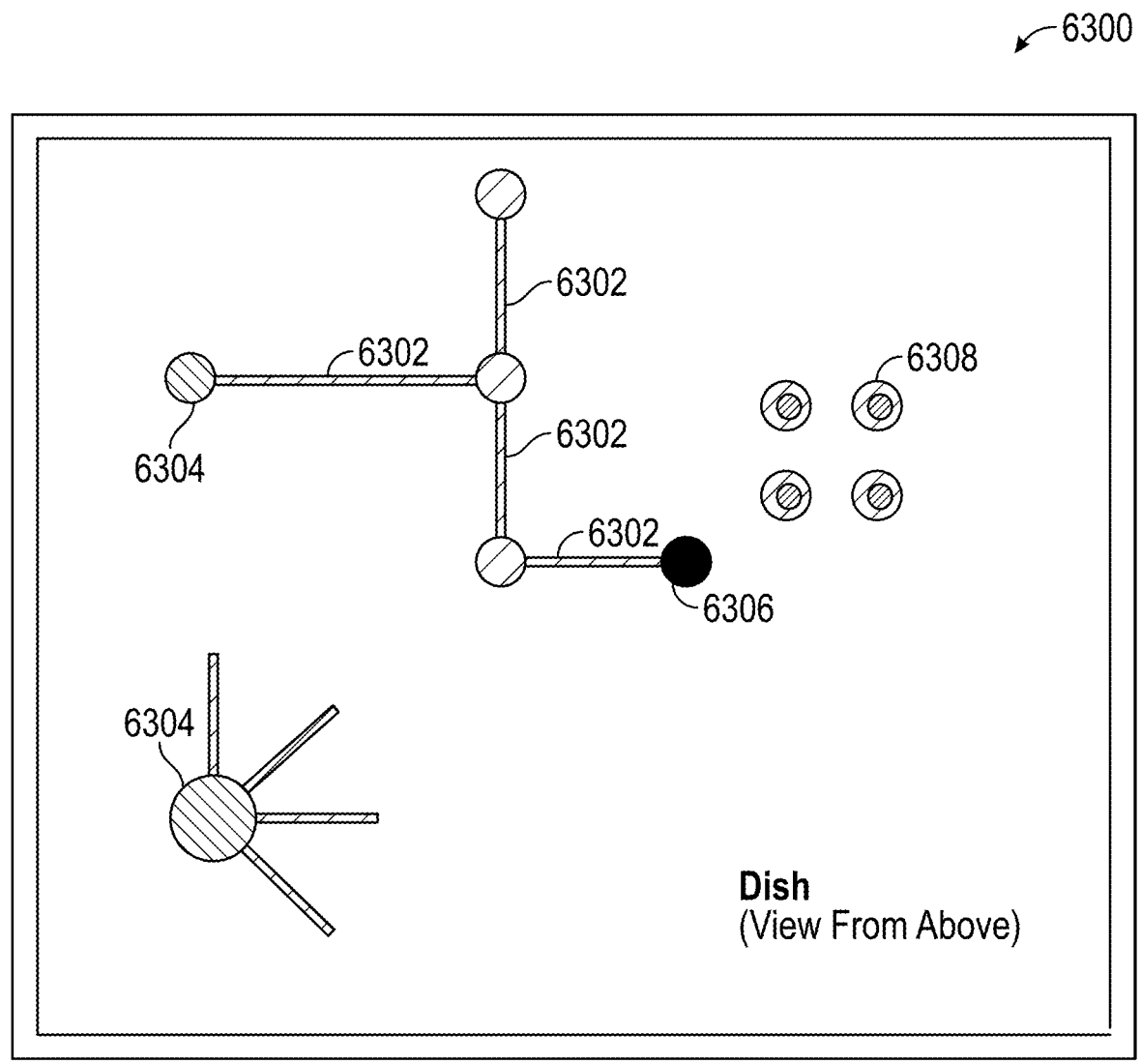
FIG. 63, illustrates swim-up-free, centrifugation-free, microfluidics-free robotic sperm preparation using horizontal swim-out.

Referring to FIG. 63, swim-up-free, centrifugation-free, microfluidics-free robotic sperm preparation using horizontal swim-out is presented 6300. The robotic system of the IVF/ICSI platform may prepare the dish and monitor the swim-out. Once a predetermined number of motile spermatozoa are obtained, the channels may be interrupted by robotically making an oil bridge in the channels. Droplets of, for example, 1-10 microliter of seminal plasma either as single or multiple droplets using a circular form or star may form connections to seminal-plasma free medium droplets using a channel system of medium allowing spermatozoa to travel through medium channels under oil. Spermatozoa may be picked up singly or in a group containing multiple sperm. Other droplets containing PVP may be connected to the droplet-channel system to slow down spermatozoa that have swum out of the semen droplet. The spermatozoa which have arrived in PVP may be selected and immobilized to be prepared for ICSI. Droplets containing eggs may be present in the same dish. Medium droplets and medium filled channels 6302 may be pipetted before covering with oil overlay. Semen droplets 6304 can be placed single or in multiple configurations to improve yield in cases of poor sperm quality. The robotics of the IVF/ICSI platform may be programmed to pipette a plurality of medium culture type configurations. A heating element may be placed under the seminal plasma droplets or channels to enhance swim out. In an example configuration, the droplets and channels may be connected to a PVP droplet 6306. In another example configuration, medium droplets may be added for placement of eggs 6308 ready for ICSI. Testicular aspirates and other samples with poor counts and motility may be pipetted in larger and shallow droplets connecting to multiple medium channels to enhance yield. This may be combined with the robotics used to physically obtain the sperm.

In embodiments, the semen preparation module may use narrow capillary tube or capillary tube-like tips to move spermatozoa from liquefied semen or semen mixed with some culture medium by visualizing spermatozoa in an automated fashion using pipetting systems and a robot, or plurality of robots that quickly focuses on spermatozoa and removes the spermatozoa by suction. In embodiments, these robotic processes may be combined with DL/CV based sperm selection software, if needed. Spermatozoa extracted from the semen samples may be deposited in culture medium droplets with slightly increased viscosity using dextran or PVP or equivalent viscous substance. This may allow case of pipetting until the final process. After such processes, the spermatozoa may be deposited in culture medium, for example, for later use or the PVP solution ready for ICSI.

In embodiments of the present invention, the IVF/ICSI platform, as described herein, may include automated semen preparation without layering or centrifugation.

In embodiments of the present invention, the IVF/ICSI platform, as described herein, may include such a system that is potentially applicable to any semen or surgically retrieved sperm sample.

In embodiments of the present invention, the IVF/ICSI platform, as described herein, may include an automated built-in system to reduce viscosity and promote liquefaction.

In embodiments of the present disclosure, the semen preparation module may include a robotic system for semen preparation (swim-up), retrieval and movement to ICSI dish. In embodiments of the present disclosure, the semen preparation module may include AI/ML for automated detection, identification, and classification. In embodiments of the present disclosure, the semen preparation module may include AI/ML for automated measurement and testing. In embodiments of the present disclosure, the semen preparation module may include AI/ML for optimization. In embodiments of the present disclosure, the semen preparation module may include AI/ML for prediction. In embodiments of the present disclosure, the semen preparation module may include AI/ML for selection/ranking. In embodiments of the present disclosure, the semen preparation module may include AI/ML for semi-autonomous, supervised, or autonomous robotics. In embodiments of the present disclosure, the semen preparation module may include AI/ML for system configuration and control. In embodiments of the present disclosure, the semen preparation module may include fully autonomous AI/ML. In embodiments of the present disclosure, the semen preparation module may include optical and machine vision components, systems, and processes. In embodiments of the present disclosure, the semen preparation module may include robotic handling systems and processes. In embodiments of the present disclosure, the semen preparation module may include sensor components, systems, and processes. In embodiments of the present disclosure, the semen preparation module may include sperm preparation components, systems, and processes. In embodiments of the present disclosure, the semen preparation module may include specimen management components, systems, and processes. In embodiments of the present disclosure, the semen preparation module may include Laser components, systems, and processes.

In embodiments of the present invention, the IVF/ICSI platform, as described herein, may include an egg preparation module that is fully automated, uses robotics for the handling and movement of materials, including biological specimens, and is connected to a network infrastructure, as described herein, for remotely controlling the activities of the egg preparation module as one component of the fully automated and robotic IVF/ICSI platform.

In embodiments, in a clinical setting follicle stimulating hormone (FSH) may be administered to a patient to stimulate the ovary/ies to grow multiple follicles, and an ultrasound-guided transvaginal procedure used, entailing aspiration of the growing follicles, while the patient is under sedation. The follicles are punctured using a thin needle, and the fluid within is aspirated into tubes. A mature antral follicle at ovulation may measure ~25 mm in diameter and contains ~50 million granulosa cells and ~7 ml of follicular fluid. Follicular fluid is often opaque yellow in color and contains hormones (e.g., estrogen, progesterone, androgens, etc.), growth factors, cytokines, metabolites (e.g., glucose, pyruvate, lactate, etc.), ions (e.g., sodium, potassium, calcium, etc.), and proteins (e.g., albumin, transferrin, etc.) among other factors. Cellular components of the follicular fluid may include granulosa cells: As an (antral) follicle develops, distinct classes of functionally different granulosa cells are generated depending on the position of the granulosa cells relative to the oocyte. The cells closest to the oocyte are cumulus granulosa cells, while mural granulosa cells are further away from the oocyte and line the follicle wall. In response to ovulation trigger, cumulus cells secrete an extracellular matrix primarily made up of hyaluronan (therefore hyaluronidase-sensitive) that causes expansion of the cumulus cells in a process called mucification. Mucified or expanded cumulus masses appear translucent and distinct from mural granulosa cells, which maintain their sheet-like tight-knit morphology with a darker appearance and thus can be visually distinguished from cumulus even with a naked eye.

In embodiments, biologic material obtained from a patient during egg retrieval may include an oocyte-cumulus-corona-complex (OCCC) or cumulus-oocyte-complex (COC): *Corona radiata* cells are the layer of cells that directly contact the zona pellucida, the acellular glycoprotein moiety or "shell" surrounding the oocyte via cytoplasmic projections. During cumulus expansion, the *Corona radiata* cells may be separated from the zona pellucida but they are still recognizable as a distinct layer of cells surrounding the oocyte. They do not undergo mucification and usually appear darker than the cumulus cells, facilitating visual identification of oocytes. Hyperstimulated ovaries have increased vascularity and the follicles are more prone to bleeding when punctured by the retrieval needle. This can lead to mixing of blood with follicular fluid.

In embodiments, oocytes isolated from follicular fluid may be at different stages of nuclear maturation, for example, fully mature (at metaphase II or MII of meiosis with a first polar body present), intermediately mature (at metaphase I of meiosis; no polar body) and immature (at prophase I of meiosis, containing a large nucleus called a germinal vesicle or GV). Depending on the level of nuclear maturity, the cumulus masses can appear with different morphology: expanded and translucent in MII oocytes; somewhat darker and more tightly organized in MI oocytes; and very dark, tight, and small in GV oocytes. Nuclear maturity may be estimated based on the appearance of the cumulus and corona cells.

In embodiments, the IVF/ICSI platform may autonomously and robotically perform oocyte search and isolation, replacing the traditional egg retrieval procedure performed by a human operator. In the traditional egg retrieval procedure performed by a human operator, the processes listed in Table 2, below, are generally followed.

TABLE 2

| Action | Human operator role |
|---|---|
| Patient identification | Document verification; patient contact; Human judgment |
| Planning case preparation | Human judgment |
| Preparation of dishes for oocyte retrieval procedure (Wash dishes, culture dishes) | Pipetting, transport |
| Preparation of tubes for follicle flushing | Pipetting |
| Verification of patient identity on dishes | Witnessing; Human judgment |
| Receiving tubes with follicular aspirates from the operating theatre | Manual handling of tubes |
| Decanting tube contents in one or more dishes | Manual handling of tubes |
| Scanning dishes for cumulus complexes | Macroscopic examination |
| Identifying cumulus complexes containing oocytes | Microscopic examination (LP) |
| Picking up the OCCCs ad placing them in a wash dish | Pipetting; (PASTEUR) changing dishes |
| Repeating the process and counting number of OCCCs | Manual handling of tubes/dishes; pipetting (PASTEUR) Changing dishes |
| Dissecting blood- stained cumulus masses | Macro-manual; microscopic observation |
| Placing OCCCs in culture dish/es | Pipetting; change of dish |
| Placing dish/es in designated incubator | Transport and knowledge of correct location |
| Data entry on paper/EMR | Macro-manual |

In embodiments, aspirates of follicular fluid may be searched under a stereo microscope by an embryologist to identify and isolate COCs. The cumulus investment of eggs may be dissected using hypodermic needles to remove blood clots or unhealthy-appearing cells or to simply reduce its size before incubation.

In embodiments, pipetting in the context of egg retrieval may entail aspiration and expelling and container-to-container transfer of individual or multiple COCs. Pipetting is fundamental to IVF laboratory techniques and may be carried out in a sterile fashion, without creating air bubbles that could be disruptive, lead to loss of cells, or create potentially infectious aerosols. Different types of pipettes may be used by the automated, robotic pipetting systems and methods of the IVF/ICSI platform, as described herein, during egg retrieval procedures, including but not limited to Pasteur pipettes, Eppendorf pipettes, capillary tube tips, or some other type of pipette. Pasteur pipettes are made of borosilicate glass, usually in two lengths (short or 5.75 inches and long or 9 inches) and may be used in conjunction with rubber pipette bulbs, to transfer smaller volumes of fluids with or without cells. These pipettes can be "pulled" over a flame to create very narrow bores for handling eggs and embryos. Eppendorf pipettes are instruments equipped with a piston and a spring-loaded tip cone, single channel and adjustable volumes (1-1000 µL units with specific ranges), used in conjunction with Eppendorf tips, to aspirate and dispense precise (usually low) volumes. capillary tube tips refer to pipette tips used in conjunction with capillary tube pipettors: Tips are made from flexible medical grade plastic to prevent scratching of plastic Petri dishes. The tips are manufactured in different inner diameters, ranging from 75 µm to 600 µm, with the most commonly used sizes being 155-200 µm for denudation of eggs and handling eggs and embryos, and 300 µm for handling blastocysts.

The automated IVF/ICSI platform may use robotics for isolation, handling and movement of eggs with their investments (COCs) from follicular fluid. The follicular aspirates may be decanted in a dish and placed on a motorized stage of an inverted microscope. The dish may be automatically scanned in a predetermined pattern, using computer vision, in combination with AI/ML and/or computer vision and optics, as described herein, in order to identify the COC. Once identified, the COC may be automatically retrieved with a pipette, washed, and transferred to a new dish containing fresh handling medium.

In embodiments, an example, simplified sequence for oocyte isolation is presented below, each element of which may be performed autonomously and robotically by the IVF/ICSI platform, as described herein:

A "wash" dish (e.g., 1×35 mm) with handling medium and an oil overlay (to prevent evaporation) may be received by the IVF/ICSI platform and placed on a stage of an inverted microscope, or some other type of microscope, fitted with a "dish holder" (e.g., a rectangular piece with cut-outs to fit one 60 mm and 2×35 mm culture dishes).

The IVF/ICSI platform may begin a sequence with movement of the stage as computer vision is used to scan the dish, for example, in a pre-determined zig-zag pattern from top to bottom.

AI/ML may identify cumulus masses containing eggs. Each aspirate may contain zero to multiple eggs. This is partly dependent on the method of aspiration used by the surgeon and the size of the follicles being aspirated. Individual follicles may be aspirated into each tube or multiple follicles may be aspirated at the same time into one tube. The ratio of eggs to tubes may be other than 1:1; there may be more tubes of aspirates and flushing medium than eggs; or multiple eggs in one tube. The robotics of the IVF/ICSI platform, as described herein, may be able to distinguish among the different contents and identify the eggs. In embodiments, processes 3 and 4 may or may not occur in parallel. In an example, while the dish is being scanned, computer vision, optics and/or AI/ML may be used to search for and identify COCs, or the process might also stop the scanning at a given position to interact with the computer vision, optics and/or AI/ML, and/or the IVF/ICSI platform might obtain images of the follicular fluid in the scanning process and after finalizing the scan, query the computer vision, optics and/or AI/ML to determine if there are any COCs present.

Once identified, a pipette held in a microtool holder may be lowered into the follicular fluid dish and placed immediately adjacent to the cumulus mass. In an embodiment, the pipette tip may be lowered at a distance from the COC, and once inside the liquid it may approach the COC, and then begin aspiration.

Negative pressure may then be applied and the cumulus mass along with some fluid may be aspirated into the pipette.

The amount of fluid may be precisely controlled based on the outer physical limits of the mass. Aspiration may stop once the full mass is inside the pipette. Then the pipette may be lifted out of the dish and remain stationary.

The stage may then move toward the first dish with handling medium.

Once in place, the pipette may be lowered into the wash dish, positive pressure may be applied, and the cumulus mass/follicular fluid may be expelled into the medium. The volume may be precisely controlled so that positive pressure stops once the entire mass exits the pipette.

The pipette may then be lifted out of the dish and remain stationary.

In embodiments, the egg preparation module may receive a follicular fluid specimen and automatically place the specimen for viewing with a microscope, computer or machine vision, or some other imaging device, in order to perform cumulus oocyte complex (COC) identification, discovery, analysis and evaluation. In an example embodiment, the specimen may be viewed within the egg preparation module using an inverted microscope, a digital microscope, or some other type of microscope. In embodiments, the inverted microscope may include components and adapted robotics to be used as part of an automated ICSI procedure, as described herein, and may include digital microscopes both under and over of the plates, dishes or other type of vessels containing the samples. The follicular fluid specimen may be automatically scanned using computer vision, machine vision and the like, in combination with AI/ML in order to perform the COC identification. This imaging in combination with AI/ML may allow differentiating of cell types, such as that of blood cells from COCs.

Figure 36:
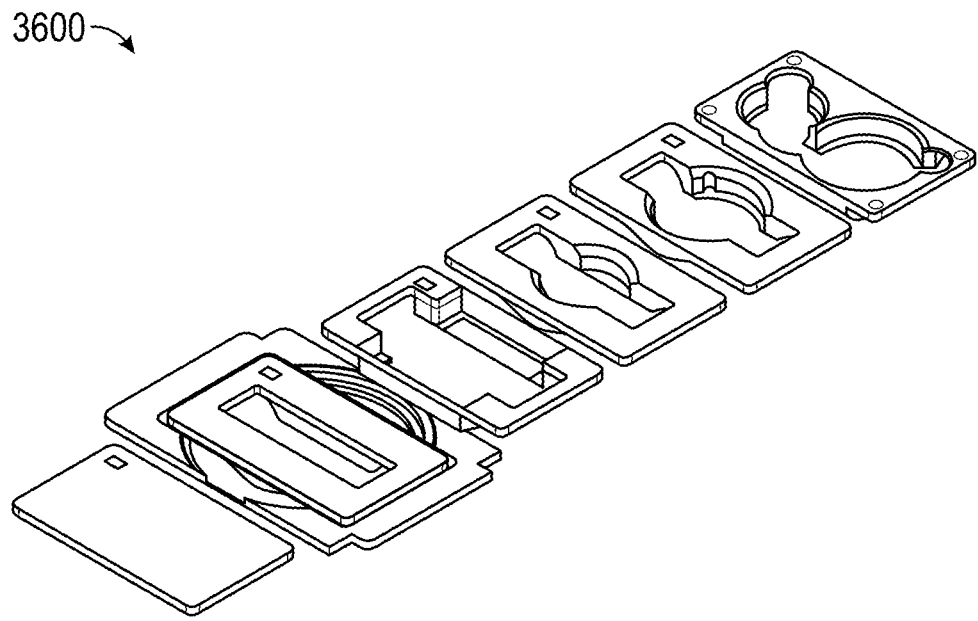
FIGS. 36 and 37 illustrate example forms of dish holders that may be used by the egg preparation module for holding a specimen dish, receptacle or vessel.
Figure 37:
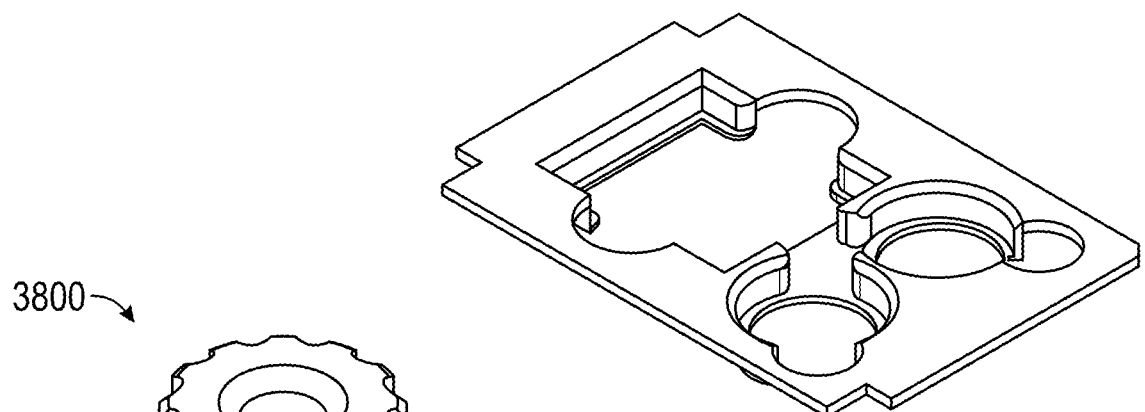

In embodiments, during the COC identification stage, the egg preparation module may autonomously and robotically place the dish, receptacle or vessel in which the follicular fluid specimen is located on a stage, plate or other surface that is motorized to provide movement to the dish, receptacle or vessel in which the follicular fluid specimen is located. FIGS. 36 and 37 illustrate example forms of dish holders that may be used by the egg preparation module for holding a specimen dish, receptacle or vessel 3600, 3700. As the imaging and AI/ML procedures are carried out on the follicular fluid specimen, the egg preparation module may automatically adjust the positioning of the dish, receptacle or vessel in which the follicular fluid specimen is located in order to optimize, for example, the angle, height, or portion of the specimen as it is imaged. The stage, plate or other surface may move in any axis of movement and may rotate along any axis or plane of operation.

In embodiments, imaging of the specimen within the egg preparation module may be made independently of the microscope or through the microscope. For example, one set of imaging equipment may be used to evaluate and analyze the positioning of certain equipment independent of the microscope, such as the position of a dish, receptacle or vessel being used within the egg preparation module. In embodiments, imaging may be made through the optics of the microscope as well, for example, by fitting a camera or plurality of cameras to the microscope viewing apparatus, such as binocular scopes. In embodiments, during imaging, the egg preparation module may automatically adjust the frequency, intensity, angle, distance or some other factor of artificial lighting that is used to image the specimen. The adjustment of the frequency, intensity, angle, distance or some other factor of artificial lighting that is used to image the specimen may be based at least in part on the AI/ML processes used to evaluate the imagery obtained of the follicular fluid sample by the egg preparation module.

In embodiments, once at least one COC is identified, for example by using the inverted microscope in combination with imaging and AI/ML, as described herein, a pipette may vertically descend into the follicular fluid specimen and extract at least one COC and transfer the selected COC to a second dish, receptacle or vessel within the egg preparation module that contains culture media. The dish, receptacle or vessel into which the COC(s) are placed may reside on or in the vicinity of a plate that is capable of temperature control, such as providing the dish, receptacle or vessel a constant 37-degree Celsius (or some other target temperature) environment during the performance of the COC washing and preparation. During this process, if more than one COC is identified within the specimen, the egg preparation module may further separate the COCs into additional dishes, receptacles or vessels to provide for a single COC per each divided sample, or some other targeted number of COCs per divided sample.

In embodiments, during the COC identification and separation stage, the egg preparation module may automatically apply compounds to the specimen in order to facilitate COC separation and extraction. In an example, if the imaging and AI/ML procedures of the egg preparation module detect the presence or probability of blood or blood clotting in the follicular fluid sample, the egg preparation module may robotically select an amount of heparin, or other clot prevention therapeutic, and add the heparin to the follicular fluid sample to facilitate COC extraction. The type of clot prevention therapeutic, the amount of clot prevention therapeutic, the timing of the addition of the clot prevention therapeutic to the follicular fluid sample, and other factors, may be determined at least in part automatically using the imaging and AI/ML processes of the IVF/ICSI platform, as described herein.

In embodiments, once the COCs have been autonomously and robotically placed in the dish, receptacle or vessel containing the culture media, the COCs may then be moved to a new dish, receptacle or vessel where the egg preparation module performs an autonomous and robotic series of washes of the COCs. Following the washing of the COCs, the dish, receptacle or other vessel in which the COCs are contained may be automatically transferred to an incubator.

In embodiments, after a period of culture of COCs, the egg preparation module may autonomously and robotically initiate an oocyte denudation process.

In embodiments, automation, as used herein, includes robotics and AI/ML-assisted processes so that processes in the egg denudation procedures that ordinarily require a human operator may be performed by the intelligent robotic system of the IVF/ICSI platform. Table 3 outlines such processes involved in traditional oocyte denudation:

TABLE 3

| Action |
| --- |
| Enzyme and wash dish preparation |
| Determination of timing of denudation in relation to ovulation trigger |
| Transfer of dish with oocytes from the incubator to the laminar flow hood |
| Verification of patient identity on all dishes |
| Transfer of eggs in groups of 1-5 (based on total number of eggs) from incubation dish to the enzyme dish/well |
| Gentle pick up and expelling of OCCCs in and out of the pipette |
| Allowing the enzyme to dissociate/disperse cumulus cells |
| Moving the oocyte-corona complexes with loosely arranged or fully dissociated cumulus cells out of the enzyme drop/well & into a clean medium drop/well |
| Removing corona cells mechanically using sequentially smaller capillary tube tips (200 to 155 um) |
| Moving the corona-free eggs to a new well/drop with fresh medium & repeat |
| Assessing nuclear maturity of the eggs |
| Separate MII from MI and GV oocytes in different wells/drops |
| Use MII eggs for ICSI or MII and MI eggs for vitrification |
| Placing dish/es in designated incubator |
| Data entry/EMR |

As an (antral) follicle develops, distinct classes of functionally different granulosa cells are generated depending on the position of the granulosa cells relative to the oocyte. The cells closest to the oocyte are called cumulus cells (or cumulus oophorous). Immediately surrounding the oocyte are *Corona radiata* cells which directly contact the zona pellucida via cytoplasmic projections. During cumulus expansion (following ovulation trigger), the *Corona radiata* cells are separated from the zona pellucida (the projections are mostly withdrawn) but they are still recognizable as a distinct layer of cells surrounding the oocyte. They do not undergo mucification and usually appear darker than the cumulus cells, facilitating visual identification of oocytes.

In embodiments, oocytes isolated from follicular fluid may be at different stages of nuclear maturation: fully mature (at metaphase II or MII of meiosis with a first polar body present), intermediately mature (at metaphase I of meiosis; no polar body) and immature (at prophase I of meiosis, containing a large nucleus called a germinal vesicle or GV). Depending on the level of nuclear maturity, the cumulus masses may appear with different morphology: expanded and translucent in MII oocytes; somewhat darker and more tightly organized in MI oocytes; and very dark, tight, and small in GV oocytes. While nuclear maturity may be reasonably estimated based on the appearance of the cumulus and corona cells, oocyte development potential cannot be assessed in this way.

In embodiments, prior to injecting oocytes with sperm, the cumulus-corona complex may be removed so the egg can be visualized and micromanipulated. Complete removal of cumulus and corona cells is called denudation. This is accomplished enzymatically and mechanically. The enzyme hyaluronidase may be used to dissociate cumulus cells. This is possible because the expanded cumulus is a hyaluronan (HA)-rich extracellular matrix. *Corona* cells, on the other hand, may be removed mechanically since they do not undergo mucification. Mechanical removal may be accomplished by repeated aspiration/expelling using small inner diameter pipettes, for example 155-200 uM capillary tube tips or hand-drawn Pasteur pipettes.

In embodiments, pipetting in the context of denudation may entail aspiration and expelling and container-to-container transfer of individual or multiple OCCCs and oocytes. Pipetting is fundamental to all IVF laboratory techniques and may be carried out in a sterile fashion, without creating air bubbles that could be disruptive, lead to loss of cells, or create potentially infectious aerosols. Different types of pipettes may be used during denudation procedures, including but not limited to: Pasteur pipettes: Made of borosilicate glass, for example in two lengths (short or 5.75 inches and long or 9 inches) and used in conjunction with rubber pipette bulbs, to transfer smaller volumes of fluids with or without cells. These pipettes can be "pulled" over a flame to create very narrow bores for handling eggs and embryos. Eppendorf pipettes: Instruments equipped with a piston and a spring-loaded tip cone, single channel and adjustable volumes (1-1000 μL units with specific ranges), used in conjunction with Eppendorf tips, to aspirate and dispense precise (usually low) volumes. Capillary Tube Tips: Pipette tips used in conjunction with "Stripper" or "EZ-grip" pipettors: Tips are made from flexible medical grade plastic to prevent scratching of plastic Petri dishes. The tips may be manufactured in different inner diameters, ranging from 75 μm to 600 μm, with the commonly used sizes being 155-200 μm for denudation of eggs and handling eggs and embryos, and 300 μm for handling blastocysts.

In embodiments, an example hardware set up for denudation related processes may include, but is not limited to, the following equipment that may be integrated within the IVF/ICSI platform, as described herein:
Inverted Microscope (Olympus IX81)
Stage movement controller (Prior H117P2IX)
Microscope Dino-Lite Edge (5mp Series)
ArduCam (IMX477 12MP)
Stage Heating & Controller (TokaiHit)
Micromanipulators (Eppendorf; TransferMan 4r)
Range of 12,500 μm for each axis
Max speed of 10,000 μm per second
Microinjector (Narishige IM-21)
10 μL per turn
400 μL total
W127-147×D56×H78 mm
Microtool Holder (HI-7)
W140×D8×H78 mm
2 Stepper motors (5PCS Nema 17)
LCPlanFI 20× Olympus
UPlanFLN 4× Olympus
Motor controller BTT SKR Mini E3 v3.0

In embodiments, the automated oocyte, AI/ML-assisted identification and isolation system of the IVF/ICSI platform may minimize and/or eliminate the need for a skilled embryologist for denudation of oocytes in preparation for ICSI or cryopreservation.

Figure 38:
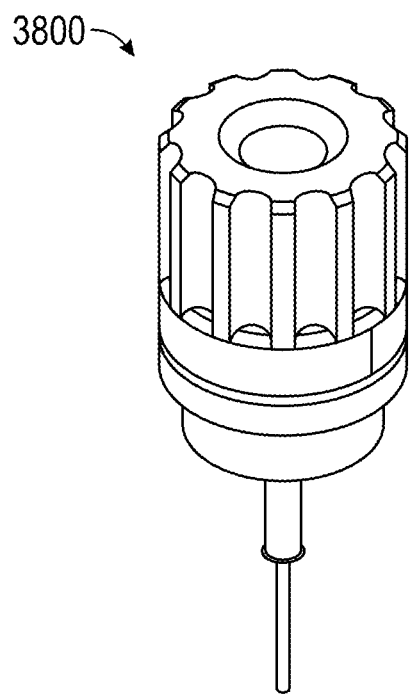
FIG. 38 illustrates an adapter to use single cell holders with standard needle holders within the egg preparation module.

In embodiments, during the denudation process, a stereomicroscope, an inverted microscope, or some other microscope type, may be used to image the specimen that is held within a dish, including a flat dish and/or a dish having a plurality of wells, for example four or more wells within the dish. A first well may contain an enzyme that allows for the removal of the cumulus cells from the oocyte. A pipette may be used to, in repetition, draw the oocyte from the well into the pipette and then expel the oocyte from the pipette allowing for removal of cumulus and corona cells via enzymatic action and also from the mechanical force of the pipette drawing and expelling the oocyte in an automated manner using robotic processing. In an example, the egg preparation module may also facilitate denudation by automatically using the pipette, or other device, to perturb the fluid in which the COCs are held. As the process of denudation progresses, the imaging and AI/ML processes, as described herein, may be used to periodically, or continuously, evaluate and analyze the extent of the corona cell removal and indicate once a targeted end point is reached or surpassed, at which time the corona cell removal process may be ended. Because prolonged exposure to enzymes has the potential to damage the oocyte, usage of the imaging and AI/ML processes may facilitate reducing the time of exposure by allowing for the rapid identification of completed preparation and reduce stress to the egg. In embodiments, the egg preparation module may use an adapter 3800 to use single cell holders with standard needle holders 3800, as shown in a sample embodiment in FIG. 38.

Figure 39:
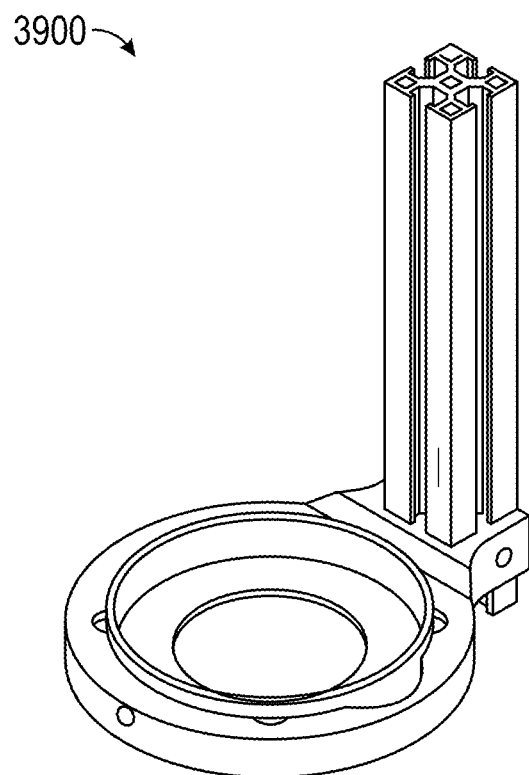
FIG. 39 depicts an ISCI dish adapter that may be coupled to an aluminum extrusion and used by the egg preparation module.

FIG. 39 depicts an ICSI dish adapter 3900 that may be coupled to and used by the egg preparation module 3900.

Figure 40:
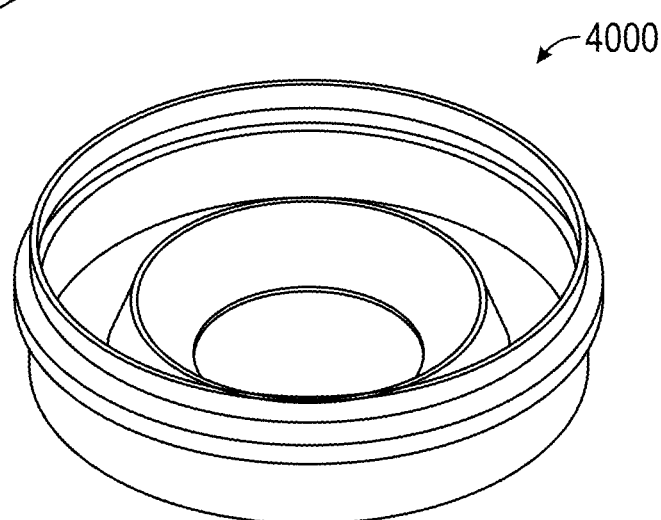
FIG. 40 depicts a mechanical barrier to interact with organic compounds.

FIG. 40 depicts a mechanical barrier 4000 to interact with organic compounds.

In embodiments, once the corona cells have been adequately removed from the COC, the egg preparation module may autonomously and robotically begin a washing process, using a number of wells within a dish, receptacle or vessel in which to perform the washing. Following washing the egg preparation module may automatically assess the maturity of an egg using imaging and AI/ML processes, as described herein. In one aspect, the imaging and AI/ML processes may evaluate the morphology of the egg to assist in determining the maturity, for example, determining if the egg has a polar body or not. If the imaging and AI/ML processes determine that there is a polar body present, the egg may be considered mature by the IVF/ICSI platform and considered as eligible to proceed to the insemination module of the IVF/ICSI platform, as described herein. If the imaging and AI/ML processes determine that there is no polar body present, the egg may be considered immature by the IVF/ICSI platform and automatically returned for further incubation, and a subsequent round of maturity assessment performed by the imaging and AI/ML processes once a further incubation cycle is completed. In embodiments, continuous monitoring using time-lapse may be used for assessment.

In embodiments, the egg preparation module and incubation module may be operatively coupled components of the intelligent, automated system of the IVF/ICSI platform. The egg preparation module may be responsible for the retrieval, identification, classification, measurement, testing, optimization, prediction, selection/ranking, and handling of eggs, employing AI/ML processes, robotic handling systems, and advanced microscopy systems to perform these tasks, as described herein. In an example, once the egg preparation module has completed the tasks of identifying and retrieving an egg, the egg may be automatically and robotically transferred to the incubation module. The incubation module may include components and systems for incubation, sensor components for monitoring the conditions within the module, and specimen management components for handling the egg during the incubation process. The incubation module may also employ AI/ML processes for automated measurement and testing, optimization, prediction, selection/ranking, and system configuration and control, and include robotic handling systems and advanced microscopy, imaging and optics systems, including computer and machine vision systems. In embodiments, the egg preparation module and the incubation module may work in tandem to ensure the eggs are properly prepared, handled, and incubated. The use of AI/ML processes in both modules automates these processes, reducing the potential for human error and increasing the efficiency and effectiveness of the IVF procedures, and the integration of these modules may allow for a streamlined and efficient process, from the initial preparation of the eggs to their incubation. This integration may be facilitated by the use of interconnected robotic IVF modules, which allow for the automated transfer of materials and data between the modules, ensuring that the eggs are handled and processed in a consistent and controlled manner necessary for the success of the IVF procedures.

In embodiments, as part of the imaging and AI/ML processes used to determine the egg's morphology and, for example the presence or absence of a polar body, a three-dimensional reconstruction model may be constructed to show the full physical entity of the oocyte, as opposed to being limited to, for example, a two-dimensional view obtained through a microscopic image. In an example, the three-dimensional view of the oocyte may be constructed through images taken from a plurality of angles of the oocyte, such as images made while physically moving the oocyte to obtain a view from multiple sides of the oocyte. Viewing multiple sides of the oocyte may be achieved by the egg preparation module by automatically manipulating the egg to view different sides of the oocyte, or it may be achieved by physically moving an imaging apparatus, such as a microscope, around a stationary oocyte. In another example, the three-dimensional view of the oocyte may be based at least in part on inferred data and predictive modeling of the oocyte. Such inference and predictive modeling may be based in part on prior data derived from egg imaging made by the IVF/ICSI platform. In an embodiment, optical coherence tomography (OCT), optical coherence microscopy (OCM), near-infrared light tomography, or some other technique may be used by the egg preparation module for oocyte imaging. OCT may be used by the IVF/ICSI platform to assess the maturity of oocytes. By providing three-dimensional images of the oocytes, OCT may identify the presence and position of the polar body, a structure that indicates the maturity of the egg. This information may be used to guide the ICSI process, as described herein, ensuring that the needle is introduced at the ideal position (as used herein, "insemination process," "insemination system," "insemination" and the like includes ICSI, IDEM on ICSI and all related ICSI systems, processes and protocols). In embodiments, the OCT system of the IVF/ICSI platform may be used in combination with the AI/ML system of the IVF/ICSI platform to take planar views of an oocyte throughout its development, allowing for more detailed tracking of its maturity, and be used to visualize multiple eggs simultaneously, providing a more efficient method of assessing egg maturity over traditional methods performed by human operators.

In embodiments, the egg preparation module may use polarized light and/or polarized sensitive OCT to automatically locate the presence or absence of a meiotic spindle and define best positioning of the oocyte during injection and to assess membrane integrity to allow identification of a successful injection. In embodiments, the maturity of the egg may be measured based at least in part by automatically identifying the meiotic spindle using imaging and AI/ML processes as described herein. In embodiments, meiotic spindle inspection may also be used to form a predictive algorithm for assisting in determining the probability of whether an egg is going to adequately mature, and when it might mature with further incubation.

In embodiments of the present disclosure, the egg preparation module may include egg retrieval components, systems, and processes. In embodiments of the present disclosure, the egg preparation module may include AI/ML for automated detection, identification, and classification. In embodiments of the present disclosure, the egg preparation module may include AI/ML for automated measurement and testing. In embodiments of the present disclosure, the egg preparation module may include AI/ML for optimization. In embodiments of the present disclosure, the egg preparation module may include AI/ML for prediction. In embodiments of the present disclosure, the egg preparation module may include AI/ML for selection/ranking. In embodiments of the present disclosure, the egg preparation module may include AI/ML for semi-autonomous, supervised, or autonomous robotics. In embodiments of the present disclosure, the egg preparation module may include AI/ML for system configuration and control. In embodiments of the present disclosure, the egg preparation module may include fully autonomous AI/ML. In embodiments of the present disclosure, the egg preparation module may include optical and machine vision components, systems, and processes. In embodiments of the present disclosure, the egg preparation module may include robotic handling systems and processes. In embodiments of the present disclosure, the egg preparation module may include sensor components, systems, and processes. In embodiments of the present disclosure, the egg preparation module may include specimen management components, systems, and processes. In embodiments of the present disclosure, the egg preparation module may include enzymatic oocyte denudation processes, systems and components. In embodiments of the present disclosure, the egg preparation module may include advanced microscopy systems and components.

The present disclosure provides an automated ICSI platform that uses robotics and AI/ML, including machine vision, to perform ICSI in an automated fashion. The system aims to enhance the consistency and success rate of ICSI procedures. The automated ICSI platform comprises both hardware and software components. The hardware includes an inverted microscope, a stage movement controller, cameras, micromanipulators, a laser objective, a motor controller, injectors, a piezoelectric actuator, microtool holders, and a 3D printed dish holder. The software components include software to operate the AI/ML, optics and the microscope and added devices. The system may operate by performing a sequence of pre-programmed processes, which may be initiated with a single command issued from a computer. The procedure may also be performed with multiple commands, each intended for a specific process in the procedure. The person operating the computer may do so remotely and the manipulators and/or the microscope used throughout the process may be handled robotically. Imaging throughout the process may be visualized on a computer screen.

The IVF/ICSI platform may automate the ICSI procedure, including sperm preparation and immobilization, egg handling, zona pellucida ablation, oolemma breaking, sperm deposition, and egg release. The system may also provide controls for microscope focusing, pressure control in the pipettes, and movement of the stage and pipettes.

After the automated ICSI procedure, a human operator may remove the ICSI dish from the microscope stage, wash the eggs using manual pipetting, and place the eggs in culture in an incubator. Alternatively, these processes of removing the ICSI dish from the microscope stage, washing the eggs using pipetting, and placing the eggs in culture in an incubator may be performed automatically and robotically by the IVF/ICSI platform.

The disclosed system may provide a more consistent and reliable approach to ICSI. By automating these processes, the system may reduce variability, improve the success rate of ICSI procedures, and potentially increase the efficiency of ART.

In the context of ICSI, automation includes the use of robotics and AI/ML-assistance, as described herein, so that certain processes in the microinjection procedure that ordinarily require a highly skilled human operator are performed by an intelligent robotic system of the IVF/ICSI platform.

In embodiments of the present invention, the IVF/ICSI platform may complete fertilization of a human egg. Human eggs may be inseminated in vitro to achieve fertilization. Fertilization may be achieved by adding several thousand sperm to one or more eggs (referred to as conventional or standard IVF), with their cumulus and corona cells intact, in a dish. Alternatively, fertilization may be achieved by microsurgical injection of a single sperm in a single egg from which all somatic cell investments-cumulus and corona cells—have been removed (referred to as intracytoplasmic sperm injection or ICSI). ICSI is a technique involving microinjection of a single (immobilized) sperm directly into the oocyte cytoplasm in order to achieve fertilization. Although this procedure was developed primarily for treatment of male factor infertility where sperm may be unable to fertilize the egg 'naturally', it is being increasingly applied for treatment of non-male factor infertility/subfertility, as well as for vitrified/warmed eggs. Thus, ICSI may be the treatment of choice for essentially all patients seeking ART. To fertilize an egg, the sperm may get through the zona pellucida surrounding the egg, attach to the oolemma and enter the cytoplasm. In ICSI, the zona pellucida and the oolemma are bypassed and the sperm is directly delivered to the cytoplasm, where it starts a cascade of fertilization and development events. Spermatozoa are motile by virtue of oscillations of their tail. This characteristic is important in achieving fertilization in vivo, as sperm may traverse the reproductive tract in the female to reach the egg. Prior to injecting a sperm cell into an egg during ICSI, the movement of the cell may be stopped. This is referred to as immobilization and it can be achieved using mechanical pressure on the tail by the ICSI needle or a laser shot. A laser, including but not limited to a 1460 nm, infrared solid-state diode, class 1 laser delivered through a 40× objective on an inverted microscope may be used by the IVF/ICSI platform as part of performing ICSI and processes related to ICSI. This laser may ablate the zona pellucida without harming the egg or embryo. Zona pellucida ablation may be used for different purposes. In the case of ICSI with Piezo, it may be used to facilitate passage of the ICSI needle through the zona (by reducing its thickness) and avoid mechanical stress on the egg. A piezoelectric actuator is a transducer that converts electrical energy into mechanical displacement. The ICSI procedure with Piezo may be modified compared to conventional ICSI. The piezo drive unit may be attached to the microtool holder and deliver pulses through the ICSI needle, traverse the zona pellucida and reach the oolemma and pressed past the mid-point in the egg. The pulse may break the membrane and allow release of sperm in the cytoplasm.

In embodiments, polyvinylpyrrolidone (PVP) is a high molecular weight molecule used in solution for slowing down the movement of sperm. This is to facilitate capture, immobilization, and pick up of sperm for injection into an egg as well as prevent 'sticking' of cells or cytoplasm to micromanipulation needles and pipettes.

In embodiments, pipetting is fundamental to IVF laboratory techniques and may be carried out in a sterile fashion, without creating air bubbles that could be disruptive, lead to loss of cells, or create potentially infectious aerosols. Pipetting in the context of ICSI entails aspiration and expelling and container-to-container transfer of individual or multiple eggs as well as fluids. The types of pipettes that may be used automatically and robotically by the IVF/ICSI platform include, but are not limited 1) plastic capillaries with narrow bores (e.g., 175 um in inner diameter) for moving eggs from dish to dish; 2) glass (Pasteur) pipettes pulled over heat to create narrow bores for moving eggs from dish to dish; and 3) microsurgical pipettes or needles to hold eggs in place and to perform sperm injection.

In embodiments, different types of pipettes may also be used automatically and robotically by the IVF/ICSI platform during ICSI including, but not limited to 1) Eppendorf pipettes (e.g., used during preparation of dishes): Instruments equipped with a piston and a spring-loaded tip cone, single channel and adjustable volumes (1-1000 μL units with specific ranges), used in conjunction with Eppendorf tips, to aspirate and dispense precise (usually low) volumes; 2) capillary tips: Tips are made from flexible medical grade plastic to prevent scratching of plastic Petri dishes. The tips are manufactured in different inner diameters, ranging from 75 μm to 600 μm, with the most commonly used sizes being 155-200 μm for denudation of eggs and handling eggs and embryos, and 300 μm for handling blastocysts; 3) microsurgical pipettes used in conjunction with micromanipulators: Microsurgical pipettes like a holding pipette or ICSI needle/pipette, and biopsy needle are ultra-fine glass instruments that are manufactured with specific outer and inner diameters in order to hold or manipulate oocytes and embryos during microsurgical procedures on a micromanipulator.

In embodiments, a holding pipette may have an outer diameter of 65-180 μm and inner diameter of 15-30 μm.

In embodiments, an ICSI needle (or pipette) may have an inner diameter of 5-6 μm, a spike at the tip, and a 30-degree bend approximately 1 mm from the tip, to accommodate use in a flat dish during micromanipulation.

In embodiments, the IVF/ICSI platform may automate ICSI processes using robotics, optics and AI/ML (including machine vision) to perform ICSI in a fully automated fashion. The entire ICSI procedure may be performed with a single command-issued from a computer locally or remotely. For example, a command may initiate a sequence of pre-programmed ICSI processes, as described herein. The procedure may also be performed with multiple commands, each intended for a specific process in the procedure.

In embodiments, the IVF/ICSI platform may use components in the performance of ICSI processes, including but not limited to:
  Inverted Microscope
  Stage movement controller
  Camera(s)
  Stage heating & controller
  Micromanipulators
  Range of 12,500 um for each axis
  Max speed of 10,000 um per second
  Laser objective
  Motor controller
  Injector (air) for holding pipette
  Eppendorf injector (oil) for injecting needle
  Piezoelectric actuator
  3D printed dish holder (with orientation marker)
  Stepper motors for microinjectors
  Microtool holders
  Condenser
  3D printed dish holder with orientation In embodiments, the IVF/ICSI platform may use software to automatically operate the AI/ML, optics, robotics and microscope and other added devices.

In embodiments, an example of actions taken by the IVF/ICSI platform when performing ICSI and related processes may include, but is not limited to:
1. Perform microtool and droplet position calibration.
2. Place one or more eggs in a prepared dish and place the dish on the heated stage of the inverted microscope, an OCT or OCM, or other forms of microscopy, including lens-less microscopy.
3. Begin the sequence of ICSI processes by issuing a single command from a computer based at least in part on AI/ML processes, outputs or results. Alternatively, individual commands may be issued manually or automatically for each process of the procedure.
4. The person operating the computer may do so remotely. The operator does not directly use the manipulators or the microscope. Images may be visualized on a computer screen, or through the incorporation of extended realities (e.g. mixed, virtual realities).
5. Commands may be presented on a user interface, such as a computer screen (IDEM), as "buttons" where, for example, one set of commands may be for directing the IVF/ICSI platform in the handling of sperm, such as:
   a. Prepare needle (the injection needle may be lowered into a PVP drop, and "primed" with a predetermined volume of PVP, meaning that PVP is aspirated into the needle in preparation for sperm pick up)
   b. Go to sperm droplet (The IVF/ICSI platform may automatically place relevant cells and instruments in position for actions such as immobilization, loading, injection, plunging, or some other action. For example, based on the initial calibration, the AI/ML/robotics may recognize the location of the sperm drop and automatically move the needle to that location, automatically select, for example, the 40× objective, and adjust the focus so that the sperm cells are brought into focus and are well distinguishable.)
   c. Immobilize sperm (AI/ML/robotics may evaluate and score the motility pattern of sperm cells in the field of vision, selecting the "best" sperm according to an algorithm, and move the stage so that the selected sperm may be targeted by a laser for immobilization; a laser shot may be released toward the tail to stop or slow the sperm movement, i.e., the sperm is immobilized. AI/ML-guided sperm immobilization may be based on real-time segmentation purposefully incorporated to assess morphology and select best position for tapping or laser shot for immobilization.)
   d. Needle in pick up position (AI/ML/robotics may determine the best position to pick up the sperm by the tail-end)
   e. Load sperm (AI/ML/robotics may perform controlled aspiration of the sperm while evaluating the position of the sperm being aspirated in the needle leaving the sperm in a predetermined position in the needle based at least in part on computer-vision guided by AI/ML, for example, algorithms based on controls (e.g., pressure, fluid dynamics, or other calculations.)
   f. Needle out of droplet (The needle may be lifted out of the sperm/PVP droplet (e.g., on the Z plane and may remain stationary in a pre-determined position, such as positioning for a next step (e.g. needle/instrument alignment and ICSI))
6. Another set of commands may be for directing the IVF/ICSI platform, for example the optics, relevant instruments, and stage, alone or combined with the goal to position cells and appropriate instruments in the handling of eggs, such as:
   a. Go to egg (The stage may move so that the egg is brought to the field of vision at, for example 4×; AI/ML/robotics may identify and locate the egg, change magnification, for example to 40×, and adjust the focus so that the zona pellucida is brought into sharp focus.)
   b. Hold the egg (The egg may be held in place either through a physical barrier (e.g. the bottom of a dish, a designed wall, or a blunt concave pipette), or by means of a holding pipette. In an example, the holding pipette may be lowered into the droplet, the AI/ML/robotics may determine the best area to hold the egg and bring the holding pipette to that position; AI/ML/robotics may apply negative pressure in the pipette to pick up and hold the egg on the holding pipette.)
   c. Open Zona Pellucida (AI/ML/robotics and optics, as described herein, may determine the location and the amount of zona in need for ablation and where zona ablation should be performed and move the egg to the target location and generate a laser shot to ablate a pre-designated section and depth of the zona pellucida. The AI/ML/robotics may be able to assess the thickness of the zona and determine the intensity and radius needed for a single or multiple shots to effectively ablate and/or how many laser shots are necessary to ablate an adequate portion of the zona to facilitate the entry of the ICSI needle through the zona without distorting the egg.)

d. Define injection path (AI/ML/robotics may determine the best path for the injection, including the initial (outside the zona) and final (intracytoplasmic) position of the needle, for example, based on a plane image (real-time) and/or through previously loaded information based on 3-D modelling and/or imaging of the egg. OCT may identify the equatorial plane of an egg and assist in programming a path of the needle from the site of entrance to where the tip of the needle should stop once the membrane has been pierced.)

e. Sperm at tip (AI/ML/robotics may apply a combination of injection/suction (or positive and negative pressures) to position the sperm at a desired position. For example, positive pressure in the ICSI needle may push the sperm to the tip of the needle in preparation for injection into the cytoplasm, aiming to reduce, if desired, the PVP volume (or other foreign media) that is injected into the egg cytoplasm.)

f. Penetrate egg (AI/ML/robotics may move the needle forward and into the egg at a pre-determined and controlled speed, stopping once it reaches the end point of the path. This may be predetermined by conventional microscopy, OCT, OCM, or other means, including using a 3D reconstruction of the egg), and may or may not be adjusted in real-time based on AI/ML-modeled characteristics.)

g. Break oolemma (The egg membrane (oolemma) may be broken using a piezoelectric pulse. AI/ML/robotics may be used to determine if a piezo pulse is needed to break the membrane and how many pulses are required.)

h. Deposit sperm (AI/ML/robotics may control and apply positive pressure in the ICSI needle to deposit the sperm in the egg.)

i. Exit egg (AI/ML/robotics may determine that the sperm is out of the needle and move the needle out of the egg.)

j. Release egg (AI/ML/robotics may control and apply positive pressure in the holding pipette until the egg is released into the droplet.)

In embodiments, other commands, including, for example, "piezo pulse" and "shoot laser" may be available and intended for human interaction/intervention with the IVF/ICSI platform if necessary.

In an example, user interface of the IVF/ICSI platform, controls may be available for magnification level; microscope focusing; incremental negative and positive pressure control in the holding pipette; and positioning of the holding pipette. Controls may also be available for movement of the stage; incremental negative and positive pressure control in the ICSI needle; and positioning of the ICSI needle.

The IVF/ICSI platform may automatically remove the ICSI dish from the microscope stage, wash the eggs using automated pipetting and place the eggs in a culture dish in an incubator. Alternatively, the removal of the ICSI dish may be performed by a human operator.

Table 4 presents a comparison of Conventional ICSI and Piezo ICSI. (P) designates processes that are exclusive to Piezo-assisted ICSI (including ICSIA).

TABLE 4

| Action | Conventional ICSI | Piezo-assisted ICSI | Remains human operator dependent with ICSIA | Micromanipulation skill required? |
|---|---|---|---|---|
| Oocyte denudation and preparation for injection | + | + | Yes | No |
| Semen preparation with isolation of motile spermatozoa from seminal fluid | + | + | Yes | No |
| ICSI dish preparation | + | + | Yes | No |
| Placement and alignment of microtools on microtool holders | + | + | Yes | Yes |
| Placement of prepared sperm in PVP in the ICSI dish | + | + | Yes | No |
| Lowering of the ICSI needle | + | + | No | Yes, but obviated with ICSIA |
| Bring Microtools and cells into focus throughout the procedure | + | + | No | Yes |
| Selection and immobilization of a single spermatozoon | + | + | Yes | Yes |
| Aspiration of the sperm in the injection needle while controlling its position in the needle until injection | + | + | Yes | Yes |
| Centering the egg in the visual field | + | + | Yes | Yes |
| Lowering the holding pipette in the vicinity of the egg | + | + | No | Yes, but obviated with ICSIA |
| Increasing suction on the holding pipette to hold and position the egg | + | + | Yes | Yes |

TABLE 4-continued

| Action | Conventional ICSI | Piezo-assisted ICSI | Remains human operator dependent with ICSIA | Micromanipulation skill required? |
|---|---|---|---|---|
| Bringing the sperm to the tip of the needle | + | + | Yes | Yes |
| (P) Holding the sperm a safe distance from the tip of the needle | N/A | + | Yes | Yes |
| Advancing the needle toward the zona pellucida of the egg | + | + | No | Yes, but obviated with ICSIA |
| (P) Once at the zona pellucida, releasing a pulse to "drill" the zona | N/A | + | No | Yes, but obviated with ICSIA |
| Pressing against and penetrating the zona pellucida | + | N/A | N/A | Yes, but obviated with ICSIA |
| (P) Withdrawing the needle to release residual zona material & bring the sperm to the tip | N/A | + | No | Yes, but obviated with ICSIA |
| Breaking the oolemma either with aspiration or by pressure or "stirring" | + | N/A | N/A | Yes |
| (P) Reinserting the needle through the drilled zona, advancing to the oolemma and pressing until halfway in the oocyte | N/A | + | No | Yes, but obviated with ICSIA |
| (P) Delivering a pulse to break the oolemma | N/A | + | No | Yes, but obviated with ICSIA |
| Ejecting the sperm into the egg, while controlling the amount of PVP/buffer being injected | + | + | Yes | Yes |
| Withdrawing the needle from the cytoplasm | + | + | No (but intervention would be needed if sperm moves back with the needle) | Yes |
| Releasing the egg and lifting the microtools to remove the ICSI dish | + | + | Yes | Yes |
| Removing the dish from the platform & moving the injected egg/s out of the ICSI dish into a culture dish and into the incubator | + | + | Yes | No |

In embodiments of the present invention, the IVF/ICSI platform, as described herein, may include an insemination module. The insemination module may include an inverted microscope with a motorized stage on which a specimen is placed and in which the light is projected from above the specimen and the microscope lenses are below the specimen. In embodiments, the motorized stage may operate independently or in conjunction with the motorized lenses. Micromanipulators may be used by the insemination module, where the micromanipulators have motors allowing movement in three axes: X, Y, and Z.

Figure 41:
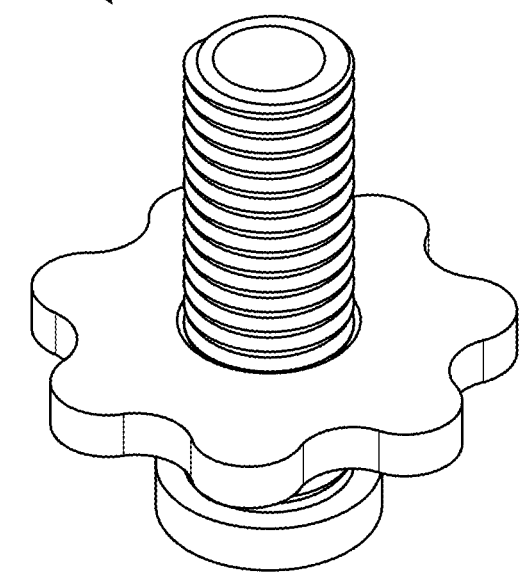
FIG. 41 depicts an example embodiment of an adapter to use ring lights with standard needle holders that may be used within the insemination module.
Figure 42:
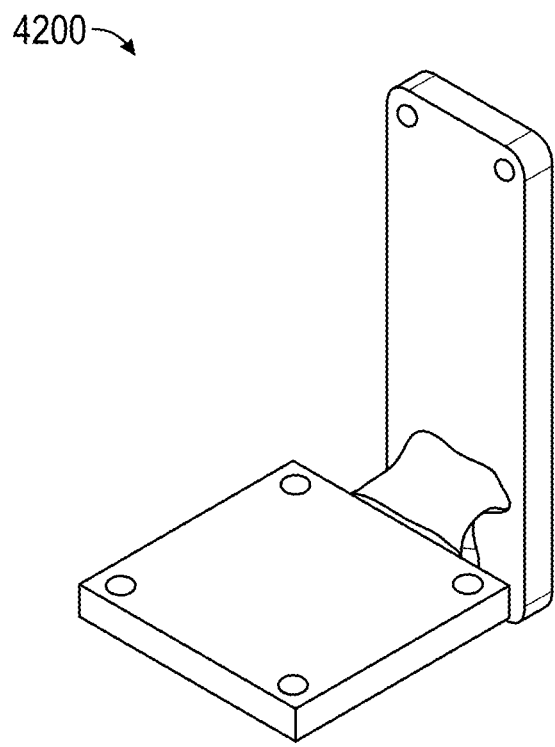
FIG. 42 depicts an adapter to use X-Y positioning systems with the neck of a microscope that may be used within the insemination module.
Figure 43:
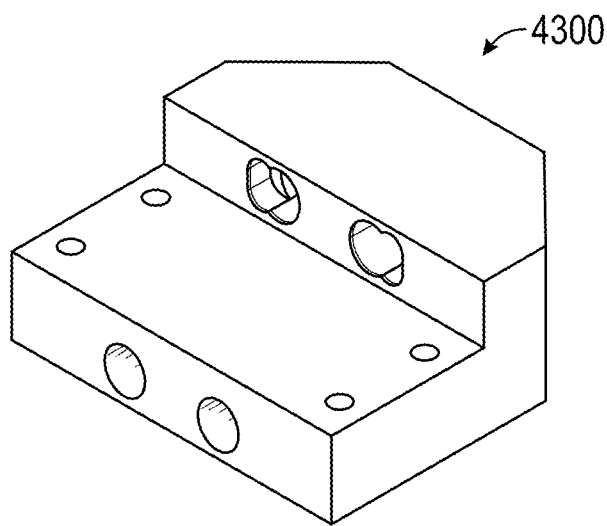
FIG. 43 depicts a mount for a cell sorter and/or cell picker for a microscope that may be used within the insemination module.
Figure 44:
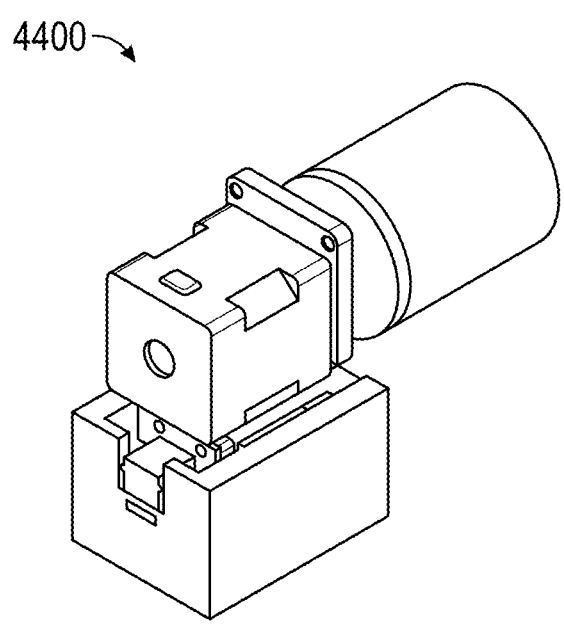
FIGS. 44 through 48 depict devices that may be used to rotate a knob or plurality of knobs of a fluid aspirator that may be used within the insemination module.
Figure 45:
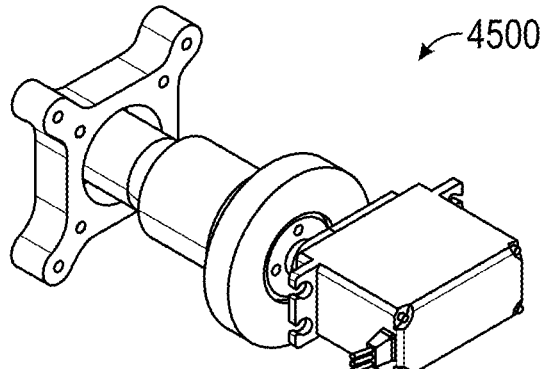
Figure 46:
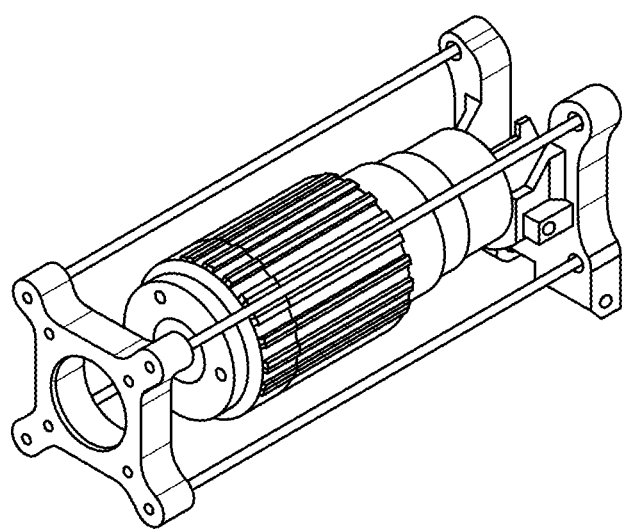
Figure 47:
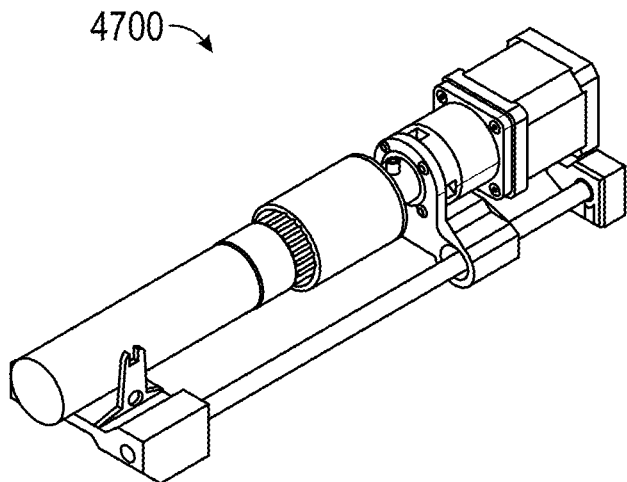
Figure 48:
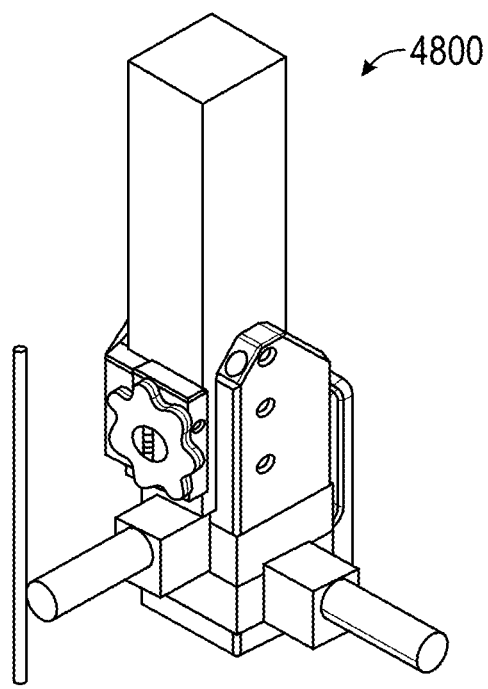

In embodiments, the insemination module may receive an ICSI dish containing a specimen and use imaging and AI/ML processes, as described herein, in association with the inverted microscope and micromanipulators. In embodiments the specimen may include a plurality of droplets, each containing at least one egg or sperm, for example, from the specimens prepared by the egg and semen preparation modules, respectively, as described herein. Sperm may be treated with PVP to slow the sperm movement. In embodiments, the ICSI dish may be overlaid with oil to minimize evaporation. Imaging may facilitate the positioning of a specimen in relation to the apparatuses of the insemination module, such as robotic devices, lighting, microscopy and other devices, permitting fully automated control of the specimen, and standardization of robotic processes. FIG. 41 depicts an example embodiment of an adapter 4100 to use ring lights with standard needle holders that may be used within the insemination module. FIG. 42 depicts an adapter to use X-Y positioning systems with the neck of a microscope that may be used within the insemination module 4200. FIG. 43 depicts a mount for a cell sorter and/or cell picker for a microscope that may be used within the insemination module 4300. In embodiments, the imaging and AI/ML processes of the insemination module may command the robotics of the insemination module to place droplets in the same locations, or near the same locations, during each insemination procedure. This may reduce the time required to locate and utilize egg and sperm located within the droplets.

In embodiments, the insemination/injection module may use a pneumatic injector that includes at least one motor for controlling aspiration and may be remotely controlled as part of the robotics of the insemination module. FIGS. 44 through 48 depict devices that may be used to rotate a knob or plurality of knobs of a fluid aspirator that may be used within the insemination module (4400-4800).

In embodiments, the insemination module may use a gaming engine or plurality of gaming engines to, for example, build computer vision algorithms to assist identification within microscope imaging, to detect an oocyte, detect the tip of a needle, detect the tip of the holding pipette, detect a sperm inside the needle, detect the oocytes at different magnifications, or detect some other objective or criterion state. In embodiments, the insemination module may use a user interface to robotically control a microscope, or plurality of microscopes, micromanipulators or the like. In an example, the insemination module may evaluate a specimen droplet in which it is known an oocyte is contained, but the exact location of the oocyte is unknown. In embodiments, the robotics of the insemination module may then use a needle to extract an oocyte from a droplet held in the ICSI dish. The insemination module may automatically adjust the magnification used by the microscope for the purpose of imaging the droplet in which the oocyte is located. Using the user interface of the insemination module, a user may initiate a command, such as by selecting to press a button in the user interface, the stage on which the specimen resides may move to a given position and then imaging and AI/ML processes, as described herein, may activate and begin searching images for an egg. If an egg is detected, the insemination module may initiate a routine that will move the stage, so the egg moves to the center. Using the imaging and AI/ML of the insemination module, the center of the oocyte may be located, and the stage may be robotically maneuvered to place the oocyte in the center. Once the oocyte is centered, the magnification of the microscope may again be automatically changed (e.g., to a 40× magnification), and the center of the egg may be used as a focusing target for the imaging and AI/ML processes. An algorithm may detect the equator of the egg which then may be used to compute positions from which the needle may enter the specimen and/or where the pipette should engage and hold the egg.

In embodiments, the machine/computer vision system on the insemination module may detect sperm, evaluate individual sperm possibly using multiple cameras placed at different angles and determine which sperm is the best candidate to use for injection into the egg. Following this identification, the selected sperm may be immobilized, for example, by automatically using a laser for interrupting the tail function or for exerting one or a few short piezo-actuator pulses. In embodiments, the imaging and AI/ML processes of the insemination module may assist in determining the best location along the sperm tail using for instance segmentation and marking specific sections of the sperm such as the midpiece and middle of the tail or the tip of the tail to direct the laser or piezo cutting or interruption and minimizing the potential of DNA damage. Following the immobilization of the sperm tail, the imaging and AI/ML processes of the insemination module may be used to detect the wanted lack of movement in the sperm. If the sperm is not sufficiently immobile, the sperm location and laser targeting of the tail procedure may be repeated on another candidate sperm and the processes repeated on a plurality of sperm candidates until the imaging and AI/ML processes of the insemination module confirm that a candidate sperm is sufficiently immobile. In embodiments, the imaging and AI/ML processes of the insemination module may also detect the positioning of the sperm, so that the robotics of the insemination module may be commanded to orient the robotic apparatuses in optimal positions for obtaining the sperm, such as robotically using a needle to capture the candidate sperm.

In embodiments, once the sperm is obtained the insemination module may activate aspiration. A control system of the insemination module may be used to aspirate and track the sperm and determine how it performs by using the imaging and AI/ML processes, as described herein.

Figure 49:
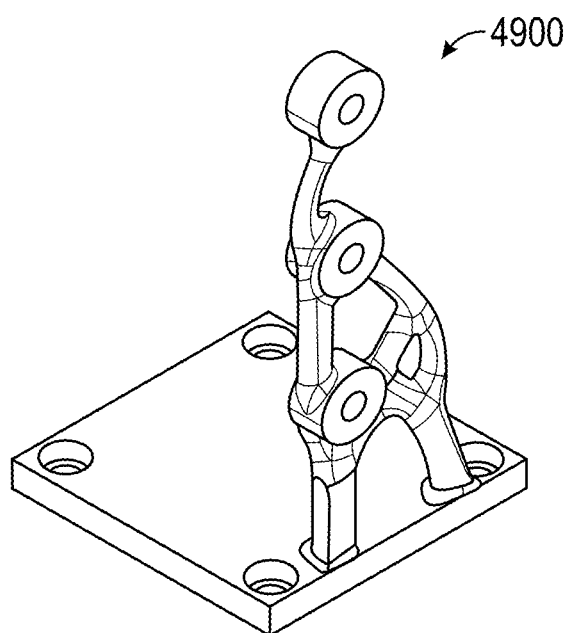
FIG. 49 depicts an adapter that may be used to couple a linear axis to an X-Y micro positioning device that may be used within the insemination module.

In embodiments, micromanipulators may hold the egg and inject the sperm. FIG. 49 depicts an adapter that may be used to couple a linear axis to an X-Y micro positioning device that may be used within the insemination module 4900. The egg may be held within the insemination module using motor-driven suction with the aspirators, and the needle may be placed at an entry point. The sperm may be placed within the tip of the needle, the needle inserted into the egg, the membrane broken, and the needle removed once the sperm is ejected from the needle. In an example embodiment, the insemination module may use laser or piezo-assisted ICSI to open a channel within the zona pellucida, through which to penetrate the egg and deposit the sperm in the egg and thereby minimize risk of deformation to the egg. The imaging and AI/ML processes of the insemination module may confirm that, following injection, the oocyte was not damaged or killed during the insemination process.

In embodiments, once the egg has been inseminated, the insemination module may prepare the fertilized egg for incubation. Once the fertilized egg is in incubation, the IVF platform may continue to incubate the embryo for a specified period of time (e.g., 5-7 days). In embodiments, the imaging and AI/ML processes of the IVF platform may be used to periodically, or continuously, monitor cell divisions occurring in the fertilized egg and algorithmically determine the health, developmental stage, viability (or other predictive factors) of the embryo. In embodiments of the present invention, the IVF/ICSI platform, as described herein, may autonomously select, immobilize and handle a single sperm cell, or multiple sperm cells, and automatically prepare such cell/cells for injection into an oocyte. In an embodiment, the IVF/ICSI platform may simultaneously, or near simultaneously, identify and select a motile sperm, immobilize the selected sperm, and aspirate the immobilized sperm into a microneedle. In an example, the IVF/ICSI platform may conduct the following processes, which may be commenced, including digitally commenced, as separate functions or commenced, including digitally commenced, as a sequence of functions using a single command, including but limited to:

(1) sperm identification (SID)
(2) motorized staging and processing
(3) autofocusing
(4) sperm tracking during handling
(5) identification and tracking of the sperm tail (segmentation)
(6) immobilization of the sperm tail by (a) laser, (b) mechanical or (c) Piezo
(7) lowering and auto-positioning of sperm injection microneedle
(8) loading and positioning of sperm in needle In embodiments of the present disclosure, the insemination module may include insemination components, systems, and processes. In embodiments of the present disclosure, the insemination module may include AI/ML for automated detection, identification, and classification. In embodiments of the present disclosure, the insemination module may include AI/ML for automated measurement and testing. In embodiments of the present disclosure, the insemination module may include AI/ML for optimization. In embodiments of the present disclosure, the insemination module may include AI/ML for prediction. In embodiments of the present disclosure, the insemination module may include AI/ML for selection/ranking. In embodiments of the present disclosure, the insemination module may include AI/ML for semi-autonomous, supervised, or autonomous robotics. In embodiments of the present disclosure, the insemination module may include AI/ML for system configuration and control. In embodiments of the present disclosure, the insemination module may include fully autonomous AI/ML. In embodiments of the present disclosure, the insemination module may include optical and machine vision components, systems, and processes. In embodiments of the present disclosure, the insemination module may include robotic handling systems and processes. In embodiments of the present disclosure, the insemination module may include sensor components, systems, and processes. In embodiments of the present disclosure, the insemination module may include specimen management components, systems, and processes.

In embodiments of the present invention, the IVF/ICSI platform, as described herein, may use robotic control to imitate human pipette handling for oocyte, sperm and embryo movement without micro-fluidics. In an example, the IVF/ICSI platform may conduct the following processes, including but limited to:

(1) Autonomous semen pipetting
(2) Viscosity testing
(3) Sperm/medium layering, for example, using a bi- or tri-layered (multi-layered) system
(4) Reduction of viscosity by pipetting and/or ultrasound
(5) Optical detection of "swim-up" efficiency by comparing clarity of upper layer before and after a period of time has transpired
(6) Automatic positioning of capillary tube-like pipette tools for egg pipetting vertically, horizontally or using an angled view. Using automation of wide-bored capillary tube pipettes while the eggs are in hyaluronidase to remove cumulus and corona cells.
(7) Visualization of tip of pipette and egg position in the pipette is not necessary to complete movement of the egg
(8) Same for embryo at any stage of development applying processes (e.g., processes 6 and 7, above)

In embodiments, the IVF/ICSI platform may use control systems, for example vision-based robotic control (visual servoing), for the control of robotic device movements, including but not limited to:

Moving a stage to specified X, Y Cartesian positions
Start/stop/reverse aspiration to specified increments
Laser sperm immobilization
Fine positioning of needle
fine positioning of holder
Sperm-in-needle positioning In an example, a control system of the IVF/ICSI platform may be used for visual servoing to position a sperm tail in a specified spot precisely in the path of a laser.

Figure 50:
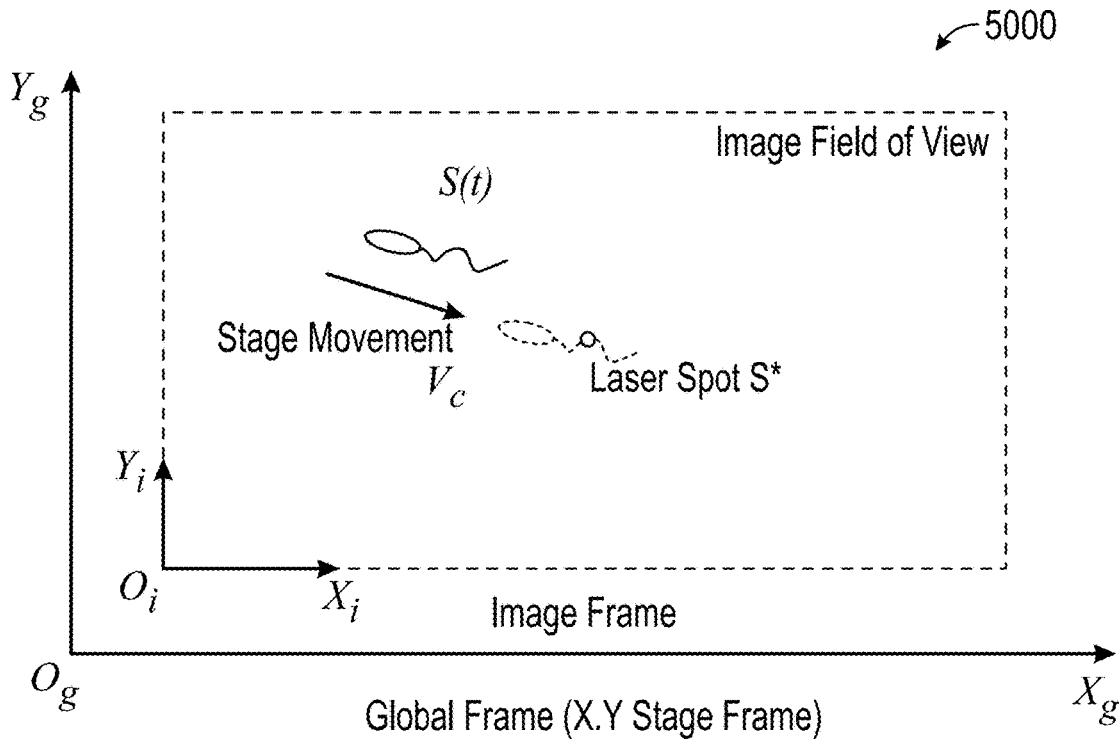
FIG. 50 illustrates an example image frame from visual servoing is to position a sperm tail in the path of a laser.
Figure 51:
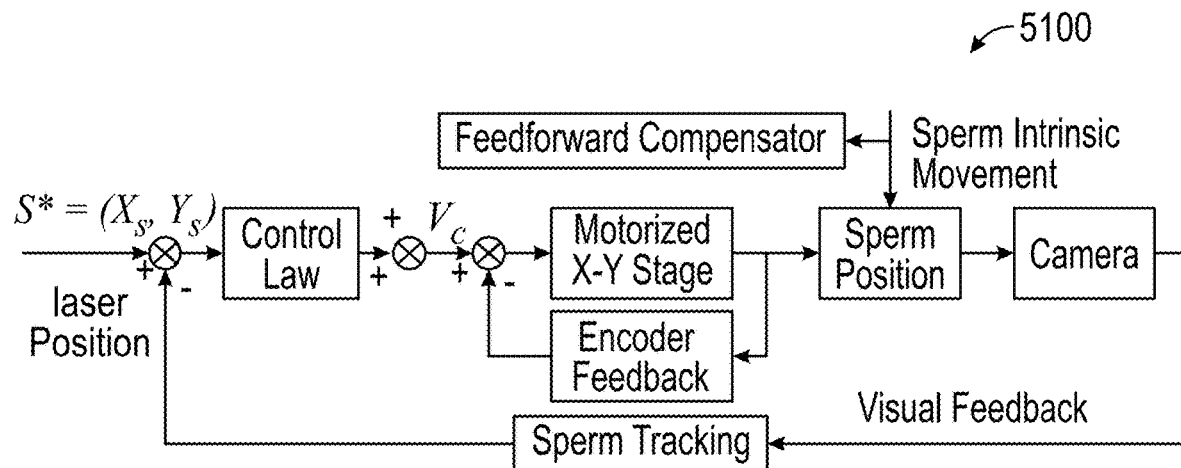
FIG. 51 illustrates an example system control diagram.

The purpose of visual servoing is to position the sperm tail in the path of a laser, as indicated by a laser spot 5000, i.e., to minimize the error e(t)

$$e(t) = s(t) - s*$$

where $s(t)=[x_{tail}, y_{tail}]^T$ is the obtained sperm tail position in the image frame $X_iO_iY_i$
(FIG. 50), and s* is the position of the laser spot in the image frame, which is a constant. FIG. 51 illustrates an example system control diagram 5100. FIG. 52 illustrates a simplified system control diagram for laser sperm ablation 5200.

In an example, a control system of the IVF/ICSI platform may be used for visual servoing to position needle, pipette, or another device. FIG. 53 illustrates a simplified system control diagram for fine positioning of a needle 5300. For example, visual servoing may be used to position a needle tip inside a designated location, i.e., to minimize the error e(t):

$$e(t) = n(t) - D^*$$

where n(t)=[xneedle,yneedle]T is the obtained needle tip position in the image frame $X_iO_iY_i$ and D* is the designated spot in the image frame, which is a constant.

Figure 54:
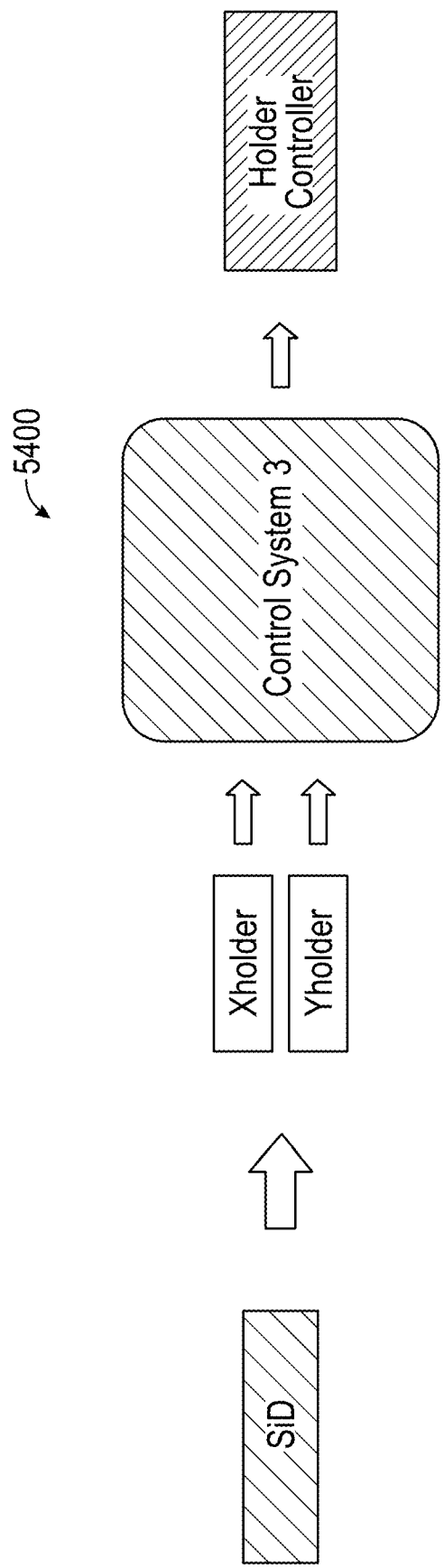
FIG. 54 illustrates a simplified system control diagram for fine positioning of a holder.

In an example, a control system of the IVF/ICSI platform may be used for visual servoing to position a holder, microtool holder, or another device. FIG. 54 illustrates a simplified system control diagram for fine positioning of a holder 5400. For example, visual servoing may be used to position a holder tip in a designated location, i.e., to minimize the error e(t):

$$e(t) = n(t) - D^*$$

where n(t)=[xholder,yholder]T is the obtained needle tip position in the image frame $X_iO_iY_i$ and D* is the designated spot in the image frame, which is a constant.

Figure 55:
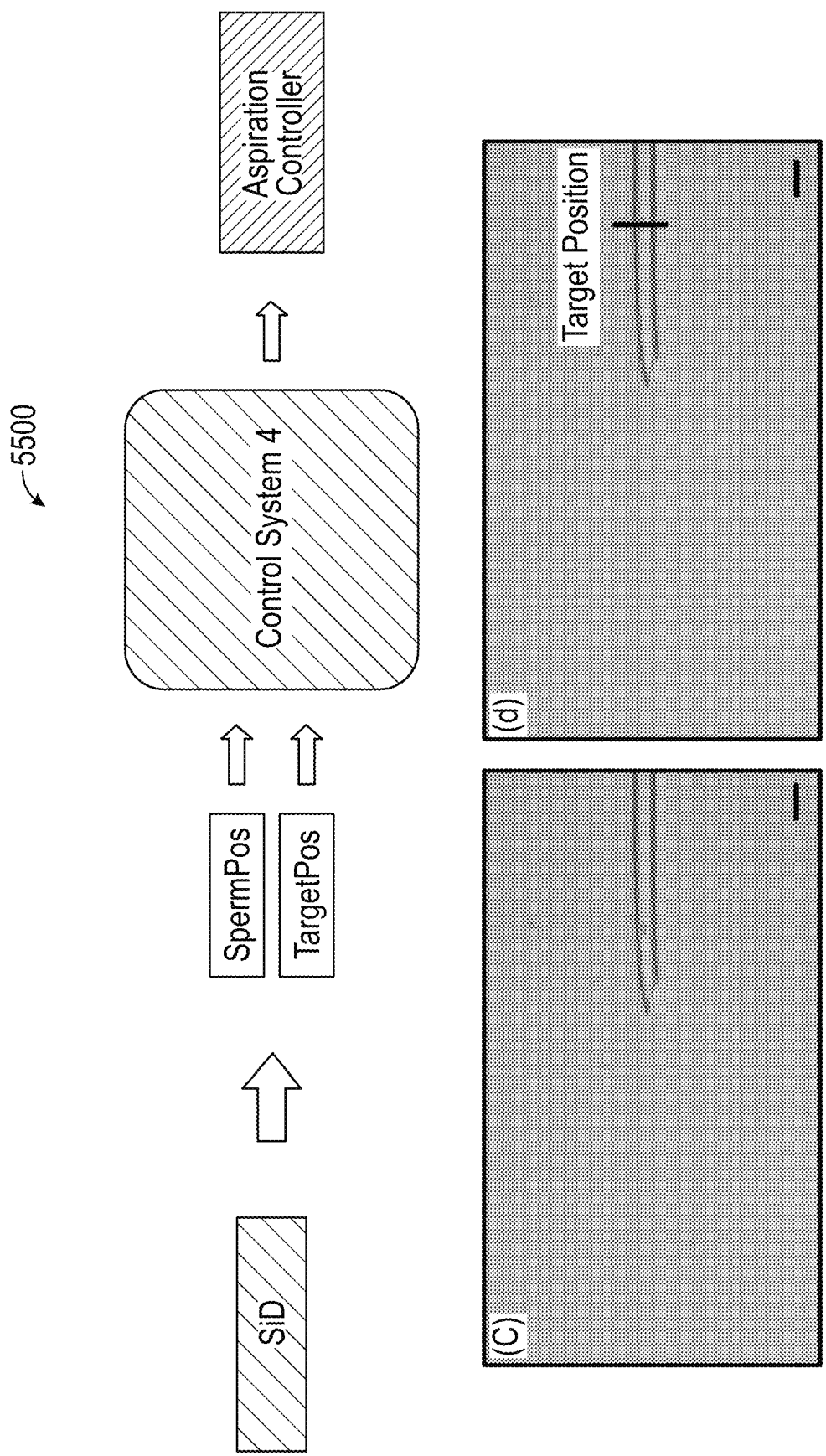
FIG. 55 illustrates a simplified system control diagram for fine positioning of a sperm within a needle.

FIG. 55 illustrates a simplified system control diagram for fine positioning of a sperm within a needle 5500.

Figure 56:
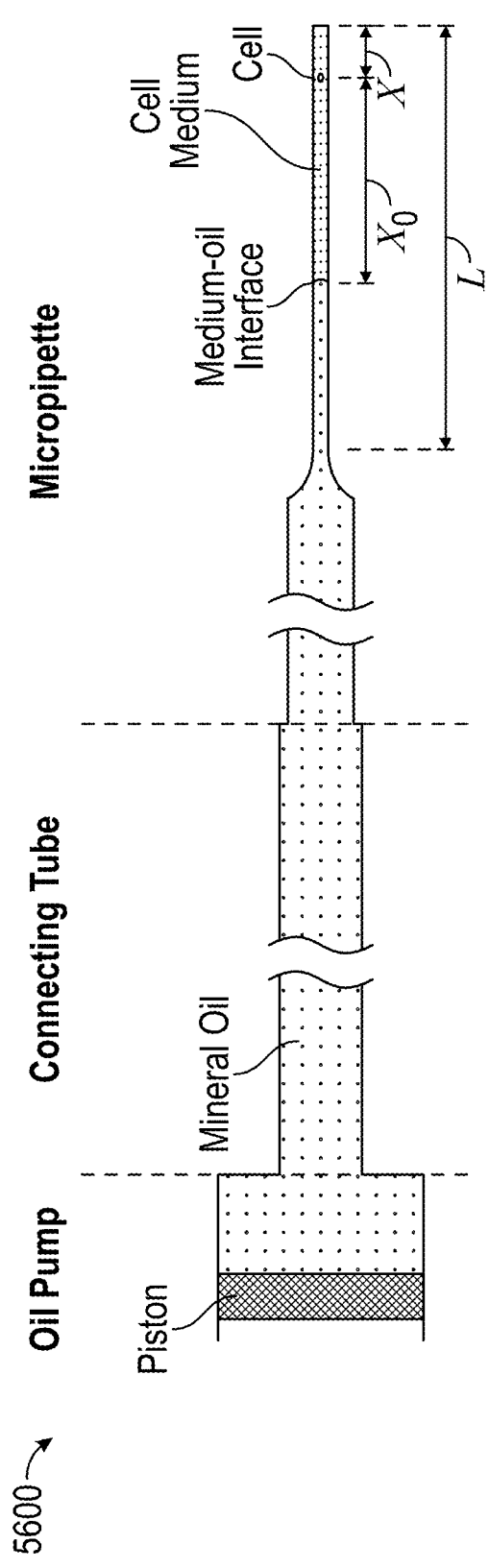
FIG. 56 illustrates a simplified system control diagram for a general cell aspiration setup.

FIG. 56 illustrates a simplified system control diagram for a general cell aspiration setup 5600 that may be used by the IVF/ICSI platform.

Figure 57:
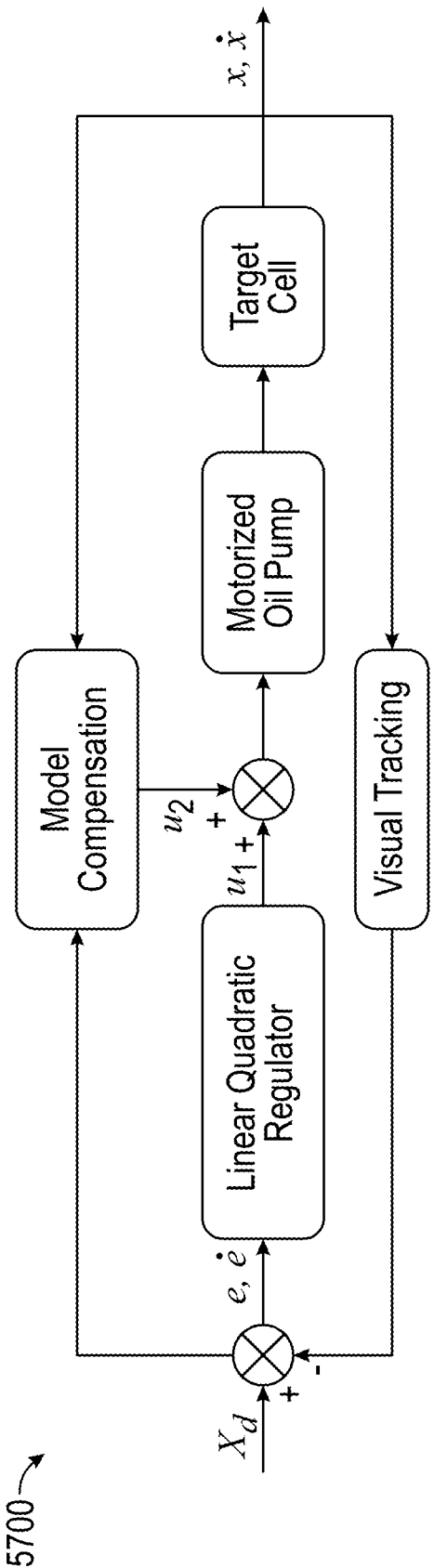
FIG. 57 illustrates a simplified diagram for a model-based adaptive control system.

FIG. 57 illustrates a simplified diagram for a model-based adaptive control system 5700 that may be used by the IVF/ICSI platform.

In an example, a control system of the IVF/ICSI platform may be used to control stage movement, for example, setting a stage position at given X, Y coordinates in pixels.

Figure 58:
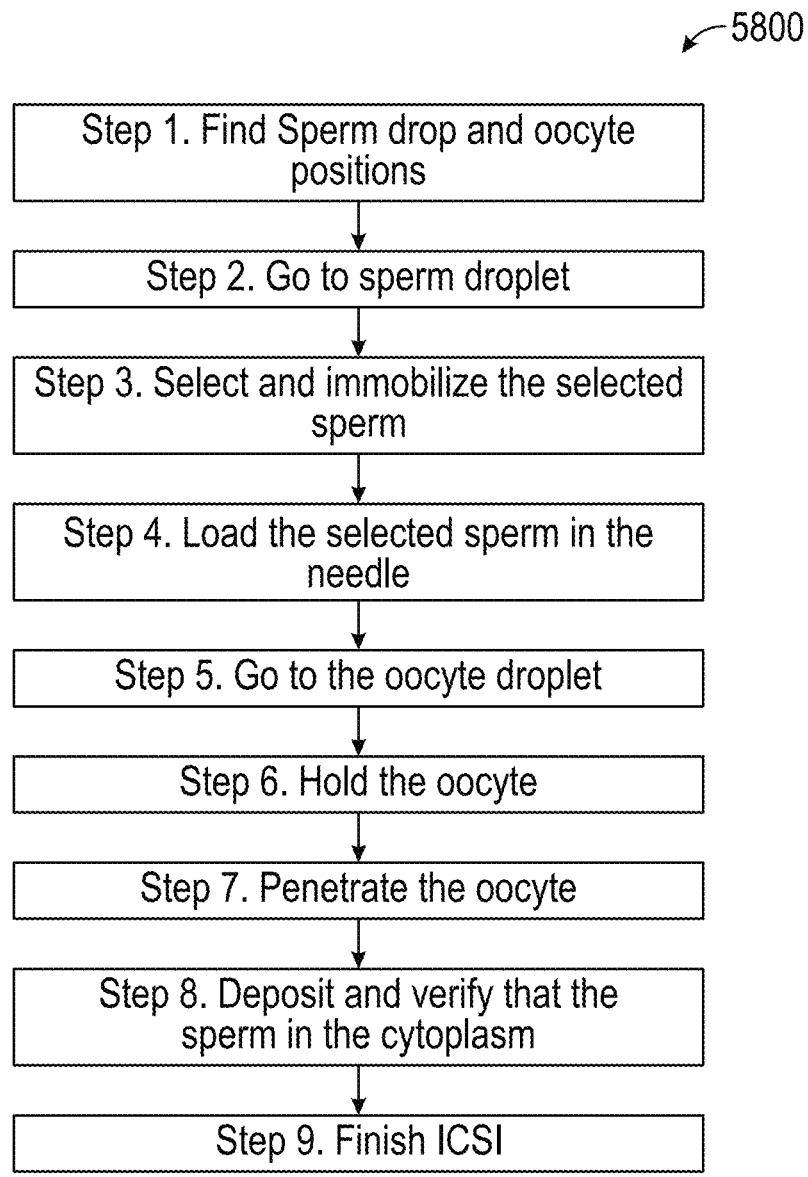
FIG. 58 illustrates a simplified workflow for finding a sperm drop and oocyte position(s) that may be used by the IVF/ICSI platform.

In an example, a control system of the IVF/ICSI platform may be used to perform a sequence of operations, including but not limited to the processes in the ICSI-related sequence below:

Find sperm drop and oocyte positions
Go to sperm droplet
Select and immobilize a selected sperm
Load the selected sperm in a needle
Go to the oocyte droplet
Hold the oocyte
Penetrate the oocyte Deposit and verify that the sperm entered the cytoplasm Finish ICSI FIG. 58 illustrates a simplified workflow for finding a sperm drop and oocyte position(s) 5800 that may be used by the IVF/ICSI platform.

In an example, the process of "Find sperm drop and oocyte positions," may involve the control system directing the automated, robotic system to initiate actions, including but not limited to:
1. Set "infocusdrop" flag to false
2. Set "Finish sweep" flat to false
3. Move stage to the initial location position using simple stage controller
4. While "Finish sweep" is false
   1. if "infocusdrop" is false
      1. Use Detect drop edge to determine if the current location is a drop edge
         1. If it is potential drop edge, then adjust the focus to achieve a clear drop edge view using focus simple controller and determine if edge drop is in focus
         2. If drop edge is confirmed, register the focus motor position for sperm (FS)
         3. Set "infocusdrop" to true
   2. If "infocusdrop" is true
      1. Determine if the current location is a sperm drop using Determine if sperm drop
   3. Determine if potential oocyte in screen using Detect Oocyte in screen
      1. If potential oocyte in screen, then adjust focus to achieve a clear view of the ZP using Determine if ZP in focus
      2. Register the focus motor position for ZP (FZ)
   4. Register on the map the type of location (none, sperm drop, oocyte in screen)
   5. Move to the next location position
   6. If reach the final location position set "Finish sweep" to true
   7. Compute outputs from the Map using connected components.
      Position of the center of the sperm drop (SDP)
      Position of the center of the oocyte (OCP)

In an example, the process of "Go to sperm droplet," may involve the control system directing the automated, robotic system to initiate actions, including but not limited to:
1. Set focus to FS using Simple Focus controller
2. Move the center of the stage to the "SDC" coordinates using simple stage controller In an example, the process of "Select and immobilize a selected sperm," may involve the control system directing the automated, robotic system to initiate actions, including but not limited to:
1. Set focus to position FS using Focus simple controller
2. Start motile sperm tracking
3. After 10 seconds,
4. Rank sperms in screen by motility and identify sperm A using sperm ranking
5. Determine the position of the tail of sperm A (STP) in this instant
6. Determine the distance DLS between STP and the laser target (LT)
7. While DLS>TOL_LS
   1. Run an iteration of the advanced stage controller that reduces the difference between DLS and the laser target LT
   2. Determine the position of the tail of sperm A STP in this instant
   3. Determine the distance DLS between STP and the laser target LT
8. Shoot laser using Trigger Laser
9. Verify that the selected sperm has been immobilized using Detect nonmotile selected sperm
10. Register the center of the sperm head position SHP In an example, the process of "Load the selected sperm in a needle," may involve the control system directing the automated, robotic system to initiate actions, including but not limited to:
1. Determine sperm pickup position SPP from the sperm head position SHP using the Detect non motile selected sperm
2. Move needle to the SPP using the simple needle controller
3. Move down the needle until it is in focus using the simple needle and Detect if needle is in focus
4. Detect needle tip NT
5. Determine the distance DNT_SPP between the needle tip NT and sperm pickup position SPP
6. While DNT_SPP>TOL_PS
   1. Run an iteration of the advanced needle controller to reduce DNT_SPP
   2. Determine DNT_SPP
7. Determine the target in-needle sperm position TNSP
8. Determine the distance D_STN between the sperm head position SHP and TNSP
9. While D_STN>TOL_SIN
   1. Run an iteration of the advanced aspiration to reduce D_STN
   2. Determine the selected sperm head position SHP in this instant using Detect non motile selected sperm and Detect sperm position inside needle
      1. Outside the needle
      2. Inside the needle
      3. Determine D_STN
10. Move the needle up until it is out of focus using simple needle and Detect in needle is in focus In an example, the process of "Go to the oocyte droplet," may involve the control system directing the automated, robotic system to initiate actions, including but not limited to:
1. Move the center of the stage to the "OCP" coordinates using simple stage controller
2. Set focus to FZ using Simple Focus controller In an example, the process of "Hold the oocyte," may involve the control system directing the automated, robotic system to initiate actions, including but not limited to:
1. Determine the oocyte holding pose using Detect the center of oocyte
2. Move stage using the simple stage controller to the oocyte holding pose
3. Determine the initial and final holding pipette holding position HPI and HPF
4. Move the holding pipette to the HPI using the simple holding pipette controller
5. Move down the holding pipette until is in in focus using the simple holding pipette controller and the Detect if holding pipette is in focus
6. Detect holding pipette tip HPT
7. Determine the distance DHPT_HP between the holding pipette tip HPT and holding position HP1
8. While DHPT_HP>TOL_HPP
   1. Run an iteration of the advanced holding pipette controller to reduce DHPT_HP
   2. Determine DHPT_HP 9. Repeat from 6 for HPF
10. Activate suction using simple holding pipette aspiration controller
11. Move the holding pipette up and down with the simple holding pipette controller while tracking the position of the tip of the holding pipette tip HPT and the center of the oocyte COO using Detect center of Oocyte and Detect holding pipette tip
12. If the coordinates of the tip of holding pipette HPT and center of the oocyte COO in the vertical direction moves similar, then stop at the original vertical coordinate In an example, the process of "Penetrate the oocyte," may involve the control system directing the automated, robotic system to initiate actions, including but not limited to:
1. Move needle to the IPP using the simple needle controller
2. Move down the needle until is in in focus using the simple needle controller and Detect if needle is in focus
3. Detect needle tip NT using Detect needle tip
4. Put the sperm to be injected in the tip of the needle using the advanced sperm aspiration controller
5. Determine the distance DNT_IPP between the needle tip NT and initial penetration position IPP
6. While DNT_IPP>TOL_IPP
    1. Run an iteration of the advanced needle controller to reduce the DNT_IPP
    2. Determine DNT_IPP
7. Determine the final penetration position FPP using the Detect center of oocyte and the Detect borders of the cytoplasm
8. Compute the distance D_FPP between the needle tip NT and the final penetration position FPP
9. While D_FPP>TOL_IPP
    1. Run an iteration of the advanced needle controller to reduce the D_FPP
    2. Determine D_FPP In an example, the process of "Deposit and verify that the sperm entered the cytoplasm," may involve the control system directing the automated, robotic system to initiate actions, including but not limited to:
1. Deposit and verify that the sperm in the cytoplasm
2. Detect needle tip NT using Detect needle tip
3. Detect the position of the sperm inside the needle SHP using Detect sperm position inside needle
4. Determine the target in-needle sperm position TNSP
5. Determine the distance D_HSTN between the sperm head position SHP and TNSP
6. While D_HSTN>TOL_TNSP
    1. Run an iteration of the advanced aspiration controller to reduce D_HSTN
    2. Determine the selected sperm head position SHP in this instant Inside the needle using Detect sperm position inside needle
    3. Determine D_HSTN
7. Determine the sperm release position SRP
8. Determine the distance D_SRP between the sperm head position SHP and SRP
9. While D_SRP>TOL_SRP
    1. Run an iteration of the advanced aspiration controller to reduce D_SRP
    2. Determine the selected sperm head position SHP in this instant Inside the needle using Detect sperm position inside needle
    3. Determine D_SRP
10. Verify that the sperm in inside the cytoplasm using Detect sperm in cytoplasm
11. Verify that the sperm is not in the injection needle using Detect sperm position inside needle In an example, the process of "Finish ISCI," may involve the control system directed the automated, robotic system to initiate actions, including but not limited to:
1. Move needle to the IPP+Delta using the simple needle controller
2. Apply negative pressure to the holding pipette using the simple holding pipette aspiration controller
3. Determine the oocyte pushing initial position OPIP using the center of the oocyte and the outer contour of the oocyte zp using Detect needle tip and Detect ZP outer
4. Move the needle to the OPIP using the simple needle controller
5. Detect the Initial Oocyte center IOC using the Detect center of
6. Move the needle to the stablished center of the oocyte coordinate IOC using the simple needle controller
7. Detect the Final oocyte center FOC it should be different from IOC
8. Move up the needle until is in not in focus using the simple needle controller the Detect if needle is in focus
9. Move up the holding pipette until is in not in focus using the simple holding pipette controller and the Detect if holding pipette is in focus In embodiments, the IVF/ICSI platform may use control systems, for example vision-based robotic control (visual servoing), for the control of robotic device movements, including but not limited to, needle controller commands, such as:
  Go to position (X, Y, Z, speedx, speedy, speedz)
  Stop
  MoveX(number of stepsx, speedx)
  MoveY(number of stepsx, speedx)
  MoveZ(number of stepsx, speedx)

In embodiments, the IVF/ICSI platform may use control systems, for example vision-based robotic control (visual servoing), for the control of robotic device movements, including but not limited to, pipette controller commands, such as:
  Go to position (X, Y, Z, speedx, speedy, speedz)
  Stop
  MoveX(number of stepsx, speedx)
  MoveY(number of stepsx, speedx)
  MoveZ(number of stepsx, speedx)

In embodiments, the IVF/ICSI platform may use control systems, for example vision-based robotic control (visual servoing), for the control of robotic device movements, including but not limited to, pipette aspiration controller commands, such as:
  Move (number of steps, speed) (where, for example, speed may be negative)
  Stop In embodiments of the present invention, the IVF platform, as described herein, may monitor the development of a plurality of embryos in the incubation module. One challenge with traditional box incubators is that when the incubator is opened, room air may move in, negatively impacting the temperature within the incubator. Also, gases may exit, impacting the pH of the culture medium. Once the incubator door is closed, time is required to recover the designated gas levels, and temperature, all of which may be detrimental to developing embryos. In part, because of this, the industry has largely moved to flat benchtop incubators with small chambers which have lower internal volume. With lower air volume, recovery rates may be faster in terms of gas and temperature recovery. In embodiments, the incubation module of the IVF platform may use universal culture media in the handling of the developing embryos, which may allow for the incubator in which the embryos are held to remain closed or be opened less frequently.

In embodiments, the incubation module of the IVF platform may use imaging and AI/ML processes, as described herein, as part of the incubation stage. In an example, images of embryos may be taken at regular or fixed intervals, continuously or some combination of fixed and continuous imaging over a selected time period. Imaging may include still images, time lapse images, simulated images, images with inferred characteristics, and/or moving images such as video or animated sequencing of still images. The imaging and AI/ML processes of the incubation module may automatically assist in the discovery of relevant events in cell and embryo division, for example when the two pronuclei "circles" are seen that confirm that there is a normal fertilization. In embodiments, the incubation system of the incubation module of the IVF platform may integrate the imaging and camera systems within the incubator. The incubator may include a double complex where the incubator has a microscopy system integrated within it, along with robotics. The double complex may have, for example, two controlled environments within the totality of the incubator, one in which the embryos may reside during development, and a second that may be used for automatically imaging individual embryos or groupings of embryos. In an example, robotics that are at least internal to the incubator may be able to automatically select a dish containing an embryo or plurality of embryos and automatically transfer the dish from a first compartment that is used to allow the embryos to develop to a second compartment in the same incubator in which microscopy and imaging may take place. Following imaging, the robotics may automatically return the dish containing the embryo or plurality of embryos from the second compartment back to the first compartment for further embryo development.

In embodiments, based at least in part on the imaging and AI/ML processes of the incubation module, the IVF/ICSI platform may automatically classify a plurality of embryos. In an example, the embryo-ranking intelligent classification assistant (ERICA), as described herein, may be used by the incubation module to classify embryos, for example, on the basis of each embryo's stage and/or quality of development. In an example, the imaging and AI/ML processes of the incubation module may take multiple planar images, cross-sections and the like of each embryo and analyze such imaging to determine the presence of appropriate cellular division, rate of division, nature of division or some other biological marker of interest. The analysis may include quantitative analysis, including but not limited to the rate of cellular division, as well as qualitative analysis, for example by determining if the division occurring is symmetric and/or the shape of the division, the proportion of the fluid area against the cellular mass, the area of the cellular mass, and the like.

In embodiments, based at least in part on the imaging and AI/ML processes of the incubation module of the IVF/ICSI platform, embryos may be identified, tagged and have their identifications bio-marked using imaging and stored, so that the IVF/ICSI platform is able to link a given embryo to the egg and sperm from which it derived, and so that the embryo upon entering cryo-storage is bio-marked such that upon removal and thawing from storage, the bio-mark of the embryo may be confirmed, and thus its identity confirmed.

In embodiments, the incubation module of the IVF/ICSI platform may provide clinical embryologists and/or andrologists an automated, robotic testing platform for conducting clinical trials, observational and other types of studies to assist in the determination of the impacts of environmental conditions related to incubation and vitrification on embryo development. The capability of the incubation module to automatically monitor, image, measure and predict aspects of embryo development, rapidly and without human intervention may allow for the rapid collection of data regarding embryo development than may be used to optimize the imaging and AI/ML processes of the incubation module, as well as inform aspects of IVF practices that may benefit parties outside of the IVF/ICSI platform. In an example, such "big data" projects may yield valuable insights that are not currently financially feasible when requiring human intervention and/or the use of human clinical embryologists and/or andrologists, including, to cite just one example, measuring the impacts of $CO_2$ exposure and timing on blastocyst formation rates. In another example, such big data may yield other insights related to the application and timing of compounds to assist and facilitate blastocyst formation. For example, individualizing micro fluids for embryos.

In an example, the ERICA system, as described herein, may score and rank embryos based at least in part on the imaging performed by the incubation module of the IVF/ICSI platform. The ERICA system may use static images, time lapse imaging, simulated images, images with inferred characteristics, continuous imaging, such as video, and/or three-dimensional imaging. In embodiments, the three-dimensional imaging used for the ERICA system may be based on real-life imaging captured automatically by the cameras of the incubation module and/or may be based on inferred, predicted, modeling or other non-real-life imaging that may be used to construct a three-dimensional model, including but not limited to a digital twin, of an embryo or plurality of embryos. In embodiments, a digital twin of a developing embryo may be advanced through a simulated life cycle and/or a predicted life cycle, based at least in part on the AI/ML processing capabilities of the incubation module that may utilize the big data as described herein. This simulated and/or predicted life cycle using a digital twin may improve the accuracy and selection of the embryo or group of embryos that has the highest probability of success to achieve a desired clinical state, such as a particular stage of development, timing of reaching a particular developmental stage, or some other criterion. Such predictive capacity may improve the differentiation of embryos that are appropriate for cryo-storage and those that are not.

In embodiments, the IVF/ICSI platform may include an intelligence layer that may include a digital twin system, which may include a set of components, processes, services, interfaces and other elements for development and deployment of digital twin capabilities for visualization of various IVF entity states, properties, processes, methods, environments, and applications, as well as for coordinated intelligence (including artificial intelligence, analytics and other capabilities) and other services and capabilities that are enabled or facilitated with a digital twin. Without limitation, a digital twin may be used for and/or applied to each of the processes that are managed, controlled, or mediated by each of the set of applications and processes of the IVF/ICSI platform, as described herein.

In embodiments, the digital twin may take advantage of the presence of multiple applications within the IVF/ICSI platform, such that a pair of applications may share data sources, and other inputs, that are collected with respect to the IVF/ICSI platform operations and processes, as well as sharing outputs, events, state information and outputs, which collectively may provide a much richer environment for enriching content in a digital twin, including through use of artificial intelligence (including any of the various expert systems, artificial intelligence systems, neural networks, supervised learning systems, machine learning systems, deep learning systems, and other systems described throughout this disclosure).

In embodiments, a digital twin may be used in connection with shared or converged processes among the various pairs of the applications of the IVF/ICSI platform, such as, the components and modules of the IVF/ICSI platform as described herein. In embodiments, converged processes may include shared data structures for multiple applications that may be connected to the digital twin such that the digital twin is updated accordingly.

In an example, the ERICA system, as described herein, may score and rank embryos based at least in part on the imaging performed by the incubation module of the IVF/ICSI platform. The ERICA system may use static images, time lapse imaging, simulated images, images with inferred characteristics, continuous imaging, such as video, and/or three-dimensional imaging to determine, for example, the amount of lipids in an embryo, and predict the impact of the detected or predicted amount of lipids present to a clinical criterion of interest, including but not limited to the probability of a successful implantation of embryo resulting in a pregnancy.

In embodiments, the dish, receptacle or vessel in which the embryo is held may be treated with oil, cellulose-based or graphite-based films, which may be transparent, to reduce the speed of gas exchange and changes in pH, providing an extra layer of safety when moving cells to and from, and within the incubator of the incubation module.

In embodiments, the imaging and AI/ML processes of the incubation module may include a sperm oocyte feature integration feature (SOFI) that may be used to classify, score and rank embryos of seemingly equivalent health based at least in part on the measured or predicted quality of the sperm (or egg) from which the embryo derives. In embodiments, SOFI can work as a stand-alone algorithm or be incorporated to improve accuracy and add explainability to embryo ranking and embryo selection algorithms.

In embodiments, the imaging and AI/ML processes of the incubation module may be used to determine the optimal timing for placing an embryo in cryo-storage.

In embodiments, the incubation module may be able to reduce the amount of cryoprotectants required to treat an embryo prior to cryo-storage and perform vitrification that reduces or removes the vapor stage of entry into the cryo-storage, speeds up the entry of the embryo into the cryo-storage, and consistently alters the angle of entry of the embryo container in such a way that the air bubble that may be generated around the container is minimized. In embodiments, the vitrification performed by the incubation module may be automatically and robotically performed by the IVF/ICSI platform.

In embodiments of the present disclosure, the incubation module may include Incubation components, systems, and processes. In embodiments of the present disclosure, the incubation module may include sensor components, systems, and processes. In embodiments of the present disclosure, the incubation module may include specimen management components, systems, and processes. In embodiments of the present disclosure, the incubation module may include AI/ML for automated measurement and testing. In embodiments of the present disclosure, the incubation module may include AI/ML for optimization. In embodiments of the present disclosure, the incubation module may include AI/ML for prediction. In embodiments of the present disclosure, the incubation module may include AI/ML for selection/ranking. In embodiments of the present disclosure, the incubation module may include AI/ML for semi-autonomous, supervised, or autonomous robotics. In embodiments of the present disclosure, the incubation module may include AI/ML for system configuration and control. In embodiments of the present disclosure, the incubation module may include fully autonomous AI/ML. In embodiments of the present disclosure, the incubation module may include robotic handling systems and processes. In embodiments of the present disclosure, the incubation module may include advanced microscopy systems and components.

In embodiments of the present invention, the IVF/ICSI platform, as described herein, may include a vitrification module that provides an equilibration and vitrification solution prior to placing the oocyte and/or embryo in or on a cryo-device. As used herein, "automation" of vitrification means vitrification processes that include robotics, optics and/or ML/AI/ML-assistance, as described herein, so that processes in the vitrification procedure that ordinarily require a human operator may be performed by the intelligent robotic system of the IVF/ICSI platform.

In the traditional vitrification procedure performed by a human operator the processes listed in Table 5, below, are generally followed.

TABLE 5

| Action | Human operator dependent | Human Operator Role |
|---|---|---|
| Preparation of vitrification solutions (bringing to 25-27 C.) | Yes | Transport |
| Preparation of cryodevices, goblets, safety goblets, cryocane tags, cryosleeves | Yes | Manual work (automated label generation possible) |
| Filling a container with LN2 | Yes | LN2 handling; transport |
| Removal of device cover and placement in LN2; placement of device on a dish | Yes | Manual work; handling of devices |
| Patient, dish, and material identification | Yes | Record review; Dish label verification; Witnessing; Human judgment |
| Preparation of 60 mm dish lid with one drop of Buffer Solution and two drops of Equilibration Solution (25-50 μL) | Yes | Pipetting (EPPENDORF) |

TABLE 5-continued

| Action | Human operator dependent | Human Operator Role |
|---|---|---|
| Transferring oocytes/embryo to BS and merging the drop with ES 1 drop | Yes | Microscopic observation (LP) Micro-pipetting (CAPILLARY TUBE TIPS) |
| 2-minute exposure to ES1 | Yes | Time keeping |
| Merging of large drop with ES2 drop | Yes | Micro-pipetting; Microscopic observation (LP) |
| 2-minute exposure | Yes | Time keeping |
| Moving oocyte/embryo to the center of the BS/ES1/ES2 drop at 1 minute | Yes | Time keeping; Microscopic observation (LP) Micro-pipetting (LP) (CAPILLARY TUBE TIPS) |
| Placing 300 μL of ES in a new dish lid, avoiding air bubbles, while completing the last minute of exposure | Yes | Time keeping; Pipetting (EPPENDORF OR PASTEUR) |
| Transferring oocytes/embryo to the new ES drop | Yes | Time keeping; Micro-pipetting; Microscopic observation (LP) (CAPILLARY TUBE TIPS) |
| 10-minute exposure | Yes | Time keeping; Intermittent Microscopic observation (HP) |
| Preparation of two Vitrification Solution drops during the last 30-60 s of exposure while avoiding air bubbles | Yes | Pipetting (EPPENDORF) |
| Preparing Vitriplate by placing 300 μL ES in Well 1 while avoiding air bubbles | Yes | Pipetting (EPPENDORF) |
| Aspirating oocytes/embryo in the tip of the pipette and transferring from culture dish to ES1 at the top (in the center), allowing to drop to the bottom of Well 1 (about 30 s) | Yes | Micro-pipetting; Microscopic observation (LP) (CAPILLARY TUBE TIPS) |
| Assessing shrinkage (at 90 s) followed by full recovery and morphology by ~2 minutes | Yes | Microscopic observation (HP); Human judgment |
| Setting a timer to count up and assessing oocytes/embryo at around 8 minutes | Yes | Time keeping; Intermittent Microscopic observation (HP) |
| Assessment of recovery at 8 minutes; decision whether to stop or continue exposure after 10 minutes | Yes | Microscopic observation (HP) Human Judgment |
| Setting a timer for 60 seconds | Yes | Time-keeping |
| Aspirating the oocytes/embryo with small amount of ES; | Yes | Micro-pipetting; Microscopic observation (LP) (CAPILLARY TUBE TIPS) |
| Depositing oocytes/embryo in VS1 (left side); expelling remaining ES; rinsing pipette with VS1 | Yes | Micro-pipetting; Microscopic observation (HP) (CAPILLARY TUBE TIPS) |
| Observing oocytes/embryo as they float to the surface of VS1; | Yes | Micro-pipetting; Microscopic observation (HP) (CAPILLARY TUBE TIPS) |
| Aspirating VS1 and then oocytes/embryo and depositing on the bottom of VS1 well; expelling remaining VS1 | Yes | Micro-pipetting; Microscopic observation (LP) (CAPILLARY TUBE TIPS) |
| Observing oocytes/embryo as they float to middle depth of VS1 well | Yes | Microscopic observation (HP) |
| Aspirating fresh VS2 and expelling; repeating once more | Yes | Micro-pipetting; (CAPILLARY TUBE TIPS) |
| Aspirating oocytes/embryo from VS1 into the tip of the capillary tube | Yes | Micro-pipetting; (CAPILLARY TUBE TIPS) |
| Placing the oocytes/embryo at middle depth of VS2 (COMPLETE REMOVAL OF ES) | Yes | Micro-pipetting; Microscopic observation (LP) (CAPILLARY TUBE TIPS) |
| Rinsing micropipette with VS2; repeating once or twice | Yes | Micro-pipetting; Microscopic observation (LP) (CAPILLARY TUBE TIPS) |
| Stirring solution around the oocytes/embryos to facilitate cryoprotectant penetration | Yes | Micro-pipetting; Microscopic observation (LP) (CAPILLARY TUBE TIPS) |
| Aspirating oocytes/embryo in the tip of the micropipette and depositing onto the device | Yes | Micro-pipetting; Microscopic observation (LP) (CAPILLARY TUBE TIPS) |
| (Assessing and adjusting volume of cryoprotectant on the device) | Yes | Micro-pipetting; Microscopic observation (LP) (CAPILLARY TUBE TIPS) |
| Plunging the device in LN2 at an angle and moving back and forth to prevent gas formation at the point of immersion (Leidenfrost effect) | Yes | Manual handling of devices |
| Picking up each device and replacing cover while the tip is submerged in LN2 using forceps | Yes | Manual handling of devices |

TABLE 5-continued

| Action | Human operator dependent | Human Operator Role |
|---|---|---|
| Placing each covered cryo-device into a labeled (previously submerged) goblet with the tip facing the bottom of the goblet | Yes | Manual handling of devices |
| Moving the security goblet down the cane using forceps until the two goblets are almost in contact - 5 mm gap between the two | Yes | Manual handling of devices |
| Rapidly transfer cryocane to LN2 dewar (in a cryosleeve) | Yes | Manual handling of devices |

In embodiments, human reproductive cells and tissues may be preserved at cryogenic temperatures indefinitely for future clinical or research use. Cellular functions stop once the cells are cryopreserved. To cryopreserve eggs and embryos, cryoprotectant solutions (colloquially referred to as "anti-freeze") may be used to avoid cell death. Currently, a mixture of dimethyl sulfoxide (DMSO) and ethylene glycol (EG) may be used as "penetrating" (i.e., diffuses into the cell) cryoprotectants combined with trehalose (or sucrose) as a "non-penetrating" cryoprotectant (i.e., remains outside the cell). The solutions also contain protein and macromolecules such as ficoll or Hydroxypropyl cellulose (HPC). Cryopreserved human reproductive cells and tissues may be stored at ultra-low (cryogenic) temperatures (e.g., $-196°$ C.) to maintain their cryopreserved state. Cryo-storage may be done in specialized tanks and is dependent on liquid nitrogen (LN2) or nitrogen vapor. Water is a major component of cells and its solidification (ice crystal formation) during cryopreservation it may be controlled to avoid damage to cellular organelles and membranes. Vitrification (as opposed to slow-freezing) is a method of cryopreservation that avoids ice crystal formation by changing liquids into a glassy state, using high concentrations of cryoprotectants, ultra-rapid cooling rates (plunging into LN2 from room temperature) and suspension of cells in minute volumes of cryoprotectant (<1 µL). Human oocytes and embryos can be efficiently and successfully cryopreserved using vitrification, with >90% survival. Immediate survival means an intact membrane in the case of eggs (no lysis), 50% or more of cells surviving in a cleavage stage embryo, and a majority of cells remaining intact in a blastocyst. Ultimately, survival means retaining viability (e.g., fertilizability in the case of eggs, and continued development in the case of embryos).

In embodiments, an equilibration solution (ES; non-vitrifying) may be used. In an example, exposure to ES may introduce cryoprotectants (CPs; osmotic pressure ~2400) into the cell (osmotic pressure ~300). Intracellular water may flow out due to this difference between intra- and extracellular osmotic pressure. At the same time, CPs may penetrate the cell membrane and enter the cell. As intra- and extracellular osmotic pressures equilibrate, these reactions may occur simultaneously but the rate at which water flows out of the cell is slightly faster than that of CPs entering the cell thus the oocyte/embryo may first shrink and then return to its original volume with water having been replaced with CPs. Successful completion of equilibration may be indicated by complete recovery of the cell's volume.

In embodiments, vitrification Solutions 1 and 2 (VS1 and VS2) may be used. The purpose of VS1 is to replace all intracellular ES with VS. This process is complete when the osmolarity/density in the cell and VS1 are equal. The purpose of VS2 is to confirm that ES has been completely replaced by VS. This is confirmed when the oocyte/embryo shrink completely (into a moon/kidney shape).

In embodiments, human oocytes may be vitrified in groups of 2-4 on current cryo-devices. For clinical use, standard protocol includes vitrification of MII oocytes but MI oocytes may also be vitrified. Human embryos may be vitrified at different stages of development, including pronuclear stage (after fertilization), cleavage stages, and blastocyst stage. Blastocysts may be vitrified following trophectoderm biopsy for preimplantation genetic testing. Tested blastocysts may be vitrified individually, maintaining their original identity. Non-tested blastocysts or other stages of embryos may be vitrified in groups of 2-4.

In embodiments, pipetting in the context of vitrification may entail aspiration, expelling and container-to-container transfer of individual or multiple eggs and embryos as well as fluids. Pipetting is fundamental to IVF laboratory techniques and may be carried out in a sterile fashion, without creating air bubbles that could be disruptive, lead to loss of cells, or create potentially infectious aerosols.

In embodiments, a plurality of pipette types may be used for different purposes during vitrification, including but not limited to Eppendorf pipettes, capillary tube tips, and micropipettes. Eppendorf pipettes are instruments equipped with a piston and a spring-loaded tip cone, single channel and adjustable volumes (1-1000 µL units with specific ranges), used in conjunction with Eppendorf tips, to aspirate and dispense precise (usually low) volumes. capillary tube tips refer to pipette tips used in conjunction with capillary tube pipettors: Tips are made from flexible medical grade plastic to prevent scratching of plastic Petri dishes. The tips are manufactured in different inner diameters, ranging from 75 µm to 600 µm, with the most commonly used sizes being 155-200 µm for denudation of eggs and handling eggs and embryos, and 300 µm for handling blastocysts. Micropipettes may also be used by the automated, robotic pipette system of the IVF/ICSI platform. Micropipettes, such as a holding pipette, are ultra-fine glass instruments that are manufactured with specific outer and inner diameters in order to hold or manipulate oocytes and embryos during microsurgical procedures on a micromanipulator. A micro-holding pipette may, for example, have an outer diameter of 65-180 µm and inner diameter of 15-30 µm.

In an example embodiment, of a vitrification process of the IVF/ICSI platform system, a sample hardware set up may include:
- Calibration dish (marked positions of CM, ES, VS1, VS2 and finish position with a diamond pen)
- Inverted Microscope
- Motorized stage
- Digital Microscope (low magnification)
- Optical sensor
- Stage heating & controller Micromanipulators
Range of 12,500 µm for each axis
Max speed of 10,000 µm per second
20× Objective
4× Objective
Step motors controller In embodiments, the IVF/ICSI platform may use a controllable motorized pipettor having, in an example, an assembly of 1) the functional components of a motorized pipettor (non-proprietary), consisting of a plunger, spring with lubrication, and the body/cylinder (non-proprietary); 2) high precision motor that drives the plunger; 3) a single axis motorized slider (proprietary) that moves the pipettor assembly in the Z direction. The components may be moved at a controlled speed and acceleration using proprietary software.

In embodiments, an example of automated and robotic vitrification sequence is described below. Each of the elements of the sequence may be performed autonomously by the IVF/ICSI platform.

1. The system may be calibrated by assigning locations in the dish where vitrification solutions, eggs and embryos will be placed.
2. The solutions for vitrification may be placed in a plate: Equilibration Solution(ES) in one Well and Vitrification Solution (VS) in a second Well. These wells may serve as the reservoir of solutions for the vitrification procedure.
3. The IVF/ICSI platform may dispense a 15 µL drop of Buffer Solution (BS) in a dish and transfers egg/embryo/s to be vitrified into the drop.
4. The IVF/ICSI platform may place this dish with the egg/embryo/s on the stage of the microscope.
5. The automated system may begin a vitrification protocol with a command issued by a human operator from a computer-either locally or remotely.
6. A motorized pipettor with a disposable tip may be positioned above Well 1 as the stage moves to a specified coordinate; the pipettor may lower into the Well (Z axis) at a specified depth and apply negative pressure to aspirate 30 µL of ES. The pipettor may move up (Z axis) raising the tip out and above the well and remains stationary, as the stage moves to bring the dish to a specified position directly under the pipette tip. The pipettor may lower onto the dish, stopping just before hitting the bottom, and the AI/ML may apply positive pressure to deposit the entire volume of ES contained in the tip onto the dish in a pre-specified position. The pipettor may move up (Z axis) raising the tip out and above the well and remain stationary while the stage moves to position Well 2 containing VS directly beneath the pipette tip. The same aspiration and expelling sequence may repeat, for example, twice, with a different pre-specified volume, creating two 100 µL drops of VS (VS1 and VS2) in the dish.
7. The distance between the center of one drop to the next drop may be predetermined and programmed for the specific purpose of allowing merging of these drops during the vitrification procedure. Multiple different distances may be used, for example, between BS and ES; ES and VS 1; and VS 1 and VS 2.
8. Once the last solution is dispensed, the pipettor may move up (Z axis) and out of the drop and return to its original position and remain stationary throughout the rest of the procedure.
9. The stage may then move to bring the egg/embryo/s to the field of vision of the optics system of the IVF/ICSI platform.
10. AI/ML, as described herein, may be used to identify the egg/s or embryo/s and the exact position is visualized and confirmed.
11. A micro-holding pipette, being held in a tool holder to the side of the stage may lower precisely near the egg/embryo (Z axis); AI/ML may inform the application of negative pressure automatically via a motorized microinjector and the egg/embryo may be secured on the holding pipette with the zona pellucida held by negative pressure. The pressure may be automatically controlled so it remains constant for the egg or embryo.
12. Opposite the microtool holder, to the side of the stage may be an adapted tool holder holding a wand that acts as a holder for the cryo-device (the "mitogen racket"). "The racket' may be a micro-mesh/grid the surface of which can be used for 'containing' egg/s and embryo/s while suspended in LN2 or N2 vapor.
13. With the egg on the holding pipette, immersed in BS, AI/ML may be used to assist the performance of the following: the racket may be lowered into the same drop and positioned in the same plane, the microtool holder moves forward toward the racket, is raised slightly, moves further forward until it reaches the middle of the Racket, then lowers the egg onto the racket while still holding the egg in place. From here on, the holding pipette holding the egg and the Racket remain together stationery while the stage moves (X axis), moving the entire 'assembly' through the solutions in a predetermined order and for pre-determined lengths of time. The process of moving the egg or embryo/racket assembly between drops leads to a "fluid bridge" between the drops that leads to merging of the drops. This allows gradual exposure of egg/embryo/s to solutions that have increasing concentrations of cryoprotectant.
14. The egg or embryo/Racket assembly may remain in each drop for a predetermined length of time. For example, 1 minute in ES; 30 seconds in VS1 and another 30 seconds in VS2.
15. After, for example, 30 seconds in VS2, AI/ML may be used to assist the movement of the stage so that the egg or embryo/racket assembly moves downward (Y axis) in the dish, creating a trail of VS2 and reducing the volume of VS2 on the racket and around the egg.
16. AI/ML may then be used to assist stopping the stage in a predetermined position.
17. AI/ML may then be used to guide the release of the egg from the holding pipette onto the grid and the racket/holder assembly is ready to be removed and plunged into LN2.
18. AI/ML may then be used to guide the lifting of the holding pipette, which may remain in a predetermined position, stationary.
19. AI/ML may then be used to guide lifting the racket which remains in a predetermined position so that it can be removed from the micromanipulator.

Figure 64:
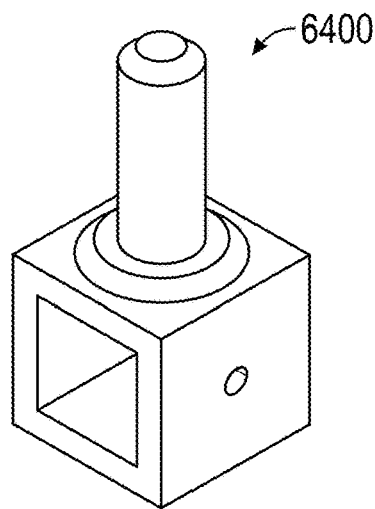
FIG. 64 depicts an adapter that may couple a handheld microscope to a metal extrusion.
Figure 65:
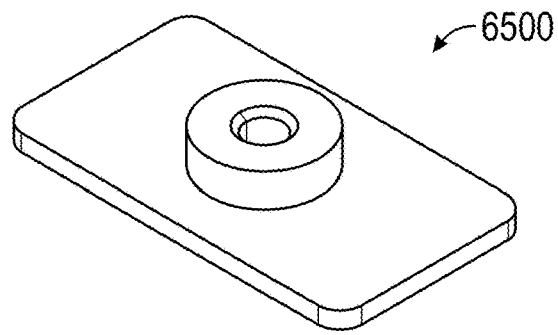
FIG. 65 depicts an adapter for using an Eppendorf micromanipulator with metal extrusions.
Figure 66:
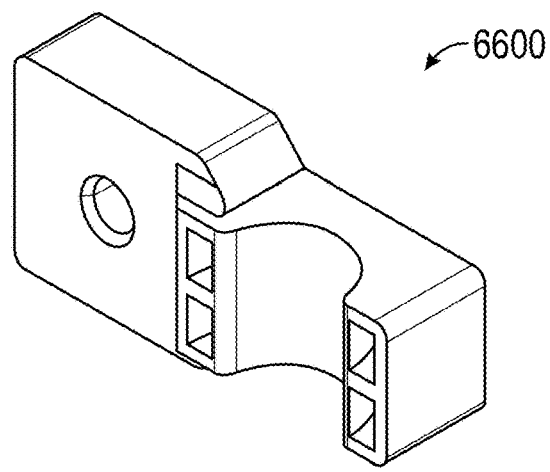
FIG. 66 depicts an adapter for using a rod-shaped source of light with metal extrusions.
Figure 68:
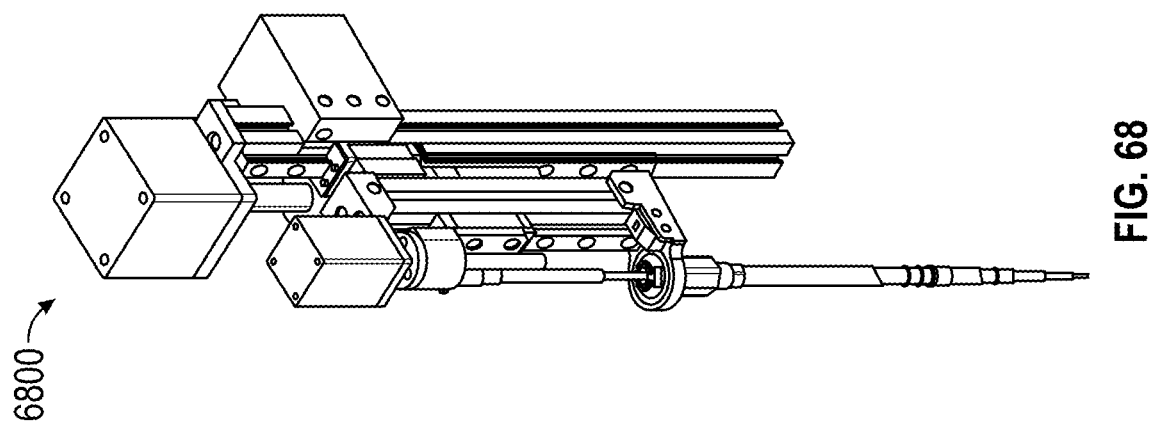
FIG. 68 depicts a device with independent Z movement and pipetting capabilities that may be attached to the neck of a microscope.
Figure 67:
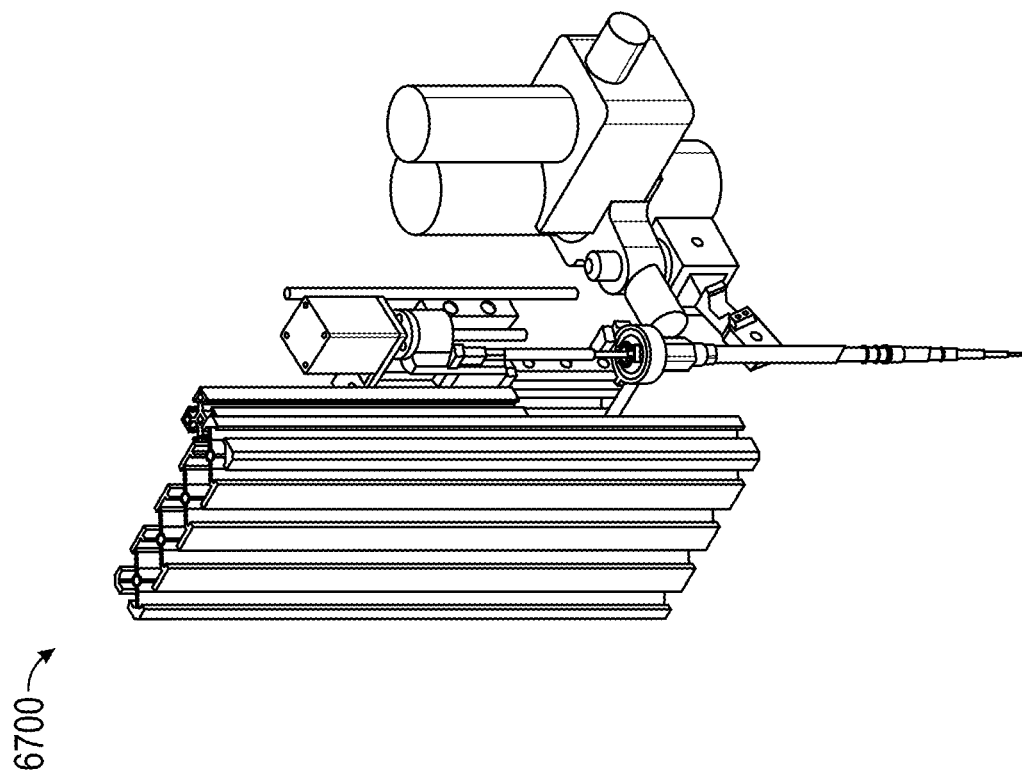
FIG. 67 depicts a device capable of vision, XYZ movement, and micromanipulator movements with aspiration capabilities and independent Z control and a variable volume pipette.
Figure 86:
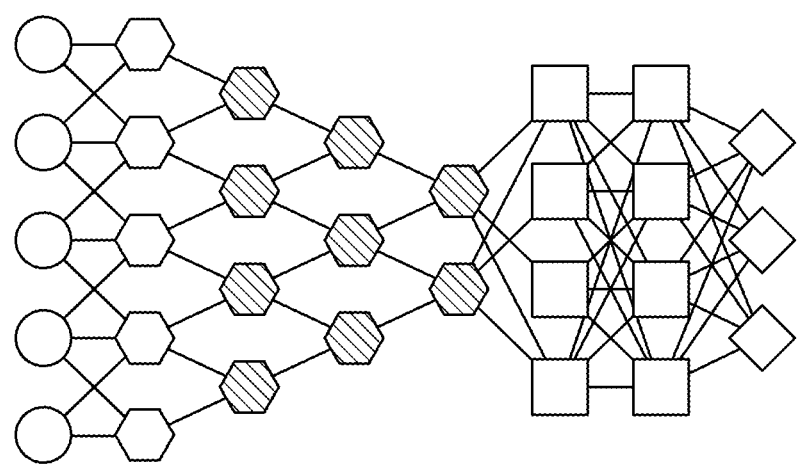
Figure 87:
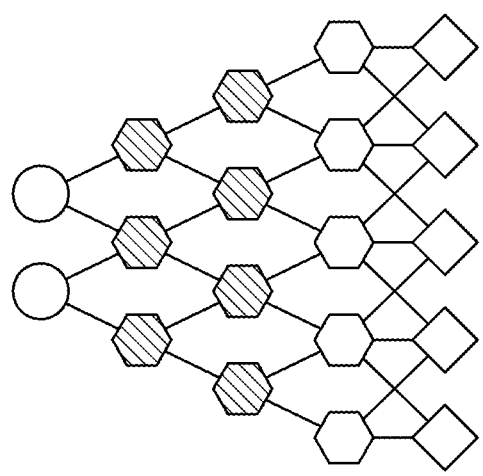

The IVF/ICSI platform may automatically remove the holder with the racket from the micromanipulator and plunge it in LN2 using a robotic plunging system. In embodiments of the present invention, the IVF/ICSI platform, as described herein, may include a vitrification module that provides modifications to use an inverted microscope at magnifications that allow visualization of samples and cells in their preservation medium for manipulation. In embodiments, the vitrification module may use selection devices to avoid the shadows that may be produced on enlarged viewing scales, as well as the characteristics of the cell to be selected. In embodiments, the microscope may be adjusted and moved automatically, as opposed to the object carrying the egg along with the solutions, to allow for immobilization in the preservation medium. FIG. 64 depicts an adapter that may couple a microscope to a metal extrusion 6400. FIG. 65 depicts an adapter for using an Eppendorf micromanipulator with metal extrusions 6500. FIG. 66 depicts an adapter for using a rod-shaped source of light with metal extrusions 660. FIG. 67 depicts a device capable of vision, XYZ movement, and micromanipulator movements with aspiration capabilities and independent Z control and a variable volume pipette 6700. FIG. 68 depicts a device with independent Z movement and pipetting capabilities that may be attached to the neck of a microscope 6800.

In embodiments, the imaging and AI/ML processes of the vitrification module may provide an algorithm, or plurality of algorithms, that determines the buoyancy capacity of the cells to preserve and assign the buoyancy and depth value where cells may be preserved.

In embodiments, the imaging and AI/ML processes of the vitrification module may provide an algorithm, or plurality of algorithms, that determines an optimal depth at which cells should be placed for preservation.

In embodiments, the vitrification module may include robotics for plunging a specimen in liquid nitrogen and then transferring it to a cryo-storage container (for example, a dewar or tank). The robotics may include an arm, handle, or other device type that is capable of attaching to a vessel containing a specimen and automatically moving the specimen into the cryo-storage, placing it at an optimal depth, or other location coordinate, including a location coordinate that is derived by the AI/ML processes, as described herein, and releasing the specimen within the cryo-storage container. In embodiments, the release of the specimen may be achieved by disengaging a magnet from the magnetized specimen vessel so that it is no longer magnetically bound and held by the robotic device. In embodiments, the vitrification module may include a plurality of robotic arms or other robotic devices for simultaneously processing a plurality of specimens and transferring each specimen to cryo-storage.

In embodiments, the vitrification module may automatically pair the microscope focus on the cell specimen with the tip of a pipette, so the vitrification module does not need to inform the robotic arm where it is. The robotic arm may be informed of the specimen's location because they are paired and moving together, so if the cell moves, for example it goes deeper, this does not create an imaging or other problem for the vitrification module, because it remains aligned. This processing and pairing may reduce miscalculations.

In embodiments, a cryo-storage device of the IVF/ICSI platform may include cameras that may be able to automatically guide the robotic positioning of a specimen within the cryo-storage and/or confirm the correct placement of a specimen.

In embodiments of the present disclosure, the vitrification and cryo-storage module may include freezing components, systems, and processes. In embodiments of the present disclosure, the vitrification and cryo-storage module may include AI/ML for automated measurement and testing. In embodiments of the present disclosure, the vitrification and cryo-storage module may include AI/ML for optimization. In embodiments of the present disclosure, the vitrification and cryo-storage module may include AI/ML for system configuration and control. In embodiments of the present disclosure, the vitrification and cryo-storage module may include AI/ML for semi-autonomous, supervised, or autonomous robotics. In embodiments of the present disclosure, the vitrification and cryo-storage module may include fully autonomous AI/ML. In embodiments of the present disclosure, the vitrification and cryo-storage module may include sensor components, systems, and processes. In embodiments of the present disclosure, the vitrification and cryo-storage module may include specimen management components, systems, and processes. In embodiments of the present disclosure, the vitrification and cryo-storage module may include robotic handling systems and processes. In embodiments of the present disclosure, the vitrification and cryo-storage module may include storage components, systems, and processes. In embodiments of the present disclosure, the vitrification and cryo-storage module may include AI/ML for automated measurement and testing. In embodiments of the present disclosure, the vitrification and cryo-storage module may include AI/ML for optimization. In embodiments of the present disclosure, the vitrification and cryo-storage module may include AI/ML for system configuration and control. In embodiments of the present disclosure, the vitrification and cryo-storage module may include AI/ML for semi-autonomous, supervised, or autonomous robotics. In embodiments of the present disclosure, the vitrification and cryo-storage module may include Fully autonomous AI/ML. In embodiments of the present disclosure, the vitrification and cryo-storage module may include sensor components, systems, and processes. In embodiments of the present disclosure, the vitrification and cryo-storage module may include specimen management components, systems, and processes. In embodiments of the present disclosure, the vitrification and cryo-storage module may include robotic handling systems and processes.

Referring to FIG. 69 through FIG. 96, in embodiments of the present disclosure, the IVF/ICSI platform, as described herein, may include expert systems, self-organization, machine learning, artificial intelligence, and the like, and may benefit from the use of a neural net, such as a neural net trained for pattern recognition, for classification of one or more parameters, characteristics, or phenomena, for support of autonomous control, and other purposes. References to a neural net throughout this disclosure should be understood to encompass a wide range of different types of neural networks, machine learning systems, artificial intelligence systems, and the like, such as feed forward neural networks, radial basis function neural networks, self-organizing neural networks (e.g., Kohonen self-organizing neural networks), recurrent neural networks, modular neural networks, artificial neural networks, physical neural networks, multi-layered neural networks, convolutional neural networks, hybrids of neural networks with other expert systems (e.g., hybrid fuzzy logic-neural network systems), Autoencoder neural networks, probabilistic neural networks, time delay neural networks, convolutional neural networks, regulatory feedback neural networks, radial basis function neural networks, recurrent neural networks, Hopfield neural networks, Boltzmann machine neural networks, self-organizing map (SOM) neural networks, learning vector quantization (LVQ) neural networks, fully recurrent neural networks, simple recurrent neural networks, echo state neural networks, long short-term memory neural networks, bi-directional neural networks, hierarchical neural networks, stochastic neural networks, genetic scale RNN neural networks, committee of machines neural networks, associative neural networks, physical neural networks, instantaneously trained neural networks, spiking neural networks, neocognitron neural networks, dynamic neural networks, cascading neural networks, neuro-fuzzy neural networks, compositional pattern-producing neural networks, memory neural networks, hierarchical temporal memory neural networks, deep feed forward neural networks, gated recurrent unit (GCU) neural networks, auto encoder neural networks, variational auto encoder neural networks, de-noising auto encoder neural networks, sparse auto-encoder neural networks, Markov chain neural networks, restricted Boltzmann machine neural networks, deep belief neural networks, deep convolutional neural networks, de-convolutional neural networks, deep convolutional inverse graphics neural networks, generative adversarial neural networks, liquid state machine neural networks, extreme learning machine neural networks, echo state neural networks, deep residual neural networks, support vector machine neural networks, neural Turing machine neural networks, and/or holographic associative memory neural networks, or hybrids or combinations of the foregoing, or combinations with other expert systems, such as rule-based systems, model-based systems (including ones based on physical models, statistical models, flow-based models, biological models, biomimetic models, and the like).

In embodiments, FIGS. 70-96 depicts example neural networks that may be used by the IVF/ICSI platform and FIG. 69 depicts a legend showing the various components of the neural networks depicted throughout FIGS. 70-96. FIG. 69 depicts various neural net components depicted in cells that are assigned functions and requirements 6900. In embodiments, the various neural net examples may include back fed data/sensor cells, data/sensor cells, noisy input cells, and hidden cells. The neural net components also include probabilistic hidden cells, spiking hidden cells, output cells, match input/output cells, recurrent cells, memory cells, different memory cells, kernels, and convolution or pool cells.

Figure 88:
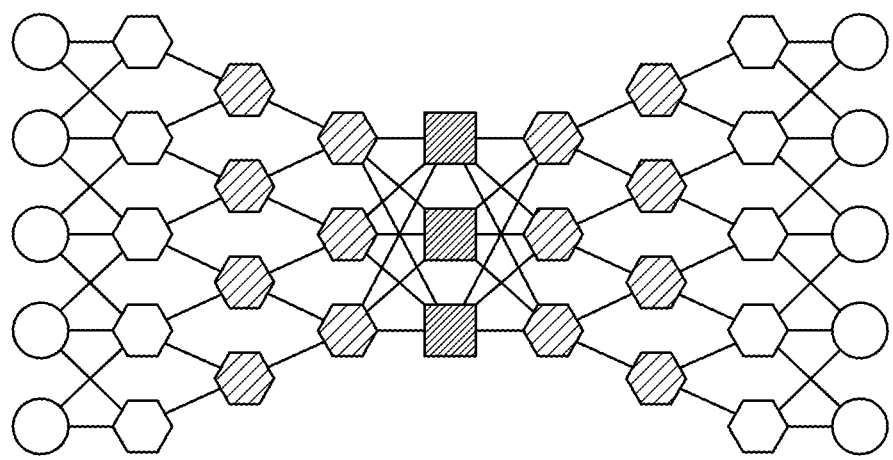
Figure 89:
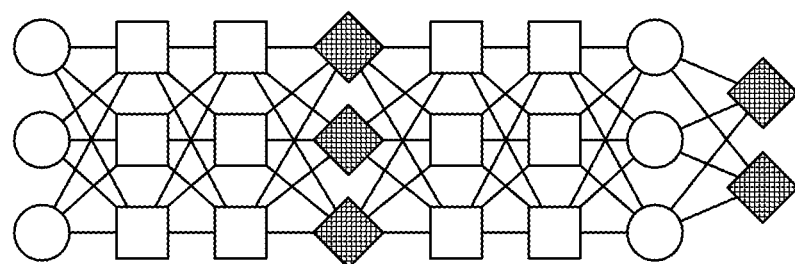
Figure 91:
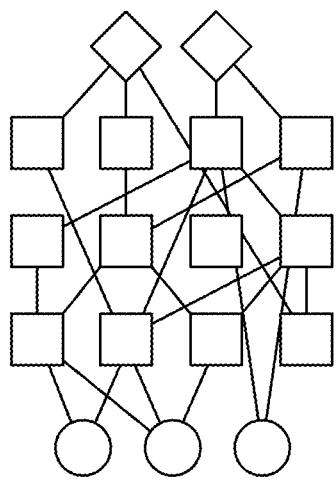
Figure 93:
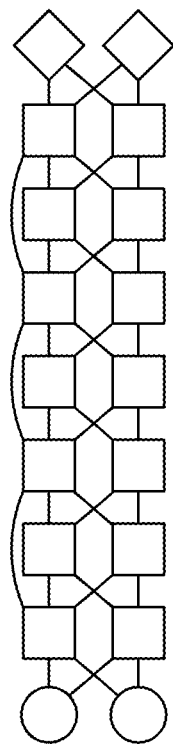
Figure 90:
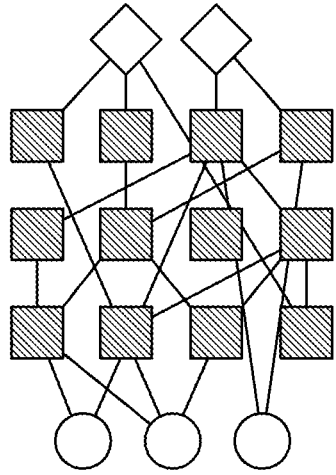
Figure 92:
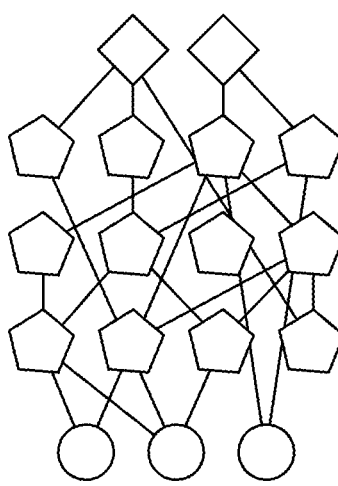
Figure 94:
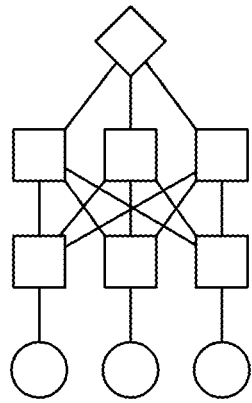
Figure 95:
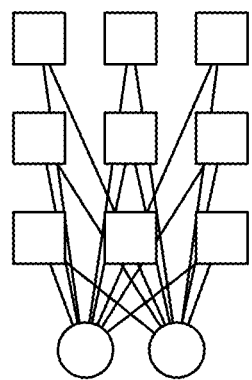
Figure 96:
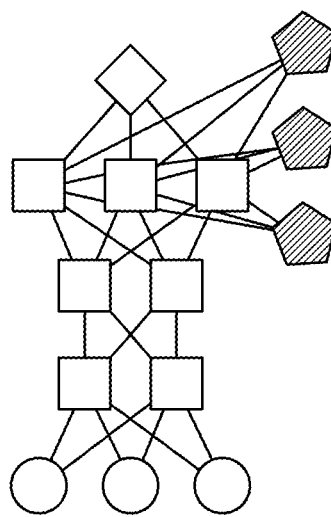

In embodiments, FIG. 70 depicts an example perceptron neural network 7000 that may connect to, integrate with, or interface with the IVF/ICSI platform. The platform may also be associated with further neural net systems such as a feed forward neural network 7100 (FIG. 71), a radial basis neural network 7200 (FIG. 72), a deep feed forward neural network 7300 (FIG. 73), a recurrent neural network 7400 (FIG. 74), a long/short term neural network 7500 (FIG. 75), and a gated recurrent neural network 7600 (FIG. 76). The platform may also be associated with further neural net systems such as an auto encoder neural network 7700 (FIG. 77), a variational neural network 7800 (FIG. 78), a denoising neural network 7900 (FIG. 79), a sparse neural network 8000 (FIG. 80), a Markov chain neural network 8100 (FIG. 81), and a Hopfield network neural network 8200 (FIG. 82). The platform may further be associated with additional neural net systems such as a Boltzmann machine neural network 8300 (FIG. 83), a restricted BM neural network 8400 (FIG. 84), a deep belief neural network 8500 (FIG. 85), a deep convolutional neural network 8600 (FIG. 86), a deconvolutional neural network 8700 (FIG. 87), and a deep convolutional inverse graphics neural network 8800 (FIG. 88). The platform may also be associated with further neural net systems such as a generative adversarial neural network 8900 (FIG. 89), a liquid state machine neural network 9000 (FIG. 90), an extreme learning machine neural network 9100 (FIG. 91), an echo state neural network 9200 (FIG. 92), a deep residual neural network 9300 (FIG. 93), a Kohonen neural network 9400 (FIG. 94), a support vector machine neural network 9500 (FIG. 95), and a neural Turing machine neural network 9600 (FIG. 96).

The foregoing neural networks may have a variety of nodes or neurons, which may perform a variety of functions on inputs, such as inputs received from sensors or other data sources, including other nodes. Functions may involve weights, features, feature vectors, and the like. Neurons may include perceptrons, neurons that mimic biological functions (such as of the human senses of touch, vision, taste, hearing, and smell), and the like. Continuous neurons, such as with sigmoidal activation, may be used in the context of various forms of neural net, such as where backpropagation is involved.

In many embodiments, an expert system or neural network may be trained, such as by a human operator or supervisor, or based on a data set, model, or the like. Training may include presenting the neural network with one or more training data sets that represent values, such as sensor data, event data, parameter data, and other types of data (including the many types described throughout this disclosure), as well as one or more indicators of an outcome, such as an outcome of a process, an outcome of a calculation, an outcome of an event, an outcome of an activity, or the like. Training may include training in optimization, such as training a neural network to optimize one or more systems based on one or more optimization approaches, such as Bayesian approaches, parametric Bayes classifier approaches, k-nearest-neighbor classifier approaches, iterative approaches, interpolation approaches, Pareto optimization approaches, algorithmic approaches, and the like. Feedback may be provided in a process of variation and selection, such as with a genetic algorithm that evolves one or more solutions based on feedback through a series of rounds.

In embodiments, a plurality of neural networks may be deployed in a cloud platform that receives data streams and other inputs collected (such as by mobile data collectors) in one or more transactional environments and transmitted to the cloud platform over one or more networks, including using network coding to provide efficient transmission. In the cloud platform, optionally using massively parallel computational capability, a plurality of different neural networks of various types (including modular forms, structure-adaptive forms, hybrids, and the like) may be used to undertake prediction, classification, control functions, and provide other outputs as described in connection with expert systems disclosed throughout this disclosure. The different neural networks may be structured to compete with each other (optionally including use evolutionary algorithms, genetic algorithms, or the like), such that an appropriate type of neural network, with appropriate input sets, weights, node types and functions, and the like, may be selected, such as by an expert system, for a specific task involved in a given context, workflow, environment process, system, or the like.

In embodiments, methods and systems described herein that involve an expert system or self-organization capability may use a feed forward neural network, which moves information in one direction, such as from a data input, like a data source related to at least one resource or parameter related to a transactional environment, such as any of the data sources mentioned throughout this disclosure, through a series of neurons or nodes, to an output. Data may move from the input nodes to the output nodes, optionally passing through one or more hidden nodes, without loops. In embodiments, feed forward neural networks may be constructed with various types of units, such as binary McCulloch-Pitts neurons, the simplest of which is a perceptron.

In embodiments, methods and systems described herein that involve an expert system or self-organization capability may use a capsule neural network, such as for prediction, classification, or control functions with respect to a transactional environment, such as relating to one or more of the machines and automated systems described throughout this disclosure.

In embodiments, methods and systems described herein that involve an expert system or self-organization capability may use a radial basis function (RBF) neural network, which may be ideal in some situations involving interpolation in a multi-dimensional space (such as where interpolation is helpful in optimizing a multi-dimensional function, such as for optimizing a data marketplace as described here, optimizing the efficiency or output of a power generation system, a factory system, or the like, or other situation involving multiple dimensions. In embodiments, each neuron in the RBF neural network stores an example from a training set as a "prototype." Linearity involved in the functioning of this neural network offers RBF the advantage of not typically suffering from problems with local minima or maxima.

In embodiments, methods and systems described herein that involve an expert system or self-organization capability may use a radial basis function (RBF) neural network, such as one that employs a distance criterion with respect to a center (e.g., a Gaussian function). A radial basis function may be applied as a replacement for a hidden layer, such as a sigmoidal hidden layer transfer, in a multi-layer perceptron. An RBF network may have two layers, such as where an input is mapped onto each RBF in a hidden layer. In embodiments, an output layer may comprise a linear combination of hidden layer values representing, for example, a mean predicted output. The output layer value may provide an output that is the same as or similar to that of a regression model in statistics. In classification problems, the output layer may be a sigmoid function of a linear combination of hidden layer values, representing a posterior probability. Performance in both cases is often improved by shrinkage techniques, such as ridge regression in classical statistics. This corresponds to a prior belief in small parameter values (and therefore smooth output functions) in a Bayesian framework. RBF networks may avoid local minima, because the only parameters that are adjusted in the learning process are the linear mapping from hidden layer to output layer. Linearity ensures that the error surface is quadratic and therefore has a single minimum. In regression problems, this may be found in one matrix operation. In classification problems, the fixed non-linearity introduced by the sigmoid output function may be handled using an iteratively re-weighted least squares function or the like. RBF networks may use kernel methods such as support vector machines (SVM) and Gaussian processes (where the RBF is the kernel function). A non-linear kernel function may be used to project the input data into a space where the learning problem may be solved using a linear model.

In embodiments, an RBF neural network may include an input layer, a hidden layer, and a summation layer. In the input layer, one neuron appears in the input layer for each predictor variable. In the case of categorical variables, N−1 neurons are used, where N is the number of categories. The input neurons may, in embodiments, standardize the value ranges by subtracting the median and dividing by the interquartile range. The input neurons may then feed the values to each of the neurons in the hidden layer. In the hidden layer, a variable number of neurons may be used (determined by the training process). Each neuron may consist of a radial basis function that is centered on a point with as many dimensions as a number of predictor variables. The spread (e.g., radius) of the RBF function may be different for each dimension. The centers and spreads may be determined by training. When presented with the vector of input values from the input layer, a hidden neuron may compute a Euclidean distance of the test case from the neuron's center point and then apply the RBF kernel function to this distance, such as using the spread values. The resulting value may then be passed to the summation layer. In the summation layer, the value coming out of a neuron in the hidden layer may be multiplied by a weight associated with the neuron and may add to the weighted values of other neurons. This sum becomes the output. For classification problems, one output is produced (with a separate set of weights and summation units) for each target category. The value output for a category is the probability that the case being evaluated has that category. In training of an RBF, various parameters may be determined, such as the number of neurons in a hidden layer, the coordinates of the center of each hidden-layer function, the spread of each function in each dimension, and the weights applied to outputs as they pass to the summation layer. Training may be used by clustering algorithms (such as k-means clustering), by evolutionary approaches, and the like.

In embodiments, a recurrent neural network may have a time-varying, real-valued (more than just zero or one) activation (output). Each connection may have a modifiable real-valued weight. Some of the nodes are called labeled nodes, some output nodes, and others hidden nodes. For supervised learning in discrete time settings, training sequences of real-valued input vectors may become sequences of activations of the input nodes, one input vector at a time. At each time step, each non-input unit may compute its current activation as a nonlinear function of the weighted sum of the activations of all units from which it receives connections. The system may explicitly activate (independent of incoming signals) some output units at certain time steps.

In embodiments, methods and systems described herein that involve an expert system or self-organization capability may use a self-organizing neural network, such as a Kohonen self-organizing neural network, such as for visualization of views of data, such as low-dimensional views of high-dimensional data. The self-organizing neural network may apply competitive learning to a set of input data, such as from one or more sensors or other data inputs from or associated with a transactional environment, including any machine or component that relates to the transactional environment. In embodiments, the self-organizing neural network may be used to identify structures in data, such as unlabeled data, such as in data sensed from a range of data sources about or sensors in or about in a transactional environment, where sources of the data are unknown (such as where events may be coming from any of a range of unknown sources). The self-organizing neural network may organize structures or patterns in the data, such that they may be recognized, analyzed, and labeled, such as identifying market behavior structures as corresponding to other events and signals.

In embodiments, methods and systems described herein that involve an expert system or self-organization capability may use a recurrent neural network, which may allow for a bi-directional flow of data, such as where connected units (e.g., neurons or nodes) form a directed cycle. Such a network may be used to model or exhibit dynamic temporal behavior, such as involved in dynamic systems, such as a wide variety of the automation systems, machines and devices described throughout this disclosure, such as an automated agent interacting with a marketplace for purposes of collecting data, testing spot market transactions, execution transactions, and the like, where dynamic system behavior involves complex interactions that a user may desire to understand, predict, control and/or optimize. For example, the recurrent neural network may be used to anticipate the state of a market, such as one involving a dynamic process or action, such as a change in state of a resource that is traded in or that enables a marketplace of transactional environment. In embodiments, the recurrent neural network may use internal memory to process a sequence of inputs, such as from other nodes and/or from sensors and other data inputs from or about the transactional environment, of the various types described herein. In embodiments, the recurrent neural network may also be used for pattern recognition, such as for recognizing a machine, component, agent, or other item based on a behavioral signature, a profile, a set of feature vectors (such as in an audio file or image), or the like. In a non-limiting example, a recurrent neural network may recognize a shift in an operational mode of a marketplace or machine by learning to classify the shift from a training data set consisting of a stream of data from one or more data sources of sensors applied to or about one or more resources.

In embodiments, methods and systems described herein that involve an expert system or self-organization capability may use a modular neural network, which may comprise a series of independent neural networks (such as ones of various types described herein) that are moderated by an intermediary. Each of the independent neural networks in the modular neural network may work with separate inputs, accomplishing subtasks that make up the task the modular network as whole is intended to perform. For example, a modular neural network may comprise a recurrent neural network for pattern recognition, such as to recognize what type of machine or system is being sensed by one or more sensors that are provided as input channels to the modular network and an RBF neural network for optimizing the behavior of the machine or system once understood. The intermediary may accept inputs of each of the individual neural networks, process them, and create output for the modular neural network, such an appropriate control parameter, a prediction of state, or the like.

Combinations among any of the pairs, triplets, or larger combinations, of the various neural network types described herein, are encompassed by the present disclosure. This may include combinations where an expert system uses one neural network for recognizing a pattern (e.g., a pattern indicating a problem or fault condition) and a different neural network for self-organizing an activity or workflow based on the recognized pattern (such as providing an output governing autonomous control of a system in response to the recognized condition or pattern). This may also include combinations where an expert system uses one neural network for classifying an item (e.g., identifying a machine, a component, or an operational mode) and a different neural network for predicting a state of the item (e.g., a fault state, an operational state, an anticipated state, a maintenance state, or the like). Modular neural networks may also include situations where an expert system uses one neural network for determining a state or context (such as a state of a machine, a process, a workflow, a marketplace, a storage system, a network, a data collector, or the like) and a different neural network for self-organizing a process involving the state or context (e.g., a data storage process, a network coding process, a network selection process, a data marketplace process, a power generation process, a manufacturing process, a refining process, a digging process, a boring process, or other process described herein).

In embodiments, methods and systems described herein that involve an expert system or self-organization capability may use a physical neural network where one or more hardware elements is used to perform or simulate neural behavior. In embodiments, one or more hardware neurons may be configured to stream voltage values, current values, or the like that represent sensor data, such as to calculate information from analog sensor inputs representing energy consumption, energy production, or the like, such as by one or more machines providing energy or consuming energy for one or more transactions. One or more hardware nodes may be configured to stream output data resulting from the activity of the neural net. Hardware nodes, which may comprise one or more chips, microprocessors, integrated circuits, programmable logic controllers, application-specific integrated circuits, field-programmable gate arrays, or the like, may be provided to optimize the machine that is producing or consuming energy, or to optimize another parameter of some part of a neural net of any of the types described herein. Hardware nodes may include hardware for acceleration of calculations (such as dedicated processors for performing basic or more sophisticated calculations on input data to provide outputs, dedicated processors for filtering or compressing data, dedicated processors for de-compressing data, dedicated processors for compression of specific file or data types (e.g., for handling image data, video streams, acoustic signals, thermal images, heat maps, or the like), and the like. A physical neural network may be embodied in a data collector, including one that may be reconfigured by switching or routing inputs in varying configurations, such as to provide different neural net configurations within the data collector for handling different types of inputs (with the switching and configuration optionally under control of an expert system, which may include a software-based neural net located on the data collector or remotely). A physical, or at least partially physical, neural network may include physical hardware nodes located in a storage system, such as for storing data within a machine, a data storage system, a distributed ledger, a mobile device, a server, a cloud resource, or in a transactional environment, such as for accelerating input/output functions to one or more storage elements that supply data to or take data from the neural net. A physical, or at least partially physical, neural network may include physical hardware nodes located in a network, such as for transmitting data within, to or from an industrial environment, such as for accelerating input/output functions to one or more network nodes in the net, accelerating relay functions, or the like. In embodiments, of a physical neural network, an electrically adjustable resistance material may be used for emulating the function of a neural synapse. In embodiments, the physical hardware emulates the neurons, and software emulates the neural network between the neurons. In embodiments, neural networks complement conventional algorithmic computers. They are versatile and may be trained to perform appropriate functions without the need for any instructions, such as classification functions, optimization functions, pattern recognition functions, control functions, selection functions, evolution functions, and others.

In embodiments, methods and systems described herein that involve an expert system or self-organization capability may use a multilayered feed forward neural network, such as for complex pattern classification of one or more items, phenomena, modes, states, or the like. In embodiments, a multilayered feed forward neural network may be trained by an optimization technique, such as a genetic algorithm, such as to explore a large and complex space of options to find an optimum, or near-optimum, global solution. For example, one or more genetic algorithms may be used to train a multilayered feed forward neural network to classify complex phenomena, such as to recognize complex operational modes of machines, such as modes involving complex interactions among machines (including interference effects, resonance effects, and the like), modes involving non-linear phenomena, modes involving critical faults, such as where multiple, simultaneous faults occur, making root cause analysis difficult, and others. In embodiments, a multilayered feed forward neural network may be used to classify results from monitoring of a marketplace, such as monitoring systems, such as automated agents, that operate within the marketplace, as well as monitoring resources that enable the marketplace, such as computing, networking, energy, data storage, energy storage, and other resources.

In embodiments, methods and systems described herein that involve an expert system or self-organization capability may use a feed-forward, back-propagation multi-layer perceptron (MLP) neural network, such as for handling one or more remote sensing applications, such as for taking inputs from sensors distributed throughout various transactional environments. In embodiments, the MLP neural network may be used for classification of transactional environments and resource environments, such as spot markets, forward markets, energy markets, renewable energy credit (REC) markets, networking markets, advertising markets, spectrum markets, ticketing markets, rewards markets, compute markets, and others mentioned throughout this disclosure, as well as physical resources and environments that produce them, such as energy resources (including renewable energy environments, mining environments, exploration environments, drilling environments, and the like, including classification of geological structures (including underground features and above ground features), classification of materials (including fluids, minerals, metals, and the like), and other problems. This may include fuzzy classification.

In embodiments, methods and systems described herein that involve an expert system or self-organization capability may use a structure-adaptive neural network, where the structure of a neural network is adapted, such as based on a rule, a sensed condition, a contextual parameter, or the like. For example, if a neural network does not converge on a solution, such as classifying an item or arriving at a prediction, when acting on a set of inputs after some amount of training, the neural network may be modified, such as from a feed forward neural network to a recurrent neural network, such as by switching data paths between some subset of nodes from unidirectional to bi-directional data paths. The structure adaptation may occur under control of an expert system, such as to trigger adaptation upon occurrence of a trigger, rule, or event, such as recognizing occurrence of a threshold (such as an absence of a convergence to a solution within a given amount of time) or recognizing a phenomenon as requiring different or additional structure (such as recognizing that a system is varying dynamically or in a non-linear fashion). In one non-limiting example, an expert system may switch from a simple neural network structure like a feed forward neural network to a more complex neural network structure like a recurrent neural network, a convolutional neural network, or the like upon receiving an indication that a continuously variable transmission is being used to drive a generator, turbine, or the like in a system being analyzed.

In embodiments, methods and systems described herein that involve an expert system or self-organization capability may use an autoencoder, autoassociator or Diabolo neural network, which may be similar to a multilayer perceptron (MLP) neural network, such as where there may be an input layer, an output layer and one or more hidden layers connecting them. However, the output layer in the auto-encoder may have the same number of units as the input layer, where the purpose of the MLP neural network is to reconstruct its own inputs (rather than just emitting a target value). Therefore, the auto encoders may operate as an unsupervised learning model. An auto encoder may be used, for example, for unsupervised learning of efficient codings, such as for dimensionality reduction, for learning generative models of data, and the like. In embodiments, an auto-encoding neural network may be used to self-learn an efficient network coding for transmission of analog sensor data from a machine over one or more networks or of digital data from one or more data sources. In embodiments, an auto-encoding neural network may be used to self-learn an efficient storage approach for storage of streams of data.

In embodiments, methods and systems described herein that involve an expert system or self-organization capability may use a probabilistic neural network (PNN), which, in embodiments, may comprise a multi-layer (e.g., four-layer) feed forward neural network, where layers may include input layers, hidden layers, pattern/summation layers and an output layer. In an embodiment of a PNN algorithm, a parent probability distribution function (PDF) of each class may be approximated, such as by a Parzen window and/or a non-parametric function. Then, using the PDF of each class, the class probability of a new input is estimated, and Bayes' rule may be employed, such as to allocate it to the class with the highest posterior probability. A PNN may embody a Bayesian network and may use a statistical algorithm or analytic technique, such as Kernel Fisher discriminant analysis technique. The PNN may be used for classification and pattern recognition in any of a wide range of embodiments disclosed herein. In one non-limiting example, a probabilistic neural network may be used to predict a fault condition of an engine based on collection of data inputs from sensors and instruments for the engine.

In embodiments, methods and systems described herein that involve an expert system or self-organization capability may use a time delay neural network (TDNN), which may comprise a feed forward architecture for sequential data that recognizes features independent of sequence position. In embodiments, to account for time shifts in data, delays are added to one or more inputs, or between one or more nodes, so that multiple data points (from distinct points in time) are analyzed together. A time delay neural network may form part of a larger pattern recognition system, such as using a perceptron network. In embodiments, a TDNN may be trained with supervised learning, such as where connection weights are trained with back propagation or under feedback. In embodiments, a TDNN may be used to process sensor data from distinct streams, such as a stream of velocity data, a stream of acceleration data, a stream of temperature data, a stream of pressure data, and the like, where time delays are used to align the data streams in time, such as to help understand patterns that involve understanding of the various streams (e.g., changes in price patterns in spot or forward markets).

In embodiments, methods and systems described herein that involve an expert system or self-organization capability may use a convolutional neural network (referred to in some cases as a CNN, a ConvNet, a shift invariant neural network, or a space invariant neural network), wherein the units are connected in a pattern similar to the visual cortex of the human brain. Neurons may respond to stimuli in a restricted region of space, referred to as a receptive field. Receptive fields may partially overlap, such that they collectively cover the entire (e.g., visual) field. Node responses may be calculated mathematically, such as by a convolution operation, such as using multilayer perceptrons that use minimal preprocessing. A convolutional neural network may be used for recognition within images and video streams, such as for recognizing a type of machine in a large environment using a camera system disposed on a mobile data collector, such as on a drone or mobile robot. In embodiments, a convolutional neural network may be used to provide a recommendation based on data inputs, including sensor inputs and other contextual information, such as recommending a route for a mobile data collector. In embodiments, a convolutional neural network may be used for processing inputs, such as for natural language processing of instructions provided by one or more parties involved in a workflow in an environment. In embodiments, a convolutional neural network may be deployed with a large number of neurons (e.g., 100,000, 500,000 or more), with multiple (e.g., 4, 5, 6 or more) layers, and with many (e.g., millions) of parameters. A convolutional neural net may use one or more convolutional nets.

In embodiments, methods and systems described herein that involve an expert system or self-organization capability may use a regulatory feedback network, such as for recognizing emergent phenomena (such as new types of behavior not previously understood in a transactional environment).

In embodiments, methods and systems described herein that involve an expert system or self-organization capability may use a self-organizing map (SOM), involving unsupervised learning. A set of neurons may learn to map points in an input space to coordinates in an output space. The input space may have different dimensions and topology from the output space, and the SOM may preserve these while mapping phenomena into groups.

In embodiments, methods and systems described herein that involve an expert system or self-organization capability may use a learning vector quantization neural net (LVQ). Prototypical representatives of the classes may parameterize, together with an appropriate distance measure, in a distance-based classification scheme.

In embodiments, methods and systems described herein that involve an expert system or self-organization capability may use an echo state network (ESN), which may comprise a recurrent neural network with a sparsely connected, random hidden layer. The weights of output neurons may be changed (e.g., the weights may be trained based on feedback). In embodiments, an ESN may be used to handle time series patterns, such as, in an example, recognizing a pattern of events associated with a market, such as the pattern of price changes in response to stimuli.

In embodiments, methods and systems described herein that involve an expert system or self-organization capability may use a Bi-directional, recurrent neural network (BRNN), such as using a finite sequence of values (e.g., voltage values from a sensor) to predict or label each element of the sequence based on both the past and the future context of the element. This may be done by adding the outputs of two RNNs, such as one processing the sequence from left to right, the other one from right to left. The combined outputs are the predictions of target signals, such as ones provided by a teacher or supervisor. A bi-directional RNN may be combined with a long short-term memory RNN.

In embodiments, methods and systems described herein that involve an expert system or self-organization capability may use a hierarchical RNN that connects elements in various ways to decompose hierarchical behavior, such as into useful subprograms. In embodiments, a hierarchical RNN may be used to manage one or more hierarchical templates for data collection in a transactional environment.

In embodiments, methods and systems described herein that involve an expert system or self-organization capability may use a stochastic neural network, which may introduce random variations into the network. Such random variations may be viewed as a form of statistical sampling, such as Monte Carlo sampling.

In embodiments, methods and systems described herein that involve an expert system or self-organization capability may use a genetic scale recurrent neural network. In such embodiments, an RNN (often an LSTM) is used where a series is decomposed into a number of scales where every scale informs the primary length between two consecutive points. A first order scale consists of a normal RNN, a second order consists of all points separated by two indices and so on. The Nth order RNN connects the first and last node. The outputs from all the various scales may be treated as a committee of members, and the associated scores may be used genetically for the next iteration.

In embodiments, methods and systems described herein that involve an expert system or self-organization capability may use a committee of machines (COM), comprising a collection of different neural networks that together "vote" on a given example. Because neural networks may suffer from local minima, starting with the same architecture and training, but using randomly different initial weights often gives different results. A CoM tends to stabilize the result.

In embodiments, methods and systems described herein that involve an expert system or self-organization capability may use an associative neural network (ASNN), such as involving an extension of a committee of machines that combines multiple feed forward neural networks and a k-nearest neighbor technique. It may use the correlation between ensemble responses as a measure of distance amid the analyzed cases for the kNN. This corrects the bias of the neural network ensemble. An associative neural network may have a memory that may coincide with a training set. If new data become available, the network instantly improves its predictive ability and provides data approximation (self-learns) without retraining. Another important feature of ASNN is the possibility to interpret neural network results by analysis of correlations between data cases in the space of models.

In embodiments, methods and systems described herein that involve an expert system or self-organization capability may use an instantaneously trained neural network (ITNN), where the weights of the hidden and the output layers are mapped directly from training vector data.

In embodiments, methods and systems described herein that involve an expert system or self-organization capability may use a spiking neural network, which may explicitly consider the timing of inputs. The network input and output may be represented as a series of spikes (such as a delta function or more complex shapes). SNNs may process information in the time domain (e.g., signals that vary over time, such as signals involving dynamic behavior of markets or transactional environments). They are often implemented as recurrent networks.

In embodiments, methods and systems described herein that involve an expert system or self-organization capability may use a dynamic neural network that addresses nonlinear multivariate behavior and includes learning of time-dependent behavior, such as transient phenomena and delay effects. Transients may include behavior of shifting market variables, such as prices, available quantities, available counterparties, and the like.

In embodiments, cascade correlation may be used as an architecture and supervised learning algorithm, supplementing adjustment of the weights in a network of fixed topology. Cascade-correlation may begin with a minimal network, then automatically trains, and adds new hidden units one by one, creating a multi-layer structure. Once a new hidden unit has been added to the network, its input-side weights may be frozen. This unit then becomes a permanent feature-detector in the network, available for producing outputs or for creating other, more complex feature detectors. The cascade-correlation architecture may learn quickly, determine its own size and topology, and retain the structures it has built even if the training set changes and requires no back-propagation.

In embodiments, methods and systems described herein that involve an expert system or self-organization capability may use a neuro-fuzzy network, such as involving a fuzzy inference system in the body of an artificial neural network. Depending on the type, several layers may simulate the processes involved in a fuzzy inference, such as fuzzification, inference, aggregation and defuzzification. Embedding a fuzzy system in a general structure of a neural net as the benefit of using available training methods to find the parameters of a fuzzy system.

In embodiments, methods and systems described herein that involve an expert system or self-organization capability may use a compositional pattern-producing network (CPPN), such as a variation of an associative neural network (ANN) that differs the set of activation functions and how they are applied. While typical ANNs often contain only sigmoid functions (and sometimes Gaussian functions), CPPNs may include both types of functions and many others. Furthermore, CPPNs may be applied across the entire space of possible inputs, so that they may represent a complete image. Since they are compositions of functions, CPPNs in effect encode images at infinite resolution and may be sampled for a particular display at whatever resolution is optimal.

This type of network may add new patterns without re-training. In embodiments, methods and systems described herein that involve an expert system or self-organization capability may use a one-shot associative memory network, such as by creating a specific memory structure, which assigns each new pattern to an orthogonal plane using adjacently connected hierarchical arrays.

In embodiments, methods and systems described herein that involve an expert system or self-organization capability may use a hierarchical temporal memory (HTM) neural network, such as involving the structural and algorithmic properties of the neocortex. HTM may use a biomimetic model based on memory-prediction theory. HTM may be used to discover and infer the high-level causes of observed input patterns and sequences.

In embodiments, methods and systems described herein that involve an expert system or self-organization capability may use a holographic associative memory (HAM) neural network, which may comprise an analog, correlation-based, associative, stimulus-response system. Information may be mapped onto the phase orientation of complex numbers. The memory is effective for associative memory tasks, generalization and pattern recognition with changeable attention.

In embodiments, various embodiments involving network coding may be used to code transmission data among network nodes in a neural net, such as where nodes are located in one or more data collectors or machines in a transactional environment.

In embodiments, one or more of the controllers, circuits, systems, data collectors, storage systems, network elements, or the like as described throughout this disclosure may be embodied in or on an integrated circuit, such as an analog, digital, or mixed signal circuit, such as a microprocessor, a programmable logic controller, an application-specific integrated circuit, a field programmable gate array, or other circuits, such as embodied on one or more chips disposed on one or more circuit boards, such as to provide in hardware (with potentially accelerated speed, energy performance, input-output performance, or the like) one or more of the functions described herein. This may include setting up circuits with up to billions of logic gates, flip-flops, multiplexers, and other circuits in a small space, facilitating high speed processing, low power dissipation, and reduced manufacturing cost compared with board-level integration. In embodiments, a digital IC, typically a microprocessor, digital signal processor, microcontroller, or the like may use Boolean algebra to process digital signals to embody complex logic, such as involved in the circuits, controllers, and other systems described herein. In embodiments, a data collector, an expert system, a storage system, or the like may be embodied as a digital integrated circuit, such as a logic IC, memory chip, interface IC (e.g., a level shifter, a serializer, a deserializer, and the like), a power management IC and/or a programmable device; an analog integrated circuit, such as a linear IC, RF IC, or the like, or a mixed signal IC, such as a data acquisition IC (including A/D converters, D/A converter, digital potentiometers) and/or a clock/timing IC.

In embodiments of the present invention, may include a platform for facilitating a self-contained AI/ML-driven robotic in vitro fertilization (IVF) system.

In embodiments of the present invention, may include an IVF-as-a-service platform.

In embodiments of the present invention, a self-contained AI/ML-driven robotic IVF system and platform may have a semen preparation system, an egg retrieval system, an insemination system, an incubation system, a freezing system, and a storage system.

In embodiments of the present invention, a platform for facilitating a self-contained AI/ML-driven robotic IVF system and platform may have a software development kit (SDK) for development or configuration of a set of services for integration with the system.

In embodiments of the present invention, a platform for facilitating a self-contained AI/ML-driven robotic IVF system and platform may have a data storage system.

In embodiments of the present invention, a platform for facilitating a self-contained AI/ML-driven robotic IVF system and platform may have a machine learning and/or artificial intelligence system configured to reduce the cost of an IVF treatment per patient.

In embodiments of the present invention, a platform for facilitating a self-contained AI/ML-driven robotic IVF system and platform may have a machine learning and/or artificial intelligence system configured to reduce lab expenses per cycle of IVF.

In embodiments of the present invention, a platform for facilitating a self-contained AI/ML-driven robotic IVF system and platform may have a machine learning and/or artificial intelligence system configured to reduce lab expenses per baby.

In embodiments of the present invention, a platform for facilitating a self-contained AI/ML-driven robotic IVF system and platform may have a machine learning and/or artificial intelligence system configured to reduce the time required for pregnancy per patient.

In embodiments of the present invention, a platform for facilitating a self-contained AI/ML-driven robotic IVF system and platform may have a machine learning and/or artificial intelligence system configured to reduce the average number of cycles required for pregnancy per patient.

In embodiments of the present invention, a platform for facilitating a self-contained AI/ML-driven robotic IVF system and platform may have a machine learning and/or artificial intelligence system configured to reduce the number of medication injections required per patient for an IVF treatment.

In embodiments of the present invention, a platform for facilitating a self-contained AI/ML-driven robotic IVF system and platform may have a machine learning and/or artificial intelligence system configured to reduce complications from IVF treatments.

In embodiments of the present invention, a platform for facilitating a self-contained AI/ML-driven robotic IVF system and platform may have a machine learning and/or artificial intelligence system configured to reduce the cost to manufacture IVF equipment.

In embodiments of the present invention, a platform for facilitating a self-contained AI/ML-driven robotic IVF system and platform may have a machine learning and/or artificial intelligence system configured to optimize the egg to embryo yield.

In embodiments of the present invention, a platform for facilitating a self-contained AI/ML-driven robotic IVF system and platform may have a machine learning and/or artificial intelligence system configured to optimize the number of viable embryos available for transfer.

In embodiments of the present invention, a platform for facilitating a self-contained AI/ML-driven robotic IVF system and platform may have a machine learning and/or artificial intelligence system configured to optimize CPA loading.

In embodiments of the present invention, a platform for facilitating a self-contained AI/ML-driven robotic IVF system and platform may have a machine learning and/or artificial intelligence system configured to reduce sample management errors.

In embodiments of the present invention, a platform for facilitating a self-contained AI/ML-driven robotic IVF system and platform may have a machine learning and/or artificial intelligence system configured to optimize hyaluronidase exposure.

In embodiments of the present invention, a platform for facilitating a self-contained AI/ML-driven robotic IVF system and platform may have a machine learning and/or artificial intelligence system configured to reduce the number of inadvertently discarded eggs.

In embodiments of the present invention, a platform for facilitating a self-contained AI/ML-driven robotic IVF system and platform may have a machine learning and/or artificial intelligence system configured to improve embryo formation.

In embodiments of the present invention, a platform for facilitating a self-contained AI/ML-driven robotic IVF system and platform may have a machine learning and/or artificial intelligence system configured to reduce harmful crystallizations.

In embodiments of the present invention, a platform for facilitating a self-contained AI/ML-driven robotic IVF system and platform may have a machine learning and/or artificial intelligence system configured to reduce the use of toxic chemicals.

In embodiments of the present invention, a platform for facilitating a self-contained AI/ML-driven robotic IVF system and platform may have a machine learning and/or artificial intelligence system configured to reduce embryo misplacement.

In embodiments of the present invention, a platform for facilitating a self-contained AI/ML-driven robotic IVF system and platform may have a machine learning and/or artificial intelligence system configured to improve the level of detail in IVF imaging.

In embodiments of the present invention, a platform for facilitating a self-contained AI/ML-driven robotic IVF system and platform may have a machine learning and/or artificial intelligence system configured to optimize the ovarian response rate.

In embodiments of the present invention, a platform for facilitating a self-contained AI/ML-driven robotic IVF system and platform may have a machine learning and/or artificial intelligence system configured to optimize the egg retrieval rate.

In embodiments of the present invention, a platform for facilitating a self-contained AI/ML-driven robotic IVF system and platform may have a machine learning and/or artificial intelligence system configured to optimize the egg fertilization rate.

In embodiments of the present invention, a platform for facilitating a self-contained AI/ML-driven robotic IVF system and platform may have a machine learning and/or artificial intelligence system configured to optimize the embryo development rate.

In embodiments of the present invention, a platform for facilitating a self-contained AI/ML-driven robotic IVF system and platform may have a machine learning and/or artificial intelligence system configured to optimize embryo quality.

In embodiments of the present invention, a platform for facilitating a self-contained AI/ML-driven robotic IVF system and platform may have a machine learning and/or artificial intelligence system configured to improve the proportion of viable embryos produced per cycle.

In embodiments of the present invention, a platform for facilitating a self-contained AI/ML-driven robotic IVF system and platform may have a machine learning and/or artificial intelligence system configured to optimize the pregnancy rate.

In embodiments of the present invention, a platform for facilitating a self-contained AI/ML-driven robotic IVF system and platform may have a machine learning and/or artificial intelligence system configured to optimize the live birth rate.

In embodiments of the present invention, a platform for facilitating a self-contained AI/ML-driven robotic IVF system and platform may have a machine learning and/or artificial intelligence system configured to optimize the blastocyst formation rate.

In embodiments of the present invention, a platform for facilitating a self-contained AI/ML-driven robotic IVF system and platform may have a machine learning and/or artificial intelligence system configured to increase the embryos produced per treatment cycle.

In embodiments of the present invention, a platform for facilitating a self-contained AI/ML-driven robotic IVF system and platform may have a machine learning and/or artificial intelligence system configured to optimize safety.

In embodiments of the present invention, a platform for facilitating a self-contained AI/ML-driven robotic IVF system and platform may have a machine learning and/or artificial intelligence system configured to reduce damage to egg cells during denudation.

In embodiments of the present invention, a platform for facilitating a self-contained AI/ML-driven robotic IVF system and platform may have a machine learning and/or artificial intelligence system configured to optimize the degree and/or rate of tilting of a container.

In embodiments of the present invention, a platform for facilitating a self-contained AI/ML-driven robotic IVF system and platform may have a machine learning and/or artificial intelligence system configured to predict fertilization of an egg.

In embodiments of the present invention, a platform for facilitating a self-contained AI/ML-driven robotic IVF system and platform may have a machine learning and/or artificial intelligence system configured to predict blastocyst formation.

In embodiments of the present invention, a platform for facilitating a self-contained AI/ML-driven robotic IVF system and platform may have a machine learning and/or artificial intelligence system configured to predict embryo quality.

In embodiments of the present invention, a platform for facilitating a self-contained AI/ML-driven robotic IVF system and platform may have a machine learning and/or artificial intelligence system configured to predict embryo development.

In embodiments of the present invention, a platform for facilitating a self-contained AI/ML-driven robotic IVF system and platform may have a machine learning and/or artificial intelligence system configured to predict the movement and/or location of a sperm cell.

In embodiments of the present invention, a platform for facilitating a self-contained AI/ML-driven robotic IVF system and platform may have a machine learning and/or artificial intelligence system configured to perform a 3D reconstruction of cells.

In embodiments of the present invention, a platform for facilitating a self-contained AI/ML-driven robotic IVF system and platform may have a machine learning and/or artificial intelligence system configured to measure the non-inferiority of an IVF treatment.

In embodiments of the present invention, a platform for facilitating a self-contained AI/ML-driven robotic IVF system and platform may have a machine learning and/or artificial intelligence system configured to measure embryo quality.

In embodiments of the present invention, a platform for facilitating a self-contained AI/ML-driven robotic IVF system and platform may have a machine learning and/or artificial intelligence system configured to measure sperm cell quality.

In embodiments of the present invention, a platform for facilitating a self-contained AI/ML-driven robotic IVF system and platform may have a machine learning and/or artificial intelligence system configured to measure sperm viscosity.

In embodiments of the present invention, a platform for facilitating a self-contained AI/ML-driven robotic IVF system and platform may have a machine learning and/or artificial intelligence system configured to measure egg cell quality.

In embodiments of the present invention, a platform for facilitating a self-contained AI/ML-driven robotic IVF system and platform may have a machine learning and/or artificial intelligence system configured to measure ovarian response rate.

In embodiments of the present invention, a platform for facilitating a self-contained AI/ML-driven robotic IVF system and platform may have a machine learning and/or artificial intelligence system configured to measure egg retrieval rate.

In embodiments of the present invention, a platform for facilitating a self-contained AI/ML-driven robotic IVF system and platform may have a machine learning and/or artificial intelligence system configured to measure egg fertilization rate.

In embodiments of the present invention, a platform for facilitating a self-contained AI/ML-driven robotic IVF system and platform may have a machine learning and/or artificial intelligence system configured to measure embryo development rate.

In embodiments of the present invention, a platform for facilitating a self-contained AI/ML-driven robotic IVF system and platform may have a machine learning and/or artificial intelligence system configured to measure pregnancy rate.

In embodiments of the present invention, a platform for facilitating a self-contained AI/ML-driven robotic IVF system and platform may have a machine learning and/or artificial intelligence system configured to measure live birth rate.

In embodiments of the present invention, a platform for facilitating a self-contained AI/ML-driven robotic IVF system and platform may have a machine learning and/or artificial intelligence system configured to measure blastocyst formation rate.

In embodiments of the present invention, a platform for facilitating a self-contained AI/ML-driven robotic IVF system and platform may have a machine learning and/or artificial intelligence system configured to measure the maturity and/or denudation of an egg cell.

In embodiments of the present invention, a platform for facilitating a self-contained AI/ML-driven robotic IVF system and platform may have a machine learning and/or artificial intelligence system configured to confirm a successful injection.

In embodiments of the present invention, a platform for facilitating a self-contained AI/ML-driven robotic IVF system and platform may have a machine learning and/or artificial intelligence system configured to rank and/or select embryos.

In embodiments of the present invention, a platform for facilitating a self-contained AI/ML-driven robotic IVF system and platform may have a machine learning and/or artificial intelligence system configured to rank and/or select sperm.

In embodiments of the present invention, a platform for facilitating a self-contained AI/ML-driven robotic IVF system and platform may have a machine learning and/or artificial intelligence system configured to rank and/or select eggs and/or oocytes.

In embodiments of the present invention, a platform for facilitating a self-contained AI/ML-driven robotic IVF system and platform may have a machine learning and/or artificial intelligence system configured to select a sperm cell for desired embryo attributes.

In embodiments of the present invention, a platform for facilitating a self-contained AI/ML-driven robotic IVF system and platform may have a machine learning and/or artificial intelligence system configured to select eggs for desired embryo attributes.

In embodiments of the present invention, a platform for facilitating a self-contained AI/ML-driven robotic IVF system and platform may have a machine learning and/or artificial intelligence system configured to guide a needle so that sperm may be loaded.

In embodiments of the present invention, a platform for facilitating a self-contained AI/ML-driven robotic IVF system and platform may have a machine learning and/or artificial intelligence system configured to guide a needle during injection.

In embodiments of the present invention, a platform for facilitating a self-contained AI/ML-driven robotic IVF system and platform may have a machine learning and/or artificial intelligence system configured to sort sperm.

In embodiments of the present invention, a platform for facilitating a self-contained AI/ML-driven robotic IVF system and platform may have a machine learning and/or artificial intelligence system configured to control the tilting of a container.

In embodiments of the present invention, a platform for facilitating a self-contained AI/ML-driven robotic IVF system and platform may have a machine learning and/or artificial intelligence system configured to control the depth of penetration of a pipette into a sample.

In embodiments of the present invention, a platform for facilitating a self-contained AI/ML-driven robotic IVF system and platform may have a machine learning and/or artificial intelligence system to control the position and/or rotation of the stage.

In embodiments of the present invention, a platform for facilitating a self-contained AI/ML-driven robotic IVF system and platform may have a machine learning and/or artificial intelligence system to control the plunging time and/or angle of a cryodevice.

In embodiments of the present invention, a platform for facilitating a self-contained AI/ML-driven robotic IVF system and platform may have a machine learning and/or artificial intelligence system configured to identify sperm.

In embodiments of the present invention, a platform for facilitating a self-contained AI/ML-driven robotic IVF system and platform may have a machine learning and/or artificial intelligence system configured to identify parts of a sperm cell.

In embodiments of the present invention, a platform for facilitating a self-contained AI/ML-driven robotic IVF system and platform may have a machine learning and/or artificial intelligence system configured to identify egg cells.

In embodiments of the present invention, a platform for facilitating a self-contained AI/ML-driven robotic IVF system and platform may have a machine learning and/or artificial intelligence system configured to identify embryos.

In embodiments of the present invention, a platform for facilitating a self-contained AI/ML-driven robotic IVF system and platform may have an artificial intelligence system for enabling semi-autonomous and supervised robotics.

In embodiments of the present invention, a platform for facilitating a self-contained AI/ML-driven robotic IVF system and platform may have fully autonomous artificial intelligence.

In embodiments of the present invention, a platform for facilitating a self-contained AI/ML-driven robotic IVF system and platform may have a digital twin system for providing a set of digital twins representing an IVF system.

In embodiments of the present invention, a platform for facilitating a self-contained AI/ML-driven robotic IVF system and platform may have a digital twin system for providing a set of digital twins representing a semen preparation system.

In embodiments of the present invention, a platform for facilitating a self-contained AI/ML-driven robotic IVF system and platform may have a digital twin system for providing a set of digital twins representing an egg discovery system.

In embodiments of the present invention, a platform for facilitating a self-contained AI/ML-driven robotic IVF system and platform may have a digital twin system for providing a set of digital twins representing an insemination system.

In embodiments of the present invention, a platform for facilitating a self-contained AI/ML-driven robotic IVF system and platform may have a digital twin system for providing a set of digital twins representing an incubation system.

In embodiments of the present invention, a platform for facilitating a self-contained AI/ML-driven robotic IVF system and platform may have a digital twin system for providing a set of digital twins representing a freezing system.

In embodiments of the present invention, a platform for facilitating a self-contained AI/ML-driven robotic IVF system and platform may have a digital twin system for providing a set of digital twins representing a storage system.

In embodiments of the present invention, a platform for facilitating a self-contained AI/ML-driven robotic IVF system and platform may have a digital twin system for providing a set of digital twins representing an IVF system and/or subsystem may have a system for visualizing temperature data in the set of digital twins.

In embodiments of the present invention, a platform for facilitating a self-contained AI/ML-driven robotic IVF system and platform may have a digital twin system for providing a set of digital twins representing an IVF process.

In embodiments of the present invention, a platform for facilitating a self-contained AI/ML-driven robotic IVF system and platform may have a digital twin system for providing a set of digital twins representing a set of sperm cells.

In embodiments of the present invention, a platform for facilitating a self-contained AI/ML-driven robotic IVF system and platform may have a digital twin system for providing a set of digital twins representing a set of egg cells.

In embodiments of the present invention, a platform for facilitating a self-contained AI/ML-driven robotic IVF system and platform may have a digital twin system for providing a set of digital twins representing a set of embryos.

In embodiments of the present invention, a platform for facilitating a self-contained AI/ML-driven robotic IVF system and platform may have a digital twin system for providing a set of digital twins representing an IVF system and/or subsystem may have a system for visualizing time lapse imaging data relating to a set of embryos in the set of digital twins.

In embodiments of the present invention, a platform for facilitating a self-contained AI/ML-driven robotic IVF system and platform may have proprietary data.

In embodiments of the present invention, a platform for facilitating a self-contained AI/ML-driven robotic IVF system and platform may have a robotic process automation system trained by experts to execute an IVF process.

In embodiments of the present invention, a platform for facilitating a self-contained AI/ML-driven robotic IVF system and platform may have a robotic process automation system trained by experts to execute a semen preparation process.

In embodiments of the present invention, a platform for facilitating a self-contained AI/ML-driven robotic IVF system and platform may have a robotic process automation system trained by experts to execute an egg retrieval process.

In embodiments of the present invention, a platform for facilitating a self-contained AI/ML-driven robotic IVF system and platform may have a robotic process automation system trained by experts to execute an insemination process.

In embodiments of the present invention, a platform for facilitating a self-contained AI/ML-driven robotic IVF system and platform may have a robotic process automation system trained by experts to execute an incubation process.

In embodiments of the present invention, a platform for facilitating a self-contained AI/ML-driven robotic IVF system and platform may have a robotic process automation system trained by experts to execute a freezing process.

In embodiments of the present invention, a platform for facilitating a self-contained AI/ML-driven robotic IVF system and platform may have a robotic process automation system trained by experts to execute a storage process.

In embodiments of the present invention, a platform for facilitating a self-contained AI/ML-driven robotic IVF system and platform may have models and/or expert systems for enabling an IVF system.

In embodiments of the present invention, a platform for facilitating a self-contained AI/ML-driven robotic IVF system and platform may have models and/or expert systems for enabling a semen preparation system.

In embodiments of the present invention, a platform for facilitating a self-contained AI/ML-driven robotic IVF system and platform may have models and/or expert systems for enabling an egg retrieval system.

In embodiments of the present invention, a platform for facilitating a self-contained AI/ML-driven robotic IVF system and platform may have models and/or expert systems for enabling an insemination system.

In embodiments of the present invention, a platform for facilitating a self-contained AI/ML-driven robotic IVF system and platform may have models and/or expert systems for enabling an incubation system.

In embodiments of the present invention, a platform for facilitating a self-contained AI/ML-driven robotic IVF system and platform may have models and/or expert systems for enabling a freezing system.

In embodiments of the present invention, a platform for facilitating a self-contained AI/ML-driven robotic IVF system and platform may have models and/or expert systems for enabling a storage system.

In embodiments of the present invention, a platform for facilitating a self-contained AI/ML-driven robotic IVF system and platform may have an IVF-in-a-box kit.

In embodiments of the present invention, a self-contained AI/ML-driven robotic semen preparation system for in vitro fertilization (IVF).

In embodiments of the present invention, a self-contained AI/ML-driven robotic egg retrieval system for in vitro fertilization (IVF).

In embodiments of the present invention, a self-contained AI/ML-driven robotic insemination system for in vitro fertilization (IVF).

In embodiments of the present invention, a self-contained AI/ML-driven robotic incubation system for in vitro fertilization (IVF).

In embodiments of the present invention, a self-contained AI/ML-driven robotic freezing system for in vitro fertilization (IVF).

In embodiments of the present invention, a self-contained AI/ML-driven robotic storage system for in vitro fertilization (IVF).

In embodiments of the present invention, a self-contained AI/ML-driven robotic IVF system and platform may have a set of robotic handling systems.

In embodiments of the present invention, a self-contained AI/ML-driven robotic IVF system and platform may have a set of robotic handling systems configured to handle liquids.

In embodiments of the present invention, a self-contained AI/ML-driven robotic IVF system and platform may have a set of robotic handling systems configured to handle sperm.

In embodiments of the present invention, a self-contained AI/ML-driven robotic IVF system and platform may have a set of robotic tilting systems configured to tilt containers.

In embodiments of the present invention, a self-contained AI/ML-driven robotic IVF system and platform may have a set of robotic pipetting machines.

In embodiments of the present invention, a self-contained AI/ML-driven robotic IVF system and platform may have a robotic swim-up system integrated with a set of robotic pipetting machines.

In embodiments of the present invention, a self-contained AI/ML-driven robotic IVF system and platform may have a robotic swim-up system integrated with a set of robotic pipetting machines and integrated with a microfluidic sperm and/or seminal plasma separation device.

In embodiments of the present invention, a self-contained AI/ML-driven robotic IVF system and platform may have a robotic handling system configured for egg retrieval.

In embodiments of the present invention, a self-contained AI/ML-driven robotic IVF system and platform may have a robotic handling system configured for egg and/or oocyte isolation.

In embodiments of the present invention, a self-contained AI/ML-driven robotic IVF system and platform may have a set of vibrating needles.

In embodiments of the present invention, a self-contained AI/ML-driven robotic IVF system and platform may have a robotic incubator.

In embodiments of the present invention, a self-contained AI/ML-driven robotic IVF system and platform may have a robotic handling system for separating sperm from toxic material.

In embodiments of the present invention, a self-contained AI/ML-driven robotic IVF system and platform may have a robotic intracytoplasmic sperm injection (ICSI) system.

In embodiments of the present invention, a self-contained AI/ML-driven robotic IVF system and platform may have a robotic laser-assisted intracytoplasmic sperm injection (ICSI) system.

In embodiments of the present invention, a self-contained AI/ML-driven robotic IVF system and platform may have a robotic intracytoplasmic sperm injection (ICSI) system may have piezo-assisted drilling.

In embodiments of the present invention, a self-contained AI/ML-driven robotic IVF system and platform may have a robotic intracytoplasmic sperm injection (ICSI) system configured for partially denuded eggs.

In embodiments of the present invention, a self-contained AI/ML-driven robotic IVF system and platform may have a robotic intracytoplasmic sperm injection (ICSI) system configured for fully denuded eggs.

In embodiments of the present invention, a self-contained AI/ML-driven robotic IVF system and platform may have a system for exposing an egg cell to sperm.

In embodiments of the present invention, a self-contained AI/ML-driven robotic IVF system and platform may have a robotic handling system configured for robotic oocyte denudation.

In embodiments of the present invention, a self-contained AI/ML-driven robotic IVF system and platform may have a robotic handling system configured for robotic oocyte denudation and may have a system configured to provide hyaluronidase.

In embodiments of the present invention, a self-contained AI/ML-driven robotic IVF system and platform may have a robotic handling system configured for vitrification.

In embodiments of the present invention, a self-contained AI/ML-driven robotic IVF system and platform may have a robotic handling system configured for the loading and/or unloading of cryoprotectant.

In embodiments of the present invention, a self-contained AI/ML-driven robotic IVF system and platform may have a robotic handling system configured for robotic egg handling and/or retrieval.

In embodiments of the present invention, a self-contained AI/ML-driven robotic IVF system and platform may have a robotic dish preparation system.

In embodiments of the present invention, a self-contained AI/ML-driven robotic IVF system and platform may have a robotic sterilization system.

In embodiments of the present invention, a self-contained AI/ML-driven robotic IVF system and platform may have a robotic waste handling system.

In embodiments of the present invention, a self-contained AI/ML-driven robotic IVF system and platform may have a micromanipulator.

In embodiments of the present invention, a self-contained AI/ML-driven robotic IVF system and platform may have a robotic dish holder for holding a dish in a desired position.

In embodiments of the present invention, a self-contained AI/ML-driven robotic IVF system and platform may have a fluid handling system.

In embodiments of the present invention, a self-contained AI/ML-driven robotic IVF system and platform may have an environmental chamber.

In embodiments of the present invention, a self-contained AI/ML-driven robotic IVF system and platform may have a machine vision system configured to select, mobilize, and/or load sperm.

In embodiments of the present invention, a self-contained AI/ML-driven robotic IVF system and platform may have a machine vision system configured to rank sperm.

In embodiments of the present invention, a self-contained AI/ML-driven robotic IVF system and platform may have a machine vision system configured to rank eggs.

In embodiments of the present invention, a self-contained AI/ML-driven robotic IVF system and platform may have a machine vision system configured to rank embryos.

In embodiments of the present invention, a self-contained AI/ML-driven robotic IVF system and platform may have a machine vision system configured to identify a sperm cell.

In embodiments of the present invention, a self-contained AI/ML-driven robotic IVF system and platform may have a machine vision system configured to identify parts of a sperm cell.

In embodiments of the present invention, a self-contained AI/ML-driven robotic IVF system and platform may have a machine vision system configured to identify an egg cell.

In embodiments of the present invention, a self-contained AI/ML-driven robotic IVF system and platform may have a machine vision system configured to enable robotic insemination.

In embodiments of the present invention, a self-contained AI/ML-driven robotic IVF system and platform may have a machine vision system configured to confirm that a pipette tip is filled properly.

In embodiments of the present invention, a self-contained AI/ML-driven robotic IVF system and platform may have a machine vision system configured to detect the tip of a hollow pipette.

In embodiments of the present invention, a self-contained AI/ML-driven robotic IVF system and platform may have a machine vision system configured to detect the tip of a needle.

In embodiments of the present invention, a self-contained AI/ML-driven robotic IVF system and platform may have a machine vision system configured to detect the inside of a needle.

In embodiments of the present invention, a self-contained AI/ML-driven robotic IVF system and platform may have a machine vision system configured to identify structures under a microscope.

In embodiments of the present invention, a self-contained AI/ML-driven robotic IVF system and platform may have a machine vision system configured to determine optimal location to position a needle for penetration.

In embodiments of the present invention, a self-contained AI/ML-driven robotic IVF system and platform may have a machine vision system configured to determine the optimal location to shoot a sperm.

In embodiments of the present invention, a self-contained AI/ML-driven robotic IVF system and platform may have a machine vision system configured to detect the orientation of a sperm cell.

In embodiments of the present invention, a self-contained AI/ML-driven robotic IVF system and platform may have a machine vision system configured to detect droplets.

In embodiments of the present invention, a self-contained AI/ML-driven robotic IVF system and platform may have a machine vision system configured to detect the successful fertilization of an egg.

In embodiments of the present invention, a self-contained AI/ML-driven robotic IVF system and platform may have a machine vision system configured to identify characteristics of blastocysts.

In embodiments of the present invention, a self-contained AI/ML-driven robotic IVF system and platform may have a machine vision system configured to determine the location of a sample submerged in liquid nitrogen.

In embodiments of the present invention, a self-contained AI/ML-driven robotic IVF system and platform may have a machine vision system configured to detect a cumulus-oocyte complex (COC).

In embodiments of the present invention, a self-contained AI/ML-driven robotic IVF system and platform may have a machine vision system configured to detect a successful egg denudation.

In embodiments of the present invention, a self-contained AI/ML-driven robotic IVF system and platform may have a machine vision system configured to detect the maturity of an egg.

In embodiments of the present invention, a self-contained AI/ML-driven robotic IVF system and platform may have advanced optics to eliminate the need for egg denudation.

In embodiments of the present invention, a self-contained AI/ML-driven robotic IVF system and platform may have advanced optics to determine whether chromosomes are complete in an embryo or egg.

In embodiments of the present invention, a self-contained AI/ML-driven robotic IVF system and platform may have an optical coherence tomography (oct) system for oocyte discovery and/or selection.

In embodiments of the present invention, a self-contained AI/ML-driven robotic IVF system and platform may have an inverted microscope.

In embodiments of the present invention, a self-contained AI/ML-driven robotic IVF system and platform may have an inverted microscope and may have a set of motorized lenses.

In embodiments of the present invention, a self-contained AI/ML-driven robotic IVF system and platform may have an inverted microscope and may have a set of micromanipulators.

In embodiments of the present invention, a self-contained AI/ML-driven robotic IVF system and platform may have advanced microscopes that are outside the range of visible light.

In embodiments of the present invention, a self-contained AI/ML-driven robotic IVF system and platform may have a system for enabling time-lapse microscopy.

In embodiments of the present invention, a self-contained AI/ML-driven robotic IVF system and platform may have a microfluidic chamber for enabling semen preparation.

In embodiments of the present invention, a self-contained AI/ML-driven robotic IVF system and platform may have a set of laser systems.

In embodiments of the present invention, a self-contained AI/ML-driven robotic IVF system and platform may have a set of laser immobilization systems.

In embodiments of the present invention, a self-contained AI/ML-driven robotic IVF system and platform may have a specimen management system.

In embodiments of the present invention, a self-contained AI/ML-driven robotic IVF system and platform may have a specimen management system that uses QR codes for tracking specimens.

In embodiments of the present invention, a self-contained AI/ML-driven robotic IVF system and platform may have a specimen management system that uses RFID tags for tracking specimens.

In embodiments of the present invention, a self-contained AI/ML-driven robotic IVF system and platform may have a specimen management system that uses sample ids to identify samples.

In embodiments of the present invention, a self-contained AI/ML-driven robotic IVF system and platform may have a set of temperature sensors.

In embodiments of the present invention, a self-contained AI/ML-driven robotic IVF system and platform may have a set of pH sensors.

In embodiments of the present invention, a self-contained AI/ML-driven robotic IVF system and platform may have a set of oxygen sensors.

In embodiments of the present invention, a self-contained AI/ML-driven robotic IVF system and platform may have a set of carbon dioxide sensors.

In embodiments of the present invention, a self-contained AI/ML-driven robotic IVF system and platform may have a set of nitrogen sensors.

In embodiments of the present invention, a self-contained AI/ML-driven robotic IVF system and platform may have a set of light sensors.

In embodiments of the present invention, a self-contained AI/ML-driven robotic IVF system and platform may have a set of cameras.

In embodiments of the present invention, a self-contained AI/ML-driven robotic IVF system and platform may have a set of humidity sensors.

In embodiments of the present invention, a self-contained AI/ML-driven robotic IVF system and platform may have a set of pressure sensors.

In embodiments of the present invention, a self-contained AI/ML-driven robotic IVF system and platform may have a set of vibration sensors.

In embodiments of the present invention, a self-contained AI/ML-driven robotic IVF system and platform may have edge computing systems.

In embodiments of the present invention, a self-contained AI/ML-driven robotic IVF system and platform may have connectivity systems.

In embodiments of the present invention, a self-contained AI/ML-driven robotic IVF system and platform may have cloud systems.

In embodiments of the present invention, a self-contained AI/ML-driven robotic IVF system and platform may have proprietary consumables that hold cells.

In embodiments of the present invention, a self-contained AI/ML-driven robotic IVF system and platform may have a thawing system for thawing specimens.

In embodiments of the present invention, a self-contained AI/ML-driven robotic IVF system and platform may have a timing system for personalizing the timing of a biological event at the egg level.

In embodiments of the present invention, a self-contained AI/ML-driven robotic IVF system and platform may have an ultrasound system configured to break up protein structures in sperm.

In embodiments of the present invention, a self-contained AI/ML-driven robotic IVF system and platform may have a hot plate system.

In embodiments of the present invention, a self-contained AI/ML-driven robotic IVF system and platform may have an emergency stop system that shuts off motors and heaters.

In embodiments of the present invention, a self-contained AI/ML-driven robotic IVF system and platform may have an air filter system.

In embodiments of the present invention, a self-contained AI/ML-driven robotic IVF system and platform may have a motorized stage system.

In embodiments of the present invention, a self-contained AI/ML-driven robotic IVF system and platform may have a motorized stage system and may have a system for rotating a dish.

In embodiments of the present invention, a self-contained AI/ML-driven robotic IVF system and platform may have an aspiration system to hold cells in place.

In embodiments of the present invention, a self-contained AI/ML-driven robotic IVF system and platform may have a graphite-based film system for covering culture media in the incubator.

In embodiments of the present invention, a self-contained AI/ML-driven robotic IVF system and platform may have a cryodevice for enabling vitrification of cells may have a magnetic end attached to a magnetic handle, which enables the release of the cryodevice.

In embodiments of the present invention, a self-contained AI/ML-driven robotic IVF system and platform may have a system for removing water from an embryo.

In embodiments of the present invention, a platform for facilitating a self-contained AI/ML-driven robotic IVF system and platform may have a liquid immersion cooling tank system may have a system for integrating with third party systems.

In embodiments of the present invention, a platform for facilitating a self-contained AI/ML-driven robotic IVF system and platform may have end user interfaces.

In embodiments of the present invention, a platform for facilitating a self-contained AI/ML-driven robotic IVF system and platform may have an application programming interface (API) system that manages one or more APIs of the platform, so as to expose the APIs to one or more related applications or third-party systems.

In embodiments of the present invention, a platform for facilitating a self-contained AI/ML-driven robotic IVF system and platform may have a user interface.

In embodiments of the present invention, a platform for facilitating a self-contained AI/ML-driven robotic IVF system and platform may have a notification system for providing notifications to platform users.

In embodiments of the present invention, a platform for facilitating a self-contained AI/ML-driven robotic IVF system and platform may have a system for integrating with a mobile application.

In embodiments of the present invention, a platform for facilitating a self-contained AI/ML-driven robotic IVF system and platform wherein platform services are accessible via the web.

In embodiments of the present invention, a platform for facilitating a self-contained AI/ML-driven robotic IVF system and platform may have a mobile application for enabling mobile access to the platform.

In embodiments of the present invention, a platform for facilitating a self-contained AI/ML-driven robotic IVF system and platform may have a dashboard and/or visualization system.

In embodiments of the present invention, a platform for facilitating a self-contained AI/ML-driven robotic IVF system and platform may have a dashboard and/or visualization system wherein the dashboard and/or visualization system presents time-lapsed image data for a set of embryos.

In embodiments of the present invention, a platform for facilitating a self-contained AI/ML-driven robotic IVF system and platform may have healthcare system application programming interfaces (APIs).

In embodiments of the present invention, a platform for facilitating a self-contained AI/ML-driven robotic IVF system and platform may have ob-gyn interfaces.

In embodiments of the present invention, an IVF lab-as-a-service platform.

In embodiments of the present invention, a platform for facilitating a self-contained AI/ML-driven robotic IVF system and platform may have data integration and connectivity with and among the semen preparation system, the egg retrieval system, the insemination system, the incubation system, the freezing system, and the storage system.

In embodiments of the present invention, a platform for facilitating a self-contained AI/ML-driven robotic IVF system and platform may have systems integration with healthcare data and/or information systems.

In embodiments of the present invention, a platform for facilitating a self-contained AI/ML-driven robotic IVF system and platform may have systems integration with payor (insurer) and/or financial systems.

In embodiments of the present invention, a platform for facilitating a self-contained AI/ML-driven robotic IVF system and platform may have systems integration with ObGyn office systems.

In embodiments of the present invention, a platform for facilitating a self-contained AI/ML-driven robotic IVF system and platform may have systems integration with other healthcare laboratories.

In embodiments of the present invention, a platform for facilitating a self-contained AI/ML-driven robotic IVF system and platform may have a quality assurance system.

In embodiments of the present invention, a method for facilitating self-contained AI/ML-driven robotic in vitro fertilization (IVF) may have a semen preparation process, an egg retrieval process, an insemination process, an incubation process, a freezing process, and a storage process.

In embodiments of the present invention, a method for facilitating self-contained AI/ML-driven robotic in vitro fertilization (IVF) may have a hormonal preparation process.

In embodiments of the present invention, a method for facilitating self-contained AI/ML-driven robotic in vitro fertilization (IVF) may have an embryology process.

In embodiments of the present invention, a method for facilitating self-contained AI/ML-driven robotic semen preparation.

In embodiments of the present invention, a method for facilitating self-contained AI/ML-driven egg retrieval.

In embodiments of the present invention, a method for facilitating self-contained
AI/ML-driven insemination.

In embodiments of the present invention, a method for facilitating self-contained AI/ML-driven incubation.

In embodiments of the present invention, a method for facilitating self-contained AI/ML-driven freezing of IVF specimens.

In embodiments of the present invention, a method for facilitating self-contained
AI/ML-driven thawing of IVF specimens.

In embodiments of the present invention, a method for facilitating self-contained AI/ML-driven surgical sperm retrieval.

In embodiments of the present invention, a method for facilitating self-contained AI/ML-driven transferring of IVF specimens.

In embodiments of the present invention, a method for facilitating self-contained AI/ML-driven storage of IVF specimens.

In embodiments of the present invention, a method for facilitating self-contained AI/ML-driven robotic in vitro fertilization (IVF) may have workgroup processes for approval and governance.

In embodiments of the present invention, a method for facilitating self-contained AI/ML-driven robotic in vitro fertilization (IVF) may have data privacy processes.

In embodiments of the present invention, a platform for facilitating a self-contained AI/ML-driven robotic IVF system and platform may have a system for managing operational control workflows.

In embodiments of the present invention, a platform for facilitating a self-contained AI/ML-driven robotic IVF system and platform may have a system for managing hormone support and monitoring workflows.

In embodiments of the present invention, a platform for facilitating a self-contained AI/ML-driven robotic IVF system and platform may have a system for managing the timing and sequencing of the IVF process.

In embodiments of the present invention, a platform for facilitating a self-contained AI/ML-driven robotic IVF system and platform may have a system for measuring and/or detecting the readiness for each process in the IVF/ICSI platform.

In embodiments of the present invention, a platform for facilitating a self-contained AI/ML-driven robotic IVF system and platform may have a system for managing supervised autonomy workflows.

In embodiments of the present invention, a platform for facilitating a self-contained AI/ML-driven robotic IVF system and platform may have a system for managing the washing and incubation of a cumulus-oocyte complex (COC).

In embodiments of the present invention, a method for 3D printing self-contained AI/ML-driven robotic IVF system and platform may have software and data enablement of 3D printed components and manufacturing processes.

In embodiments of the present invention, a 3D printed self-contained AI/ML-driven robotic in vitro fertilization (IVF) system.

In embodiments of the present invention, a self-contained AI/ML-driven robotic IVF system and platform may have 3D printed components.

In embodiments of the present invention, a platform for facilitating a self-contained AI/ML-driven robotic IVF system and platform may have a system configured to perform seminal plasma contamination testing.

In embodiments of the present invention, a platform for facilitating a self-contained AI/ML-driven robotic IVF system and platform may have a system configured to perform sperm motility testing.

In embodiments of the present invention, a platform for facilitating a self-contained AI/ML-driven robotic IVF system and platform may have a system configured to perform semen analysis.

In embodiments of the present invention, a platform for facilitating a self-contained AI/ML-driven robotic IVF system and platform may have a system configured to perform DNA fragmentation testing.

In embodiments of the present invention, a platform for facilitating a self-contained AI/ML-driven robotic IVF system and platform may have a system configured to perform ai-assisted DNA fragmentation testing.

In embodiments of the present invention, a platform for facilitating a self-contained AI/ML-driven robotic IVF system and platform may have a system configured to perform oocyte activation testing after denudation.

In embodiments of the present invention, a platform for facilitating a self-contained AI/ML-driven robotic IVF system and platform may have biological materials.

In embodiments of the present invention, a platform for facilitating a self-contained AI/ML-driven robotic IVF system and platform may have a protein rich liquid for combination with sperm.

In embodiments of the present invention, a platform for facilitating a self-contained AI/ML-driven robotic IVF system and platform may have hormonal agents.

In embodiments of the present invention, a platform for facilitating a self-contained AI/ML-driven robotic IVF system and platform may have chemical materials.

In embodiments of the present invention, a self-contained AI/ML-driven robotic IVF system and platform may have a system for automatically providing hyaluronidase for enzymatic denudation of oocytes.

In embodiments of the present invention, a self-contained AI/ML-driven robotic IVF system and platform may have a system for enabling oocyte denudation by exposure to sticky culture media.

In embodiments of the present invention, a self-contained AI/ML-driven robotic IVF system and platform may have a system for enabling oocyte denudation by stage movement using a dish with 3D printed mesh.

In embodiments, provided herein is a self-contained AI/ML-driven robotic IVF system having a sperm preparation system, an egg retrieval system, COC location/preparation (e.g., identification, isolation from follicular fluid, placement into media for culture, maturity and quality assessment, denudation, and preparation for fertilization or cryopreservation), insemination system, an incubation system, a freezing system, and a storage system.

In embodiments, provided herein is a self-contained AI/ML-driven robotic IVF system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a software development kit (SDK) for development or configuration of a set of services for integration with the system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a data storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce the cost of an IVF treatment per patient.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce lab expenses per cycle of IVF.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce lab expenses per baby.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce the time required for pregnancy per patient.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce the average number of cycles required for pregnancy per patient.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce the number of medication injections required per patient for an IVF treatment.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce complications from IVF treatments.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce the cost to manufacture IVF equipment.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the egg to embryo yield.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the number of viable embryos available for transfer.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize CPA loading.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce sample management errors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize hyaluronidase exposure.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce the number of inadvertently discarded eggs.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to improve embryo formation.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce harmful crystallizations.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce the use of toxic chemicals.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce embryo misplacement.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to improve the level of detail in IVF imaging.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the ovarian response rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the egg retrieval rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the egg fertilization rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the embryo development rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize embryo quality.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to improve the proportion of viable embryos produced per cycle.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the pregnancy rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the live birth rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the blastocyst formation rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to increase the embryos produced per treatment cycle.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize safety.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to reduce damage to egg cells during denudation.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to optimize the degree and/or rate of tilting of a container.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to predict fertilization of an egg.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to predict blastocyst formation.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to predict embryo quality.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to predict embryo development.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to predict the movement and/or location of a sperm cell.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to perform a 3D reconstruction of cells.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure the non-inferiority of an IVF treatment.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure embryo quality.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure sperm cell quality.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure sperm viscosity.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure egg cell quality.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure ovarian response rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure egg retrieval rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure egg fertilization rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure embryo development rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure pregnancy rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure live birth rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure blastocyst formation rate.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to measure the maturity and/or denudation of an egg cell.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to confirm a successful injection.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to rank and/or select embryos.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to rank and/or select sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to rank and/or select eggs and/or oocytes.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to select a sperm cell for desired embryo attributes.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or storage system and having a machine learning and/or artificial intelligence system configured to select eggs for desired embryo attributes.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to guide a needle so that sperm may be loaded.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to guide a needle during injection.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to sort sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to control the tilting of a container.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to control the depth of penetration of a pipette into a sample.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system to control the position and/or rotation of the stage.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system to control the plunging time and/or angle of a cryodevice.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to identify sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to identify parts of a sperm cell.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to identify egg cells.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine learning and/or artificial intelligence system configured to identify embryos.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an artificial intelligence system for enabling semi-autonomous and supervised robotics.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having fully autonomous artificial intelligence.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing an IVF system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing a sperm preparation system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing an egg discovery system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing an insemination system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing an incubation system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing a freezing system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing a storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing an IVF system and/or subsystem having a system for visualizing temperature data in the set of digital twins.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing an IVF process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing a set of sperm cells.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing a set of egg cells.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing a set of embryos.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a digital twin system for providing a set of digital twins representing an IVF system and/or subsystem having a system for visualizing time lapse imaging data relating to a set of embryos in the set of digital twins.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having proprietary data.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic process automation system trained by experts to execute an IVF process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic process automation system trained by experts to execute a sperm preparation process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic process automation system trained by experts to execute an egg retrieval process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic process automation system trained by experts to execute an insemination process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic process automation system trained by experts to execute an incubation process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic process automation system trained by experts to execute a freezing process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic process automation system trained by experts to execute a storage process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having models and/or expert systems for enabling an IVF system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having models and/or expert systems for enabling a sperm preparation system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having models and/or expert systems for enabling an egg retrieval system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having models and/or expert systems for enabling an insemination system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having models and/or expert systems for enabling an incubation system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having models and/or expert systems for enabling a freezing system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having models and/or expert systems for enabling a storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an IVF-in-a-box kit.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of robotic handling systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of robotic handling systems configured to handle liquids.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of robotic handling systems configured to handle sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of robotic tilting systems configured to tilt containers.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of robotic pipetting machines.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic swim-up system integrated with a set of robotic pipetting machines.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic swim-up system integrated with a set of robotic pipetting machines and integrated with a microfluidic sperm and/or seminal plasma separation device.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic handling system configured for egg retrieval.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic handling system configured for egg and/or oocyte isolation.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of vibrating needles.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic incubator.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic handling system for separating sperm from toxic material.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic intracytoplasmic sperm injection (ICSI) system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic laser-assisted intracytoplasmic sperm injection (ICSI) system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic intracytoplasmic sperm injection (ICSI) system having Piezo-assisted drilling.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic intracytoplasmic sperm injection (ICSI) system configured for partially denuded eggs.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic intracytoplasmic sperm injection (ICSI) system configured for fully denuded eggs.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for exposing an egg cell to sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic handling system configured for robotic oocyte denudation.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic handling system configured for robotic oocyte denudation and having a system configured to provide hyaluronidase.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic handling system configured for vitrification.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic handling system configured for the loading and/or unloading of cryoprotectant.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic handling system configured for robotic egg handling and/or retrieval.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic dish preparation system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic sterilization system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic waste handling system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a micromanipulator.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a robotic dish holder for holding a dish in a desired position.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a fluid handling system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an environmental chamber.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to select, mobilize, and/or load sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to rank sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to rank eggs.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to rank embryos.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to identify a sperm cell.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to identify parts of a sperm cell.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to identify an egg cell.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to enable robotic insemination.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to confirm that a pipette tip is filled properly.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to detect the tip of a hollow pipette.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to detect the tip of a needle.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to detect the inside of a needle.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to identify structures under a microscope.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to determine optimal location to position a needle for penetration.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to determine the optimal location to shoot a sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to detect the orientation of a sperm cell.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to detect droplets.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to detect the successful fertilization of an egg.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to identify characteristics of blastocysts.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to determine the location of a sample submerged in liquid nitrogen.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to detect a cumulus-oocyte complex (COC).

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to detect a successful egg denudation.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a machine vision system configured to detect the maturity of an egg.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having advanced optics to eliminate the need for egg denudation.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having advanced optics to determine whether chromosomes are complete in an embryo or egg.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an optical coherence tomography (OCT) system for oocyte discovery and/or selection.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an inverted microscope.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an inverted microscope having a set of motorized lenses.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an inverted microscope having a set of micromanipulators.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having advanced microscopes that are outside the range of visible light.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for enabling time-lapse microscopy.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a microfluidic chamber for enabling sperm preparation.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of laser systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of laser immobilization systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a specimen management system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a specimen management system that uses QR codes for tracking specimens.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a specimen management system that uses RFID tags for tracking specimens.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a specimen management system that uses sample IDs to identify samples.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of temperature sensors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of pH sensors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of oxygen sensors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of carbon dioxide sensors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of nitrogen sensors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of light sensors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of cameras.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of humidity sensors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of pressure sensors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a set of vibration sensors.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having edge computing systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having connectivity systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having cloud systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having proprietary consumables that hold cells.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a thawing system for thawing specimens.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a timing system for personalizing the timing of a biological event at the egg level.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an ultrasound system configured to break up protein structures in sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a hot plate system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an emergency stop system that shuts off motors and heaters.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an air filter system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a motorized stage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a motorized stage system having a system for rotating a dish.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an aspiration system to hold cells in place.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a graphite-based film system for covering culture media in the incubator.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a cryodevice for enabling vitrification of cells having a magnetic end attached to a magnetic handle, which enables the release of the cryodevice.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for removing water from an embryo.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a liquid immersion cooling tank system having a system for integrating with third party systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having end user interfaces.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an application programming interface (API) system that manages one or more APIs of the platform, so as to expose the APIs to one or more related applications or third-party systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a user interface.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a notification system for providing notifications to platform users.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for integrating with a mobile application.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and wherein platform services are accessible via the web.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a mobile application for enabling mobile access to the platform.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a dashboard and/or visualization system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a dashboard and/or visualization system wherein the dashboard and/or visualization system presents time-lapsed image data for a set of embryos.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having healthcare system application programming interfaces (APIs).

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having OB-GYN interfaces.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having data integration and connectivity with and among the sperm preparation system, the egg retrieval system, the insemination system, the incubation system, the freezing system, and the storage system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having systems integration with healthcare data and/or information systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having systems integration with payor (insurer) and/or financial systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having systems integration with OBGYN office systems.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having systems integration with other healthcare laboratories.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a quality assurance system.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a sperm preparation process, an egg retrieval process, an insemination process, an incubation process, a freezing process, and a storage process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a hormonal preparation process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having an embryology process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having workgroup processes for approval and governance.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having data privacy processes.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for managing operational control workflows.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for managing hormone support and monitoring workflows.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for managing the timing and sequencing of the IVF process.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for measuring and/or detecting the readiness for each process of the IVF/ICSI platform.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for managing supervised autonomy workflows.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for managing the washing and incubation of a cumulus-oocyte complex (COC).

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having software and data enablement of 3D printed components and manufacturing processes.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having 3D printed components.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system configured to perform seminal plasma contamination testing.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system configured to perform sperm motility testing.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system configured to perform semen analysis.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system configured to perform DNA fragmentation testing.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system configured to perform AI-assisted DNA fragmentation testing.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system configured to perform oocyte activation testing after denudation.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having biological materials.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a protein rich liquid for combination with sperm.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having hormonal agents.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having chemical materials.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for automatically providing hyaluronidase for enzymatic denudation of oocytes.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for enabling oocyte denudation by exposure to sticky culture media.

In embodiments, provided herein is a self-contained AI/ML-driven robotic in vitro fertilization (IVF) system having a sperm preparation system, an egg retrieval system, COC location/preparation (e.g., identification, isolation from follicular fluid, placement into media for culture, maturity and quality assessment, denudation, and preparation for fertilization or cryopreservation), an insemination system, an incubation system, a freezing system, and a storage system and having a system for enabling oocyte denudation by stage movement using a dish with 3D printed mesh.

Figures 97, 98:
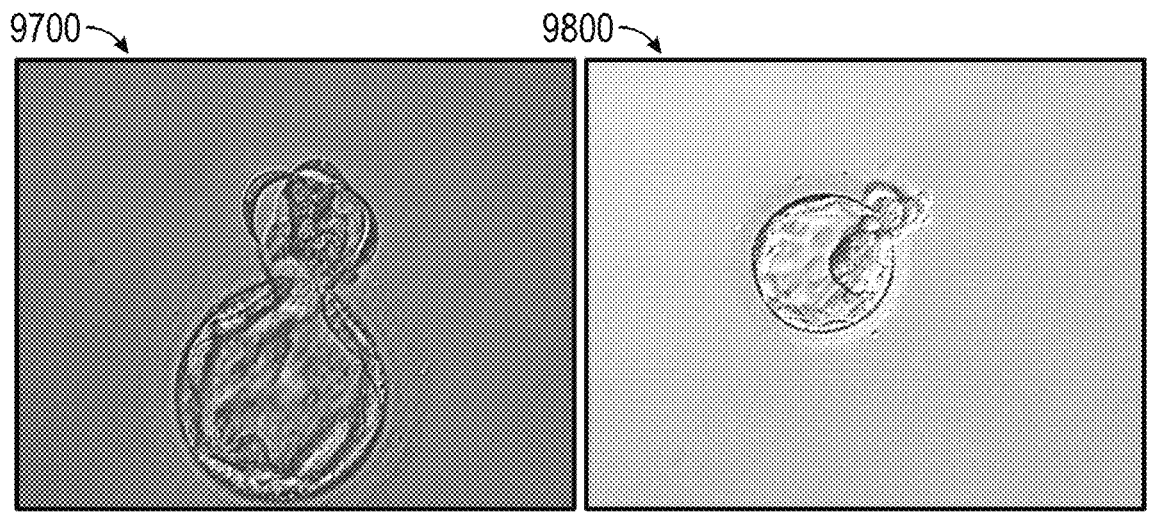
FIG. 97 is an electron microscope view of a non-standardized image used as input for the method based on image standardization, for the classification of human embryonic cells.
FIG. 98 is an electron microscope view of a second non-standardized image that is used as input for the method based on the standardization of images, for the classification of human embryonic cells.
Figures 99, 100:
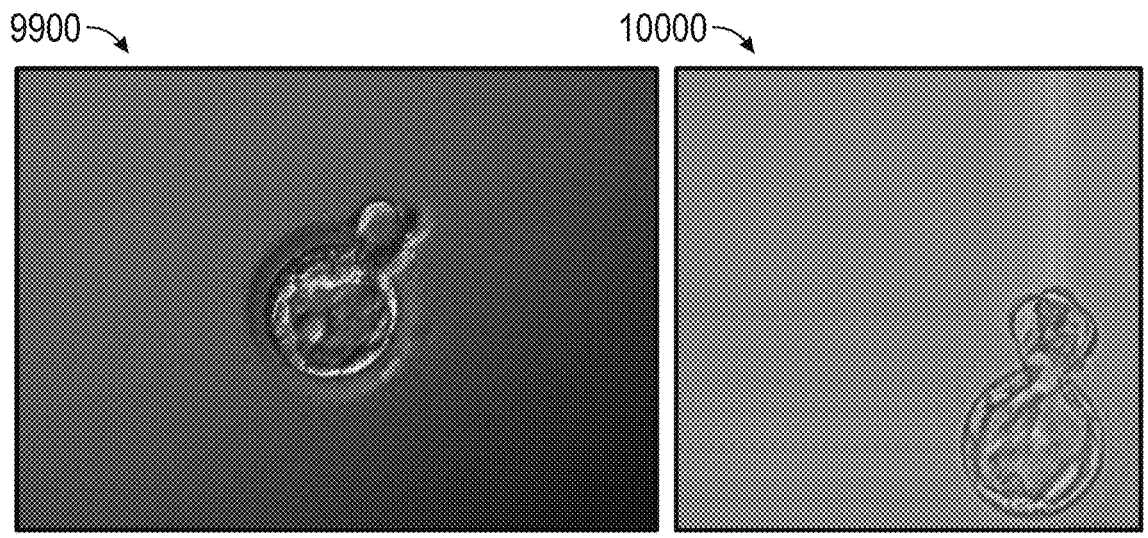
FIG. 99 is an electron microscope view of a third non-standardized image that is used as input for the method based on image standardization, for the classification of human embryonic cells.
FIG. 100 is an electron microscope view of the first image with pre-processing and/or conditioning treatment, where they have been pre-processed with the standardization parameters used in the method based on the standardization of images, for the classification of human embryonic cells.
Figures 101, 102:
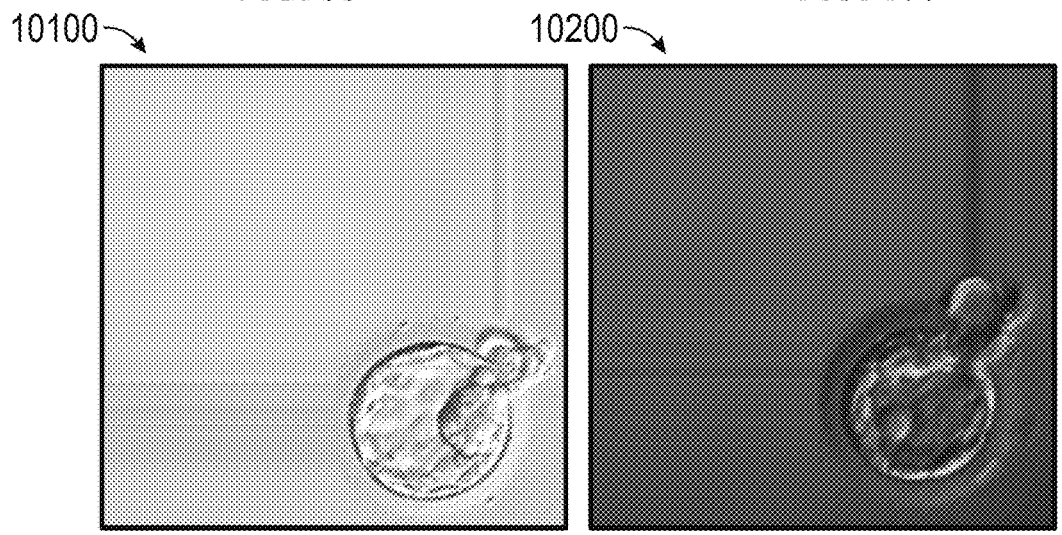
FIG. 101 is an electron microscope view of the second image with pre-processing and/or conditioning treatment, where they have been pre-processed with the standardization parameters used in the method based on the standardization of images, for the classification of human embryonic cells.
FIG. 102 is an electron microscope view of the third image with pre-processing and/or conditioning treatment, where they have been pre-processed with the standardization parameters used in the method based on the standardization of images, for the classification of human embryonic cells.
Figure 103:
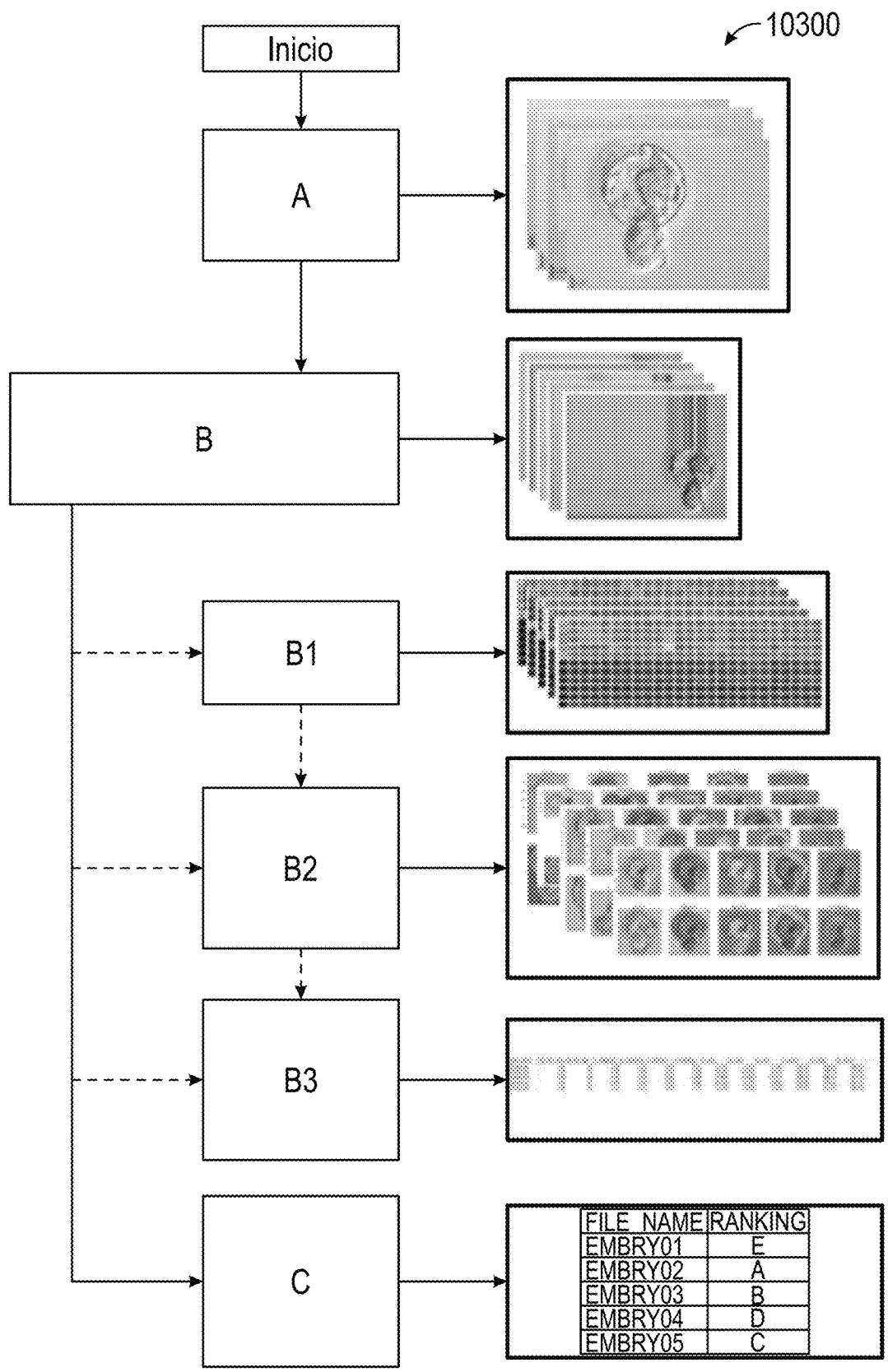
FIG. 103 is a view of the elements that make up example 1 of the method based on the conditioning and pre-processing of images, for the classification of human embryonic cells.
Figure 104:
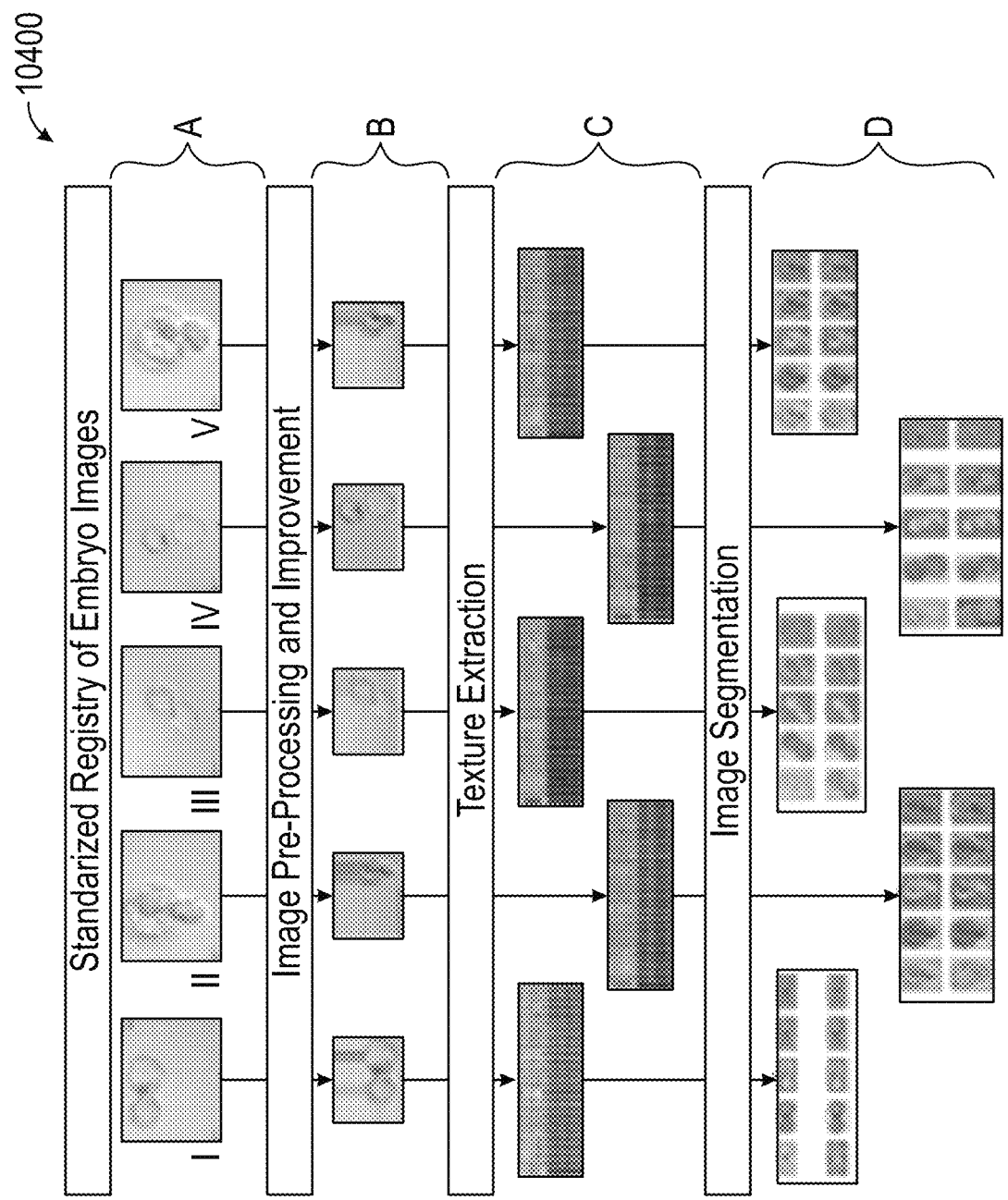
FIG. 104 depicts image segmentation using a registry of embryo images.

In embodiments of the present invention, FIG. 97 depicts an electron microscope view 9700 of a non-standardized image used as input for the method based on image standardization for the classification of human embryonic cells using the IVF/ICSI platform, as described herein. FIG. 98 depicts an electron microscope view 9800 of a second non-standardized image that may be used as input for the method based on the standardization of images, and/or for the classification of human embryonic cells. FIG. 99 depicts an electron microscope view 9900 of a third non-standardized image that may be used as input for the method based on image standardization, and/or for the classification of human embryonic cells. FIG. 100 depicts an electron microscope view 10000 of the first image with pre-processing and/or conditioning treatment, where it has been pre-processed with the standardization parameters used in the method based on the standardization of images, and/or for the classification of human embryonic cells. FIG. 101 depicts an electron microscope view 10100 of the second image with pre-processing and/or conditioning treatment, where it has been pre-processed with the standardization parameters used in the method based on the standardization of images, and/or for the classification of human embryonic cells. FIG. 102 depicts an electron microscope view 10200 of the third image with pre-processing and/or conditioning treatment, where it has been pre-processed with the standardization parameters used in the method based on the standardization of images for the classification of human embryonic cells. FIG. 103 depicts a view 10300 of the elements that make up example 1 with the steps of the method based on the conditioning and pre-processing of images for the classification of human embryonic cells. FIG. 104 depicts image segmentation using a registry of embryo images 10400.

In embodiments of the present invention, the method based on image conditioning and pre-processing for the classification of human embryonic cells, using the IVF/ICSI platform as described herein, may comprise the processes of:

1. Obtaining independent micrographies of one or at least one set of embryos: At this stage, a collection of micrographs may be made, at least one of which may correspond to an embryo (in the case of being a plurality of images, each set of they may be classified by each of the embryos independently), these images may come from the same or different equipment from which they have been obtained and in the same way their resolution and magnification may be different, in such a way that in this stage, a standardization of them may be carried out as follows:
   a. Each image may correspond to a single embryo.
   b. Each image may be individually analyzed and manipulated until the pixel to square micrometer or voxel to micrometer ratio is achieved. Cubic may be the same for the entire set of images, using interpolation techniques for this process;
   c. The image of the embryo may correspond to the blastocyst stage, generally between days 5 to 7 after the day of fertilization of the development of the embryo, each image may be obtained prior to any physical intervention such as freezing and/or biopsy that is intended to be performed;
   d. The images of the embryos may be taken in 2, 3 or 4 dimensions (3 spatial dimensions and one temporal) with any pixel or voxel reconstruction techniques. In the case that the micrograph is in 2 dimensions, the thickest area of the embryo may be identified defining the agenda of the longest possible diameter of the embryo seen in two dimensions; that the area of focus of the microscope is in the area of greatest diameter of the embryo; the focal plane is at the height of the embryo that represents the largest diameter in its 2D or 3D representation; it may be obtained manually, moving the vertical position of the focal plane, until it is close to the point of greatest diameter, in such a way that the trophectoderm may be observed as sharp as possible (that is, can be observed in clearly defined edges; obtain the minimum of blurring in the image), using a range of light, in such a way that the structures can be clearly observed and a contrast is obtained that allows the sharpness described above; The embryo may appear complete within the image and without obstructions, for example objects such as instruments, text added to the image, superimposed structures, among others, may not appear in it;

At the end of this stage there may be a plurality of independent images (in 2, 3 or 4 dimensions) pre-processed and improved (regardless of the source that produces it) with microscopy, high-definition digital cameras or other specialized techniques for image reconstruction. This stage of the process may be carried out separately for the purpose that the plurality of images show the modifications of the embryos in the period of time;
2. Pre-processing and improvement of images. Using a computer, artificial vision and/or machine learning strategies may be defined until a standardized image of the embryo is obtained; Through the use of deep learning techniques (deep learning) and/or artificial vision, relevant characteristics may be identified such as the ratio of pixel to square micrometer or voxel to cubic micrometer, the intensity distribution of the pixels or voxels, the responses to previously given convolutional filters, or other previously defined mathematical models that allow the identification of intensity patterns in 2, 3 or 4 dimensions such as roughness, contrast, brightness, saturation, smoothness, or particular shapes, for the prediction of embryonic characteristics such as the degree of collapse, or degradation, as well as the stage of the embryo. The parameters may be based on filters to identify a plurality of textures and/or other metrics based on the segmentation of cell types: where the plurality of textures can be at least those where one or a combination of detector masks are used of textures such as in 2 dimensions those of LAWS (where the energy of LAWS is obtained by detecting textures in images of the embryo that can be standardized, or improved by means of artificial vision strategies such as energy filters, of Gaussian, Laplacian and edge detectors) to identify textures on the original image and at least one variant of the original. To generate the variants, entropy filters with different radii of influence and Gaussian blur may be used. Once this activity has been carried out, the automatic cropping technique may be implemented, that is, the calculated textures are used, the k-means algorithm is used with a value of k of at least 2 to identify the pixels that belong to the background of which they belong the embryo or any instrument or material present in the photograph other than the embryo. Based on this 2—, 3- or 4-dimensional mask, the method may detect the edges to crop the image containing the embryo. As an alternative to automatic cropping based on the k-means algorithm, it is also possible to use an object identifier based on artificial intelligence, which allows the identification and subtraction of instruments, letters or other artifacts foreign to the embryo from the image. For the identification of the development stages of the embryo, a model of deep convolutional neural networks may be used that can classify embryos in one of three phases: a) expansion, b) hatching and c) hatched; or it can function as a regressor defining the percentage that is within the zona pellucida and that which is outside. With the classifier technique, a probability value [0-1] may be obtained where an image corresponds to one of these three classes with a prediction according to the model used.

For the identification of embryos that are collapsed (a natural process of embryos), a previously trained classifier may be used, which is identified with a probability index, or by means of a regressor that allows to identify the percentage of collapse that shows the image of the embryo. To identify the degree of degradation of an embryo, a previously trained classifier that uses a probability index that a given image falls within the class of "degraded" or "normal" may be used, or a previously trained regressor may be used, that allows to identify the percentage of degradation that the embryo presents through the image.

To identify the degree of snuffing out of an embryo within a development curve, a previously trained classifier may be used that uses a probability index that a given image falls within one or more classes that are associated with the degree of evolution or growth of the embryo according to the expected growth given the conditions of the embryo. As an alternative to the classifier, a previously trained regressor may be used that allows identifying the percentile in which it is found according to its growth and development, according to a reference of healthy embryos, or alternatively, statistical data can be used to locate the image of the embryo within a distribution of statistical parameters of growth such as the size of the different areas. In such a way that at the end of this stage there is an algorithm implemented in a computer that allows identifying the pixels or voxels that belong to at least one of the following five areas: i) background, ii) zona pellucida, iii) trophectoderm, iv) blastocele and/or v) inner cell mass. The supervised training may be carried out by means of manual labels on the texture vectors for each pixel or voxel, where from the predictions made at the pixel or voxel level, the predictions are subjected to a process to generate more homogeneous areas for each label, which involves the extraction of the blobs of a k-means (k=20) and of a process of erosion and expansion of the areas. An alternative to identify the different zones is to use a neural network model that contains an encoder and a decoder that manages to associate each pixel or voxel to one of the five labels: i) background, li) zona pellucida, iii) trophectoderm, iv) blastocele and/or v) Internal cell mass;

3. Assign feasibility potential. With the algorithm of the previous stage, in addition to the descriptors related to the phases, slow collapse and degradation, other descriptors may be obtained based on the following: original image, image with entropy filters, image with highlighted edges, polar image to starting from a centroid, and the areas identified by the segmentation methodology. Statistical descriptors may be used, or a fraction of them selected by descriptor selection methods, associated with the distribution of the data as measures of central tendency, dispersion, kurtosis, only for being illustrative but not limiting; in such a way that with the list of descriptors obtained from each embryo, together with patient history data (age and hours between fertilization and the image or images), the source of the embryo (laboratory preset: microscope, and objective), a deep, sequential neural network is trained, which may allow each embryo to be classified into one of two classes: good prognosis and poor prognosis. As an alternative, another classification algorithm such as vector support machines, decision trees or some other may be used. Understanding as a good prognosis as a euploid and/or transferred embryo with (beta fraction of human chorionic gonadotropin) b-hCG>=20 units (beta positive, pregnancy, 7 days after transfer) and/or presence of gestational sac at least three weeks after transfer, observed by imaging techniques and/or presence of heartbeat at least five weeks after transfer and/or evidence of live birth; and one with a poor prognosis such as aneuploid or with a b-hCG value <20 and/or spontaneous abortion after having implanted the embryo. In case of conflict in the criteria for classifying images of embryos (e.g., euploid with b-hCG<20) priority is given to ploidy status.

A set of embryos may be ordered in a descending (or ascending) manner according to the probability of having a good prognosis; in such a way that a health care team evaluates the results obtained by the algorithm, together with the patient's history and decides which embryos will be transferred.

In order to demonstrate the inventive activity in the present invention, examples that demonstrate the preceding method are presented below in an enunciative way, but not limiting.

Example 1. Using a conventional computer system, the process may begin with the evaluation that is made of the conventional images (Start) of an embryo in the blastocyst stage (between days 5 to 7 after the day of fertilization of the development of the embryo), which were obtained from a patient whose eggs had not been intervened either physically and/or biopsy. With these characteristics, stage A of the method based on conditioning and pre-processing of images of human embryo classification.

The classification of human embryonic cells where a collection of micrographs of a single embryo coming, in this example, from the same equipment and that already have the same resolution, in such a way that the conditioning and pre-processing is a minimal manipulation stage since the images correspond to a single embryo but nevertheless they are only manipulated so that the contents of each pixel or voxel of them are homogeneous in the whole series of images, using interpolation techniques. Once the thickest area of the embryo is identified in two dimensions; images are positioned in such a way that the focus area of the microscope is in the area of greatest diameter of the embryo; the focal plane is at the height of the embryo that represents the largest diameter in its 2D representation. It is important that the trophectoderm is observed as clearly as possible (that is, it can be observed in clearly defined edges, leaving the entire embryo within the image and without obstructions. The intervention is then carried out in stage B of pre-processing and/or image improvement, where artificial vision and/or machine learning strategies are used until a standardized image of the embryo is obtained. Based on filters to identify a plurality of B1 textures and/or other metrics based on type segmentation of cells; carried out this activity, the automatic clipping technique is implemented; in this case, 275 calculated textures are shown, the k-means algorithm is used with k=2 to identify the pixels or voxels that belong to the "background" of those that belong to the embryo. Based on this mask, the edges may be detected to cut the B2 image that contains the embryo; characteristics are extracted or using artificial vision and/or artificial intelligence where for the identification of the development phases of the embryo a model of deep convolutional neural networks B3 is used that identifies embryos in one of three phases: a) expansion, b) hatching and c) hatched. With this technique, a probability value [0-1] is obtained where an image corresponds to one of these three classes with a precision of 95%. Furthermore, this model may identify embryos that are collapsed (a natural process of embryos), which is also identified with a probability factor that allows at least three models to be independently separated: a) development phases; b) collapsed embryos and c) degraded embryos. Once the previous stage is concluded, they are obtained from the B3 descriptors related to the phases, slow collapse and degradation, other descriptors are obtained based on the following: original image, image with entropy filters, edge detection with "canny" algorithm, polar image from a centroid, and the areas identified by the segmentation methodology to use these descriptors associated with the distribution of the data as measures of central tendency, dispersion, kurtosis, only for being illustrative but not limiting and with this ordered set of C embryos in a descending manner according to the probability of having a good forecast; in such a way that the health care team evaluates the results obtained by the algorithm, together with the patient's history and decides which embryos will be transferred, as the case may be.

Example 2. A comparison was made between the selection of the embryo in a conventional way by a team of embryologists, with the selection process that is proposed for registration, by means of a case study. The starting point is a particular case of a treatment in which it was possible to obtain five blastocysts.

For this case, the genetic study was used as the gold standard, where a euploid result is considered a good prognosis and an aneuploid result is considered a poor prognostic result. In addition, the level of b-hCG (beta fraction of human chorionic gonadotropin) in serum seven days after embryo transfer was used as a reference.

Selection of the Embryo by Conventional Methods.

Starting from the achievement of five embryos in the blastocyst stage, the embryology team qualifies each embryo based on four characteristics: i) the day the embryo matured to the blastocyst stage (commonly they are day five or day six), ii) the blastocyst agenda (using a scale from 1 to 5 where 1 is the smallest and 5 is the largest), ii) quality of the internal cell mass (measured on a scale of 1 to 3, where 1 is the best quality and 3 is the lowest quality), and v) cell form and content in trophectoderm (measured on a scale of 1 to 3, where 1 is the best quality and 3 is the lowest quality). The results of the evaluation are observed in Table 6:

TABLE 6

Evaluation results

| Embryo | Day in which the embryo matured to the blastocyst stage | Size | Quality of the inner cell mass | Trophectoderm quality |
| --- | --- | --- | --- | --- |
| 1 | 6 | 5 | 1 | 1 |
| 2 | 5 | 5 | 1 | 1 |
| 3 | 5 | 5 | 2 | 2 |
| 4 | 5 | 5 | 2 | 1 |
| 5 | 6 | 5 | 1 | 1 |

According to these characteristics, the embryology team chose embryo 2 as the most suitable to carry out the transfer, even without knowing their ploidy status. Selection of the embryo using the system.

The following procedure was applied for each of the five images.

Although, the images were taken with similar characteristics of microscope, light and optical filters, as can be seen in FIG. 102, they were taken with different objectives (200× and 400×), which causes a heterogeneous relationship of micrometer ratios per pixel (embryos 2 and 5 with 400×, and the rest at 200×) 10200.

The proposed registration system carried out as a first step, the pro-processing and improvement of the image, which causes the homogenization of the micrometer-to-pixel rotation. In this case it has been set to one micrometer per pixel. In addition, pro-processing identifies the embryo and cuts it out of the image. Next, a filling scheme is made to homogenize the size of the images by copying the values of the image border. In this case, it has been adjusted to 400×400 pixels 10300 as shown in FIG. 103. The processed images are introduced to a previously trained neural network model to identify the phase of each of the embryos and their collapse. This resulted in the correct identification of the stage of each embryo as shown in Table 7 of results.

TABLE 7

Pro-processed and evaluated images of the embryos.

| Embryo | Expansion | Hatched | Hatching | Collapsing |
| --- | --- | --- | --- | --- |
| 1 | <0.01 | <0.01 | 0.96 | 0.03 |
| 2 | 0.10 | <0.01 | 0.81 | 0.09 |
| 3 | <0.01 | <0.01 | 0.99 | <0.01 |
| 4 | <0.01 | <0.01 | 0.99 | <0.01 |
| 5 | <0.01 | <0.01 | 0.74 | 0.25 |

The system then proceeds to identify 275 textures for each pre-processed image, using the 25 Laws masks of 5×5 size. The Laws masks are obtained by calculating the product (vertical×horizontal) of all the combinations between the following vectors: i) 1, 4, 6, 4, 1, II) −1, −2, 0, 2, 1, iii) −1, 0, 2, 0, −1, iv) 1, −4, 6, −4, 1, and v)−1, 2, 0, −2, 1. Some previous filters have been applied to apply the convolution of the Laws masks, with the intention of highlighting characteristics or patterns in the images, which consist of the application of entropy filters with radii between 2 and 20 pixels, as well as square Gaussian filters of sizes between 5 and 11 pixels. This process then creates a vector of 275 features for each pixel. All of these vectors are introduced to a previously trained neural network model to classify the pixels into one of four categories: i) background, i) zona pellucida, iii) trophectoderm, and iv) internal region. With this information, a binary image was reconstructed for each of the four categories.

These vectors were then used to classify in an unsupervised manner into 20 groups using the k-means algorithm. Next, for each group of pixels that belong to the same group identified by k-means, and that are contiguously in the image, the predominant category (background, zona pellucida, trophectoderm or internal region) was identified, and it was homogenized between all the pixels in that group. With this information, four binary masks corresponding to each of these four categories (fundus, zona pellucida, trophectoderm, or Internal region) were created. The zona pellucida mask was subsequently treated with two dilations, five erosions and three dilations with a size of 3×3 for each case.

Next, the extraction stage of the characteristics consists of the computation of statistical descriptors for the pixels that belong to i) the entire embryo, II) zona pellucida, iii) trophectoderm, and iv) internal region. Parameters may be associated with the distribution of the data such as mean, variance, coefficient of variation, range, percentiles, among others, resulting in a total of 81 parameters.

Next, the proposed system uses the list of characteristics previously described and introduces them to a previously trained AI model to predict the prognosis of each embryo. This resulted in a list of probability values that each list of characteristics associated with each embryo photo belongs to the class of good prognosis. The embryos are ranked in descending order according to their probability value of belonging to the class of good prognosis using ordered alphabet letters, such that the letter A * is assigned to the embryo with the best prognosis. The results of the hierarchy are shown in the following Table 8.

TABLE 8

The results of the hierarchy of the embryos.

| Embryo | Probability of belonging to the good prognosis class | Ranking |
|---|---|---|
| 1 | 0.86 | D |
| 2 | 0.28 | E |
| 3 | 0.97 | A |
| 4 | 0.93 | C |
| 5 | 0.94 | B |

This resulted in the selection of embryo 3 as the one with the best prognosis followed by 5, 4, 1 and 2 in that order. This means that embryo 2 was assigned the worst prognosis.

The results of the genetic study with the embryos selected by the embryology team were then compared with that of the system (which had been blind up to now for both the embryology team and the system proposed here). The results of the genetic study are shown in the following Table 9.

TABLE 9

Results of the genetic study are shown in the following.

| Embryo | Ploidy | Genus |
|---|---|---|
| 1 | Euploid | Male |
| 2 | Aneuploid | — |
| 3 | Euploid | Female |
| 4 | Euploid | Female |
| 5 | Euploid | Male |

The genetic results showed that embryo 2 was the only aneuploid, indicating that, if the embryo had been selected using the criteria of the embryology team, it would have selected the aneuploid and the procedure would have been unsuccessful. On the other hand, the system identified embryo 2 as the one with the lowest probability of having a good prognosis.

The client decided to have embryo 5 transferred based on gender and the result of the genetic study.

The transfer of embryo 5 was carried out without any risk factor. Seven days after the transfer, a blood sample and measurement of b-hCG were taken, which resulted in a value of 110 mIU/ml. A second b-hCG sample was taken two days later in reference to the last one, where a blood value of 275 mIU/ml was obtained. This is interpreted as a healthy pregnancy.

26 days after embryo transfer 5, a routine ultrasound was performed, where the expected size structures (Yolk sac and embryo) were observed, which is an indicator of normal pregnancy development.

Example 3. This example shows how the process is viable for the hierarchization of other types of cells (ovules); where the method allows to identify other characteristics present in cell structures and that they allow to select and rank them; then the method with ovules is carried out to show the industrial application and the inventive step of the process.

1. Obtaining independent micrographs of one or at least one set of eggs: At this stage, a collection of micrographs is made, at least one of which may correspond to a single ovule (in the case of a plurality of images, each set of they may be classified by each one of the ovules independently), these images can come from the same or different equipment from which they have been obtained and in the same way their resolution and magnification can be completely different, in such a way that in this stage a standardization of each is carried out as follows: a. Each image may correspond to a single ovule. b. Each image is individually analyzed and manipulated until the pixel to square micrometer or voxel to cubic micrometer ratio is the same for the entire set of images, using interpolation techniques for this process; c. The image of the ovum may correspond to a mature ovum, each image may be obtained prior to any physical intervention such as freezing; d. The images of the ovules can be taken in 2, 3 or 4 dimensions (3 spatial dimensions and one temporal) with any pixel or voxel reconstruction techniques. In the case that the micrograph is in 2 dimensions, the thickest area of the ovule is identified defining the size of the longest possible diameter of the ovule seen in two dimensions; that the focus area of the microscope is in the area with the largest diameter of the ovule; the focal plane is at the height of the ovule that represents the largest diameter in its 2D representation; it may be obtained manually, moving the vertical position of the focal plane, until it is close to the point of greatest diameter, in such a way that the cell membrane and the area can be observed as sharp as possible (that is, it can be observed in clearly defined edges; obtain the minimum of blur in the Image), using a range of light, in such a way that the structures can be clearly observed and a contrast is obtained that allows the clarity described above; f. The ovule may appear complete within the image and without obstructions, that is, objects such as instruments, text added to the image, superimposed structures, among others, do not appear on it.

In such a way that at the end of this stage there is a plurality of independent images (in 2, 3 or 4 dimensions) pre-processed and improved (regardless of the source that produces it) with microscopy, high-definition digital cameras or other specialized techniques for image reconstruction. This stage of the process is carried out separately for the purpose that the plurality of images show the modifications of the ovules in the period of time;

2. Pre-processing and improvement of images. Using a computer, artificial vision and/or machine learning strategies (machine learning) are defined until a standardized image of the ovum is obtained; Through the use of deep learning techniques (deep learning) and/or artificial vision, relevant characteristics are identified such as the pixel to square micrometer or voxel to cubic micrometer ratio, the intensity distribution of the pixels or voxels, the responses to previously given convolutional filters, or other previously defined mathematical models that allow the identification of intensity patterns in 2, 3 or 4 dimensions such as roughness, contrast, brightness, saturation, smoothness, or particular shapes, for the prediction of ovule characteristics such as its internal diameter, the thickness of the zona pellucida, granularity, the presence of vacuoles, the presence and position of the meiotic spindle, among others; the parameters may be filter-based to identify a plurality of textures and/or other metrics based on the structure segmentation: where the plurality of textures can be at least those where one or a combination of texture detector masks are used, such as LAWS (for example 25, where the LAWS energy is obtained by detecting textures in Images of the ovule that can be standardized, or enhanced by means of artificial vision strategies such as energy filters, Gaussian type, Laplacian and edge detectors) to identify textures on the original image and at least one variant of the original. Entropy filters with different radii of influence and Gaussian blurring are used to generate the variants; Once this activity has been carried out, the automatic cropping technique is implemented, that is, the calculated textures are used, the k-means algorithm is used with a k value of at least 2 to identify the pixels or voices that belong to the background of the that belong to the ovule or some instrument or material present in the photograph other than the ovule. Based on this mask, the edges are detected to cut out the image containing the ovum. As an alternative to automatic cropping based on the k-means algorithm, it is also possible to use an object identifier based on artificial intelligence, which allows the identification and subtraction of instruments, letters or other artifacts other than the ovule from the image. To identify the ovule maturation phases, a deep convolutional neural network model is used that can classify ovules into one of the following phases: a) presence of a germinal vesicle, b) meiosis I, or c) meiosis II; With the classifier technique, a probability value [0-1] is obtained where an image corresponds to one of these three classes with a precision according to the model used.

For the identification of the position of the polar body of the ovules, a previously trained classifier can be used, which is identified with a probability index.

To identify the degree of degradation of an egg, a pre-trained classifier can be used that uses a probability index that a given image falls within the class of "degraded" or normal, or a pre-trained regressor can be used, which enables identification of the percentage of degradation that the ovule presents through the image.

To identify the degree of development of an ovum within a development curve, a previously trained classifier can be used that uses a probability index that a given image is within one or more classes that are associated with the degree of evolution or growth of the ovum according to the expected growth given the conditions of the ovum. As an alternative to the classifier, a previously trained regressor can be used to identify the percentile in which it is located according to its growth and development, according to a reference of healthy eggs, or alternatively, statistical data can be used to locate to the image of the ovule within a distribution of statistical growth parameters such as the size of the different areas.

In such a way that at the end of this stage there is an algorithm implemented in a computer that allows to identify the pixels or voxels that belong to different structures.

The supervised training was carried out by means of manual labels on the texture vectors for each pixel or voxel; where from the predictions made at the pixel or voxel level, the predictions are subjected to a process to generate more homogeneous areas for each label, which involves the extraction of blobs from a k-means and a process of erosion and dilation of the zones.

An alternative to identify the different zones is to use a model of neural networks that contains an encoder and a decoder that manages to associate each pixel or voxel to one of the structures of interest.

3. Assign feasibility potential. With the algorithm of the previous stage, in addition to the descriptors related to the maturation and degradation phases, other descriptors are obtained based on the following: original image, image with entropy filters, image with highlighted edges, polar image from of a centroid, and the areas identified by the segmentation methodology.

Statistical descriptors are used, or a fraction of them selected by descriptor selection methods, associated with the distribution of the data as measures of central tendency, dispersion, kurtosis, only for being illustrative but not limiting; in such a way that with the list of descriptors obtained from each ovule, together with patient history data (age and hours between fertilization and the image or images), the source of the ovule (laboratory preset: microscope, and objective), a neuron network may be trained which allows each ovum to be classified into one of two classes: good prognosis and poor prognosis. As an alternative, another classification algorithm such as vector support machines, decision trees or some other can be used.

Understanding as a good prognosis as an ovum that successfully achieved fertilization, or that managed to develop into an euploid embryo and/or transferred with (beta fraction of human canonical gonadotropin) b-hCG>=20 units (beta positive, pregnancy, 7 days after transfer) and/or presence of heartbeat at least five weeks after transfer and/or evidence of live birth; and one with a poor prognosis such as an ovum that did not mature to the stage of meiosis I or meiosis II, which did not achieve normal fertilization, one that generated an aneuploid embryo or with a b-hCG value<20 and/or spontaneous abortion after having implanted the embryo.

Finally, there is an ordered set of eggs in a descending (or ascending) way according to the probability of having a good prognosis; in such a way that the health care team evaluates the results obtained by the algorithm, in conjunction with the patient's history and will favor subsequent decision-making.

In embodiments of the present invention, use of the IVF/ICSI platform, as described herein, may include the real-time automatic quantitative evaluation, assessment and/or classification system of individual spermatozoa, intended for ICSI, and other fertilization procedures, which allows the selection of a single spermatozoa, requires a conventional method, sample preparation consisting of further sperm collection and regardless of the production method (e.g. masturbation, prostate massage, surgical extraction) the following steps are generally followed before selecting sperm for ICSI: a. The semen sample is prepared using standard sperm capacitation techniques including centrifugation and swim-up, gradients, or microfluidics (WHO REF manual). This step is usually skipped when sperm are present at low concentrations without the presence of seminal plasma as is the case when spermatozoa have been surgically retrieved. b. For manipulation, the sperm are placed in specialized culture media. As an example, a common preparation uses a 10 pL drop with the Multipurpose Handling Medium (MHM) solution. c. A commonly employed step involves the transfer of several sperm aspirated from the previous preparation and released into a new drop with a specialized solution intended to reduce sperm motility. A commonly used means for such a purpose is a polyvinylpyrrolidone (PVP) solution with or without HSA (human serum albumin) d. Other methods could be added as part of the semen preparation and sperm selection process. These may include but are not limited to the use of hyaluronic acid binding, magnetically activated cell sorting (MACS), microfluidics, and surface charge Zeta potential.

The preparation steps mentioned above are not mandatory and, when applicable, can be used as stand-alone steps or in combination with other steps not included in this description. Semen preparation protocols may vary based on individual laboratory protocols.

Once the sample has been prepared following what has been described, the automatic quantitative evaluation system in real time, assessment and/or classification of individual spermatozoa, aimed at ICSI or other fertilization procedures, requires the selection of a single spermatozoa, and, using the IVF/ICSI platform as described herein, includes the following stages:
  I. Localization of spermatozoa in images. Which can comprise two different image inputs: 1 a. Image processing using digital filters; 1 b. Image processing using convolutional neural networks;
  II. Characterization of sperm patterns.
  III. Evaluation of the quality of the spermatozoa and generation of the recommendation of the best spermatozoa to inject.

Figure 105:
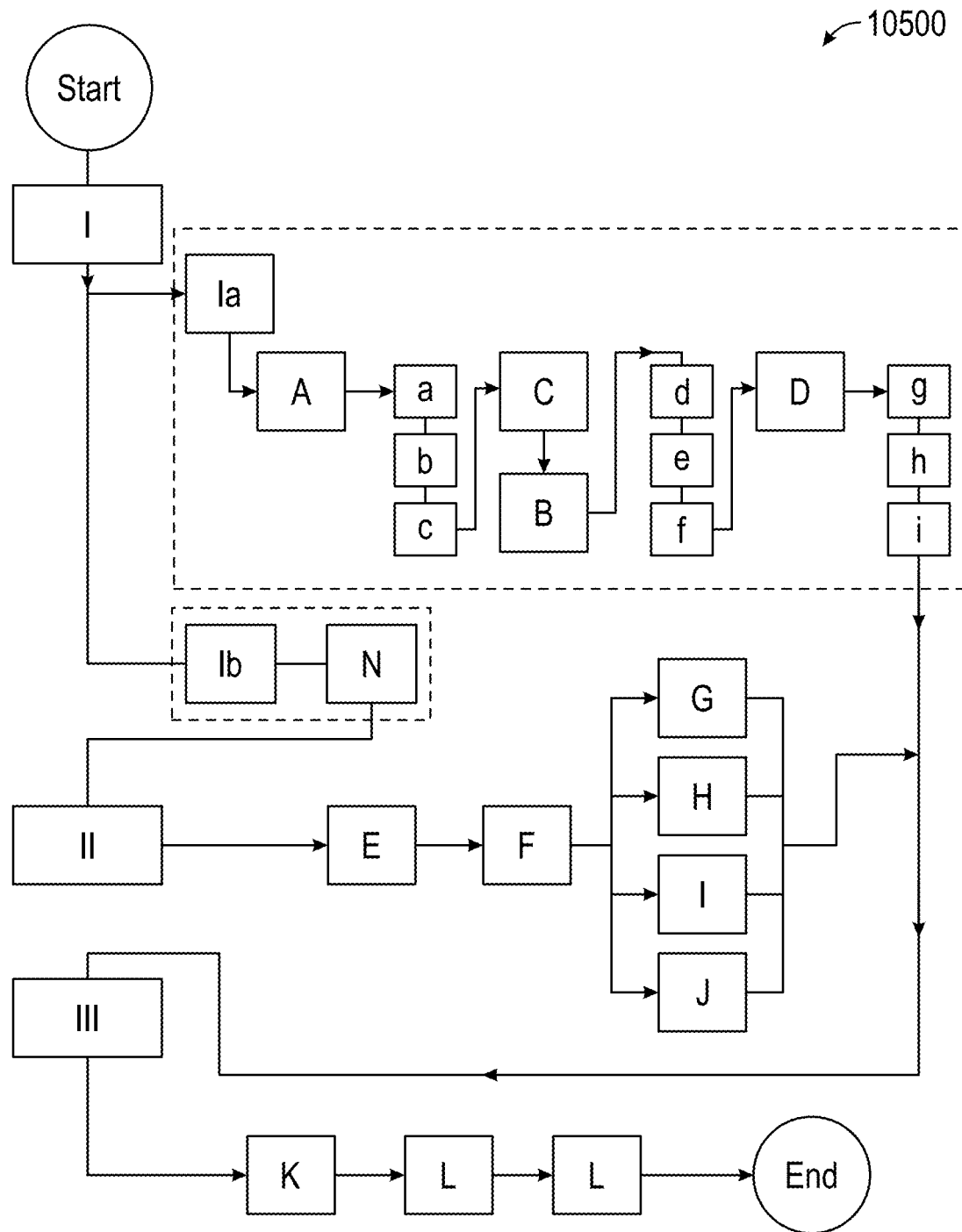
FIG. 105 is a diagram representing the system for real-time automated quantitative evaluation, assessment, and/or classification of individual sperm.

FIG. 105 is a diagram 10500 representing the system for real-time automated quantitative evaluation, assessment, and/or classification of individual sperm. Where to start the previous process, it is required to prepare the sample before taking images to be processed in the microscope.

Figure 106:
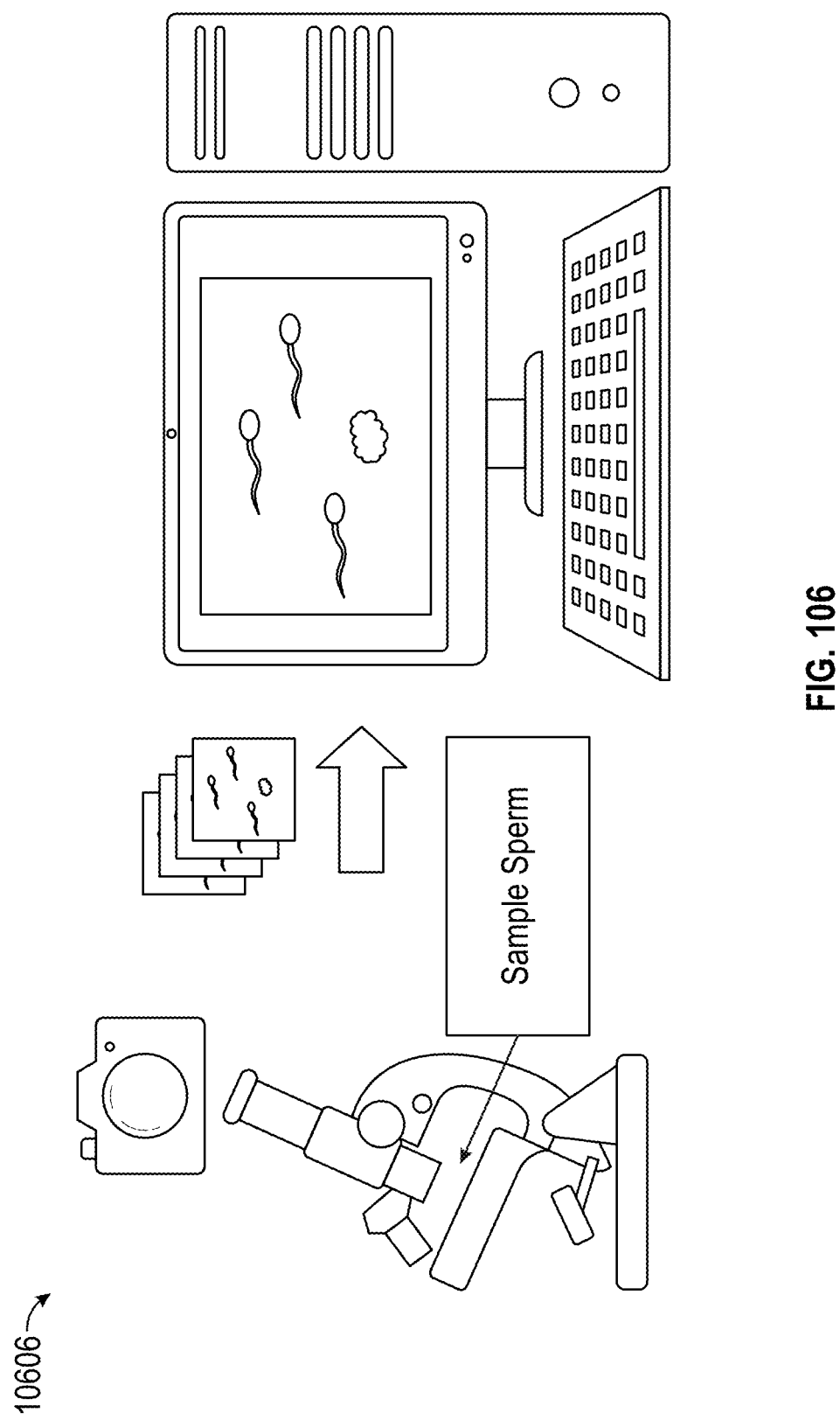
FIG. 106 is a representation of equipment (camera and microscope) that generates the images of the system for the evaluation, assessment and/or automatic quantitative classification in real time of individual spermatozoa.

The invented system takes as input a sequence of images or frames. These images 100 may come from a conventional digital camera 200, or an imaging scanner that is connected to a camera on the microscope 300 where the sperm sample is viewed or delivered to the system as a video file 10600 (FIG. 106).

The system for the real-time automatic quantitative evaluation, assessment and/or classification of individual spermatozoa, aimed at ICSI, and other fertilization procedures, which require the selection of a single spermatozoa, consists of three parts:

Location of the sperm in images. Once at least two images 100 have been obtained, they can be processed in either of the following two ways:

Image Processing Through Digital Filters

In this stage, each one of the images 100 consists of a matrix of pixels of size n×m, which represents the image that is being observed by the microscope at a given instant; in each pair of arrays 101 and 102, the first array 101 is compared with the second array 102, establishing the differences in the intensity values of each pixel; this difference allows establishing a parameter that is compared with a predefined value that determines if the changes between the first arrangement 101 and the other 102 are significant and therefore evidence a possible movement of an element in the microscope. Then it is necessary to discriminate from those movements that are real or not, in such a way that if the difference only appears in one pixel, then it is digital noise and in case the movement is from a set in the neighborhood of changes, then it is an actual motion; the actual movements are represented in a third arrangement 103 whose inputs are a set of movement registers R1, this process is repeated with the total set of images 100, in such a way that all the R1 are registered as a set of indicators, among which are, dimension, area, eccentricity, height, width, convexity, etc. in such a way that these indicators are compared with pre-established patterns to determine their nature, among which can be characterized as sperm, manipulation pipette, epithelial cells just to mention a few and only those that represent sperm that are associated with their indicators are selected in the register R2, in such a way that these registers R2 pass to the next stage;

Image Processing Through Convolutional Neural Networks

The images 100 are provided to a convolutional neural network N, which is located in a conventional logic processing unit 104 where a mathematical algorithm is housed that allows the association of specific indicators among which are dimension, area, eccentricity, height, width, convexity, among others; in such a way that these indicators are compared with pre-established patterns to determine their nature, in which they can be characterized as sperm, manipulation pipette, epithelial cells just to mention a few and only those that represent sperm that are associated with their indicators are selected in register R2, such that these registers R2 have a unique identification number D1 and are provided to the next step;

Characterization of Sperm Patterns

In this stage, we seek to identify the trajectory of each sperm and characterize it to turn it into indicators, at least of, trajectory, morphological characteristics such as head, tail, head movement patterns, tail movement patterns and include:

The R2 records of Stage II are compared (which may be by means of conventional arithmetic operations) in such a way as to establish a relationship of correspondence between the parameters associated with each sperm in such a way that if the correspondence is significant, the trajectory T1 is established by means of coordinates of a Cartesian plane, associated to each register R2, thus establishing a sequence of coordinates S1 that are translated as a geometric trajectory; but if the correspondence is not significant through the unique record of each spermatozoon, it allows defining whether it is a spermatozoon that enters the visual field of the microscope 300 or is one of those that were previously in the visual field; in such a way that now each record R1 is associated with a path T1, since each of these could be present and associated with different records R1 which are discriminated by the identifier D1; With these associations of "R1+D1+T1", a digital representation 400 is generated for each sperm in the processing logic unit 104, and provided to different threads: a. Path pattern descriptor generation thread W, in each association R1+D1+T1 of each sperm, allows generating at least one indicator such as velocity, trajectory, linearity, curvature; b. Thread for the generation of descriptors of movement patterns X, in each digital representation 400 of each spermatozoon, allows generating at least one indicator of movement of the head, movement of the tail; c. Subprocess of characterization of the morphology of the sperm And, in each digital representation 400 of each sperm, it allows to characterize it at least one indicator of the shape of the head, size of the tail, presence of anomalies; d. The texture characterization thread Z, using at least one set of Laws masks, allows characterizing spermatozoa by their textures. All these records have uniquely characterized each sperm since R1+D1+T1 is associated with at least its trajectory pattern descriptors W, movement pattern descriptors X, characterization of sperm morphology Y, and texture Z, generating a digital array P that represents the input of the next stage of the process.

Evaluation of the Quality of the Sperm and Generation of Recommendation of the Best Sperm to Inject In this stage, the aim is to relate the indicators generated in STAGE II with a quality index for each sperm analyzed, which allows defining a recommended order for the selection of sperm to be injected, which is presented on screen 500 of the computer in where the analysis is performed.

The digital context P that identifies each sperm is provided to a mathematical algorithm that determines an index Q for each sperm, which represents the quality of the sperm. The values of the Q indices of all the spermatozoa analyzed are ordered to generate an R list, from highest to lowest, in such a way that the first elements of the list correspond to the highest quality spermatozoa to provide a live product of pregnancy. Finally, a set of spermatozoa (at least three) with the Q index values that appear in the list (those with the highest indices) are identified and a digital indicator is generated for each of the spermatozoa according to their R2 register. and corresponding S1, which is overlaid on the most recently acquired image 100 and displayed on the screen 500 of the computer where the analysis is performed.

Therefore, when a user asks the system for help in selecting the best sperm to inject during an ICSI procedure, the system performs: K. calculating a quality metric for each sperm; L the calculation of a classification of the quality of the spermatozoa detected; and M. the user denotation of the highest ranked sperm. The calculation of a quality metric for each sperm (K process) consists of assigning a numerical value to each sperm evaluating the sets W, X, Y and Z using a mathematical model that can be generated by an expert or by using the Machine learning or artificial intelligence algorithms include, but are not limited to, neural networks, linear classifiers, probabilistic classifiers, trees, logistic regression, clustering methods, and deep learning classifiers.

Computing a sperm quality ranking of the detected sperm (process L) consists of ranking the sperm according to the quality metric generated in step K.

User denotation of top ranked sperm (M) consists of, based on measurements and ranking, superimposing graphical elements over the locations of the selected sperm in each frame of the video stream in real time and displaying them to the user, from system invented by using 500. Examples of 500 include a computer screen, mobile phone, tablet, or with a virtual or augmented reality headset or goggles. using the IVF/ICSI platform using the IVF/ICSI platform using the IVF/ICSI platform.

Figure 107:
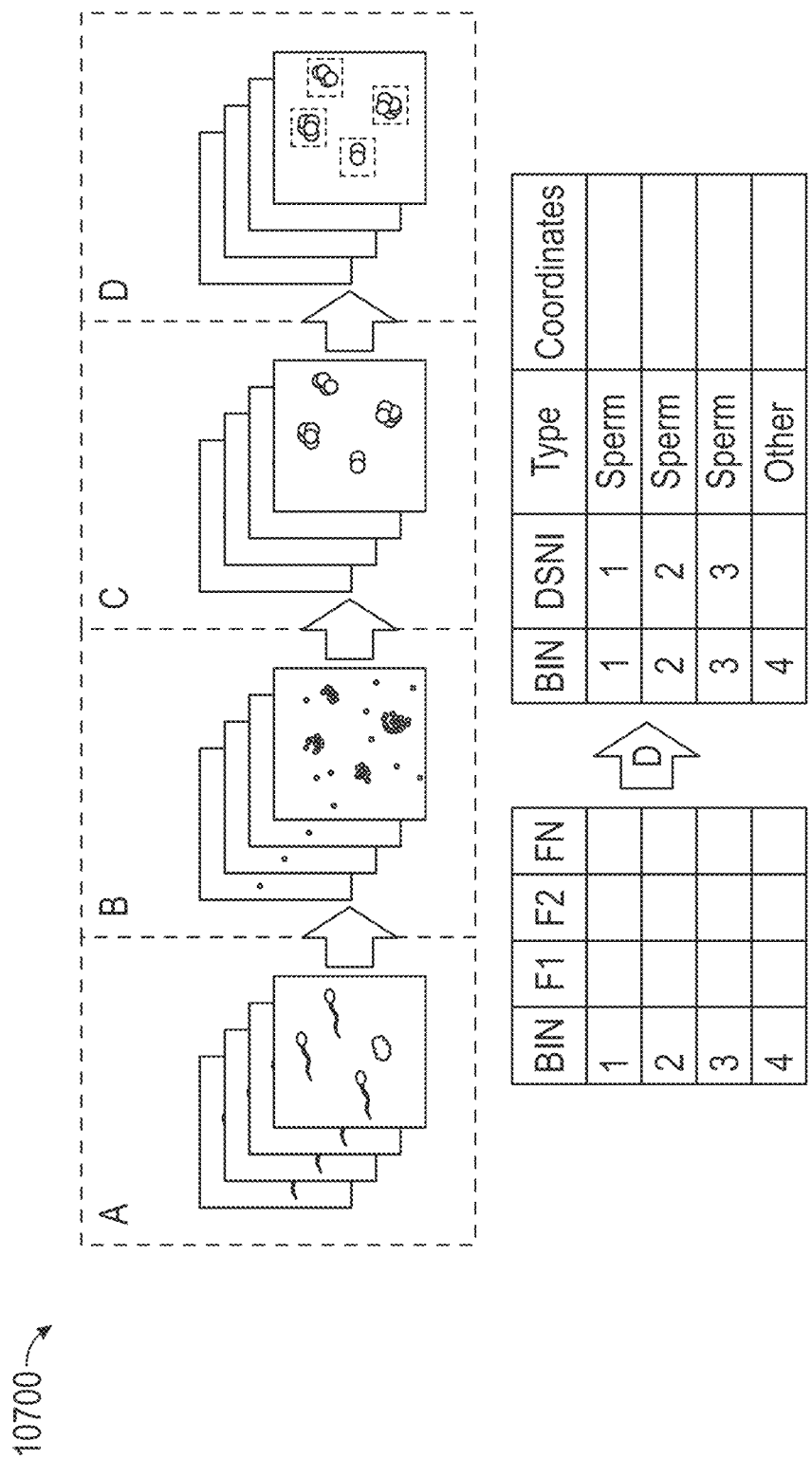
FIG. 107 is a representation of the semantic segmentation of sperm in a video sequence.

FIG. 107 is a representation of the semantic segmentation of sperm in a video sequence 10700.

Figure 108:
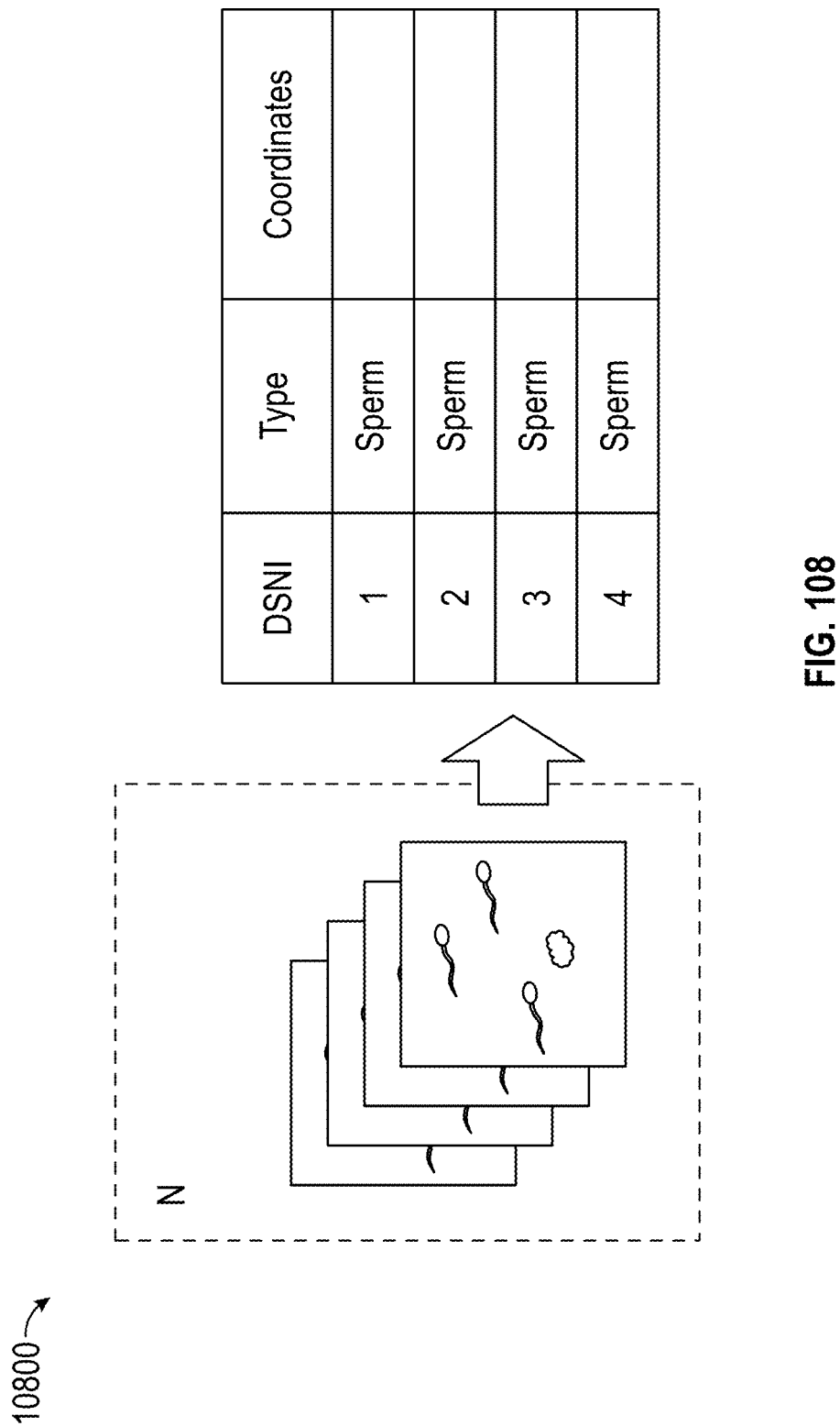
FIG. 108 is a representation of the semantic segmentation of sperm in a video sequence using a neural network architecture.

FIG. 108 is a representation of the semantic segmentation of sperm in a video sequence using a neural network architecture 10800.

FIG. 109 is a representation of the process to verify the correspondence of the identity of a sperm within successive frames 10900.

Figure 110:
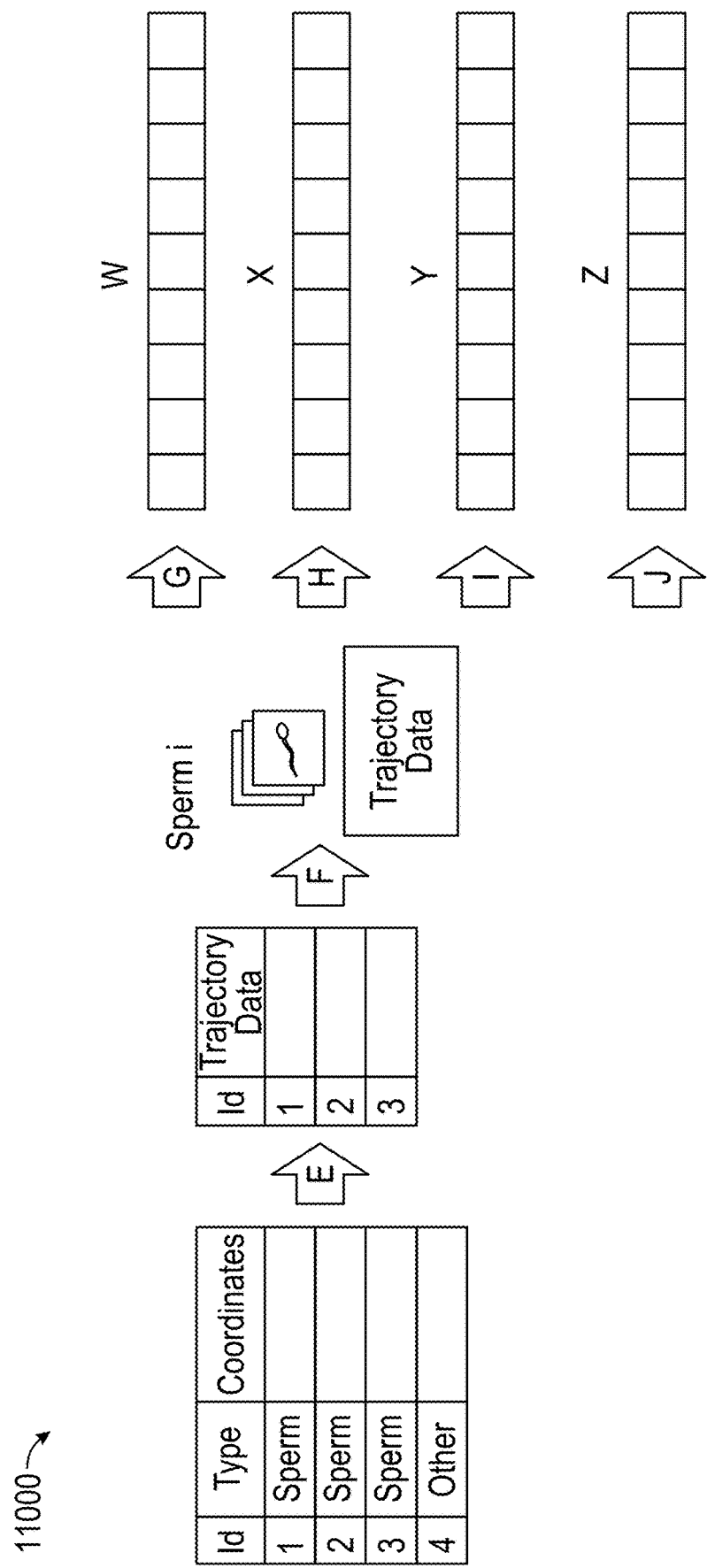
FIG. 110 is a diagram with examples of inputs and outputs for procedures described herein.

FIG. 110 is a diagram with examples of inputs and outputs for procedures described herein 11000.

Figure 111:
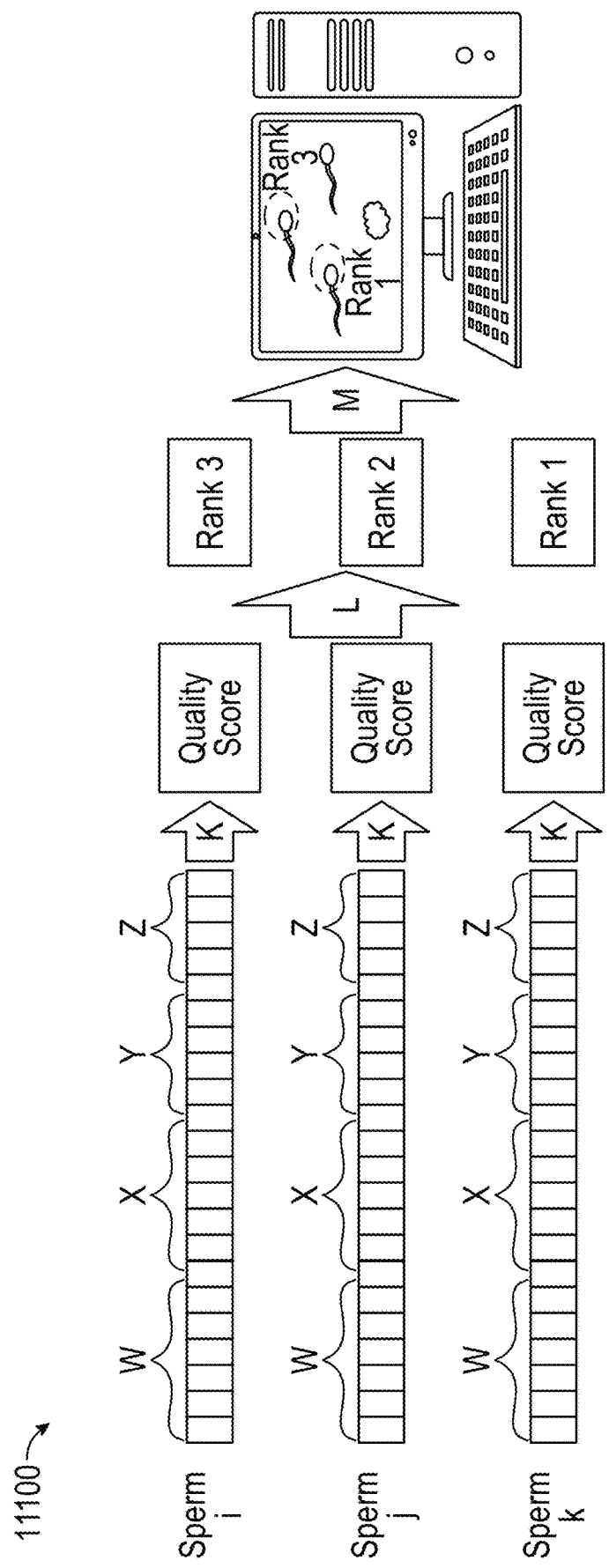
FIG. 111 is a diagram with examples of inputs and outputs for procedures described herein.

FIG. 111 is a diagram with examples of inputs and outputs for procedures described herein 11100.

While only a few embodiments of the disclosure have been shown and described, it will be obvious to those skilled in the art that many changes and modifications may be made thereunto without departing from the spirit and scope of the disclosure as described in the following claims. All patent applications and patents, both foreign and domestic, and all other publications referenced herein are incorporated herein in their entireties to the full extent permitted by law.

The methods and systems described herein may be deployed in part or in whole through machines that execute computer software, program codes, and/or instructions on a processor. The disclosure may be implemented as a method on the machine(s), as a system or apparatus as part of or in relation to the machine(s), or as a computer program product embodied in a computer readable medium executing on one or more of the machines. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like, including a central processing unit (CPU), a general processing unit (GPU), a logic board, a chip (e.g., a graphics chip, a video processing chip, a data compression chip, or the like), a chipset, a controller, a system-on-chip (e.g., an RF system on chip, an AI system on chip, a video processing system on chip, or others), an integrated circuit, an application specific integrated circuit (ASIC), a field programmable gate array (FPGA), an approximate computing processor, a quantum computing processor, a parallel computing processor, a neural network processor, or other type of processor. The processor may be or may include a signal processor, digital processor, data processor, embedded processor, microprocessor or any variant such as a co-processor (math co-processor, graphic co-processor, communication co-processor, video co-processor, AI co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, network-attached storage, server-based storage, and the like.

A processor may include one or more cores that may enhance speed and performance of a multiprocessor. In embodiments, the process may be a dual core processor, quad core processors, other chip-level multiprocessor and the like that combine two or more independent cores (sometimes called a die).

The methods and systems described herein may be deployed in part or in whole through machines that execute computer software on various devices including a server, client, firewall, gateway, hub, router, switch, infrastructure-as-a-service, platform-as-a-service, or other such computer and/or networking hardware or system. The software may be associated with a server that may include a file server, print server, domain server, internet server, intranet server, cloud server, infrastructure-as-a-service server, platform-as-a-service server, web server, and other variants such as secondary server, host server, distributed server, failover server, backup server, server farm, and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for the execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network with multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, 4G, 5G, LTE, EVDO, mesh, or other network types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic book readers, music players and the like. These devices may include, apart from other components, a storage medium such as flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, network-attached storage, network storage, NVME-accessible storage, PCIE connected storage, distributed storage, and the like.

The methods and systems described herein may transform physical and/or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable code using a processor capable of executing program instructions stored thereon as a monolithic software structure, as standalone software modules, or as modules that employ external routines, code, services, and so forth, or any combination of these, and all such implementations may be within the scope of the disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices, artificial intelligence, computing devices, networking equipment, servers, routers and the like. Furthermore, the elements depicted in the flow chart and block diagrams, or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described in the disclosure may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described in the disclosure, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the devices described in the disclosure, as well as heterogeneous combinations of processors, processor architectures, or combinations of different hardware and software, or any other machine capable of executing program instructions. Computer software may employ virtualization, virtual machines, containers, dock facilities, portainers, and other capabilities.

Thus, in one aspect, methods described in the disclosure and combinations thereof may be embodied in computer executable code that, when executing on one or more computing devices, performs the steps thereof. In another aspect, the methods may be embodied in systems that perform the steps thereof and may be distributed across devices in a number of ways, or all of the functionalities may be integrated into a dedicated, standalone device or other hardware. In another aspect, the means for performing the steps associated with the processes described in the disclosure may include any of the hardware and/or software described in the disclosure. All such permutations and combinations are intended to fall within the scope of the disclosure.

While the disclosure has been disclosed in connection with the various embodiments shown and described in detail, various modifications and improvements thereon will become readily apparent to those skilled in the art. Accordingly, the spirit and scope of the disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "with," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosure and does not pose a limitation on the scope of the disclosure unless otherwise claimed. The term "set" may include a set with a single member. No language in the specification should be construed as indicating any non-claimed element as essential to the practice of the disclosure.

While the foregoing written description enables one skilled to make and use what is considered presently to be the best mode thereof, those skilled in the art will understand and appreciate the existence of variations, combinations, and equivalents of the specific embodiment, method, and examples herein. The disclosure should therefore not be limited by the above-described embodiment, method, and examples, but by all embodiments and methods within the scope and spirit of the disclosure.

All documents referenced herein are hereby incorporated by reference as if fully set forth herein.

The invention claimed is:

1. A method for automated, artificial-intelligence-based intracytoplasmic sperm injection (ICSI), the method comprising:
   receiving a droplet containing an egg in a dish placed on a stage;
   using an artificial intelligence/machine learning system (AI/ML system) and an imaging system to detect a zona pellucida, wherein the imaging system includes a microscopy system, a camera system, and a lighting system;
   holding the egg using a robotic microtool;
   lowering a robotic pipettor into the droplet;
   using the AI/ML system and the imaging system to determine an area at which to hold the egg and positioning the robotic microtool to that area;
   using the AI/ML system to instruct the robotic microtool to apply negative pressure to hold the egg to the robotic pipettor;
   using the AI/ML system and the imaging system to determine a target location where zona ablation should be performed;
   moving the egg to the target location;
   using the AI/ML system and the imaging system to assess a thickness of the zona pellucida and determine an ablation action;
   generating a laser to produce the ablation action to ablate the zona pellucida at the target location, wherein a depth of the ablation action is based on the assessed thickness;
   using the AI/ML system and the imaging system to define an injection path into the egg; and
   injecting a sperm, along the injection path, into the egg.

2. The method of claim 1 wherein the stage is a microscope stage.

3. The method of claim 2 wherein the microscopy system includes an inverted microscope.

4. The method of claim 2 wherein the microscopy system includes a stereomicroscope.

5. The method of claim 2 wherein the microscopy system includes a movable microscope.

6. The method of claim 2 wherein the microscopy system includes an optical coherence tomography device.

7. The method of claim 2 wherein the microscopy system includes an optical coherence microscopy device.

8. The method of claim 2 wherein the microscopy system includes a lens-less microscope.

9. The method of claim 1 wherein the robotic microtool is a second robotic pipettor configured to hold the egg.

10. The method of claim 1 wherein:
    the robotic pipettor includes a plurality of pipettes, and
    lowering the robotic pipettor into the droplet includes lowering at least one of the plurality of pipettes into the droplet.

11. The method of claim 1 further comprising heating the dish.

12. The method of claim 1 wherein the imaging system produces at least one image having a mixed reality in which simulated imagery and real-life imagery are combined.

13. The method of claim 1 wherein the ablation action is produced at an intensity and radius needed to ablate an adequate portion of the zona pellucida to facilitate an entry of an ICSI needle through the zona pellucida without distorting the egg.

14. The method of claim 1 wherein injecting the sperm includes moving a needle forward into the egg along the injection path.

15. The method of claim 14 wherein moving the needle includes moving the needle at a controlled speed and stopping once the needle reaches an end point of the injection path.

16. The method of claim 14 wherein injecting the sperm includes using the AI/ML system to apply positive pressure in a needle to deposit the sperm in the egg.

17. The method of claim 16 further comprising using the AI/ML system and the imaging system to (i) confirm that the sperm is out of the needle and (ii) move the needle out of the egg.

18. The method of claim 1 further comprising using the AI/ML system and the imaging system to apply positive pressure in the robotic microtool until the egg is released into a droplet.

19. The method of claim 1 further comprising breaking a membrane of the egg using a set of piezoelectric pulses, wherein the AI/ML system is configured to determine a number of pulses in the set of piezoelectric pulses.

20. The method of claim 1 wherein using the AI/ML system and the imaging system to determine the target location is performed based on at least one of conventional microscopy, optical coherence tomography, optical coherence microscopy, or three-dimensional simulation of morphology of the egg.

* * * * *